United States Patent
Fortman et al.

(10) Patent No.: US 9,856,461 B2
(45) Date of Patent: Jan. 2, 2018

(54) PRODUCING ALPHA-OLEFINS USING POLYKETIDE SYNTHASES

(71) Applicant: The Regents of the University of California, Oakland, CA (US)

(72) Inventors: Jeffrey L. Fortman, San Francisco, CA (US); Leonard Katz, Oakland, CA (US); Eric J. Steen, Berkeley, CA (US); Jay D Keasling, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 14/853,821

(22) Filed: Sep. 14, 2015

(65) Prior Publication Data
US 2016/0068827 A1 Mar. 10, 2016

Related U.S. Application Data

(63) Continuation of application No. 13/876,727, filed as application No. PCT/US2011/053787 on Sep. 28, 2011, now abandoned.

(60) Provisional application No. 61/387,435, filed on Sep. 28, 2010.

(51) Int. Cl.
*C12N 9/10* (2006.01)
*C12P 5/00* (2006.01)
*C12P 5/02* (2006.01)
*C12N 15/52* (2006.01)

(52) U.S. Cl.
CPC .......... *C12N 9/1029* (2013.01); *C12N 15/52* (2013.01); *C12P 5/005* (2013.01); *C12P 5/007* (2013.01); *C12P 5/026* (2013.01); *C12Y 203/01* (2013.01)

(58) Field of Classification Search
CPC ....... C12N 9/1029; C12N 15/52; C12P 5/007; C12P 5/026; C12P 5/005; C12Y 203/01
See application file for complete search history.

(56) References Cited

U.S. PATENT DOCUMENTS 6,558,942 B1 * 5/2003 Khosla ................ C07D 309/36
435/253.5
2007/0281343 A9 12/2007 Arslanian et al.
2008/0076167 A1 3/2008 Gokarn et al.
2009/0111151 A1 4/2009 Julien et al.
(Continued)

FOREIGN PATENT DOCUMENTS

JP 2004-520008 A 7/2004
JP 2007-533308 A 11/2007
(Continued)

OTHER PUBLICATIONS

GenBank Accession No. AAT70108.1, version GI_50082961, "CurM [Lyngbya majuscule]." Chang et al., Jun. 14, 2004. Retrieved from ncbi.nlm.nih.gov/protein/50082961 on Mar. 26, 2013.
(Continued)

*Primary Examiner* — Alexander Kim
(74) *Attorney, Agent, or Firm* — Kilpatrick Townsend & Stockton LLP

(57) ABSTRACT

The present invention provides for a polyketide synthase (PKS) capable of synthesizing an α-olefin, such as 1-hexene or butadiene. The present invention also provides for a host cell comprising the PKS and when cultured produces the α-olefin.

12 Claims, 19 Drawing Sheets

DEBS.LD-Nys.m5 CurM

(56) References Cited

U.S. PATENT DOCUMENTS

2010/0330642 A1* 12/2010 Ridley .................. C12P 5/026
                                                                                                                                                  435/167
2011/0091952 A1     4/2011 Sherman et al.

FOREIGN PATENT DOCUMENTS

| WO | 02/12534 A2 | 2/2002 |
| WO | 2005/103279 A2 | 11/2005 |
| WO | 2009/121066 A1 | 10/2009 |
| WO | 2009/134899 A1 | 11/2009 |
| WO | WO 2011/005548 A1 | 1/2011 |

OTHER PUBLICATIONS

Alber et al., *J. Biol. Chem.* 277(5): 12137-12143 (2002).
Carreras et al., "Engineering of Modular Polyketide Synthases to Produce Novel Polyketides", *Current Opinion in Biotechnology* 9(4): 403-411 (1998).
Chang et al., *J. Nat. Prod.* 67: 1356-1367 (2004).
Chen et al., *J. Bacteriol*, 188(11): 4024-4036 (2006).
Choi et al., "Isolation of the biosynthetic gene cluster for tautomycetin, a linear polyketide T cell-specific immunomodulator from *Streptomyces* sp. CK4412", *Journal of Biotechnology* 136:S57 (2008).
Erb et al.; "Carboxylation mechanism and stereochemistry of crotonyl-CoA carboxylase/reductase, a carboxylating enoyl-thioester reductase"; *Proc. Natl. Acad. Sci. USA* 106(22):8871-8876 (2009).
Gu et al.; "Polyketide decarboxylative chain termination preceded by o-sulfonation in curacin a biosynthesis"; *J. Am. Chem. Soc.* 131(44):16033-16035 (2009).
Mendez-Perez et al., "Modular synthase-encoding gene involved in [akoga]-olefin biosynthesis of *Synechococcus* sp. Strain PCC 7002", *Applied and Environmental Microbiology* 77(12): 4264-4267 (2011).
Wilkinson et al., "Biosynthetic engineering of polyketide synthases", *Expert Opinion on Therapeurtic Patents* 13(10): 1579-1606 (2003).
Zhang et al., "A phosphopantetheinylatingpolyketide synthase producing a linear polyene to initiate enediyne antitumor antibiotic biosynthesis", Proceedings of the National Academy of Sciences 105(5):.1460-1465 (2008).
The International Search Report from PCT/US2011/053787, dated Apr. 26, 2012.
Extended European Search Report dated Feb. 27, 2014 issued for EP 11833081.0, 8 pages.

* cited by examiner

DEBS.LD-Nys.m5 CurM

FIG. 4A

R=
benzene
p-aminobenzene
p-hydroxybenzene

Final product
Styrene
p-aminostyrene
p-hydroxystyrene

FIG. 4B

Non-native R groups incorporated by the avermectin loading domain

R² =

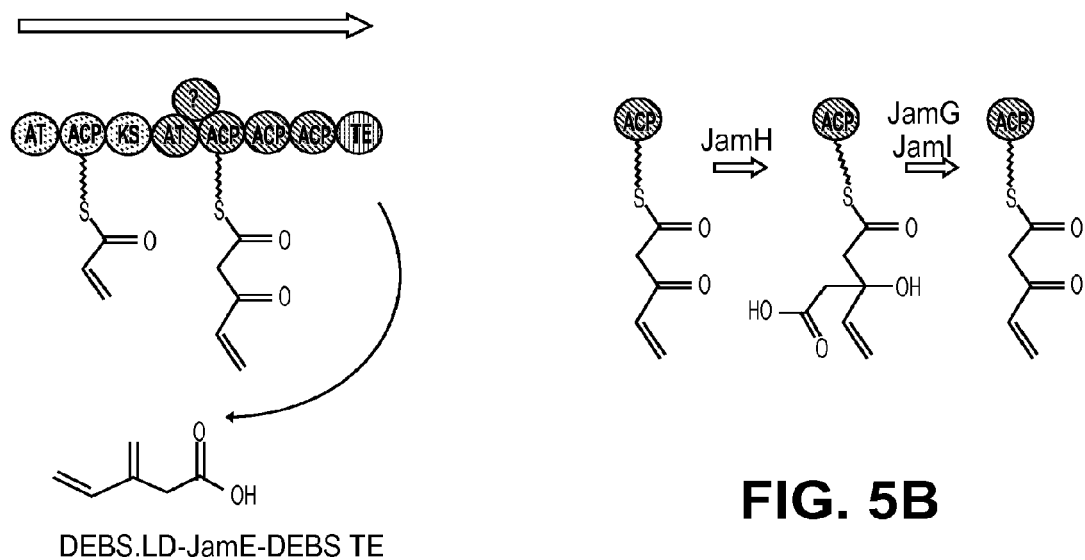
FIG. 5A
FIG. 5B
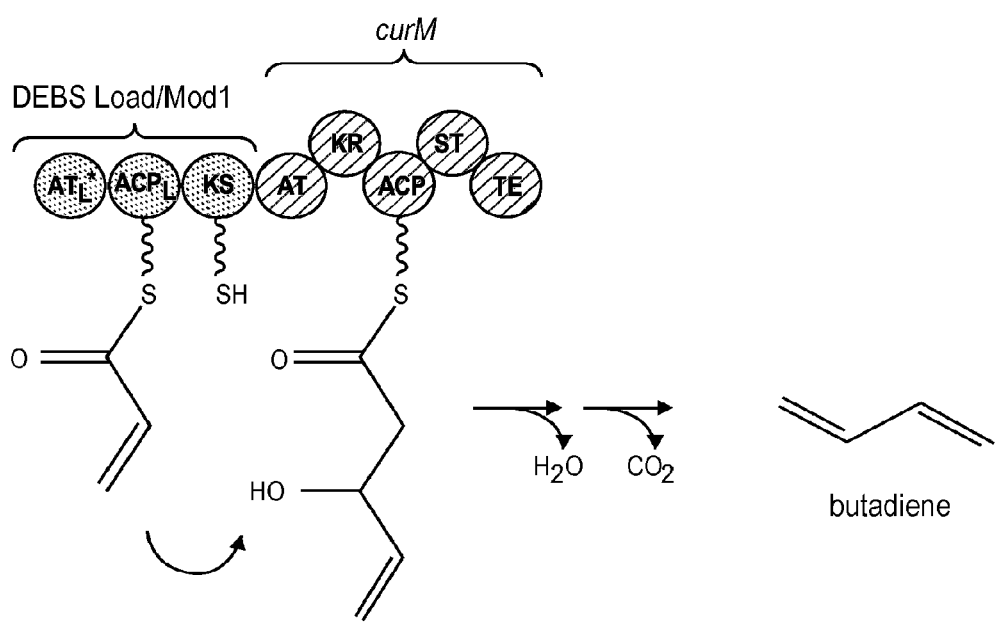
FIG. 6

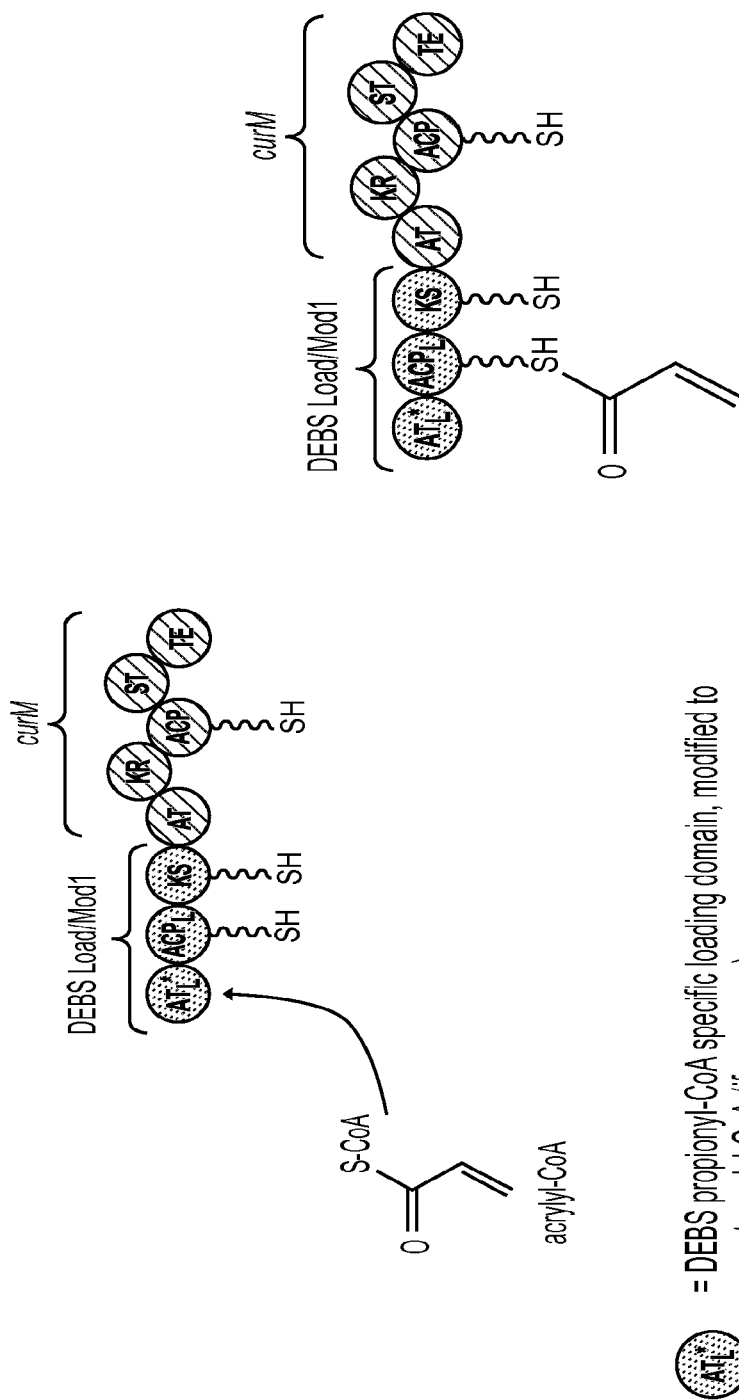

Specifies binding of malonyl-CoA and transfer to ACP domain

Thiotransfer of acrylate moiety to KS domain

Catalyzes reduction of the β-carbonyl group

Catalyzes condensation with release of $CO_2$

SEQUENCE LISTING

```
<160> NUMBER OF SEQ ID NOS: 19

<210> SEQ ID NO 1
<211> LENGTH: 2211
<212> TYPE: PRT
<213> ORGANISM: Lyngbya majuscula

<400> SEQUENCE: 1

Met Ser Asn Val Ser Lys Thr Thr Gln Gln Asp Val Ser Ser Gln Glu
1               5                   10                  15

Val Leu Gln Val Leu Gln Glu Met Arg Ser Arg Leu Glu Ala Val Asn
            20                  25                  30
```

-continued

```
Lys Ala Lys Thr Glu Pro Ile Ala Ile Val Gly Met Ala Cys Arg Phe
     35                  40                  45
Pro Gly Gly Ala Asn Asp Pro Ser Thr Tyr Trp Arg Leu Leu His Asp
 50                  55                  60
Gly Ile Asp Ala Ile Thr Pro Val Pro Pro His Arg Trp Asp Val Asn
 65                  70                  75                  80
Ala His Tyr Glu Pro Asn Pro Glu Ile Pro Gly Lys Ala Tyr Thr Lys
                 85                  90                  95
Gln Gly Gly Phe Ile Glu Gln Val Asp Gln Phe Asp Pro Leu Phe Phe
            100                 105                 110
Gly Ile Ser Pro Arg Glu Ala Ile Ser Leu Asp Pro Gln Tyr Arg Leu
        115                 120                 125
Leu Leu Glu Val Thr Trp Glu Ala Leu Glu Asn Ala Gly Gln Thr Trp
130                 135                 140
Thr Asn Leu Lys Asn Ser Lys Thr Ser Val Phe Met Gly Val Ser Thr
145                 150                 155                 160
Asp Asp Tyr Ala Ser Leu Ser Asn Pro Ile Leu Ile Asn Asn Arg Ser
                165                 170                 175
Leu Gly Val Gly Arg Ile Ser His Leu Leu Gly Leu Gln Gly Ser Asn
            180                 185                 190
Ile Gln Leu Asp Thr Ala Cys Ser Ser Leu Val Ala Ile His Leu
        195                 200                 205
Ala Cys Gln Ser Leu Arg Ser Gly Glu Ser Asn Leu Ala Leu Val Gly
    210                 215                 220
Gly Val Asn Leu Ile Leu Ser Pro Ile Ser Thr Ile Gly Arg Cys Thr
225                 230                 235                 240
Met Lys Ala Leu Ser Pro Asp Gly Arg Cys Lys Thr Phe Asp Ala Ala
                245                 250                 255
Ala Asn Gly Tyr Gly Gln Ala Glu Gly Cys Gly Val Val Val Leu Lys
            260                 265                 270
Arg Leu Ser Asp Ala Ile Thr Asp Gly Asp Leu Ile Ser Ala Leu Ile
        275                 280                 285
Arg Gly Ser Ala Ile Asn His Asp Gly Pro Ser Ser Gly Leu Thr Val
    290                 295                 300
Pro Asn Gly Met Ala Gln Lys Gln Val Ile Gln Gln Ala Leu Ser Asn
305                 310                 315                 320
Ala Arg Leu Glu Pro His Gln Val Ser Tyr Leu Glu Ala His Gly Thr
                325                 330                 335
Gly Thr Ala Leu Gly Asp Pro Ile Glu Ile Glu Ala Leu Ala Ala Ile
            340                 345                 350
Tyr Gly Lys Asn Arg Pro Val Asp Gln Pro Leu Val Val Gly Ser Val
        355                 360                 365
Lys Thr Asn Ile Gly His Leu Glu Ala Ala Gly Val Ser Ala Leu
    370                 375                 380
Ile Lys Val Val Leu Ala Leu Gln His Gln Glu Ile Pro Pro His Leu
385                 390                 395                 400
His Leu Lys Gln Pro Asn Pro Tyr Val Asp Trp Asp Lys Leu Pro Ile
                405                 410                 415
Lys Ile Pro Thr Ser Leu Met Pro Trp Asn Cys Glu Ala Lys Pro Arg
            420                 425                 430
Ile Ala Gly Ile Ser Ser Phe Gly Ile Ser Gly Thr Asn Ala His Leu
        435                 440                 445
```

```
Leu Leu Glu Glu Val Pro Glu Leu Ile Lys Gly Gln Lys Ala Lys Gly
450                 455                 460

Lys Ser Glu Asn Asp Leu Glu Arg Pro Leu His Ile Leu Thr Leu Ser
465                 470                 475                 480

Thr Lys Thr Glu Lys Ala Leu Glu Glu Leu Val Ser Arg Tyr Gln Asn
                    485                 490                 495

His Trp Glu Thr Tyr Pro Glu Leu Ala Ile Ser Asp Val Cys Tyr Thr
                500                 505                 510

Ala Asn Thr Gly Arg Ala Gln Phe Asn His Arg Leu Ala Val Ile Ala
            515                 520                 525

Ser Gly Ser Glu Glu Leu Thr Gln Lys Leu Arg Gln His Thr Ala Gly
530                 535                 540

Glu Glu Val Val Gly Val Phe Ser Gly Lys Val Pro Asn Ser Gly Ser
545                 550                 555                 560

Glu Ser Lys Val Ala Phe Leu Phe Thr Gly Gln Gly Ser Gln Tyr Leu
                565                 570                 575

Asn Met Gly Arg Gln Leu Tyr Glu Thr Gln Pro Thr Phe Arg Gln Ala
            580                 585                 590

Leu Asp Thr Cys Asp His Ile Leu Arg Pro Tyr Leu Asp Asn Pro Leu
            595                 600                 605

Leu Glu Ile Leu Tyr Pro Gln Asp Ala Gln Lys Ser Asn Asp Ser Pro
610                 615                 620

Leu Asp Gln Thr Gly Tyr Thr Gln Pro Ala Leu Phe Ser Ile Glu Tyr
625                 630                 635                 640

Ala Leu Leu Lys Leu Trp Glu Ser Trp Gly Ile Lys Pro Asn Val Val
                645                 650                 655

Met Gly His Ser Val Gly Glu Tyr Val Ala Ala Thr Val Ala Gly Val
            660                 665                 670

Phe Ser Leu Glu Asp Gly Leu Lys Leu Ile Ala Ala Arg Gly Arg Leu
            675                 680                 685

Met Gln Gly Leu Pro Ala Gly Gly Glu Met Val Ser Val Met Ala Ser
690                 695                 700

Glu Ser Lys Val Leu Glu Thr Leu Lys Ala Met Ser Leu Glu Asp Lys
705                 710                 715                 720

Val Ala Ile Ala Ala Ile Asn Gly Pro Glu Ser Ile Val Ile Ser Gly
                725                 730                 735

Glu Ala Glu Ala Ile Arg Ala Met Ala Thr His Leu Glu Ser Val Gly
            740                 745                 750

Ile Lys Thr Lys Gln Leu Gln Val Ser His Ala Phe His Ser Pro Leu
            755                 760                 765

Met Glu Pro Met Leu Ala Glu Phe Glu Ala Val Ala Asn Gln Ile Thr
            770                 775                 780

Tyr His Gln Pro Arg Ile Pro Ile Ile Ser Asn Val Thr Gly Thr Lys
785                 790                 795                 800

Ala Asp Lys Ser Ile Ala Thr Ala Gln Tyr Trp Val Asn His Val Arg
                805                 810                 815

Gln Pro Val Arg Phe Ala Gln Gly Met Ala Thr Leu His Gln Gln Gly
            820                 825                 830

Tyr Glu Thr Phe Leu Glu Ile Gly Ala Lys Pro Ile Leu Leu Gly Met
            835                 840                 845

Gly Lys Gln Cys Leu Ser Pro Asp Val Gly Val Trp Leu Pro Ser Leu
850                 855                 860
```

```
Arg His Gly Val Asp Glu Trp Gln Gln Ile Leu Ser Ser Leu Gly Gln
865                 870                 875                 880

Leu Tyr Val Gln Gly Ala Lys Val Asp Trp Ser Gly Phe Asp Arg Asp
                885                 890                 895

Tyr Ser Arg Glu Lys Val Val Leu Pro Thr Tyr Pro Phe Gln Arg Glu
            900                 905                 910

Arg Tyr Trp Val Glu Thr Ser Ile Asn Gln Gln Gln Val Val Cys Ser
            915                 920                 925

Gly Glu Pro Asn Leu Gln Gly Thr Pro Glu Gly Thr Ser Thr Thr Ile
930                 935                 940

Val Lys Leu Leu Ser Gln Gly Asn Thr Lys Glu Leu Ala Glu Lys Val
945                 950                 955                 960

Glu Lys Thr Ser Asp Leu Pro Pro Glu Gln Leu Lys Leu Leu Pro Asp
            965                 970                 975

Leu Leu Ala Ser Leu Ser Gln Gln His Gln Gln Glu Leu Ala Arg Leu
            980                 985                 990

Thr Thr Lys Lys Trp Phe Tyr Lys  Val Gln Trp Ile Ser  Gln Ala Ile
            995                 1000                1005

Lys Pro  Gln Arg Asn Lys Ser  Asn Asn Gln Val Cys  His Trp Leu
1010                1015                1020

Ile Leu  Thr Asp Ser Lys Gly  Leu Gly Lys Ser Leu  Ala Thr His
1025                1030                1035

Leu Gln  Gln Leu Gly Asn Glu  Cys Ser Val Val Tyr  Gln Ala Asp
1040                1045                1050

Asn Tyr  Gln Asn Tyr Glu Pro  Gly Ile Tyr His Ile  Asn Pro Ser
1055                1060                1065

His Pro  Gln Glu Phe Glu Gln  Val Tyr Gln Thr Ile  Phe Glu Asn
1070                1075                1080

Gly Lys  Leu Pro Leu Gln Lys  Val Ile His Leu Trp  Ser Leu Asp
1085                1090                1095

Thr Ala  Ser Glu Gln Asp Leu  Thr Thr Glu Thr Leu  Glu Gln Ala
1100                1105                1110

Gln Leu  Trp Gly Cys Gly Ser  Thr Leu His Leu Leu  Gln Thr Leu
1115                1120                1125

Val Lys  Asn Pro Asn Ser Thr  Pro Pro Lys Leu Trp  Met Ile Thr
1130                1135                1140

Arg Gly  Thr Gln Pro Val Leu  Ser Pro Thr Glu Lys  Leu Thr Val
1145                1150                1155

Ala Thr  Ser Pro Leu Trp Gly  Leu Gly Arg Thr Ile  Ala Ser Glu
1160                1165                1170

His Pro  Gln Leu Trp Gly Gly  Leu Val Asp Leu Asp  Pro Gln Gly
1175                1180                1185

Ser Glu  Asp Glu Val Glu Val  Leu Leu Gln Gln Ile  Ile Asp Ser
1190                1195                1200

Gln Lys  Glu Asp His Leu Ala  Val Arg Asn Arg Lys  Ile Tyr Val
1205                1210                1215

Ala Arg  Leu Leu Lys His Ile  Pro Gln Glu Ser Gln  Pro Leu Ser
1220                1225                1230

Leu Arg  Ser Asp Ala Thr Tyr  Leu Ile Thr Gly Gly  Leu Gly Ala
1235                1240                1245

Leu Gly  Leu Lys Thr Ala Ala  Trp Met Ala Glu Lys  Gly Ala Arg
1250                1255                1260
```

-continued

```
Asn Leu Val Leu Ile Ser Arg Arg Gln Pro Ser Glu Gln Ala Gln
    1265                1270                1275

Gln Thr Ile Gln Ser Leu Glu Glu Leu Gly Thr Gln Val Lys Val
    1280                1285                1290

Leu Ser Ala Asp Ile Ser Val Glu Ser Asp Val Ala Asn Ile Leu
    1295                1300                1305

Glu Gln Ile Gln Thr Ser Leu Pro Pro Leu Leu Gly Val Ile His
    1310                1315                1320

Ala Ala Gly Val Leu Asp Asp Gly Leu Leu Gln Gln Thr Asn Trp
    1325                1330                1335

Glu Arg Phe Thr Lys Val Met Ala Pro Lys Val Asn Gly Thr Trp
    1340                1345                1350

Asn Leu His Lys Leu Thr Gln His Leu Ser Leu Asp Phe Phe Val
    1355                1360                1365

Cys Phe Ser Ser Met Ser Ser Leu Leu Gly Ser Pro Gly Gln Gly
    1370                1375                1380

Asn Tyr Ala Ala Ala Asn Ala Phe Met Asp Ala Val Val His Tyr
    1385                1390                1395

Arg Arg Glu Met Gly Leu Pro Gly Leu Ser Ile Asn Trp Gly Gly
    1400                1405                1410

Trp Ser Glu Gly Gly Met Ala Thr Arg Leu Ala Ser Gln His Gln
    1415                1420                1425

Asn Arg Met Gln Thr Ala Gly Ile Ser Leu Ile Ser Pro Glu Gln
    1430                1435                1440

Gly Ile Gln Val Leu Glu Glu Leu Val Arg Thr Gln Ser Thr Ala
    1445                1450                1455

Gln Val Gly Val Leu Pro Val Asp Trp Ser Val Leu Ala Lys Gln
    1460                1465                1470

Phe Ser Ser Ala Asn Pro Ser Ser Leu Leu Leu Glu Leu Leu Gln
    1475                1480                1485

Gln Glu Thr Ser Ser Glu Lys Thr Asp Glu Arg Ile Leu Glu Lys
    1490                1495                1500

Leu Gln Ala Ala Pro Ile Thr Glu Arg Gln Asp Ile Leu Lys Asn
    1505                1510                1515

Tyr Ile Gln Leu Val Val Ala Lys Thr Leu Gly Ile Asn Pro Ser
    1520                1525                1530

Lys Ile Ser Thr Asp Asp Asn Phe Val Glu Leu Gly Met Asp Ser
    1535                1540                1545

Leu Met Gly Met Glu Val Val Asn Lys Leu Ser Gly Asp Leu Asp
    1550                1555                1560

Phe Ile Ile Tyr Pro Arg Glu Phe Tyr Glu Arg Pro Thr Ile Asp
    1565                1570                1575

Ser Leu Thr Gln Tyr Leu Ser Ala Glu Leu Ser Glu Asp Asn Leu
    1580                1585                1590

Ala Thr Gln Pro Ser Pro Thr Ser Leu Glu Ile Phe Ala Thr Lys
    1595                1600                1605

Ser Ser Pro Ser Gly Asn Ser Ala Arg Pro Ala Ser Val Ser Ser
    1610                1615                1620

Arg Leu Pro Gly Ile Ile Phe Ile Leu Ser Ser Pro Arg Ser Gly
    1625                1630                1635

Ser Thr Leu Leu Arg Val Met Leu Ala Gly His Ser Ser Leu Phe
    1640                1645                1650
```

-continued

```
Ser Pro Pro Glu Leu His Leu Leu Pro Phe Asn Thr Met Lys Glu
1655                1660                1665

Arg Gln Glu Gln Leu Asn Leu Ser Tyr Leu Gly Glu Gly Leu Gln
1670                1675                1680

Lys Thr Phe Met Glu Val Lys Asn Leu Asp Ala Thr Ala Ser Gln
1685                1690                1695

Ala Leu Ile Lys Asp Leu Glu Ser Gln Asn Leu Ser Ile Gln Gln
1700                1705                1710

Val Tyr Gly Met Leu Gln Glu Asn Ile Ala Pro Arg Leu Leu Val
1715                1720                1725

Asp Lys Ser Pro Thr Tyr Ala Met Glu Pro Thr Ile Leu Glu Arg
1730                1735                1740

Gly Glu Ala Leu Phe Ala Asn Ser Lys Tyr Ile Tyr Leu Val Arg
1745                1750                1755

His Pro Tyr Ser Val Ile Glu Ser Phe Val Arg Met Arg Met Gln
1760                1765                1770

Lys Leu Val Gly Leu Gly Glu Asn Pro Tyr Arg Val Ala Glu
1775                1780                1785

Gln Val Trp Ala Lys Ser Asn Gln Asn Ile Leu Asn Phe Leu Ser
1790                1795                1800

Gln Leu Glu Pro Glu Arg Gln His Gln Ile Arg Tyr Glu Asp Leu
1805                1810                1815

Val Lys Lys Pro Gln Gln Val Leu Ser Gln Leu Cys Asp Phe Leu
1820                1825                1830

Asn Val Pro Phe Glu Pro Glu Leu Leu Gln Pro Tyr Gln Gly Asp
1835                1840                1845

Arg Met Thr Gly Gly Val His Gln Lys Ser Leu Ser Ile Ser Asp
1850                1855                1860

Pro Asn Phe Leu Lys His Asn Thr Ile Asp Glu Ser Leu Ala Asp
1865                1870                1875

Lys Trp Lys Thr Ile Gln Leu Pro Tyr Pro Leu Lys Ser Glu Thr
1880                1885                1890

Gln Arg Ile Ala Ser Gln Leu Ser Tyr Glu Leu Pro Asn Leu Val
1895                1900                1905

Thr Thr Pro Thr Asn Gln Gln Pro Gln Val Ser Thr Thr Pro Ser
1910                1915                1920

Thr Glu Gln Pro Ile Met Glu Glu Lys Phe Leu Glu Phe Gly Gly
1925                1930                1935

Asn Gln Ile Cys Leu Cys Ser Trp Gly Ser Pro Glu His Pro Val
1940                1945                1950

Val Leu Cys Ile His Gly Ile Leu Glu Gln Gly Leu Ala Trp Gln
1955                1960                1965

Glu Val Ala Leu Pro Leu Ala Ala Gln Gly Tyr Arg Val Val Ala
1970                1975                1980

Pro Asp Leu Phe Gly His Gly Arg Ser Ser His Leu Glu Met Val
1985                1990                1995

Thr Ser Tyr Ser Ser Leu Thr Phe Leu Ala Gln Ile Asp Arg Val
2000                2005                2010

Ile Gln Glu Leu Pro Asp Gln Pro Leu Leu Val Gly His Ser
2015                2020                2025

Met Gly Ala Met Leu Ala Thr Ala Ile Ala Ser Val Arg Pro Lys
2030                2035                2040
```

```
Lys Ile Lys Glu Leu Ile Leu Val Glu Leu Pro Leu Pro Ala Glu
    2045                2050                2055

Glu Ser Lys Lys Glu Ser Ala Val Asn Gln Leu Thr Thr Cys Leu
    2060                2065                2070

Asp Tyr Leu Ser Ser Thr Pro Gln His Pro Ile Phe Pro Asp Val
    2075                2080                2085

Ala Thr Ala Ala Ser Arg Leu Arg Gln Ala Ile Pro Ser Leu Ser
    2090                2095                2100

Glu Glu Phe Ser Tyr Ile Leu Ala Gln Arg Ile Thr Gln Pro Asn
    2105                2110                2115

Gln Gly Gly Val Arg Trp Ser Trp Asp Ala Ile Ile Arg Thr Arg
    2120                2125                2130

Ser Ile Leu Gly Leu Asn Asn Leu Pro Gly Gly Arg Ser Gln Tyr
    2135                2140                2145

Leu Glu Met Leu Lys Ser Ile Gln Val Pro Thr Thr Leu Val Tyr
    2150                2155                2160

Gly Asp Ser Ser Lys Leu Asn Arg Pro Glu Asp Leu Gln Gln Gln
    2165                2170                2175

Lys Met Thr Met Thr Gln Ala Lys Arg Val Phe Leu Ser Gly Gly
    2180                2185                2190

His Asn Leu His Ile Asp Ala Ala Ala Ala Leu Ala Ser Leu Ile
    2195                2200                2205

Leu Thr Ser
    2210

<210> SEQ ID NO 2
<211> LENGTH: 2694
<212> TYPE: PRT
<213> ORGANISM: Artificial sequence
<220> FEATURE:
<223> OTHER INFORMATION: EryA1 loading module + KS1 and AT-ACP from IdmO

<400> SEQUENCE: 2

Met Ala Asp Leu Ser Lys Leu Ser Asp Ser Arg Thr Ala Gln Pro Gly
1               5                   10                  15

Arg Ile Val Arg Pro Trp Pro Leu Ser Gly Cys Asn Glu Ser Ala Leu
                20                  25                  30

Arg Ala Arg Ala Arg Gln Leu Arg Ala His Leu Asp Arg Phe Pro Asp
            35                  40                  45

Ala Gly Val Glu Gly Val Gly Ala Ala Leu Ala His Asp Glu Gln Ala
        50                  55                  60

Asp Ala Gly Pro His Arg Ala Val Val Ala Ser Ser Thr Ser Glu
65                  70                  75                  80

Leu Leu Asp Gly Leu Ala Ala Val Ala Asp Gly Arg Pro His Ala Ser
                85                  90                  95

Val Val Arg Gly Val Ala Arg Pro Ser Ala Pro Val Val Phe Val Phe
            100                 105                 110

Pro Gly Gln Gly Ala Gln Trp Ala Gly Met Ala Gly Glu Leu Leu Gly
        115                 120                 125

Glu Ser Arg Val Phe Ala Ala Ala Met Asp Ala Cys Ala Arg Ala Phe
    130                 135                 140

Glu Pro Val Thr Asp Trp Thr Leu Ala Gln Val Leu Asp Ser Pro Glu
145                 150                 155                 160

Gln Ser Arg Arg Val Glu Val Val Gln Pro Ala Leu Phe Ala Val Gln
                165                 170                 175
```

```
Thr Ser Leu Ala Ala Leu Trp Arg Ser Phe Gly Val Thr Pro Asp Ala
            180                 185                 190

Val Val Gly His Ser Ile Gly Glu Leu Ala Ala His Val Cys Gly
            195                 200             205

Ala Ala Gly Ala Ala Asp Ala Ala Arg Ala Ala Ala Leu Trp Ser Arg
            210                 215                 220

Glu Met Ile Pro Leu Val Gly Asn Gly Asp Met Ala Ala Val Ala Leu
225                 230                 235                 240

Ser Ala Asp Glu Ile Glu Pro Arg Ile Ala Arg Trp Asp Asp Val
                245                 250                 255

Val Leu Ala Gly Val Asn Gly Pro Arg Ser Val Leu Leu Thr Gly Ser
            260                 265                 270

Pro Glu Pro Val Ala Arg Arg Val Gln Glu Leu Ser Ala Glu Gly Val
            275                 280                 285

Arg Ala Gln Val Ile Asn Val Ser Met Ala Ala His Ser Ala Gln Val
            290                 295                 300

Asp Asp Ile Ala Glu Gly Met Arg Ser Ala Leu Ala Trp Phe Ala Pro
305                 310                 315                 320

Gly Gly Ser Glu Val Pro Phe Tyr Ala Ser Leu Thr Gly Gly Ala Val
                325                 330                 335

Asp Thr Arg Glu Leu Val Ala Asp Tyr Trp Arg Arg Ser Phe Arg Leu
            340                 345                 350

Pro Val Arg Phe Asp Glu Ala Ile Arg Ser Ala Leu Glu Val Gly Pro
            355                 360                 365

Gly Thr Phe Val Glu Ala Ser Pro His Pro Val Leu Ala Ala Ala Leu
            370                 375                 380

Gln Gln Thr Leu Asp Ala Glu Gly Ser Ser Ala Ala Val Val Pro Thr
385                 390                 395                 400

Leu Gln Arg Gly Gln Gly Gly Met Arg Arg Phe Leu Leu Ala Ala Ala
                405                 410                 415

Gln Ala Phe Thr Gly Gly Val Ala Val Asp Trp Thr Ala Ala Tyr Asp
            420                 425                 430

Asp Val Gly Ala Glu Pro Gly Ser Leu Pro Glu Phe Ala Pro Ala Glu
            435                 440                 445

Glu Glu Asp Glu Pro Ala Glu Ser Gly Val Asp Trp Asn Ala Pro Pro
450                 455                 460

His Val Leu Arg Glu Arg Leu Leu Ala Val Val Asn Gly Glu Thr Ala
465                 470                 475                 480

Ala Leu Ala Gly Arg Glu Ala Asp Ala Glu Ala Thr Phe Arg Glu Leu
                485                 490                 495

Gly Leu Asp Ser Val Leu Ala Ala Gln Leu Arg Ala Lys Val Ser Ala
            500                 505                 510

Ala Ile Gly Arg Glu Val Asn Ile Ala Leu Leu Tyr Asp His Pro Thr
            515                 520                 525

Pro Arg Ala Leu Ala Glu Ala Leu Ala Ala Gly Thr Glu Val Ala Gln
            530                 535                 540

Arg Glu Thr Arg Ala Arg Thr Asn Glu Ala Ala Pro Gly Glu Pro Val
545                 550                 555                 560

Ala Val Val Ala Met Ala Cys Arg Leu Pro Gly Gly Val Ser Thr Pro
                565                 570                 575

Glu Glu Phe Trp Glu Leu Leu Ser Glu Gly Arg Asp Ala Val Ala Gly
            580                 585                 590

Leu Pro Thr Asp Arg Gly Trp Asp Leu Asp Ser Leu Phe His Pro Asp
```

```
                    595                 600                 605
Pro Thr Arg Ser Gly Thr Ala His Gln Arg Gly Gly Phe Leu Thr
610                 615                 620
Glu Ala Thr Ala Phe Asp Pro Ala Phe Phe Gly Met Ser Pro Arg Glu
625                 630                 635                 640
Ala Leu Ala Val Asp Pro Gln Gln Arg Leu Met Leu Glu Leu Ser Trp
                    645                 650                 655
Glu Val Leu Glu Arg Ala Gly Ile Pro Pro Thr Ser Leu Gln Ala Ser
                660                 665                 670
Pro Thr Gly Val Phe Val Gly Leu Ile Pro Gln Glu Tyr Gly Pro Arg
            675                 680                 685
Leu Ala Glu Gly Gly Glu Gly Val Glu Gly Tyr Leu Met Thr Gly Thr
690                 695                 700
Thr Thr Ser Val Ala Ser Gly Arg Ile Ala Tyr Thr Leu Gly Leu Glu
705                 710                 715                 720
Gly Pro Ala Ile Ser Val Asp Thr Ala Cys Ser Ser Leu Val Ala
                    725                 730                 735
Val His Leu Ala Cys Gln Ser Leu Arg Arg Gly Glu Ser Ser Leu Ala
                740                 745                 750
Met Ala Gly Gly Val Thr Val Met Pro Thr Pro Gly Met Leu Val Asp
            755                 760                 765
Phe Ser Arg Met Asn Ser Leu Ala Pro Asp Gly Arg Cys Lys Ala Phe
770                 775                 780
Ser Ala Gly Ala Asn Gly Phe Gly Met Ala Glu Gly Ala Gly Met Leu
785                 790                 795                 800
Leu Leu Glu Arg Leu Ser Asp Ala Arg Arg Asn Gly His Pro Val Leu
                    805                 810                 815
Ala Val Leu Arg Gly Thr Ala Val Asn Ser Asp Gly Ala Ser Asn Gly
                820                 825                 830
Leu Ser Ala Pro Asn Gly Arg Ala Gln Val Arg Val Ile Gln Gln Ala
            835                 840                 845
Leu Ala Glu Ser Gly Leu Gly Pro Ala Asp Ile Asp Ala Val Glu Ala
850                 855                 860
His Gly Thr Gly Thr Arg Leu Gly Asp Pro Ile Glu Ala Arg Ala Leu
865                 870                 875                 880
Phe Glu Ala Tyr Gly Arg Asp Arg Glu Gln Pro Leu His Leu Gly Ser
                    885                 890                 895
Val Lys Ser Asn Leu Gly His Thr Gln Ala Ala Ala Gly Val Ala Gly
                900                 905                 910
Val Ile Lys Met Val Leu Ala Met Arg Ala Gly Thr Leu Pro Arg Thr
            915                 920                 925
Leu His Ala Ser Glu Arg Ser Lys Glu Ile Asp Trp Ser Ser Gly Ala
930                 935                 940
Ile Ser Leu Leu Asp Glu Pro Glu Pro Trp Pro Ala Gly Ala Arg Pro
945                 950                 955                 960
Arg Arg Ala Gly Val Ser Ser Phe Gly Val Ser Gly Thr Asn Ala His
                    965                 970                 975
Val Ile Val Glu Glu Ala Pro Ser Ser Ala Asp Val Ala Glu
                980                 985                 990
Ser Gly Val Arg Val Pro Val Pro Val Pro Trp Val Val Ser Ala
            995                 1000                1005
Arg Ser  Ala Glu Gly Leu Ala  Ala Gln Ala Glu Arg  Leu Ala Arg
    1010             1015                 1020
```

```
Phe Val Gly Glu Arg Ser Asp Gln Asp Pro Val Asp Ile Gly Phe
    1025            1030                1035

Ser Leu Val Arg Ser Arg Ser Leu Leu Glu His Arg Ala Val Val
    1040            1045                1050

Leu Gly Lys Gly Arg Asp Asp Leu Val Ala Gly Leu Ala Ser Leu
    1055            1060                1065

Ala Ser Asp Gly Ser Ala Thr Gly Val Val Ser Gly Val Ala Arg
    1070            1075                1080

Gly Arg Ala Arg Val Ala Phe Gly Phe Ser Gly Gln Gly Ala Gln
    1085            1090                1095

Arg Val Gly Met Gly Ala Glu Leu Ala Ser Val Tyr Pro Val Phe
    1100            1105                1110

Ala Glu Ala Leu Ala Glu Val Thr Gly Ala Leu Gly Leu Asp Pro
    1115            1120                1125

Glu Val Phe Gly Asp Val Asp Arg Leu Gly Arg Thr Glu Val Thr
    1130            1135                1140

Gln Ala Ala Leu Phe Ala Phe Glu Val Ala Val Val Arg Leu Leu
    1145            1150                1155

Glu Ser Phe Gly Val Arg Pro Asp Val Leu Ile Gly His Ser Ile
    1160            1165                1170

Gly Glu Ile Ala Ala Ala Tyr Val Ala Gly Val Phe Ser Leu Gly
    1175            1180                1185

Asp Ala Ala Ala Leu Val Gly Ala Arg Gly Arg Leu Met Gln Ala
    1190            1195                1200

Leu Pro Ala Gly Gly Val Met Val Ala Val Gln Ala Gly Glu Ala
    1205            1210                1215

Glu Val Val Ala Ala Leu Glu Gly Phe Ala Asp Arg Val Ser Leu
    1220            1225                1230

Ala Ala Val Asn Gly Pro Ser Ser Val Val Val Ser Gly Glu Ala
    1235            1240                1245

Glu Ala Val Glu Gln Val Val Ala Arg Leu Gly Lys Val Lys Ser
    1250            1255                1260

Lys Arg Leu Arg Val Ser His Ala Phe His Ser Pro Leu Met Glu
    1265            1270                1275

Pro Met Leu Ala Asp Phe Arg Gln Val Ala Glu Gln Ile Thr Tyr
    1280            1285                1290

Asn Glu Pro Gln Leu Pro Val Val Ser Asn Val Ser Gly Arg Leu
    1295            1300                1305

Ala Glu Pro Gly Glu Leu Thr Thr Pro Asp Tyr Trp Val Arg His
    1310            1315                1320

Val Arg Glu Ala Val Arg Phe Gly Asp Gly Val Arg Ala Leu Ala
    1325            1330                1335

Ala Asp Gly Val Gly Val Leu Val Glu Val Gly Pro Asp Ser Val
    1340            1345                1350

Leu Thr Ala Leu Ala Arg Glu Ser Leu Asp Gly Glu Asp Gly Leu
    1355            1360                1365

Arg Ala Val Pro Leu Leu Arg Lys Asp Arg Pro Glu Pro Glu Thr
    1370            1375                1380

Leu Leu Thr Gly Val Ala Gln Ala Phe Thr His Gly Val Gln Val
    1385            1390                1395

Asp Trp Pro Ala Leu Leu Pro Gly Gly Arg Val Glu Leu Pro
    1400            1405                1410
```

```
Thr Tyr Ala Phe Gln Arg Arg Tyr Trp Leu Glu Asp Ala Asp
1415                1420                1425

Pro Thr Gly Gly Asp Pro Ala Ala Leu Gly Leu Thr Ala Ala Asp
1430                1435                1440

His Pro Leu Leu Gly Ala Ala Val Pro Leu Ala Glu Asp Gln Gly
1445                1450                1455

Ile Val Ile Thr Ser Arg Leu Ser Leu Arg Thr His Pro Trp Leu
1460                1465                1470

Ala Asp His Glu Ile Gly Gly Thr Val Leu Leu Pro Gly Ala Gly
1475                1480                1485

Leu Val Glu Ile Ala Leu Arg Ala Gly Asp Glu Val Gly Cys Gly
1490                1495                1500

Arg Val Glu Glu Leu Thr Leu Glu Ile Pro Leu Val Val Pro Gln
1505                1510                1515

Glu Gly Gly Val Thr Val Gln Ile Arg Val Gly Ala Pro Asp Glu
1520                1525                1530

Ser Gly Trp Arg Pro Met Thr Val His Ser Arg Thr Asp Pro Glu
1535                1540                1545

Glu Glu Trp Thr Arg His Val Ser Gly Val Leu Ser Pro Asp Val
1550                1555                1560

Pro Thr Glu Arg Tyr Asp Leu Gly Ala Trp Pro Pro Ala Gly Ala
1565                1570                1575

Thr Pro Val Glu Leu Asp Gly Phe Tyr Glu Ala Tyr Ala Arg Leu
1580                1585                1590

Gly Tyr Ala Tyr Gly Pro Ser Phe Gln Gly Leu Arg Ala Ala Trp
1595                1600                1605

Arg Arg Gly Asp Glu Val Phe Ala Glu Val Ser Leu Pro Val Glu
1610                1615                1620

Glu Gln Glu Thr Ala Gly Arg Phe Thr Leu His Pro Ala Leu Leu
1625                1630                1635

Asp Ala Ala Leu Gln Ser Ala Gly Ala Gly Ala Phe Phe Asp Ser
1640                1645                1650

Gly Gly Ser Met Arg Leu Pro Phe Ala Trp Ser Gly Val Ser Val
1655                1660                1665

Phe Ala Ala Gly Ala Ser Thr Val Arg Val Arg Leu Ser Pro Ala
1670                1675                1680

Gly Pro Asp Ala Val Thr Val Ala Leu Ala Asp Pro Thr Gly Ala
1685                1690                1695

Pro Val Ala Leu Val Glu Arg Leu Leu Ile Pro Glu Met Ser Pro
1700                1705                1710

Glu Gln Leu Glu Arg Val Arg Gly Glu Glu Lys Glu Ala Pro Tyr
1715                1720                1725

Val Leu Asp Trp Val Pro Val Glu Val Pro Ala Asp Asp Leu Val
1730                1735                1740

Arg Pro Glu Arg Trp Thr Leu Leu Gly Gly Ala Asp Ala Gly Val
1745                1750                1755

Gly Leu Asp Val Ala Gly Ala Phe Ala Ser Leu Glu Pro Ser Asp
1760                1765                1770

Gly Ala Pro Glu Phe Val Val Leu Pro Cys Val Pro Pro Thr Ser
1775                1780                1785

Pro Thr Arg Ala Ala Asp Val Arg Gln Ser Thr Leu Gln Ala Leu
1790                1795                1800

Thr Val Leu Gln Asn Trp Val Thr Asp Glu Arg His Ala Asp Ser
```

-continued

```
            1805                1810                1815
Arg Leu Val Leu Val Thr Arg Arg Ala Val Gly Val Gly Ala His
    1820                1825                1830
Asp Asp Val Pro Asp Leu Thr His Ala Ala Leu Trp Gly Leu Val
    1835                1840                1845
Arg Ser Ala Gln Thr Glu Asn Pro Gly Arg Phe Leu Leu Val Asp
    1850                1855                1860
Leu Asp Glu Gly Ala Glu Leu Ala Glu Val Leu Pro Gly Ala Leu
    1865                1870                1875
Gly Ser Gly Glu Ser Gln Val Ala Val Arg Ala Gly Arg Val Leu
    1880                1885                1890
Ala Ala Arg Leu Ala Arg Ser Gly Ser Gly Gly Ala Glu Leu Val
    1895                1900                1905
Pro Pro Ala Gly Ala Pro Trp Arg Leu Asp Thr Thr Ser Pro Gly
    1910                1915                1920
Thr Leu Glu Asn Leu Ala Leu Val Pro Ser Ala Glu Glu Pro Leu
    1925                1930                1935
Gly Pro Leu Asp Val Arg Val Ser Val Arg Ala Ala Gly Leu Asn
    1940                1945                1950
Phe Arg Asp Val Leu Ile Ala Leu Gly Met Tyr Pro Gly Asp Ala
    1955                1960                1965
Arg Met Gly Gly Glu Gly Ala Gly Val Val Thr Asp Val Gly Ser
    1970                1975                1980
Glu Val Thr Thr Leu Ala Pro Gly Asp Arg Val Met Gly Met Leu
    1985                1990                1995
Ser Ser Ala Phe Gly Pro Thr Ala Val Ser Asp His Arg Ala Leu
    2000                2005                2010
Val Arg Val Pro Asp Asp Trp Ser Phe Glu Gln Ala Ala Ser Val
    2015                2020                2025
Pro Thr Val Phe Ala Thr Ala Tyr Tyr Gly Leu Val Asp Leu Ala
    2030                2035                2040
Glu Leu Arg Ala Gly Gln Ser Val Leu Val His Ala Ala Ala Gly
    2045                2050                2055
Gly Val Gly Met Ala Ala Val Gln Leu Ala Arg His Leu Gly Ala
    2060                2065                2070
Glu Val Phe Gly Thr Ala Ser Thr Gly Lys Trp Asp Ser Leu Arg
    2075                2080                2085
Ala Gly Gly Leu Asp Ala Glu His Ile Ala Ser Ser Arg Thr Val
    2090                2095                2100
Glu Phe Glu Glu Thr Phe Leu Ala Ala Thr Ala Gly Arg Gly Val
    2105                2110                2115
Asp Val Val Leu Asp Ser Leu Ala Gly Glu Phe Val Asp Ala Ser
    2120                2125                2130
Leu Arg Leu Leu Pro Arg Gly Gly Arg Phe Val Glu Met Gly Lys
    2135                2140                2145
Ala Asp Ile Arg Asp Ala Glu Arg Val Ala Ala Asp His Pro Gly
    2150                2155                2160
Val Thr Tyr Arg Ser Phe Asp Leu Leu Glu Ala Gly Leu Asp Arg
    2165                2170                2175
Phe Gln Glu Ile Leu Thr Glu Val Val Arg Leu Phe Glu Arg Gly
    2180                2185                2190
Val Leu Arg His Leu Pro Val Thr Ala Trp Asp Val Arg Arg Ala
    2195                2200                2205
```

```
Ala Glu Ala Phe Arg Phe Val Ser Gln Ala Arg His Val Gly Lys
    2210            2215                2220

Asn Val Leu Val Met Pro Arg Val Trp Asp Arg Asp Gly Thr Val
    2225            2230                2235

Leu Ile Thr Gly Gly Thr Gly Ala Leu Gly Ala Leu Val Ala Arg
    2240            2245                2250

His Leu Val Ala Glu His Gly Met Arg Asn Val Leu Leu Ala Gly
    2255            2260                2265

Arg Arg Gly Val Asp Ala Pro Gly Ala Arg Glu Leu Leu Ala Glu
    2270            2275                2280

Leu Glu Thr Ala Gly Ala Gln Val Ser Val Val Ala Cys Asp Val
    2285            2290                2295

Ala Asp Arg Asp Ala Val Ala Glu Leu Ile Ala Lys Val Pro Val
    2300            2305                2310

Glu His Pro Leu Thr Ala Val Val His Thr Ala Gly Val Val Ala
    2315            2320                2325

Asp Ala Thr Leu Thr Ala Leu Asp Ala Glu Arg Val Asp Thr Val
    2330            2335                2340

Leu Arg Ala Lys Val Asp Ala Val Leu His Leu His Glu Ala Thr
    2345            2350                2355

Arg Gly Leu Asp Leu Ala Gly Phe Val Leu Phe Ser Ser Ala Ser
    2360            2365                2370

Gly Ile Phe Gly Ser Pro Gly Gln Gly Asn Tyr Ala Ala Ala Asn
    2375            2380                2385

Ser Phe Ile Asp Ala Phe Ala His His Arg Arg Ala Gln Gly Leu
    2390            2395                2400

Pro Ala Leu Ser Leu Ala Trp Gly Leu Trp Ala Arg Thr Ser Gly
    2405            2410                2415

Met Ala Gly Gln Leu Gly His Asp Asp Val Ala Arg Ile Ser Arg
    2420            2425                2430

Thr Gly Leu Ala Pro Ile Thr Asp Asp Gln Gly Met Ala Leu Leu
    2435            2440                2445

Asp Ala Ala Leu Gly Ala Gly Arg Pro Leu Leu Val Pro Val Arg
    2450            2455                2460

Leu Asp Arg Ala Ala Leu Arg Ser Gln Ala Thr Ala Gly Thr Leu
    2465            2470                2475

Pro Pro Ile Leu Arg Gly Leu Val Arg Ala Thr Val Arg Arg Ala
    2480            2485                2490

Ala Ser Thr Ala Ala Ala Gln Gly Pro Ser Leu Ala Glu Arg Leu
    2495            2500                2505

Ala Gly Leu Pro Val Thr Glu His Glu Arg Ile Val Val Glu Leu
    2510            2515                2520

Val Arg Ala Asp Leu Ala Ala Val Leu Gly His Ser Ser Ser Ala
    2525            2530                2535

Gly Ile Asp Pro Gly Arg Ala Phe Gln Asp Met Gly Ile Asp Ser
    2540            2545                2550

Leu Thr Ala Val Glu Leu Arg Asn Arg Leu Asn Gly Ala Thr Gly
    2555            2560                2565

Leu Arg Leu Ala Ala Ser Leu Val Phe Asp Tyr Pro Thr Pro Asn
    2570            2575                2580

Ala Leu Ala Thr His Ile Leu Asp Glu Leu Ala Leu Asp Thr Ala
    2585            2590                2595
```

```
Gly Ala  Gly Ala Ala Gly Glu  Pro Asp Gly Pro Ala  Pro Ala Pro
    2600             2605             2610

Ala Asp  Glu Ala Arg Phe Arg  Arg Val Ile Asn Ser  Ile Pro Leu
    2615             2620             2625

Asp Arg  Ile Arg Arg Ala Gly  Leu Leu Asp Ala Leu  Leu Gly Leu
    2630             2635             2640

Ala Gly  Thr Ser Ala Asp Thr  Ala Ala Ser Asp Asp  Phe Asp Gln
    2645             2650             2655

Glu Glu  Asp Gly Pro Ala Ile  Ala Ser Met Asp Val  Asp Asp Leu
    2660             2665             2670

Val Arg  Ile Ala Leu Gly Glu  Ser Asp Thr Thr Ala  Asp Ile Thr
    2675             2680             2685

Glu Gly  Thr Asp Arg Ser
    2690

<210> SEQ ID NO 3
<211> LENGTH: 2694
<212> TYPE: PRT
<213> ORGANISM: Artificial sequence
<220> FEATURE:
<223> OTHER INFORMATION: EryA1 loading module + KS1 and AT-ACP from IdmO

<400> SEQUENCE: 3

Met Ala Asp Leu Ser Lys Leu Ser Asp Ser Arg Thr Ala Gln Pro Gly
1               5                   10                  15

Arg Ile Val Arg Pro Trp Pro Leu Ser Gly Cys Asn Glu Ser Ala Leu
            20                  25                  30

Arg Ala Arg Ala Arg Gln Leu Arg Ala His Leu Asp Arg Phe Pro Asp
        35                  40                  45

Ala Gly Val Glu Gly Val Gly Ala Ala Leu Ala His Asp Glu Gln Ala
    50                  55                  60

Asp Ala Gly Pro His Arg Ala Val Val Ala Ser Ser Thr Ser Glu
65                  70                  75                  80

Leu Leu Asp Gly Leu Ala Ala Val Ala Asp Gly Arg Pro His Ala Ser
                85                  90                  95

Val Val Arg Gly Val Ala Arg Pro Ser Ala Pro Val Phe Val Phe
            100                 105                 110

Pro Gly Gln Gly Ala Gln Trp Ala Gly Met Ala Gly Glu Leu Leu Gly
        115                 120                 125

Glu Ser Arg Val Phe Ala Ala Met Asp Ala Cys Ala Arg Ala Phe
    130                 135                 140

Glu Pro Val Thr Asp Trp Thr Leu Ala Gln Val Leu Asp Ser Pro Glu
145                 150                 155                 160

Gln Ser Arg Arg Val Glu Val Gln Pro Ala Leu Phe Ala Val Gln
                165                 170                 175

Thr Ser Leu Ala Ala Leu Trp Arg Ser Phe Gly Val Thr Pro Asp Ala
            180                 185                 190

Val Val Gly His Ser Ile Gly Glu Leu Ala Ala Ala His Val Cys Gly
        195                 200                 205

Ala Ala Gly Ala Ala Asp Ala Ala Arg Ala Ala Ala Leu Trp Ser Arg
    210                 215                 220

Glu Met Ile Pro Leu Val Gly Asn Gly Asp Met Ala Ala Val Ala Leu
225                 230                 235                 240

Ser Ala Asp Glu Ile Glu Pro Arg Ile Ala Arg Trp Asp Asp Val
                245                 250                 255
```

```
Val Leu Ala Gly Val Asn Gly Pro Arg Ser Val Leu Thr Gly Ser
            260                 265                 270

Pro Glu Pro Val Ala Arg Arg Val Gln Glu Leu Ser Ala Glu Gly Val
        275                 280                 285

Arg Ala Gln Val Ile Asn Val Ser Met Ala Ala His Ser Ala Gln Val
    290                 295                 300

Asp Asp Ile Ala Glu Gly Met Arg Ser Ala Leu Ala Trp Phe Ala Pro
305                 310                 315                 320

Gly Gly Ser Glu Val Pro Phe Tyr Ala Ser Leu Thr Gly Gly Ala Val
                325                 330                 335

Asp Thr Arg Glu Leu Val Ala Asp Tyr Trp Arg Arg Ser Phe Arg Leu
            340                 345                 350

Pro Val Arg Phe Asp Glu Ala Ile Arg Ser Ala Leu Glu Val Gly Pro
        355                 360                 365

Gly Thr Phe Val Glu Ala Ser Pro His Pro Val Leu Ala Ala Ala Leu
    370                 375                 380

Gln Gln Thr Leu Asp Ala Glu Gly Ser Ser Ala Ala Val Val Pro Thr
385                 390                 395                 400

Leu Gln Arg Gly Gln Gly Gly Met Arg Arg Phe Leu Leu Ala Ala Ala
                405                 410                 415

Gln Ala Phe Thr Gly Gly Val Ala Val Asp Trp Thr Ala Ala Tyr Asp
            420                 425                 430

Asp Val Gly Ala Glu Pro Gly Ser Leu Pro Glu Phe Ala Pro Ala Glu
        435                 440                 445

Glu Glu Asp Glu Pro Ala Glu Ser Gly Val Asp Trp Asn Ala Pro Pro
    450                 455                 460

His Val Leu Arg Glu Arg Leu Leu Ala Val Val Asn Gly Glu Thr Ala
465                 470                 475                 480

Ala Leu Ala Gly Arg Glu Ala Asp Ala Glu Ala Thr Phe Arg Glu Leu
                485                 490                 495

Gly Leu Asp Ser Val Leu Ala Ala Gln Leu Arg Ala Lys Val Ser Ala
            500                 505                 510

Ala Ile Gly Arg Glu Val Asn Ile Ala Leu Leu Tyr Asp His Pro Thr
        515                 520                 525

Pro Arg Ala Leu Ala Glu Ala Leu Ala Ala Gly Thr Glu Val Ala Gln
    530                 535                 540

Arg Glu Thr Arg Ala Arg Thr Asn Glu Ala Ala Pro Gly Glu Pro Val
545                 550                 555                 560

Ala Val Val Ala Met Ala Cys Arg Leu Pro Gly Gly Val Ser Thr Pro
                565                 570                 575

Glu Glu Phe Trp Glu Leu Leu Ser Glu Gly Arg Asp Ala Val Ala Gly
            580                 585                 590

Leu Pro Thr Asp Arg Gly Trp Asp Leu Asp Ser Leu Phe His Pro Asp
        595                 600                 605

Pro Thr Arg Ser Gly Thr Ala His Gln Arg Gly Gly Gly Phe Leu Thr
    610                 615                 620

Glu Ala Thr Ala Phe Asp Pro Ala Phe Phe Gly Met Ser Pro Arg Glu
625                 630                 635                 640

Ala Leu Ala Val Asp Pro Gln Gln Arg Leu Met Leu Glu Leu Ser Trp
                645                 650                 655

Glu Val Leu Glu Arg Ala Gly Ile Pro Pro Thr Ser Leu Gln Ala Ser
            660                 665                 670

Pro Thr Gly Val Phe Val Gly Leu Ile Pro Gln Glu Tyr Gly Pro Arg
```

-continued

```
            675                 680                 685
Leu Ala Glu Gly Gly Glu Gly Val Glu Gly Tyr Leu Met Thr Gly Thr
            690                 695                 700
Thr Thr Ser Val Ala Ser Gly Arg Ile Ala Tyr Thr Leu Gly Leu Glu
705                 710                 715                 720
Gly Pro Ala Ile Ser Val Asp Thr Ala Cys Ser Ser Leu Val Ala
            725                 730                 735
Val His Leu Ala Cys Gln Ser Leu Arg Arg Gly Glu Ser Ser Leu Ala
            740                 745                 750
Met Ala Gly Gly Val Thr Val Met Pro Thr Pro Gly Met Leu Val Asp
            755                 760                 765
Phe Ser Arg Met Asn Ser Leu Ala Pro Asp Gly Arg Cys Lys Ala Phe
            770                 775                 780
Ser Ala Gly Ala Asn Gly Phe Gly Met Ala Glu Gly Ala Gly Met Leu
785                 790                 795                 800
Leu Leu Glu Arg Leu Ser Asp Ala Arg Arg Asn Gly His Pro Val Leu
            805                 810                 815
Ala Val Leu Arg Gly Thr Ala Val Asn Ser Asp Gly Ala Ser Asn Gly
            820                 825                 830
Leu Ser Ala Pro Asn Gly Arg Ala Gln Val Arg Val Ile Gln Gln Ala
            835                 840                 845
Leu Ala Glu Ser Gly Leu Gly Pro Ala Asp Ile Asp Ala Val Glu Ala
            850                 855                 860
His Gly Thr Gly Thr Arg Leu Gly Asp Pro Ile Glu Ala Arg Ala Leu
865                 870                 875                 880
Phe Glu Ala Tyr Gly Arg Asp Arg Glu Gln Pro Leu His Leu Gly Ser
            885                 890                 895
Val Lys Ser Asn Leu Gly His Thr Gln Ala Ala Ala Gly Val Ala Gly
            900                 905                 910
Val Ile Lys Met Val Leu Ala Met Arg Ala Gly Thr Leu Pro Arg Thr
            915                 920                 925
Leu His Ala Ser Glu Arg Ser Lys Glu Ile Asp Trp Ser Ser Gly Ala
            930                 935                 940
Ile Ser Leu Leu Asp Glu Pro Glu Pro Trp Pro Ala Gly Ala Arg Pro
945                 950                 955                 960
Arg Arg Ala Gly Val Ser Ser Phe Gly Val Ser Gly Thr Asn Ala His
            965                 970                 975
Val Ile Val Glu Glu Ala Pro Glu Ser Ser Ala Asp Ala Val Ala Glu
            980                 985                 990
Ser Gly Val Arg Val Pro Val Pro  Val Val Pro Trp Val  Val Ser Ala
            995                 1000                1005
Arg Ser  Ala Glu Gly Leu Ala  Ala Gln Ala Glu Arg  Leu Ala Arg
            1010                1015                1020
Phe Val  Gly Glu Arg Ser Asp  Gln Asp Pro Val Asp  Ile Gly Phe
            1025                1030                1035
Ser Leu  Val Arg Ser Arg Ser  Leu Leu Glu His Arg  Ala Val Val
            1040                1045                1050
Leu Gly  Lys Gly Arg Asp Asp  Leu Val Ala Gly Leu  Ala Ser Leu
            1055                1060                1065
Ala Ser  Asp Gly Ser Ala Thr  Gly Val Val Ser Gly  Val Ala Arg
            1070                1075                1080
Gly Arg  Ala Arg Val Ala Phe  Gly Phe Ser Gly Gln  Gly Ala Gln
            1085                1090                1095
```

-continued

```
Arg Val Gly Met Gly Ala Glu Leu Ala Ser Val Tyr Pro Val Phe
1100            1105                 1110

Ala Glu Ala Leu Ala Glu Val Thr Gly Ala Leu Gly Leu Asp Pro
1115            1120                 1125

Glu Val Phe Gly Asp Val Asp Arg Leu Gly Arg Thr Glu Val Thr
1130            1135                 1140

Gln Ala Ala Leu Phe Ala Phe Glu Val Ala Val Arg Leu Leu
1145            1150                 1155

Glu Ser Phe Gly Val Arg Pro Asp Val Leu Ile Gly His Ser Ile
1160            1165                 1170

Gly Glu Ile Ala Ala Ala Tyr Val Ala Gly Val Phe Ser Leu Gly
1175            1180                 1185

Asp Ala Ala Leu Val Gly Ala Arg Gly Arg Leu Met Gln Ala
1190            1195                 1200

Leu Pro Ala Gly Gly Val Met Val Ala Val Gln Ala Gly Glu Ala
1205            1210                 1215

Glu Val Val Ala Ala Leu Glu Gly Phe Ala Asp Arg Val Ser Leu
1220            1225                 1230

Ala Ala Val Asn Gly Pro Ser Ser Val Val Val Ser Gly Glu Ala
1235            1240                 1245

Glu Ala Val Glu Gln Val Val Ala Arg Leu Gly Lys Val Lys Ser
1250            1255                 1260

Lys Arg Leu Arg Val Ser His Ala Phe His Ser Pro Leu Met Glu
1265            1270                 1275

Pro Met Leu Ala Asp Phe Arg Gln Val Ala Glu Gln Ile Thr Tyr
1280            1285                 1290

Asn Glu Pro Gln Leu Pro Val Val Ser Asn Val Ser Gly Arg Leu
1295            1300                 1305

Ala Glu Pro Gly Glu Leu Thr Thr Pro Asp Tyr Trp Val Arg His
1310            1315                 1320

Val Arg Glu Ala Val Arg Phe Gly Asp Gly Val Arg Ala Leu Ala
1325            1330                 1335

Ala Asp Gly Val Gly Val Leu Val Glu Val Gly Pro Asp Ser Val
1340            1345                 1350

Leu Thr Ala Leu Ala Arg Glu Ser Leu Asp Gly Glu Asp Gly Leu
1355            1360                 1365

Arg Ala Val Pro Leu Leu Arg Lys Asp Arg Pro Glu Pro Glu Thr
1370            1375                 1380

Leu Leu Thr Gly Val Ala Gln Ala Phe Thr His Gly Val Gln Val
1385            1390                 1395

Asp Trp Pro Ala Leu Leu Pro Gly Gly Arg Arg Val Glu Leu Pro
1400            1405                 1410

Thr Tyr Ala Phe Gln Arg Arg Arg Tyr Trp Leu Glu Asp Ala Asp
1415            1420                 1425

Pro Thr Gly Gly Asp Pro Ala Ala Leu Gly Leu Thr Ala Ala Asp
1430            1435                 1440

His Pro Leu Leu Gly Ala Ala Val Pro Leu Ala Glu Asp Gln Gly
1445            1450                 1455

Ile Val Ile Thr Ser Arg Leu Ser Leu Arg Thr His Pro Trp Leu
1460            1465                 1470

Ala Asp His Glu Ile Gly Gly Thr Val Leu Leu Pro Gly Ala Gly
1475            1480                 1485
```

```
Leu Val Glu Ile Ala Leu Arg Ala Gly Asp Glu Val Gly Cys Gly
    1490            1495                1500

Arg Val Glu Glu Leu Thr Leu Glu Ile Pro Leu Val Val Pro Gln
1505                1510                1515

Glu Gly Gly Val Thr Val Gln Ile Arg Val Gly Ala Pro Asp Glu
1520                1525                1530

Ser Gly Trp Arg Pro Met Thr Val His Ser Arg Thr Asp Pro Glu
1535                1540                1545

Glu Glu Trp Thr Arg His Val Ser Gly Val Leu Ser Pro Asp Val
1550                1555                1560

Pro Thr Glu Arg Tyr Asp Leu Gly Ala Trp Pro Ala Gly Ala
1565                1570                1575

Thr Pro Val Glu Leu Asp Gly Phe Tyr Glu Ala Tyr Ala Arg Leu
1580                1585                1590

Gly Tyr Ala Tyr Gly Pro Ser Phe Gln Gly Leu Arg Ala Ala Trp
1595                1600                1605

Arg Arg Gly Asp Glu Val Phe Ala Glu Val Ser Leu Pro Val Glu
1610                1615                1620

Glu Gln Glu Thr Ala Gly Arg Phe Thr Leu His Pro Ala Leu Leu
1625                1630                1635

Asp Ala Ala Leu Gln Ser Ala Gly Ala Gly Ala Phe Phe Asp Ser
1640                1645                1650

Gly Gly Ser Met Arg Leu Pro Phe Ala Trp Ser Gly Val Ser Val
1655                1660                1665

Phe Ala Ala Gly Ala Ser Thr Val Arg Val Arg Leu Ser Pro Ala
1670                1675                1680

Gly Pro Asp Ala Val Thr Val Ala Leu Ala Asp Pro Thr Gly Ala
1685                1690                1695

Pro Val Ala Leu Val Glu Arg Leu Leu Ile Pro Glu Met Ser Pro
1700                1705                1710

Glu Gln Leu Glu Arg Val Arg Gly Glu Glu Lys Glu Ala Pro Tyr
1715                1720                1725

Val Leu Asp Trp Val Pro Val Glu Val Pro Ala Asp Asp Leu Val
1730                1735                1740

Arg Pro Glu Arg Trp Thr Leu Leu Gly Gly Ala Asp Ala Gly Val
1745                1750                1755

Gly Leu Asp Val Ala Gly Ala Phe Ala Ser Leu Glu Pro Ser Asp
1760                1765                1770

Gly Ala Pro Glu Phe Val Val Leu Pro Cys Val Pro Pro Thr Ser
1775                1780                1785

Pro Thr Arg Ala Ala Asp Val Arg Gln Ser Thr Leu Gln Ala Leu
1790                1795                1800

Thr Val Leu Gln Asn Trp Val Thr Asp Glu Arg His Ala Asp Ser
1805                1810                1815

Arg Leu Val Leu Val Thr Arg Arg Ala Val Gly Val Gly Ala His
1820                1825                1830

Asp Asp Val Pro Asp Leu Thr His Ala Ala Leu Trp Gly Leu Val
1835                1840                1845

Arg Ser Ala Gln Thr Glu Asn Pro Gly Arg Phe Leu Leu Val Asp
1850                1855                1860

Leu Asp Glu Gly Ala Glu Leu Ala Glu Val Leu Pro Gly Ala Leu
1865                1870                1875

Gly Ser Gly Glu Ser Gln Val Ala Val Arg Ala Gly Arg Val Leu
```

-continued

```
            1880                1885                1890
Ala Ala Arg Leu Ala Arg Ser Gly Ser Gly Ala Glu Leu Val
        1895                1900                1905
Pro Pro Ala Gly Ala Pro Trp Arg Leu Asp Thr Thr Ser Pro Gly
        1910                1915                1920
Thr Leu Glu Asn Leu Ala Leu Val Pro Ser Ala Glu Glu Pro Leu
        1925                1930                1935
Gly Pro Leu Asp Val Arg Val Ser Val Arg Ala Ala Gly Leu Asn
        1940                1945                1950
Phe Arg Asp Val Leu Ile Ala Leu Gly Met Tyr Pro Gly Asp Ala
        1955                1960                1965
Arg Met Gly Gly Glu Gly Ala Gly Val Val Thr Asp Val Gly Ser
        1970                1975                1980
Glu Val Thr Thr Leu Ala Pro Gly Asp Arg Val Met Gly Met Leu
        1985                1990                1995
Ser Ser Ala Phe Gly Pro Thr Ala Val Ser Asp His Arg Ala Leu
        2000                2005                2010
Val Arg Val Pro Asp Asp Trp Ser Phe Glu Gln Ala Ala Ser Val
        2015                2020                2025
Pro Thr Val Phe Ala Thr Ala Tyr Tyr Gly Leu Val Asp Leu Ala
        2030                2035                2040
Glu Leu Arg Ala Gly Gln Ser Val Leu Val His Ala Ala Ala Gly
        2045                2050                2055
Gly Val Gly Met Ala Ala Val Gln Leu Ala Arg His Leu Gly Ala
        2060                2065                2070
Glu Val Phe Gly Thr Ala Ser Thr Gly Lys Trp Asp Ser Leu Arg
        2075                2080                2085
Ala Gly Gly Leu Asp Ala Glu His Ile Ala Ser Ser Arg Thr Val
        2090                2095                2100
Glu Phe Glu Glu Thr Phe Leu Ala Ala Thr Ala Gly Arg Gly Val
        2105                2110                2115
Asp Val Val Leu Asp Ser Leu Ala Gly Glu Phe Val Asp Ala Ser
        2120                2125                2130
Leu Arg Leu Leu Pro Arg Gly Gly Arg Phe Val Glu Met Gly Lys
        2135                2140                2145
Ala Asp Ile Arg Asp Ala Glu Arg Val Ala Ala Asp His Pro Gly
        2150                2155                2160
Val Thr Tyr Arg Ser Phe Asp Leu Leu Glu Ala Gly Leu Asp Arg
        2165                2170                2175
Phe Gln Glu Ile Leu Thr Glu Val Val Arg Leu Phe Glu Arg Gly
        2180                2185                2190
Val Leu Arg His Leu Pro Val Thr Ala Trp Asp Val Arg Arg Ala
        2195                2200                2205
Ala Glu Ala Phe Arg Phe Val Ser Gln Ala Arg His Val Gly Lys
        2210                2215                2220
Asn Val Leu Val Met Pro Arg Val Trp Asp Arg Asp Gly Thr Val
        2225                2230                2235
Leu Ile Thr Gly Gly Thr Gly Ala Leu Gly Ala Leu Val Ala Arg
        2240                2245                2250
His Leu Val Ala Glu His Gly Met Arg Asn Val Leu Leu Ala Gly
        2255                2260                2265
Arg Arg Gly Val Asp Ala Pro Gly Ala Arg Glu Leu Leu Ala Glu
        2270                2275                2280
```

-continued

```
Leu Glu Thr Ala Gly Ala Gln Val Ser Val Val Ala Cys Asp Val
    2285                2290                2295

Ala Asp Arg Asp Ala Val Ala Glu Leu Ile Ala Lys Val Pro Val
    2300                2305                2310

Glu His Pro Leu Thr Ala Val Val His Thr Ala Gly Val Val Ala
    2315                2320                2325

Asp Ala Thr Leu Thr Ala Leu Asp Ala Glu Arg Val Asp Thr Val
    2330                2335                2340

Leu Arg Ala Lys Val Asp Ala Val Leu His Leu His Glu Ala Thr
    2345                2350                2355

Arg Gly Leu Asp Leu Ala Gly Phe Val Leu Phe Ser Ser Ala Ser
    2360                2365                2370

Gly Ile Phe Gly Ser Pro Gly Gln Gly Asn Tyr Ala Ala Ala Asn
    2375                2380                2385

Ser Phe Ile Asp Ala Phe Ala His His Arg Arg Ala Gln Gly Leu
    2390                2395                2400

Pro Ala Leu Ser Leu Ala Trp Gly Leu Trp Ala Arg Thr Ser Gly
    2405                2410                2415

Met Ala Gly Gln Leu Gly His Asp Asp Val Ala Arg Ile Ser Arg
    2420                2425                2430

Thr Gly Leu Ala Pro Ile Thr Asp Asp Gln Gly Met Ala Leu Leu
    2435                2440                2445

Asp Ala Ala Leu Gly Ala Gly Arg Pro Leu Leu Val Pro Val Arg
    2450                2455                2460

Leu Asp Arg Ala Ala Leu Arg Ser Gln Ala Thr Ala Gly Thr Leu
    2465                2470                2475

Pro Pro Ile Leu Arg Gly Leu Val Arg Ala Thr Val Arg Arg Ala
    2480                2485                2490

Ala Ser Thr Ala Ala Ala Gln Gly Pro Ser Leu Ala Glu Arg Leu
    2495                2500                2505

Ala Gly Leu Pro Val Thr Glu His Glu Arg Ile Val Val Glu Leu
    2510                2515                2520

Val Arg Ala Asp Leu Ala Ala Val Leu Gly His Ala Ser Ala Glu
    2525                2530                2535

Arg Val Pro Ala Asp Gln Ala Phe Ala Glu Leu Gly Val Asp Ser
    2540                2545                2550

Leu Thr Ala Val Glu Leu Arg Asn Arg Leu Asn Gly Ala Thr Gly
    2555                2560                2565

Leu Arg Leu Ala Ala Ser Leu Val Phe Asp Tyr Pro Thr Pro Asn
    2570                2575                2580

Ala Leu Ala Thr His Ile Leu Asp Glu Leu Ala Leu Asp Thr Ala
    2585                2590                2595

Gly Ala Gly Ala Ala Gly Glu Pro Asp Gly Pro Ala Pro Ala Pro
    2600                2605                2610

Ala Asp Glu Ala Arg Phe Arg Arg Val Ile Asn Ser Ile Pro Leu
    2615                2620                2625

Asp Arg Ile Arg Arg Ala Gly Leu Leu Asp Ala Leu Leu Gly Leu
    2630                2635                2640

Ala Gly Thr Ser Ala Asp Thr Ala Ala Ser Asp Asp Phe Asp Gln
    2645                2650                2655

Glu Glu Asp Gly Pro Ala Ile Ala Ser Met Asp Val Asp Asp Leu
    2660                2665                2670
```

```
Val Arg Ile Ala Leu Gly Glu Ser Asp Thr Thr Ala Asp Ile Thr
    2675                2680                2685
Glu Gly Thr Asp Arg Ser
    2690

<210> SEQ ID NO 4
<211> LENGTH: 2227
<212> TYPE: PRT
<213> ORGANISM: Artificial sequence
<220> FEATURE:
<223> OTHER INFORMATION: KS domain from IdmP and AT-TE domains from CurM

<400> SEQUENCE: 4

Met Ser Ser Ala Ser Ser Glu Lys Ile Val Glu Ala Leu Arg Ala Ser
1               5                   10                  15

Leu Thr Glu Asn Glu Arg Leu Arg Arg Leu Asn Gln Glu Leu Ala Ala
            20                  25                  30

Ala Ala His Glu Pro Val Ala Ile Val Ser Met Ala Cys Arg Phe Pro
        35                  40                  45

Gly Gly Val Glu Ser Pro Glu Asp Phe Trp Asp Leu Ile Ser Glu Gly
    50                  55                  60

Arg Asp Ala Val Ser Gly Leu Pro Asp Asn Arg Gly Trp Asp Leu Asp
65                  70                  75                  80

Ala Leu Tyr Asp Pro Asp Pro Glu Ala Gln Gly Lys Thr Tyr Val Arg
                85                  90                  95

Glu Gly Ala Phe Leu Tyr Asp Ala Ala Glu Phe Asp Ala Glu Leu Phe
            100                 105                 110

Gly Ile Ser Pro Arg Glu Ala Leu Ala Met Asp Pro Gln Gln Arg Leu
        115                 120                 125

Leu Met Glu Thr Ser Trp Glu Val Leu Glu Arg Ala Gly Ile Arg Pro
    130                 135                 140

Asp Ser Leu Arg Gly Lys Pro Val Gly Val Phe Thr Gly Gly Ile Thr
145                 150                 155                 160

Ser Asp Tyr Val Thr Arg His Tyr Ala Ser Gly Thr Ala Pro Gln Leu
                165                 170                 175

Pro Ser Gly Val Glu Ser His Phe Met Thr Gly Ser Ala Gly Ser Val
            180                 185                 190

Phe Ser Gly Arg Ile Ala Tyr Thr Tyr Gly Phe Glu Gly Pro Ala Val
        195                 200                 205

Thr Val Asp Thr Ala Cys Ser Ser Leu Val Ala Leu His Met Ala
    210                 215                 220

Ala Gln Ser Leu Arg Gln Gly Glu Cys Ser Leu Ala Phe Ala Gly Gly
225                 230                 235                 240

Val Ala Val Leu Pro Asn Pro Gly Thr Phe Val Gly Phe Ser Arg Gln
                245                 250                 255

Arg Ala Leu Ser Pro Asp Gly Arg Cys Lys Ala Phe Ser Ala Asp Ala
            260                 265                 270

Asp Gly Thr Gly Trp Gly Glu Gly Ala Gly Leu Val Leu Leu Glu Lys
        275                 280                 285

Leu Ser Asp Ala Arg Arg Asn Gly His Pro Val Leu Ala Ile Leu Arg
    290                 295                 300

Gly Ser Ala Val Asn Gln Asp Gly Ala Ser Asn Gly Leu Thr Ala Pro
305                 310                 315                 320

Asn Gly Pro Ser Gln Gln Arg Val Ile Arg Ala Ala Leu Ala Asn Ala
                325                 330                 335
```

```
Arg Leu Ser Pro Asp Asp Val Asp Val Val Glu Ala His Gly Thr Gly
                340                 345                 350
Thr Pro Leu Gly Asp Pro Ile Glu Ala Gln Ala Leu Gln Ala Thr Tyr
            355                 360                 365
Gly Arg Ser Arg Ser Ala Glu Arg Pro Leu Trp Leu Gly Ser Val Lys
370                 375                 380
Ser Asn Val Ala His Ala Gln Ala Ala Gly Val Ala Ser Val Ile
385                 390                 395                 400
Lys Val Val Met Ala Leu Arg His Arg Leu Leu Pro Lys Thr Leu His
                405                 410                 415
Ala Asp Glu Arg Ser Pro His Ile Asp Trp His Ser Gly Ala Val Glu
            420                 425                 430
Leu Leu Thr Glu Ala Arg Glu Trp Ser Arg Thr Glu Gly Arg Ala Arg
        435                 440                 445
Arg Ala Gly Val Ser Ser Phe Gly Ile Ser Gly Thr Asn Ala His Val
450                 455                 460
Ile Ile Glu Glu Ala Pro Glu Leu Ile Lys Gly Gln Lys Ala Lys Gly
465                 470                 475                 480
Lys Ser Glu Asn Asp Leu Glu Arg Pro Leu His Ile Leu Thr Leu Ser
                485                 490                 495
Thr Lys Thr Glu Lys Ala Leu Glu Glu Leu Val Ser Arg Tyr Gln Asn
            500                 505                 510
His Trp Glu Thr Tyr Pro Glu Leu Ala Ile Ser Asp Val Cys Tyr Thr
        515                 520                 525
Ala Asn Thr Gly Arg Ala Gln Phe Asn His Arg Leu Ala Val Ile Ala
530                 535                 540
Ser Gly Ser Glu Glu Leu Thr Gln Lys Leu Arg Gln His Thr Ala Gly
545                 550                 555                 560
Glu Glu Val Val Gly Val Phe Ser Gly Lys Val Pro Asn Ser Gly Ser
                565                 570                 575
Glu Ser Lys Val Ala Phe Leu Phe Thr Gly Gln Gly Ser Gln Tyr Leu
            580                 585                 590
Asn Met Gly Arg Gln Leu Tyr Glu Thr Gln Pro Thr Phe Arg Gln Ala
        595                 600                 605
Leu Asp Thr Cys Asp His Ile Leu Arg Pro Tyr Leu Asp Asn Pro Leu
610                 615                 620
Leu Glu Ile Leu Tyr Pro Gln Asp Ala Gln Lys Ser Asn Asp Ser Pro
625                 630                 635                 640
Leu Asp Gln Thr Gly Tyr Thr Gln Pro Ala Leu Phe Ser Ile Glu Tyr
                645                 650                 655
Ala Leu Leu Lys Leu Trp Glu Ser Trp Gly Ile Lys Pro Asn Val Val
            660                 665                 670
Met Gly His Ser Val Gly Glu Tyr Val Ala Ala Thr Val Ala Gly Val
        675                 680                 685
Phe Ser Leu Glu Asp Gly Leu Lys Leu Ile Ala Ala Arg Gly Arg Leu
690                 695                 700
Met Gln Gly Leu Pro Ala Gly Gly Glu Met Val Ser Val Met Ala Ser
705                 710                 715                 720
Glu Ser Lys Val Leu Glu Thr Leu Lys Ala Met Ser Leu Glu Asp Lys
                725                 730                 735
Val Ala Ile Ala Ala Ile Asn Gly Pro Glu Ser Ile Val Ile Ser Gly
            740                 745                 750
Glu Ala Glu Ala Ile Arg Ala Met Ala Thr His Leu Glu Ser Val Gly
```

755                 760                 765
Ile Lys Thr Lys Gln Leu Gln Val Ser His Ala Phe His Ser Pro Leu
    770                 775                 780

Met Glu Pro Met Leu Ala Glu Phe Glu Ala Val Ala Asn Gln Ile Thr
785                 790                 795                 800

Tyr His Gln Pro Arg Ile Pro Ile Ile Ser Asn Val Thr Gly Thr Lys
                    805                 810                 815

Ala Asp Lys Ser Ile Ala Thr Ala Gln Tyr Trp Val Asn His Val Arg
            820                 825                 830

Gln Pro Val Arg Phe Ala Gln Gly Met Ala Thr Leu His Gln Gln Gly
                835                 840                 845

Tyr Glu Thr Phe Leu Glu Ile Gly Ala Lys Pro Ile Leu Leu Gly Met
850                 855                 860

Gly Lys Gln Cys Leu Ser Pro Asp Val Gly Val Trp Leu Pro Ser Leu
865                 870                 875                 880

Arg His Gly Val Asp Glu Trp Gln Gln Ile Leu Ser Ser Leu Gly Gln
                885                 890                 895

Leu Tyr Val Gln Gly Ala Lys Val Asp Trp Ser Gly Phe Asp Arg Asp
                900                 905                 910

Tyr Ser Arg Glu Lys Val Val Leu Pro Thr Tyr Pro Phe Gln Arg Glu
            915                 920                 925

Arg Tyr Trp Val Glu Thr Ser Ile Asn Gln Gln Val Val Cys Ser
930                 935                 940

Gly Glu Pro Asn Leu Gln Gly Thr Pro Glu Gly Thr Ser Thr Thr Ile
945                 950                 955                 960

Val Lys Leu Leu Ser Gln Gly Asn Thr Lys Glu Leu Ala Glu Lys Val
                965                 970                 975

Glu Lys Thr Ser Asp Leu Pro Pro Glu Gln Leu Lys Leu Leu Pro Asp
            980                 985                 990

Leu Leu Ala Ser Leu Ser Gln Gln His Gln Gln Glu Leu Ala Arg Leu
            995                 1000                1005

Thr Thr Lys Lys Trp Phe Tyr Lys Val Gln Trp Ile Ser Gln Ala
    1010                1015                1020

Ile Lys Pro Gln Arg Asn Lys Ser Asn Asn Gln Val Cys His Trp
    1025                1030                1035

Leu Ile Leu Thr Asp Ser Lys Gly Leu Gly Lys Ser Leu Ala Thr
    1040                1045                1050

His Leu Gln Gln Leu Gly Asn Glu Cys Ser Val Val Tyr Gln Ala
    1055                1060                1065

Asp Asn Tyr Gln Asn Tyr Glu Pro Gly Ile Tyr His Ile Asn Pro
    1070                1075                1080

Ser His Pro Gln Glu Phe Glu Gln Val Tyr Gln Thr Ile Phe Glu
    1085                1090                1095

Asn Gly Lys Leu Pro Leu Gln Lys Val Ile His Leu Trp Ser Leu
    1100                1105                1110

Asp Thr Ala Ser Glu Gln Asp Leu Thr Thr Glu Thr Leu Glu Gln
    1115                1120                1125

Ala Gln Leu Trp Gly Cys Gly Ser Thr Leu His Leu Leu Gln Thr
    1130                1135                1140

Leu Val Lys Asn Pro Asn Ser Thr Pro Pro Lys Leu Trp Met Ile
    1145                1150                1155

Thr Arg Gly Thr Gln Pro Val Leu Ser Pro Thr Glu Lys Leu Thr
    1160                1165                1170

```
Val Ala Thr Ser Pro Leu Trp Gly Leu Gly Arg Thr Ile Ala Ser
1175                1180                1185

Glu His Pro Gln Leu Trp Gly Leu Val Asp Leu Asp Pro Gln
1190                1195                1200

Gly Ser Glu Asp Glu Val Glu Val Leu Leu Gln Gln Ile Ile Asp
1205                1210                1215

Ser Gln Lys Glu Asp His Leu Ala Val Arg Asn Arg Lys Ile Tyr
1220                1225                1230

Val Ala Arg Leu Leu Lys His Ile Pro Gln Glu Ser Gln Pro Leu
1235                1240                1245

Ser Leu Arg Ser Asp Ala Thr Tyr Leu Ile Thr Gly Gly Leu Gly
1250                1255                1260

Ala Leu Gly Leu Lys Thr Ala Ala Trp Met Ala Glu Lys Gly Ala
1265                1270                1275

Arg Asn Leu Val Leu Ile Ser Arg Arg Gln Pro Ser Glu Gln Ala
1280                1285                1290

Gln Gln Thr Ile Gln Ser Leu Glu Glu Leu Gly Thr Gln Val Lys
1295                1300                1305

Val Leu Ser Ala Asp Ile Ser Val Glu Ser Asp Val Ala Asn Ile
1310                1315                1320

Leu Glu Gln Ile Gln Thr Ser Leu Pro Pro Leu Leu Gly Val Ile
1325                1330                1335

His Ala Ala Gly Val Leu Asp Asp Gly Leu Leu Gln Gln Thr Asn
1340                1345                1350

Trp Glu Arg Phe Thr Lys Val Met Ala Pro Lys Val Asn Gly Thr
1355                1360                1365

Trp Asn Leu His Lys Leu Thr Gln His Leu Ser Leu Asp Phe Phe
1370                1375                1380

Val Cys Phe Ser Ser Met Ser Ser Leu Leu Gly Ser Pro Gly Gln
1385                1390                1395

Gly Asn Tyr Ala Ala Ala Asn Ala Phe Met Asp Ala Val Val His
1400                1405                1410

Tyr Arg Arg Glu Met Gly Leu Pro Gly Leu Ser Ile Asn Trp Gly
1415                1420                1425

Gly Trp Ser Glu Gly Gly Met Ala Thr Arg Leu Ala Ser Gln His
1430                1435                1440

Gln Asn Arg Met Gln Thr Ala Gly Ile Ser Leu Ile Ser Pro Glu
1445                1450                1455

Gln Gly Ile Gln Val Leu Glu Glu Leu Val Arg Thr Gln Ser Thr
1460                1465                1470

Ala Gln Val Gly Val Leu Pro Val Asp Trp Ser Val Leu Ala Lys
1475                1480                1485

Gln Phe Ser Ser Ala Asn Pro Ser Ser Leu Leu Leu Glu Leu Leu
1490                1495                1500

Gln Gln Glu Thr Ser Ser Glu Lys Thr Asp Glu Arg Ile Leu Glu
1505                1510                1515

Lys Leu Gln Ala Ala Pro Ile Thr Glu Arg Gln Asp Ile Leu Lys
1520                1525                1530

Asn Tyr Ile Gln Leu Val Val Ala Lys Thr Leu Gly Ile Asn Pro
1535                1540                1545

Ser Lys Ile Ser Thr Asp Asp Asn Phe Val Glu Leu Gly Met Asp
1550                1555                1560
```

-continued

```
Ser Leu Met Gly Met Glu Val Val Asn Lys Leu Ser Gly Asp Leu
    1565                1570                1575

Asp Phe Ile Ile Tyr Pro Arg Glu Phe Tyr Glu Arg Pro Thr Ile
    1580                1585                1590

Asp Ser Leu Thr Gln Tyr Leu Ser Ala Glu Leu Ser Glu Asp Asn
    1595                1600                1605

Leu Ala Thr Gln Pro Ser Pro Thr Ser Leu Glu Ile Phe Ala Thr
    1610                1615                1620

Lys Ser Ser Pro Ser Gly Asn Ser Ala Arg Pro Ala Ser Val Ser
    1625                1630                1635

Ser Arg Leu Pro Gly Ile Ile Phe Ile Leu Ser Ser Pro Arg Ser
    1640                1645                1650

Gly Ser Thr Leu Leu Arg Val Met Leu Ala Gly His Ser Ser Leu
    1655                1660                1665

Phe Ser Pro Pro Glu Leu His Leu Leu Pro Phe Asn Thr Met Lys
    1670                1675                1680

Glu Arg Gln Glu Gln Leu Asn Leu Ser Tyr Leu Gly Glu Gly Leu
    1685                1690                1695

Gln Lys Thr Phe Met Glu Val Lys Asn Leu Asp Ala Thr Ala Ser
    1700                1705                1710

Gln Ala Leu Ile Lys Asp Leu Glu Ser Gln Asn Leu Ser Ile Gln
    1715                1720                1725

Gln Val Tyr Gly Met Leu Gln Glu Asn Ile Ala Pro Arg Leu Leu
    1730                1735                1740

Val Asp Lys Ser Pro Thr Tyr Ala Met Glu Pro Thr Ile Leu Glu
    1745                1750                1755

Arg Gly Glu Ala Leu Phe Ala Asn Ser Lys Tyr Ile Tyr Leu Val
    1760                1765                1770

Arg His Pro Tyr Ser Val Ile Glu Ser Phe Val Arg Met Arg Met
    1775                1780                1785

Gln Lys Leu Val Gly Leu Gly Glu Glu Asn Pro Tyr Arg Val Ala
    1790                1795                1800

Glu Gln Val Trp Ala Lys Ser Asn Gln Asn Ile Leu Asn Phe Leu
    1805                1810                1815

Ser Gln Leu Glu Pro Glu Arg Gln His Gln Ile Arg Tyr Glu Asp
    1820                1825                1830

Leu Val Lys Lys Pro Gln Gln Val Leu Ser Gln Leu Cys Asp Phe
    1835                1840                1845

Leu Asn Val Pro Phe Glu Pro Glu Leu Leu Gln Pro Tyr Gln Gly
    1850                1855                1860

Asp Arg Met Thr Gly Gly Val His Gln Lys Ser Leu Ser Ile Ser
    1865                1870                1875

Asp Pro Asn Phe Leu Lys His Asn Thr Ile Asp Glu Ser Leu Ala
    1880                1885                1890

Asp Lys Trp Lys Thr Ile Gln Leu Pro Tyr Pro Leu Lys Ser Glu
    1895                1900                1905

Thr Gln Arg Ile Ala Ser Leu Ser Tyr Glu Leu Pro Asn Leu
    1910                1915                1920

Val Thr Thr Pro Thr Asn Gln Gln Pro Gln Val Ser Thr Thr Pro
    1925                1930                1935

Ser Thr Glu Gln Pro Ile Met Glu Glu Lys Phe Leu Glu Phe Gly
    1940                1945                1950

Gly Asn Gln Ile Cys Leu Cys Ser Trp Gly Ser Pro Glu His Pro
```

```
                1955                1960                1965

Val Val Leu Cys Ile His Gly Ile Leu Glu Gln Gly Leu Ala Trp
        1970                1975                1980

Gln Glu Val Ala Leu Pro Leu Ala Ala Gln Gly Tyr Arg Val Val
        1985                1990                1995

Ala Pro Asp Leu Phe Gly His Gly Arg Ser Ser His Leu Glu Met
        2000                2005                2010

Val Thr Ser Tyr Ser Ser Leu Thr Phe Leu Ala Gln Ile Asp Arg
        2015                2020                2025

Val Ile Gln Glu Leu Pro Asp Gln Pro Leu Leu Val Gly His
        2030                2035                2040

Ser Met Gly Ala Met Leu Ala Thr Ala Ile Ala Ser Val Arg Pro
        2045                2050                2055

Lys Lys Ile Lys Glu Leu Ile Leu Val Glu Leu Pro Leu Pro Ala
        2060                2065                2070

Glu Glu Ser Lys Lys Glu Ser Ala Val Asn Gln Leu Thr Thr Cys
        2075                2080                2085

Leu Asp Tyr Leu Ser Ser Thr Pro Gln His Pro Ile Phe Pro Asp
        2090                2095                2100

Val Ala Thr Ala Ala Ser Arg Leu Arg Gln Ala Ile Pro Ser Leu
        2105                2110                2115

Ser Glu Glu Phe Ser Tyr Ile Leu Ala Gly Arg Ile Thr Gln Pro
        2120                2125                2130

Asn Gln Gly Gly Val Arg Trp Ser Trp Asp Ala Ile Ile Arg Thr
        2135                2140                2145

Arg Ser Ile Leu Gly Leu Asn Asn Leu Pro Gly Gly Arg Ser Gln
        2150                2155                2160

Tyr Leu Glu Met Leu Lys Ser Ile Gln Val Pro Thr Thr Leu Val
        2165                2170                2175

Tyr Gly Asp Ser Ser Lys Leu Asn Arg Pro Glu Asp Leu Gln Gln
        2180                2185                2190

Gln Lys Met Thr Met Thr Gln Ala Lys Arg Val Phe Leu Ser Gly
        2195                2200                2205

Gly His Asn Leu His Ile Asp Ala Ala Ala Ala Leu Ala Ser Leu
        2210                2215                2220

Ile Leu Thr Ser
        2225

<210> SEQ ID NO 5
<211> LENGTH: 2740
<212> TYPE: PRT
<213> ORGANISM: Artificial sequence
<220> FEATURE:
<223> OTHER INFORMATION: Hybrid polyketide synthase capable of producing
      butene

<400> SEQUENCE: 5

Met Ala Asp Leu Ser Lys Leu Ser Asp Ser Arg Thr Ala Gln Pro Gly
1               5                   10                  15

Arg Ile Val Arg Pro Trp Pro Leu Ser Gly Cys Asn Glu Ser Ala Leu
            20                  25                  30

Arg Ala Arg Ala Arg Gln Leu Arg Ala His Leu Asp Arg Phe Pro Asp
        35                  40                  45

Ala Gly Val Glu Gly Val Gly Ala Ala Leu Ala His Asp Glu Gln Ala
    50                  55                  60
```

Asp Ala Gly Pro His Arg Ala Val Val Ala Ser Ser Thr Ser Glu
65                  70                  75                  80

Leu Leu Asp Gly Leu Ala Ala Val Ala Asp Gly Arg Pro His Ala Ser
            85                  90                  95

Val Val Arg Gly Val Ala Arg Pro Ser Ala Pro Val Val Phe Val Phe
            100                 105                 110

Pro Gly Gln Gly Ala Gln Trp Ala Gly Met Ala Gly Glu Leu Leu Gly
            115                 120                 125

Glu Ser Arg Val Phe Ala Ala Met Asp Ala Cys Ala Arg Ala Phe
    130                 135                 140

Glu Pro Val Thr Asp Trp Thr Leu Ala Gln Val Leu Asp Ser Pro Glu
145                 150                 155                 160

Gln Ser Arg Arg Val Glu Val Val Gln Pro Ala Leu Phe Ala Val Gln
            165                 170                 175

Thr Ser Leu Ala Ala Leu Trp Arg Ser Phe Gly Val Thr Pro Asp Ala
            180                 185                 190

Val Val Gly His Ser Ile Gly Glu Leu Ala Ala His Val Cys Gly
            195                 200                 205

Ala Ala Gly Ala Ala Asp Ala Ala Arg Ala Ala Leu Trp Ser Arg
210                 215                 220

Glu Met Ile Pro Leu Val Gly Asn Gly Asp Met Ala Ala Val Ala Leu
225                 230                 235                 240

Ser Ala Asp Glu Ile Glu Pro Arg Ile Ala Arg Trp Asp Asp Val
            245                 250                 255

Val Leu Ala Gly Val Asn Gly Pro Arg Ser Val Leu Leu Thr Gly Ser
            260                 265                 270

Pro Glu Pro Val Ala Arg Arg Val Gln Glu Leu Ser Ala Glu Gly Val
    275                 280                 285

Arg Ala Gln Val Ile Asn Val Ser Met Ala Ala His Ser Ala Gln Val
    290                 295                 300

Asp Asp Ile Ala Glu Gly Met Arg Ser Ala Leu Ala Trp Phe Ala Pro
305                 310                 315                 320

Gly Gly Ser Glu Val Pro Phe Tyr Ala Ser Leu Thr Gly Gly Ala Val
            325                 330                 335

Asp Thr Arg Glu Leu Val Ala Asp Tyr Trp Arg Arg Ser Phe Arg Leu
            340                 345                 350

Pro Val Arg Phe Asp Glu Ala Ile Arg Ser Ala Leu Glu Val Gly Pro
            355                 360                 365

Gly Thr Phe Val Glu Ala Ser Pro His Pro Val Leu Ala Ala Ala Leu
    370                 375                 380

Gln Gln Thr Leu Asp Ala Glu Gly Ser Ser Ala Val Val Pro Thr
385                 390                 395                 400

Leu Gln Arg Gly Gln Gly Gly Met Arg Arg Phe Leu Leu Ala Ala Ala
            405                 410                 415

Gln Ala Phe Thr Gly Gly Val Ala Val Asp Trp Thr Ala Ala Tyr Asp
            420                 425                 430

Asp Val Gly Ala Glu Pro Gly Ser Leu Pro Glu Phe Ala Pro Ala Glu
            435                 440                 445

Glu Glu Asp Glu Pro Ala Glu Ser Gly Val Asp Trp Asn Ala Pro Pro
450                 455                 460

His Val Leu Arg Glu Arg Leu Leu Ala Val Asn Gly Glu Thr Ala
465                 470                 475                 480

Ala Leu Ala Gly Arg Glu Ala Asp Ala Glu Ala Thr Phe Arg Glu Leu

```
                485                 490                 495
Gly Leu Asp Ser Val Leu Ala Ala Gln Leu Arg Ala Lys Val Ser Ala
                500                 505                 510

Ala Ile Gly Arg Glu Val Asn Ile Ala Leu Leu Tyr Asp His Pro Thr
            515                 520                 525

Pro Arg Ala Leu Ala Glu Ala Leu Ser Ser Gly Thr Glu Val Ala Gln
    530                 535                 540

Arg Glu Thr Arg Ala Arg Thr Asn Glu Ala Ala Pro Gly Glu Pro Ile
545                 550                 555                 560

Ala Val Val Ala Met Ala Cys Arg Leu Pro Gly Gly Val Ser Thr Pro
                565                 570                 575

Glu Glu Phe Trp Glu Leu Leu Ser Glu Gly Arg Asp Ala Val Ala Gly
            580                 585                 590

Leu Pro Thr Asp Arg Gly Trp Asp Leu Asp Ser Leu Phe His Pro Asp
    595                 600                 605

Pro Thr Arg Ser Gly Thr Ala His Gln Arg Gly Gly Phe Leu Thr
    610                 615                 620

Glu Ala Thr Ala Phe Asp Pro Ala Phe Phe Gly Met Ser Pro Arg Glu
625                 630                 635                 640

Ala Leu Ala Val Asp Pro Gln Gln Arg Leu Met Leu Glu Leu Ser Trp
                645                 650                 655

Glu Val Leu Glu Arg Ala Gly Ile Pro Pro Thr Ser Leu Gln Ala Ser
            660                 665                 670

Pro Thr Gly Val Phe Val Gly Leu Ile Pro Gln Glu Tyr Gly Pro Arg
    675                 680                 685

Leu Ala Glu Gly Gly Glu Gly Val Glu Gly Tyr Leu Met Thr Gly Thr
    690                 695                 700

Thr Thr Ser Val Ala Ser Gly Arg Ile Ala Tyr Thr Leu Gly Leu Glu
705                 710                 715                 720

Gly Pro Ala Ile Ser Val Asp Thr Ala Cys Ser Ser Ser Leu Val Ala
                725                 730                 735

Val His Leu Ala Cys Gln Ser Leu Arg Arg Gly Glu Ser Ser Leu Ala
            740                 745                 750

Met Ala Gly Gly Val Thr Val Met Pro Thr Pro Gly Met Leu Val Asp
    755                 760                 765

Phe Ser Arg Met Asn Ser Leu Ala Pro Asp Gly Arg Cys Lys Ala Phe
    770                 775                 780

Ser Ala Gly Ala Asn Gly Phe Gly Met Ala Glu Gly Ala Gly Met Leu
785                 790                 795                 800

Leu Leu Glu Arg Leu Ser Asp Ala Arg Arg Asn Gly His Pro Val Leu
                805                 810                 815

Ala Val Leu Arg Gly Thr Ala Val Asn Ser Asp Gly Ala Ser Asn Gly
            820                 825                 830

Leu Ser Ala Pro Asn Gly Arg Ala Gln Val Arg Val Ile Gln Gln Ala
    835                 840                 845

Leu Ala Glu Ser Gly Leu Gly Pro Ala Asp Ile Asp Ala Val Glu Ala
    850                 855                 860

His Gly Thr Gly Thr Arg Leu Gly Asp Pro Ile Glu Ala Arg Ala Leu
865                 870                 875                 880

Phe Glu Ala Tyr Gly Arg Asp Arg Glu Gln Pro Leu His Leu Gly Ser
                885                 890                 895

Val Lys Ser Asn Leu Gly His Thr Gln Ala Ala Ala Gly Val Ala Gly
            900                 905                 910
```

-continued

Val Ile Lys Met Val Leu Ala Met Arg Ala Gly Thr Leu Pro Arg Thr
            915                 920                 925

Leu His Ala Ser Glu Arg Ser Lys Glu Ile Asp Trp Ser Ser Gly Ala
    930                 935                 940

Ile Ser Leu Leu Asp Glu Pro Glu Pro Trp Pro Ala Gly Ala Arg Pro
945                 950                 955                 960

Arg Arg Ala Gly Val Ser Ser Phe Gly Ile Ser Gly Thr Asn Ala His
                965                 970                 975

Ala Ile Ile Glu Glu Ala Pro Glu Leu Ile Lys Gly Gln Lys Ala Lys
            980                 985                 990

Gly Lys Ser Glu Asn Asp Leu Glu Arg Pro Leu His Ile Leu Thr Leu
            995                 1000                1005

Ser Thr Lys Thr Glu Lys Ala Leu Glu Glu Leu Val Ser Arg Tyr
    1010                1015                1020

Gln Asn His Trp Glu Thr Tyr Pro Glu Leu Ala Ile Ser Asp Val
    1025                1030                1035

Cys Tyr Thr Ala Asn Thr Gly Arg Ala Gln Phe Asn His Arg Leu
    1040                1045                1050

Ala Val Ile Ala Ser Gly Ser Glu Glu Leu Thr Gln Lys Leu Arg
    1055                1060                1065

Gln His Thr Ala Gly Glu Val Val Gly Val Phe Ser Gly Lys
    1070                1075                1080

Val Pro Asn Ser Gly Ser Glu Ser Lys Val Ala Phe Leu Phe Thr
    1085                1090                1095

Gly Gln Gly Ser Gln Tyr Leu Asn Met Gly Arg Gln Leu Tyr Glu
    1100                1105                1110

Thr Gln Pro Thr Phe Arg Gln Ala Leu Asp Thr Cys Asp His Ile
    1115                1120                1125

Leu Arg Pro Tyr Leu Asp Asn Pro Leu Leu Glu Ile Leu Tyr Pro
    1130                1135                1140

Gln Asp Ala Gln Lys Ser Asn Asp Ser Pro Leu Asp Gln Thr Gly
    1145                1150                1155

Tyr Thr Gln Pro Ala Leu Phe Ser Ile Glu Tyr Ala Leu Leu Lys
    1160                1165                1170

Leu Trp Glu Ser Trp Gly Ile Lys Pro Asn Val Val Met Gly His
    1175                1180                1185

Ser Val Gly Glu Tyr Val Ala Ala Thr Val Ala Gly Val Phe Ser
    1190                1195                1200

Leu Glu Asp Gly Leu Lys Leu Ile Ala Ala Arg Gly Arg Leu Met
    1205                1210                1215

Gln Gly Leu Pro Ala Gly Gly Glu Met Val Ser Val Met Ala Ser
    1220                1225                1230

Glu Ser Lys Val Leu Glu Thr Leu Lys Ala Met Ser Leu Glu Asp
    1235                1240                1245

Lys Val Ala Ile Ala Ala Ile Asn Gly Pro Glu Ser Ile Val Ile
    1250                1255                1260

Ser Gly Glu Ala Glu Ala Ile Arg Ala Met Ala Thr His Leu Glu
    1265                1270                1275

Ser Val Gly Ile Lys Thr Lys Gln Leu Gln Val Ser His Ala Phe
    1280                1285                1290

His Ser Pro Leu Met Glu Pro Met Leu Ala Glu Phe Glu Ala Val
    1295                1300                1305

-continued

```
Ala Asn Gln Ile Thr Tyr His Gln Pro Arg Ile Pro Ile Ile Ser
1310                1315                1320

Asn Val Thr Gly Thr Lys Ala Asp Lys Ser Ile Ala Thr Ala Gln
1325                1330                1335

Tyr Trp Val Asn His Val Arg Gln Pro Val Arg Phe Ala Gln Gly
1340                1345                1350

Met Ala Thr Leu His Gln Gln Gly Tyr Glu Thr Phe Leu Glu Ile
1355                1360                1365

Gly Ala Lys Pro Ile Leu Leu Gly Met Gly Lys Gln Cys Leu Ser
1370                1375                1380

Pro Asp Val Gly Val Trp Leu Pro Ser Leu Arg His Gly Val Asp
1385                1390                1395

Glu Trp Gln Gln Ile Leu Ser Ser Leu Gly Gln Leu Tyr Val Gln
1400                1405                1410

Gly Ala Lys Val Asp Trp Ser Gly Phe Asp Arg Asp Tyr Ser Arg
1415                1420                1425

Glu Lys Val Val Leu Pro Thr Tyr Pro Phe Gln Arg Glu Arg Tyr
1430                1435                1440

Trp Val Glu Thr Ser Ile Asn Gln Gln Gln Val Val Cys Ser Gly
1445                1450                1455

Glu Pro Asn Leu Gln Gly Thr Pro Glu Gly Thr Ser Thr Thr Ile
1460                1465                1470

Val Lys Leu Leu Ser Gln Gly Asn Thr Lys Glu Leu Ala Glu Lys
1475                1480                1485

Val Glu Lys Thr Ser Asp Leu Pro Pro Glu Gln Leu Lys Leu Leu
1490                1495                1500

Pro Asp Leu Leu Ala Ser Leu Ser Gln Gln His Gln Gln Glu Leu
1505                1510                1515

Ala Arg Leu Thr Thr Lys Lys Trp Phe Tyr Lys Val Gln Trp Ile
1520                1525                1530

Ser Gln Ala Ile Lys Pro Gln Arg Asn Lys Ser Asn Asn Gln Val
1535                1540                1545

Cys His Trp Leu Ile Leu Thr Asp Ser Lys Gly Leu Gly Lys Ser
1550                1555                1560

Leu Ala Thr His Leu Gln Gln Leu Gly Asn Glu Cys Ser Val Val
1565                1570                1575

Tyr Gln Ala Asp Asn Tyr Gln Asn Tyr Glu Pro Gly Ile Tyr His
1580                1585                1590

Ile Asn Pro Ser His Pro Gln Glu Phe Glu Gln Val Tyr Gln Thr
1595                1600                1605

Ile Phe Glu Asn Gly Lys Leu Pro Leu Gln Lys Val Ile His Leu
1610                1615                1620

Trp Ser Leu Asp Thr Ala Ser Glu Gln Asp Leu Thr Thr Glu Thr
1625                1630                1635

Leu Glu Gln Ala Gln Leu Trp Gly Cys Gly Ser Thr Leu His Leu
1640                1645                1650

Leu Gln Thr Leu Val Lys Asn Pro Asn Ser Thr Pro Pro Lys Leu
1655                1660                1665

Trp Met Ile Thr Arg Gly Thr Gln Pro Val Leu Ser Pro Thr Glu
1670                1675                1680

Lys Leu Thr Val Ala Thr Ser Pro Leu Trp Gly Leu Gly Arg Thr
1685                1690                1695

Ile Ala Ser Glu His Pro Gln Leu Trp Gly Gly Leu Val Asp Leu
```

-continued

```
            1700                1705                1710

Asp Pro Gln Gly Ser Glu Asp Glu Val Glu Val Leu Leu Gln Gln
    1715                1720                1725

Ile Ile Asp Ser Gln Lys Glu Asp His Leu Ala Val Arg Asn Arg
    1730                1735                1740

Lys Ile Tyr Val Ala Arg Leu Leu Lys His Ile Pro Gln Glu Ser
    1745                1750                1755

Gln Pro Leu Ser Leu Arg Ser Asp Ala Thr Tyr Leu Ile Thr Gly
    1760                1765                1770

Gly Leu Gly Ala Leu Gly Leu Lys Thr Ala Ala Trp Met Ala Glu
    1775                1780                1785

Lys Gly Ala Arg Asn Leu Val Leu Ile Ser Arg Arg Gln Pro Ser
    1790                1795                1800

Glu Gln Ala Gln Gln Thr Ile Gln Ser Leu Glu Glu Leu Gly Thr
    1805                1810                1815

Gln Val Lys Val Leu Ser Ala Asp Ile Ser Val Glu Ser Asp Val
    1820                1825                1830

Ala Asn Ile Leu Glu Gln Ile Gln Thr Ser Leu Pro Pro Leu Leu
    1835                1840                1845

Gly Val Ile His Ala Ala Gly Val Leu Asp Asp Gly Leu Leu Gln
    1850                1855                1860

Gln Thr Asn Trp Glu Arg Phe Thr Lys Val Met Ala Pro Lys Val
    1865                1870                1875

Asn Gly Thr Trp Asn Leu His Lys Leu Thr Gln His Leu Ser Leu
    1880                1885                1890

Asp Phe Phe Val Cys Phe Ser Ser Met Ser Ser Leu Leu Gly Ser
    1895                1900                1905

Pro Gly Gln Gly Asn Tyr Ala Ala Ala Asn Ala Phe Met Asp Ala
    1910                1915                1920

Val Val His Tyr Arg Arg Glu Met Gly Leu Pro Gly Leu Ser Ile
    1925                1930                1935

Asn Trp Gly Gly Trp Ser Glu Gly Gly Met Ala Thr Arg Leu Ala
    1940                1945                1950

Ser Gln His Gln Asn Arg Met Gln Thr Ala Gly Ile Ser Leu Ile
    1955                1960                1965

Ser Pro Glu Gln Gly Ile Gln Val Leu Glu Glu Leu Val Arg Thr
    1970                1975                1980

Gln Ser Thr Ala Gln Val Gly Val Leu Pro Val Asp Trp Ser Val
    1985                1990                1995

Leu Ala Lys Gln Phe Ser Ser Ala Asn Pro Ser Ser Leu Leu Leu
    2000                2005                2010

Glu Leu Gln Gln Glu Thr Ser Ser Glu Lys Thr Asp Glu Arg
    2015                2020                2025

Ile Leu Glu Lys Leu Gln Ala Ala Pro Ile Thr Glu Arg Gln Asp
    2030                2035                2040

Ile Leu Lys Asn Tyr Ile Gln Leu Val Val Ala Lys Thr Leu Gly
    2045                2050                2055

Ile Asn Pro Ser Lys Ile Ser Thr Asp Asp Asn Phe Val Glu Leu
    2060                2065                2070

Gly Met Asp Ser Leu Met Gly Met Glu Val Val Asn Lys Leu Ser
    2075                2080                2085

Gly Asp Leu Asp Phe Ile Ile Tyr Pro Arg Glu Phe Tyr Glu Arg
    2090                2095                2100
```

-continued

```
Pro Thr Ile Asp Ser Leu Thr Gln Tyr Leu Ser Ala Glu Leu Ser
2105                2110                2115

Glu Asp Asn Leu Ala Thr Gln Pro Ser Pro Thr Ser Leu Glu Ile
2120                2125                2130

Phe Ala Thr Lys Ser Ser Pro Ser Gly Asn Ser Ala Arg Pro Ala
2135                2140                2145

Ser Val Ser Ser Arg Leu Pro Gly Ile Ile Phe Ile Leu Ser Ser
2150                2155                2160

Pro Arg Ser Gly Ser Thr Leu Leu Arg Val Met Leu Ala Gly His
2165                2170                2175

Ser Ser Leu Phe Ser Pro Pro Glu Leu His Leu Leu Pro Phe Asn
2180                2185                2190

Thr Met Lys Glu Arg Gln Glu Gln Leu Asn Leu Ser Tyr Leu Gly
2195                2200                2205

Glu Gly Leu Gln Lys Thr Phe Met Glu Val Lys Asn Leu Asp Ala
2210                2215                2220

Thr Ala Ser Gln Ala Leu Ile Lys Asp Leu Glu Ser Gln Asn Leu
2225                2230                2235

Ser Ile Gln Gln Val Tyr Gly Met Leu Gln Glu Asn Ile Ala Pro
2240                2245                2250

Arg Leu Leu Val Asp Lys Ser Pro Thr Tyr Ala Met Glu Pro Thr
2255                2260                2265

Ile Leu Glu Arg Gly Glu Ala Leu Phe Ala Asn Ser Lys Tyr Ile
2270                2275                2280

Tyr Leu Val Arg His Pro Tyr Ser Val Ile Glu Ser Phe Val Arg
2285                2290                2295

Met Arg Met Gln Lys Leu Val Gly Leu Gly Glu Glu Asn Pro Tyr
2300                2305                2310

Arg Val Ala Glu Gln Val Trp Ala Lys Ser Asn Gln Asn Ile Leu
2315                2320                2325

Asn Phe Leu Ser Gln Leu Glu Pro Glu Arg Gln His Gln Ile Arg
2330                2335                2340

Tyr Glu Asp Leu Val Lys Lys Pro Gln Gln Val Leu Ser Gln Leu
2345                2350                2355

Cys Asp Phe Leu Asn Val Pro Phe Glu Pro Glu Leu Leu Gln Pro
2360                2365                2370

Tyr Gln Gly Asp Arg Met Thr Gly Gly Val His Gln Lys Ser Leu
2375                2380                2385

Ser Ile Ser Asp Pro Asn Phe Leu Lys His Asn Thr Ile Asp Glu
2390                2395                2400

Ser Leu Ala Asp Lys Trp Lys Thr Ile Gln Leu Pro Tyr Pro Leu
2405                2410                2415

Lys Ser Glu Thr Gln Arg Ile Ala Ser Gln Leu Ser Tyr Glu Leu
2420                2425                2430

Pro Asn Leu Val Thr Thr Pro Thr Asn Gln Gln Pro Gln Val Ser
2435                2440                2445

Thr Thr Pro Ser Thr Glu Gln Pro Ile Met Glu Glu Lys Phe Leu
2450                2455                2460

Glu Phe Gly Gly Asn Gln Ile Cys Leu Cys Ser Trp Gly Ser Pro
2465                2470                2475

Glu His Pro Val Val Leu Cys Ile His Gly Ile Leu Glu Gln Gly
2480                2485                2490
```

-continued

```
Leu Ala Trp Gln Glu Val Ala Leu Pro Leu Ala Ala Gln Gly Tyr
    2495                2500                2505

Arg Val Val Ala Pro Asp Leu Phe Gly His Gly Arg Ser Ser His
    2510                2515                2520

Leu Glu Met Val Thr Ser Tyr Ser Ser Leu Thr Phe Leu Ala Gln
    2525                2530                2535

Ile Asp Arg Val Ile Gln Glu Leu Pro Asp Gln Pro Leu Leu Leu
    2540                2545                2550

Val Gly His Ser Met Gly Ala Met Leu Ala Thr Ala Ile Ala Ser
    2555                2560                2565

Val Arg Pro Lys Lys Ile Lys Glu Leu Ile Leu Val Glu Leu Pro
    2570                2575                2580

Leu Pro Ala Glu Glu Ser Lys Lys Glu Ser Ala Val Asn Gln Leu
    2585                2590                2595

Thr Thr Cys Leu Asp Tyr Leu Ser Ser Thr Pro Gln His Pro Ile
    2600                2605                2610

Phe Pro Asp Val Ala Thr Ala Ala Ser Arg Leu Arg Gln Ala Ile
    2615                2620                2625

Pro Ser Leu Ser Glu Glu Phe Ser Tyr Ile Leu Ala Gln Arg Ile
    2630                2635                2640

Thr Gln Pro Asn Gln Gly Gly Val Arg Trp Ser Trp Asp Ala Ile
    2645                2650                2655

Ile Arg Thr Arg Ser Ile Leu Gly Leu Asn Asn Leu Pro Gly Gly
    2660                2665                2670

Arg Ser Gln Tyr Leu Glu Met Leu Lys Ser Ile Gln Val Pro Thr
    2675                2680                2685

Thr Leu Val Tyr Gly Asp Ser Ser Lys Leu Asn Arg Pro Glu Asp
    2690                2695                2700

Leu Gln Gln Gln Lys Met Thr Met Thr Gln Ala Lys Arg Val Phe
    2705                2710                2715

Leu Ser Gly Gly His Asn Leu His Ile Asp Ala Ala Ala Ala Leu
    2720                2725                2730

Ala Ser Leu Ile Leu Thr Ser
    2735                2740

<210> SEQ ID NO 6
<211> LENGTH: 3191
<212> TYPE: PRT
<213> ORGANISM: Artificial sequence
<220> FEATURE:
<223> OTHER INFORMATION: Hybrid polyketide synthase capable of producing
      propene

<400> SEQUENCE: 6

Met Ala Gly His Gly Asp Ala Thr Ala Gln Lys Ala Gln Asp Ala Glu
1               5                   10                  15

Lys Ser Glu Asp Gly Ser Asp Ala Ile Ala Val Ile Gly Met Ser Cys
                20                  25                  30

Arg Phe Pro Gly Ala Pro Gly Thr Ala Glu Phe Trp Gln Leu Leu Ser
        35                  40                  45

Ser Gly Ala Asp Ala Val Val Thr Ala Ala Asp Gly Arg Arg Arg Gly
    50                  55                  60

Thr Ile Asp Ala Pro Ala Asp Phe Asp Ala Ala Phe Phe Gly Met Ser
65                  70                  75                  80

Pro Arg Glu Ala Ala Ala Thr Asp Pro Gln Gln Arg Leu Val Leu Glu
                85                  90                  95
```

```
Leu Gly Trp Glu Ala Leu Glu Asp Ala Gly Ile Val Pro Glu Ser Leu
            100                 105                 110

Arg Gly Glu Ala Ala Ser Val Phe Val Gly Ala Met Asn Asp Asp Tyr
            115                 120                 125

Ala Thr Leu Leu His Arg Ala Gly Ala Pro Thr Asp Thr Tyr Thr Ala
            130                 135                 140

Thr Gly Leu Gln His Ser Met Ile Ala Asn Arg Leu Ser Tyr Phe Leu
145                 150                 155                 160

Gly Leu Arg Gly Pro Ser Leu Val Val Asp Thr Gly Gln Ser Ser Ser
            165                 170                 175

Leu Val Ala Val Ala Leu Ala Val Glu Ser Leu Arg Gly Gly Thr Ser
            180                 185                 190

Gly Ile Ala Leu Ala Gly Gly Val Asn Leu Val Leu Ala Glu Glu Gly
            195                 200                 205

Ser Ala Ala Met Glu Arg Val Gly Ala Leu Ser Pro Asp Gly Arg Cys
            210                 215                 220

His Thr Phe Asp Ala Arg Ala Asn Gly Tyr Val Arg Gly Glu Gly Gly
225                 230                 235                 240

Ala Ile Val Val Leu Lys Pro Leu Ala Asp Ala Leu Ala Asp Gly Asp
            245                 250                 255

Arg Val Tyr Cys Val Val Arg Gly Val Ala Thr Gly Asn Asp Gly Gly
            260                 265                 270

Gly Pro Gly Leu Thr Val Pro Asp Arg Ala Gly Gln Glu Ala Val Leu
            275                 280                 285

Arg Ala Ala Cys Asp Gln Ala Gly Val Arg Pro Ala Asp Val Arg Phe
            290                 295                 300

Val Glu Leu His Gly Thr Gly Thr Pro Ala Gly Asp Pro Val Glu Ala
305                 310                 315                 320

Glu Ala Leu Gly Ala Val Tyr Gly Thr Gly Arg Pro Ala Asn Glu Pro
            325                 330                 335

Leu Leu Val Gly Ser Val Lys Thr Asn Ile Gly His Leu Glu Gly Ala
            340                 345                 350

Ala Gly Ile Ala Gly Phe Val Lys Ala Ala Leu Cys Leu His Glu Arg
            355                 360                 365

Ala Leu Pro Ala Ser Leu Asn Phe Glu Thr Pro Asn Pro Ala Ile Pro
            370                 375                 380

Leu Glu Arg Leu Arg Leu Lys Val Gln Thr Ala His Ala Ala Leu Gln
385                 390                 395                 400

Pro Gly Thr Gly Gly Pro Leu Leu Ala Gly Val Ser Ala Phe Gly
            405                 410                 415

Met Gly Gly Thr Asn Cys His Val Val Leu Glu Glu Thr Pro Gly Gly
            420                 425                 430

Arg Gln Pro Ala Glu Thr Gly Gln Ala Asp Ala Cys Leu Phe Ser Ala
            435                 440                 445

Ser Pro Met Leu Leu Leu Ser Ala Arg Ser Glu Gln Ala Leu Arg Ala
            450                 455                 460

Gln Ala Ala Arg Leu Arg Glu His Leu Glu Asp Ser Gly Ala Asp Pro
465                 470                 475                 480

Leu Asp Ile Ala Tyr Ser Leu Ala Thr Thr Arg Thr Arg Phe Glu His
            485                 490                 495

Arg Ala Ala Val Pro Cys Gly Asp Pro Asp Arg Leu Ser Ser Ala Leu
            500                 505                 510
```

```
Ala Ala Leu Ala Ala Gly Gln Thr Pro Arg Gly Val Arg Ile Gly Ser
            515                 520                 525

Thr Asp Ala Asp Gly Arg Leu Ala Leu Leu Phe Thr Gly Gln Gly Ala
530                 535                 540

Gln His Pro Gly Met Gly Gln Glu Leu Tyr Thr Thr Asp Pro His Phe
545                 550                 555                 560

Ala Ala Ala Leu Asp Glu Val Cys Glu Glu Leu Gln Arg Cys Gly Thr
            565                 570                 575

Gln Asn Leu Arg Glu Val Met Phe Thr Pro Asp Gln Pro Asp Leu Leu
            580                 585                 590

Asp Arg Thr Glu Tyr Thr Gln Pro Ala Leu Phe Ala Leu Gln Thr Ala
            595                 600                 605

Leu Tyr Arg Thr Leu Thr Ala Arg Gly Thr Gln Ala His Leu Val Leu
            610                 615                 620

Gly His Ser Val Gly Glu Ile Thr Ala Ala His Ile Ala Gly Val Leu
625                 630                 635                 640

Asp Leu Pro Asp Ala Ala Arg Leu Ile Thr Ala Arg Ala His Val Met
            645                 650                 655

Gly Gln Leu Pro His Gly Gly Ala Met Leu Ser Val Gln Ala Ala Glu
            660                 665                 670

His Asp Leu Asp Gln Leu Ala His Thr His Gly Val Glu Ile Ala Ala
            675                 680                 685

Val Asn Gly Pro Thr His Cys Val Leu Ser Gly Pro Arg Thr Ala Leu
            690                 695                 700

Glu Glu Thr Ala Gln His Leu Arg Glu Gln Asn Val Arg His Thr Trp
705                 710                 715                 720

Leu Lys Val Ser His Ala Phe His Ser Ala Leu Met Asp Pro Met Leu
            725                 730                 735

Gly Ala Phe Arg Asp Thr Leu Asn Thr Leu Asn Tyr Gln Pro Pro Thr
            740                 745                 750

Ile Pro Leu Ile Ser Asn Leu Thr Gly Gln Ile Ala Asp Pro Asn His
            755                 760                 765

Leu Cys Thr Pro Asp Tyr Trp Ile Asp His Ala Arg His Thr Val Arg
            770                 775                 780

Phe Ala Asp Ala Val Gln Thr Ala His His Gln Gly Thr Thr Thr Tyr
785                 790                 795                 800

Leu Glu Ile Gly Pro His Pro Thr Leu Thr Thr Leu His His Thr
                805                 810                 815

Leu Asp Asn Pro Thr Thr Ile Pro Thr Leu His Arg Glu Arg Pro Glu
            820                 825                 830

Pro Glu Thr Leu Thr Gln Ala Ile Ala Ala Val Gly Val Arg Thr Asp
            835                 840                 845

Gly Ile Asp Trp Ala Val Leu Cys Gly Ala Ser Arg Pro Arg Arg Val
850                 855                 860

Glu Leu Pro Thr Tyr Ala Phe Gln Arg Arg Thr His Trp Ala Pro Gly
865                 870                 875                 880

Leu Thr Pro Asn His Ala Pro Ala Asp Arg Pro Ala Ala Glu Pro Gln
            885                 890                 895

Arg Ala Met Ala Val Gly Pro Val Ser Arg Glu Ala Leu Val Arg Leu
            900                 905                 910

Val Gly Glu Thr Thr Ala Ser Val Leu Gly Leu Asp Gly Pro Asp Glu
            915                 920                 925

Val Ala Leu Asp Arg Pro Phe Thr Ser Gln Gly Leu Asp Ser Met Thr
```

-continued

```
            930                 935                 940
Ala Val Glu Leu Ala Gly Leu Gly Thr Ala Ala Gly Val Ala Leu
945                 950                 955                 960

Asp Pro Thr Leu Val Tyr Glu Leu Pro Thr Pro Arg Ala Val Ala Asp
                965                 970                 975

His Leu Ala Lys Thr Leu Leu Gly Glu Ser Ala Ala Asp Ala Asp Gln
            980                 985                 990

Glu Val Asn Gly Arg Thr Gly Glu Ala Glu Ala Lys Ala Gly Asp Pro
        995                 1000                1005

Ile Ala Val Ile Gly Ile Gly Cys Arg Phe Pro Gly Gly Val Ala
    1010                1015                1020

Thr Pro Asp Asp Leu Trp Glu Leu Val Ala Ser Gly Thr Asp Ala
    1025                1030                1035

Ile Ser Thr Phe Pro Thr Asp Arg Gly Trp Asp Leu Asp Gly Leu
    1040                1045                1050

Tyr Asp Pro Asp Pro Ser Thr Pro Gly Lys Ser Tyr Val Arg His
    1055                1060                1065

Gly Gly Phe Leu His Asp Ala Ala Gln Phe Asp Ala Glu Phe Phe
    1070                1075                1080

Gly Ile Ser Pro Arg Glu Ala Thr Ala Met Asp Pro Gln Gln Arg
    1085                1090                1095

Leu Leu Leu Glu Thr Ser Trp Glu Ala Leu Glu Arg Ala Gly Val
    1100                1105                1110

Val Pro Glu Ser Leu Arg Gly Gly Arg Thr Gly Val Phe Val Gly
    1115                1120                1125

Thr Thr Ala Pro Glu Tyr Gly Pro Arg Leu His Glu Gly Thr Asp
    1130                1135                1140

Gly Tyr Glu Gly Phe Leu Leu Thr Gly Thr Thr Ala Ser Val Ala
    1145                1150                1155

Ser Gly Arg Ile Ala Tyr Ala Leu Gly Thr Arg Gly Pro Ala Leu
    1160                1165                1170

Thr Val Asp Thr Ala Cys Ser Ser Ser Leu Val Ala Leu His Leu
    1175                1180                1185

Ala Val Gln Ser Leu Arg Arg Gly Glu Cys Asp Leu Ala Leu Ala
    1190                1195                1200

Gly Gly Thr Thr Val Met Ser Gly Pro Gly Met Phe Val Glu Phe
    1205                1210                1215

Ser Arg Gln Arg Gly Leu Ala Pro Asp Gly Arg Cys Lys Ala Phe
    1220                1225                1230

Ser Ala Asp Ala Asp Gly Thr Ala Trp Ala Glu Gly Val Gly Met
    1235                1240                1245

Leu Leu Val Glu Arg Leu Ser Asp Ala Glu Arg Leu Gly His Arg
    1250                1255                1260

Val Leu Ala Val Val Arg Gly Thr Ala Val Asn Gln Asp Gly Ala
    1265                1270                1275

Ser Asn Gly Leu Thr Ala Pro Ser Gly Pro Ala Gln Gln Gln Val
    1280                1285                1290

Ile Arg Asp Ala Leu Ser Asp Ala Gly Leu Ser Ala Asp Asp Ile
    1295                1300                1305

Asp Ala Val Glu Ala His Gly Thr Gly Thr Ala Leu Gly Asp Pro
    1310                1315                1320

Ile Glu Ala Gly Ala Leu Leu Ala Thr Tyr Gly His Pro Lys Arg
    1325                1330                1335
```

```
Gln Thr Pro Val Trp Leu Gly Ser Leu Lys Ser Asn Ile Gly His
    1340            1345                1350

Thr Gln Ala Ala Ala Gly Ile Ala Gly Ile Ile Lys Met Val Gln
    1355            1360                1365

Ala Leu Arg His Asp Thr Leu Pro Arg Thr Leu His Ala Asp His
    1370            1375                1380

Pro Ser Ser Lys Val Asp Trp Asp Ala Gly Pro Leu Gln Leu Leu
    1385            1390                1395

Thr Asp Ala Arg Pro Trp Pro Ala Asp Pro Asp Arg Pro Arg Arg
    1400            1405                1410

Ala Gly Ile Ser Ala Phe Gly Val Ser Gly Thr Asn Ala His Val
    1415            1420                1425

Val Leu Glu Glu Pro Pro Glu Leu Ile Lys Gly Gln Lys Ala Lys
    1430            1435                1440

Gly Lys Ser Glu Asn Asp Leu Glu Arg Pro Leu His Ile Leu Thr
    1445            1450                1455

Leu Ser Thr Lys Thr Glu Lys Ala Leu Glu Glu Leu Val Ser Arg
    1460            1465                1470

Tyr Gln Asn His Trp Glu Thr Tyr Pro Glu Leu Ala Ile Ser Asp
    1475            1480                1485

Val Cys Tyr Thr Ala Asn Thr Gly Arg Ala Gln Phe Asn His Arg
    1490            1495                1500

Leu Ala Val Ile Ala Ser Gly Ser Glu Glu Leu Thr Gln Lys Leu
    1505            1510                1515

Arg Gln His Thr Ala Gly Glu Val Val Gly Val Phe Ser Gly
    1520            1525                1530

Lys Val Pro Asn Ser Gly Ser Glu Ser Lys Val Ala Phe Leu Phe
    1535            1540                1545

Thr Gly Gln Gly Ser Gln Tyr Leu Asn Met Gly Arg Gln Leu Tyr
    1550            1555                1560

Glu Thr Gln Pro Thr Phe Arg Gln Ala Leu Asp Thr Cys Asp His
    1565            1570                1575

Ile Leu Arg Pro Tyr Leu Asp Asn Pro Leu Leu Glu Ile Leu Tyr
    1580            1585                1590

Pro Gln Asp Ala Gln Lys Ser Asn Asp Ser Pro Leu Asp Gln Thr
    1595            1600                1605

Gly Tyr Thr Gln Pro Ala Leu Phe Ser Ile Glu Tyr Ala Leu Leu
    1610            1615                1620

Lys Leu Trp Glu Ser Trp Gly Ile Lys Pro Asn Val Val Met Gly
    1625            1630                1635

His Ser Val Gly Glu Tyr Val Ala Ala Thr Val Ala Gly Val Phe
    1640            1645                1650

Ser Leu Glu Asp Gly Leu Lys Leu Ile Ala Ala Arg Gly Arg Leu
    1655            1660                1665

Met Gln Gly Leu Pro Ala Gly Gly Glu Met Val Ser Val Met Ala
    1670            1675                1680

Ser Glu Ser Lys Val Leu Glu Thr Leu Lys Ala Met Ser Leu Glu
    1685            1690                1695

Asp Lys Val Ala Ile Ala Ala Ile Asn Gly Pro Glu Ser Ile Val
    1700            1705                1710

Ile Ser Gly Glu Ala Glu Ala Ile Arg Ala Met Ala Thr His Leu
    1715            1720                1725
```

```
Glu Ser Val Gly Ile Lys Thr Lys Gln Leu Gln Val Ser His Ala
    1730                1735                1740

Phe His Ser Pro Leu Met Glu Pro Met Leu Ala Glu Phe Glu Ala
    1745                1750                1755

Val Ala Asn Gln Ile Thr Tyr His Gln Pro Arg Ile Pro Ile Ile
    1760                1765                1770

Ser Asn Val Thr Gly Thr Lys Ala Asp Lys Ser Ile Ala Thr Ala
    1775                1780                1785

Gln Tyr Trp Val Asn His Val Arg Gln Pro Val Arg Phe Ala Gln
    1790                1795                1800

Gly Met Ala Thr Leu His Gln Gln Gly Tyr Glu Thr Phe Leu Glu
    1805                1810                1815

Ile Gly Ala Lys Pro Ile Leu Leu Gly Met Gly Lys Gln Cys Leu
    1820                1825                1830

Ser Pro Asp Val Gly Val Trp Leu Pro Ser Leu Arg His Gly Val
    1835                1840                1845

Asp Glu Trp Gln Gln Ile Leu Ser Ser Leu Gly Gln Leu Tyr Val
    1850                1855                1860

Gln Gly Ala Lys Val Asp Trp Ser Gly Phe Asp Arg Asp Tyr Ser
    1865                1870                1875

Arg Glu Lys Val Val Leu Pro Thr Tyr Pro Phe Gln Arg Glu Arg
    1880                1885                1890

Tyr Trp Val Glu Thr Ser Ile Asn Gln Gln Gln Val Val Cys Ser
    1895                1900                1905

Gly Glu Pro Asn Leu Gln Gly Thr Pro Glu Gly Thr Ser Thr Thr
    1910                1915                1920

Ile Val Lys Leu Leu Ser Gln Gly Asn Thr Lys Glu Leu Ala Glu
    1925                1930                1935

Lys Val Glu Lys Thr Ser Asp Leu Pro Pro Glu Gln Leu Lys Leu
    1940                1945                1950

Leu Pro Asp Leu Leu Ala Ser Leu Ser Gln Gln His Gln Gln Glu
    1955                1960                1965

Leu Ala Arg Leu Thr Thr Lys Lys Trp Phe Tyr Lys Val Gln Trp
    1970                1975                1980

Ile Ser Gln Ala Ile Lys Pro Gln Arg Asn Lys Ser Asn Asn Gln
    1985                1990                1995

Val Cys His Trp Leu Ile Leu Thr Asp Ser Lys Gly Leu Gly Lys
    2000                2005                2010

Ser Leu Ala Thr His Leu Gln Gln Leu Gly Asn Glu Cys Ser Val
    2015                2020                2025

Val Tyr Gln Ala Asp Asn Tyr Gln Asn Tyr Glu Pro Gly Ile Tyr
    2030                2035                2040

His Ile Asn Pro Ser His Pro Gln Glu Phe Glu Gln Val Tyr Gln
    2045                2050                2055

Thr Ile Phe Glu Asn Gly Lys Leu Pro Leu Gln Lys Val Ile His
    2060                2065                2070

Leu Trp Ser Leu Asp Thr Ala Ser Glu Gln Asp Leu Thr Thr Glu
    2075                2080                2085

Thr Leu Glu Gln Ala Gln Leu Trp Gly Cys Gly Ser Thr Leu His
    2090                2095                2100

Leu Leu Gln Thr Leu Val Lys Asn Pro Asn Ser Thr Pro Pro Lys
    2105                2110                2115

Leu Trp Met Ile Thr Arg Gly Thr Gln Pro Val Leu Ser Pro Thr
```

```
                2120                2125                2130
Glu Lys Leu Thr Val Ala Thr Ser Pro Leu Trp Gly Leu Gly Arg
        2135                2140                2145
Thr Ile Ala Ser Glu His Pro Gln Leu Trp Gly Gly Leu Val Asp
        2150                2155                2160
Leu Asp Pro Gln Gly Ser Glu Asp Glu Val Glu Val Leu Leu Gln
        2165                2170                2175
Gln Ile Ile Asp Ser Gln Lys Glu Asp His Leu Ala Val Arg Asn
        2180                2185                2190
Arg Lys Ile Tyr Val Ala Arg Leu Leu Lys His Ile Pro Gln Glu
        2195                2200                2205
Ser Gln Pro Leu Ser Leu Arg Ser Asp Ala Thr Tyr Leu Ile Thr
        2210                2215                2220
Gly Gly Leu Gly Ala Leu Gly Leu Lys Thr Ala Ala Trp Met Ala
        2225                2230                2235
Glu Lys Gly Ala Arg Asn Leu Val Leu Ile Ser Arg Arg Gln Pro
        2240                2245                2250
Ser Glu Gln Ala Gln Gln Thr Ile Gln Ser Leu Glu Glu Leu Gly
        2255                2260                2265
Thr Gln Val Lys Val Leu Ser Ala Asp Ile Ser Val Glu Ser Asp
        2270                2275                2280
Val Ala Asn Ile Leu Glu Gln Ile Gln Thr Ser Leu Pro Pro Leu
        2285                2290                2295
Leu Gly Val Ile His Ala Ala Gly Val Leu Asp Asp Gly Leu Leu
        2300                2305                2310
Gln Gln Thr Asn Trp Glu Arg Phe Thr Lys Val Met Ala Pro Lys
        2315                2320                2325
Val Asn Gly Thr Trp Asn Leu His Lys Leu Thr Gln His Leu Ser
        2330                2335                2340
Leu Asp Phe Phe Val Cys Phe Ser Ser Met Ser Ser Leu Leu Gly
        2345                2350                2355
Ser Pro Gly Gln Gly Asn Tyr Ala Ala Ala Asn Ala Phe Met Asp
        2360                2365                2370
Ala Val Val His Tyr Arg Arg Glu Met Gly Leu Pro Gly Leu Ser
        2375                2380                2385
Ile Asn Trp Gly Gly Trp Ser Glu Gly Gly Met Ala Thr Arg Leu
        2390                2395                2400
Ala Ser Gln His Gln Asn Arg Met Gln Thr Ala Gly Ile Ser Leu
        2405                2410                2415
Ile Ser Pro Glu Gln Gly Ile Gln Val Leu Glu Glu Leu Val Arg
        2420                2425                2430
Thr Gln Ser Thr Ala Gln Val Gly Val Leu Pro Val Asp Trp Ser
        2435                2440                2445
Val Leu Ala Lys Gln Phe Ser Ser Ala Asn Pro Ser Ser Leu Leu
        2450                2455                2460
Leu Glu Leu Leu Gln Gln Glu Thr Ser Ser Glu Lys Thr Asp Glu
        2465                2470                2475
Arg Ile Leu Glu Lys Leu Gln Ala Ala Pro Ile Thr Glu Arg Gln
        2480                2485                2490
Asp Ile Leu Lys Asn Tyr Ile Gln Leu Val Val Ala Lys Thr Leu
        2495                2500                2505
Gly Ile Asn Pro Ser Lys Ile Ser Thr Asp Asp Asn Phe Val Glu
        2510                2515                2520
```

```
Leu Gly Met Asp Ser Leu Met Gly Met Glu Val Val Asn Lys Leu
        2525                2530                2535

Ser Gly Asp Leu Asp Phe Ile Ile Tyr Pro Arg Glu Phe Tyr Glu
        2540                2545                2550

Arg Pro Thr Ile Asp Ser Leu Thr Gln Tyr Leu Ser Ala Glu Leu
        2555                2560                2565

Ser Glu Asp Asn Leu Ala Thr Gln Pro Ser Pro Thr Ser Leu Glu
        2570                2575                2580

Ile Phe Ala Thr Lys Ser Ser Pro Ser Gly Asn Ser Ala Arg Pro
        2585                2590                2595

Ala Ser Val Ser Ser Arg Leu Pro Gly Ile Ile Phe Ile Leu Ser
        2600                2605                2610

Ser Pro Arg Ser Gly Ser Thr Leu Leu Arg Val Met Leu Ala Gly
        2615                2620                2625

His Ser Ser Leu Phe Ser Pro Pro Glu Leu His Leu Leu Pro Phe
        2630                2635                2640

Asn Thr Met Lys Glu Arg Gln Glu Gln Leu Asn Leu Ser Tyr Leu
        2645                2650                2655

Gly Glu Gly Leu Gln Lys Thr Phe Met Glu Val Lys Asn Leu Asp
        2660                2665                2670

Ala Thr Ala Ser Gln Ala Leu Ile Lys Asp Leu Glu Ser Gln Asn
        2675                2680                2685

Leu Ser Ile Gln Gln Val Tyr Gly Met Leu Gln Glu Asn Ile Ala
        2690                2695                2700

Pro Arg Leu Leu Val Asp Lys Ser Pro Thr Tyr Ala Met Glu Pro
        2705                2710                2715

Thr Ile Leu Glu Arg Gly Glu Ala Leu Phe Ala Asn Ser Lys Tyr
        2720                2725                2730

Ile Tyr Leu Val Arg His Pro Tyr Ser Val Ile Glu Ser Phe Val
        2735                2740                2745

Arg Met Arg Met Gln Lys Leu Val Gly Leu Gly Glu Glu Asn Pro
        2750                2755                2760

Tyr Arg Val Ala Glu Gln Val Trp Ala Lys Ser Asn Gln Asn Ile
        2765                2770                2775

Leu Asn Phe Leu Ser Gln Leu Glu Pro Glu Arg Gln His Gln Ile
        2780                2785                2790

Arg Tyr Glu Asp Leu Val Lys Lys Pro Gln Gln Val Leu Ser Gln
        2795                2800                2805

Leu Cys Asp Phe Leu Asn Val Pro Phe Glu Pro Glu Leu Leu Gln
        2810                2815                2820

Pro Tyr Gln Gly Asp Arg Met Thr Gly Gly Val His Gln Lys Ser
        2825                2830                2835

Leu Ser Ile Ser Asp Pro Asn Phe Leu Lys His Asn Thr Ile Asp
        2840                2845                2850

Glu Ser Leu Ala Asp Lys Trp Lys Thr Ile Gln Leu Pro Tyr Pro
        2855                2860                2865

Leu Lys Ser Glu Thr Gln Arg Ile Ala Ser Gln Leu Ser Tyr Glu
        2870                2875                2880

Leu Pro Asn Leu Val Thr Thr Pro Thr Asn Gln Gln Pro Gln Val
        2885                2890                2895

Ser Thr Thr Pro Ser Thr Glu Gln Pro Ile Met Glu Glu Lys Phe
        2900                2905                2910
```

Leu Glu Phe Gly Gly Asn Gln Ile Cys Leu Cys Ser Trp Gly Ser
    2915                2920                2925

Pro Glu His Pro Val Val Leu Cys Ile His Gly Ile Leu Glu Gln
    2930                2935                2940

Gly Leu Ala Trp Gln Glu Val Ala Leu Pro Leu Ala Ala Gln Gly
    2945                2950                2955

Tyr Arg Val Val Ala Pro Asp Leu Phe Gly His Gly Arg Ser Ser
    2960                2965                2970

His Leu Glu Met Val Thr Ser Tyr Ser Ser Leu Thr Phe Leu Ala
    2975                2980                2985

Gln Ile Asp Arg Val Ile Gln Glu Leu Pro Asp Gln Pro Leu Leu
    2990                2995                3000

Leu Val Gly His Ser Met Gly Ala Met Leu Ala Thr Ala Ile Ala
    3005                3010                3015

Ser Val Arg Pro Lys Lys Ile Lys Glu Leu Ile Leu Val Glu Leu
    3020                3025                3030

Pro Leu Pro Ala Glu Glu Ser Lys Lys Glu Ser Ala Val Asn Gln
    3035                3040                3045

Leu Thr Thr Cys Leu Asp Tyr Leu Ser Ser Thr Pro Gln His Pro
    3050                3055                3060

Ile Phe Pro Asp Val Ala Thr Ala Ala Ser Arg Leu Arg Gln Ala
    3065                3070                3075

Ile Pro Ser Leu Ser Glu Glu Phe Ser Tyr Ile Leu Ala Gln Arg
    3080                3085                3090

Ile Thr Gln Pro Asn Gln Gly Gly Val Arg Trp Ser Trp Asp Ala
    3095                3100                3105

Ile Ile Arg Thr Arg Ser Ile Leu Gly Leu Asn Asn Leu Pro Gly
    3110                3115                3120

Gly Arg Ser Gln Tyr Leu Glu Met Leu Lys Ser Ile Gln Val Pro
    3125                3130                3135

Thr Thr Leu Val Tyr Gly Asp Ser Ser Lys Leu Asn Arg Pro Glu
    3140                3145                3150

Asp Leu Gln Gln Gln Lys Met Thr Met Thr Gln Ala Lys Arg Val
    3155                3160                3165

Phe Leu Ser Gly Gly His Asn Leu His Ile Asp Ala Ala Ala Ala
    3170                3175                3180

Leu Ala Ser Leu Ile Leu Thr Ser
    3185                3190

<210> SEQ ID NO 7
<211> LENGTH: 2688
<212> TYPE: PRT
<213> ORGANISM: Artificial sequence
<220> FEATURE:
<223> OTHER INFORMATION: Hybrid polyketide synthase capable of producing
      styrene

<400> SEQUENCE: 7

Met Thr Lys Glu Tyr Thr Arg Pro Gln Ser Ala Pro Leu Thr Glu Gly
1               5                   10                  15

Asp Leu Leu Thr Leu Ile Val Ala His Leu Ala Glu Arg Leu Arg Met
                20                  25                  30

Asp Ala Arg Phe Ile Asp Val His Glu Pro Phe Ser Arg His Gly Leu
            35                  40                  45

Asp Ser Arg Gly Ala Val Asp Leu Val Val Asp Leu Arg Thr Ala Leu
        50                  55                  60

```
Gly Arg Pro Leu Ser Pro Val Val Trp Gln His Pro Thr Pro Asp
 65                  70                  75                  80

Ala Leu Ala Arg His Leu Ala Gly Gly Ala Asp Ala Arg Glu Gly Gln
                 85                  90                  95

Ala Arg Ala Asp Ser Ala Tyr Glu Arg Pro Gly Ala Pro Asn Glu Pro
                100                 105                 110

Ile Ala Ile Val Gly Met Ala Cys Arg Phe Pro Gly Ala Pro Asp Val
            115                 120                 125

Asp Ser Tyr Trp Arg Leu Leu Ser Gly Gly Val Asp Ala Val Thr Glu
        130                 135                 140

Val Pro Ala Gly Arg Trp Asp Met Asp Ala Phe Tyr Asp Arg Asp Pro
145                 150                 155                 160

Arg Ser Leu Gly Asp Val Ser Thr Leu Arg Gly Gly Phe Ile Asp Asp
                165                 170                 175

Val Asp Arg Phe Asp Ala Met Phe Phe Gly Ile Ser Pro Arg Glu Ala
                180                 185                 190

Val Ser Met Asp Pro Gln Gln Arg Leu Met Leu Glu Leu Ala Trp Glu
            195                 200                 205

Ala Leu Glu Asp Ala Gly Ile Val Ala Glu Arg Leu Lys Glu Ser Leu
        210                 215                 220

Thr Gly Val Phe Phe Gly Cys Ile Trp Asp Asp Tyr Val Thr Leu Ile
225                 230                 235                 240

His Gln Arg Gly Arg Gly Ala Ile Ala Gln His Thr Val Thr Gly Asn
                245                 250                 255

His Arg Ser Ile Ile Ala Asn Arg Val Ser Tyr Thr Leu Asp Leu Arg
            260                 265                 270

Gly Pro Ser Met Thr Val Asp Ser Ala Cys Ser Ser Ala Leu Val Thr
        275                 280                 285

Ile His Met Ala Cys Glu Ser Leu Arg Ser Gly Glu Ser Thr Leu Ala
    290                 295                 300

Leu Ala Gly Gly Val Asn Leu Asn Ile Ala Pro Glu Ser Thr Ile Gly
305                 310                 315                 320

Val His Lys Phe Gly Gly Leu Ser Pro Asp Gly Arg Cys Phe Thr Phe
                325                 330                 335

Asp Ala Arg Ala Asn Gly Tyr Val Arg Gly Glu Gly Gly Gly Val Val
            340                 345                 350

Val Leu Lys Arg Leu Ser Ser Ala Ile Ala Asp Gly Asp Pro Ile Ile
        355                 360                 365

Cys Val Ile Arg Gly Ser Ala Val Asn Asn Asp Gly Ala Ser Asn Gly
    370                 375                 380

Leu Thr Gly Pro Asn Pro Leu Ala Gln Glu Ala Val Leu Arg Thr Ala
385                 390                 395                 400

Tyr Glu Arg Ala Gly Val Asn Pro Ala Asp Val Gln Tyr Val Glu Leu
                405                 410                 415

His Gly Thr Gly Thr Gln Leu Gly Asp Pro Val Glu Ala Ser Ala Leu
            420                 425                 430

Gly Ala Val Leu Gly Lys Arg Arg Pro Ala Glu Arg Pro Leu Leu Val
        435                 440                 445

Gly Ser Ala Lys Thr Asn Val Gly His Leu Glu Gly Ala Ala Gly Ile
    450                 455                 460

Val Gly Leu Leu Lys Ala Ala Leu Cys Leu Lys His Lys Gln Leu Ala
465                 470                 475                 480
```

```
Pro Asn Leu Asn Phe Glu Thr Pro Asn Pro His Ile Pro Phe Ala Glu
            485                 490                 495

Leu Asn Leu Lys Val Gln Gly Ala Leu Gly Pro Trp Pro Asp Met Asp
        500                 505                 510

Arg Pro Leu Val Cys Gly Val Ser Ser Phe Gly Leu Gly Thr Asn
        515                 520                 525

Ala His Val Val Leu Ser Glu Trp Ala Ser Leu Glu Ala Glu Leu His
    530                 535                 540

Pro Leu Ala Ala Glu Ser Pro Glu Ala Leu Arg Glu Glu Val Gln Arg
545                 550                 555                 560

Arg Leu Leu Thr Met Thr Ser Leu Val Gly Arg Ala Pro Leu Ser Phe
                565                 570                 575

Leu Cys Gly Arg Ser Ala Ala Gln Arg Ser Ala Lys Glu His Arg Leu
            580                 585                 590

Ala Val Thr Ala Arg Ser Phe Glu Glu Leu Lys Gln Arg Leu Leu Gly
        595                 600                 605

Phe Leu Glu His Glu Lys His Val Ser Val Ser Ala Gly Arg Val Asp
    610                 615                 620

Leu Gly Ala Ala Pro Lys Val Val Phe Val Phe Ala Gly Gln Gly Ala
625                 630                 635                 640

Gln Trp Phe Gly Met Gly Arg Ala Leu Leu Gln Arg Glu Pro Val Phe
                645                 650                 655

Arg Thr Thr Ile Glu Gln Cys Ser Ser Phe Ile Gln Gln Asn Leu Gly
            660                 665                 670

Trp Ser Leu Leu Asp Glu Leu Met Thr Asp Arg Glu Ser Ser Arg Leu
        675                 680                 685

Asp Glu Ile Asp Val Ser Leu Pro Ala Ile Ile Ser Ile Glu Ile Ala
    690                 695                 700

Leu Ala Ala Gln Trp Arg Ala Trp Gly Val Glu Pro Ala Phe Val Val
705                 710                 715                 720

Gly His Ser Thr Gly Glu Ile Ala Ala His Val Ala Gly Val Leu
                725                 730                 735

Ser Ile Glu Asp Ala Met Arg Thr Ile Cys Ala Tyr Gly Arg Ile Ile
            740                 745                 750

Arg Lys Leu Arg Gly Lys Gly Met Gly Leu Val Ala Leu Ser Trp
        755                 760                 765

Glu Asp Ala Gly Lys Glu Leu Thr Gly Tyr Glu Gly Arg Leu Phe Arg
        770                 775                 780

Ala Ile Glu His Ser Ala Asp Ser Thr Val Leu Ala Gly Glu Pro Asp
785                 790                 795                 800

Ala Leu Asp Ala Leu Leu Gln Ala Leu Glu Arg Lys Asn Val Phe Cys
                805                 810                 815

Arg Arg Val Ala Met Asp Val Ala Pro His Cys Pro Gln Val Asp Cys
            820                 825                 830

Leu Arg Asp Glu Leu Phe Asp Ala Leu Arg Glu Val Arg Pro Asn Lys
        835                 840                 845

Ala Gln Ile Pro Ile Val Ser Glu Val Thr Gly Thr Ala Leu Asp Gly
    850                 855                 860

Glu Arg Phe Asp Ala Ser His Trp Val Arg Asn Phe Gly Asp Pro Ala
865                 870                 875                 880

Leu Phe Ser Thr Ala Ile Asp His Leu Leu Gln Glu Gly Phe Asp Ile
                885                 890                 895

Phe Leu Glu Leu Thr Pro His Pro Leu Ala Leu Pro Ala Ile Glu Ser
```

-continued

```
                900             905             910
Asn Leu Arg Arg Ser Gly Arg Arg Gly Val Val Leu Pro Ser Leu Arg
            915             920             925
Arg Asn Glu Asp Glu Arg Gly Val Met Leu Asp Thr Leu Gly Val Leu
        930             935             940
Tyr Val Arg Gly Ala Pro Val Arg Trp Asp Asn Val Tyr Pro Ala Ala
945             950             955             960
Phe Glu Ser Met Pro Leu Pro Ser Thr Ala Gly Gly Lys Pro Leu
                965             970             975
Pro Pro Met Pro Leu Leu Ile Ser Ala Arg Thr Asp Ala Ala Leu Ala
            980             985             990
Ala Gln Ala Ala Arg Leu Arg Ala His Leu Asp Ser His Leu Asp Leu
        995             1000            1005
Glu Leu Val Asp Val Ala Tyr Ser Leu Ala Ala Thr Arg Thr His
    1010            1015            1020
Phe Glu Arg Arg Ala Val Val Ala Arg Asp Arg Ala Gly Ile
    1025            1030            1035
Leu Asp Gly Leu Asp Ala Leu Ala His Gly Gly Ser Ala Ala Leu
    1040            1045            1050
Leu Gly Arg Ser Ala Ala His Gly Lys Leu Ala Ile Leu Phe Thr
    1055            1060            1065
Gly Gln Gly Ser Gln Arg Pro Thr Met Gly Arg Ala Leu Tyr Asp
    1070            1075            1080
Ala Phe Pro Val Phe Arg Gly Ala Leu Asp Ala Ala Ala Ala His
    1085            1090            1095
Leu Asp Arg Asp Leu Asp Arg Pro Leu Arg Asp Val Leu Phe Ala
    1100            1105            1110
Pro Asp Gly Ser Glu Gln Ala Ala Arg Leu Asp Gln Thr Ala Phe
    1115            1120            1125
Thr Gln Pro Ala Leu Phe Ala Leu Glu Val Ala Leu Phe Glu Leu
    1130            1135            1140
Leu Gln Ser Phe Gly Leu Lys Pro Ala Leu Leu Leu Gly His Ser
    1145            1150            1155
Ile Gly Glu Leu Val Ala Ala His Val Ala Gly Val Leu Ser Leu
    1160            1165            1170
Gln Asp Ala Cys Thr Leu Val Ala Ala Arg Ala Lys Leu Met Gln
    1175            1180            1185
Ala Leu Pro Gln Gly Gly Ala Met Val Thr Leu Gln Ala Ser Glu
    1190            1195            1200
Gln Glu Ala Arg Asp Leu Leu Gln Ala Ala Glu Gly Arg Val Ser
    1205            1210            1215
Leu Ala Ala Val Asn Gly His Leu Ser Thr Val Val Ala Gly Asp
    1220            1225            1230
Glu Asp Ala Val Leu Lys Ile Ala Arg Gln Val Glu Ala Leu Gly
    1235            1240            1245
Arg Lys Ala Thr Arg Leu Arg Val Ser His Ala Phe His Ser Pro
    1250            1255            1260
His Met Asp Gly Met Leu Asp Asp Phe Arg Arg Val Ala Gln Gly
    1265            1270            1275
Leu Thr Phe His Pro Ala Arg Ile Pro Ile Ile Ser Asn Val Thr
    1280            1285            1290
Gly Ala Arg Ala Thr Asp Gln Glu Leu Ala Ser Pro Glu Thr Trp
    1295            1300            1305
```

```
Val Arg His Val Arg Asp Thr Val Arg Phe Leu Asp Gly Val Arg
    1310            1315                1320

Thr Leu His Ala Glu Gly Ala Arg Ala Phe Leu Glu Leu Gly Pro
    1325            1330                1335

His Pro Val Leu Ser Ala Leu Ala Gln Asp Ala Leu Gly His Asp
    1340            1345                1350

Glu Gly Pro Ser Pro Cys Ala Phe Leu Pro Thr Leu Arg Lys Gly
    1355            1360                1365

Arg Asp Asp Ala Glu Ala Phe Thr Ala Ala Leu Gly Ala Leu His
    1370            1375                1380

Ala Ala Gly Leu Thr Pro Asp Trp Asn Ala Phe Phe Ala Pro Phe
    1385            1390                1395

Ala Pro Cys Lys Val Pro Leu Pro Thr Tyr Thr Phe Gln Arg Glu
    1400            1405                1410

Arg Phe Trp Leu Asp Ala Ser Thr Ala His Ala Ala Ser Ala Thr
    1415            1420                1425

Pro Ala Ala Ala Leu Glu Gly Arg Phe Trp Gln Ala Val Glu Ser
    1430            1435                1440

Gly Asp Ile Asp Thr Leu Ser Ser Glu Leu His Val Asp Gly Asp
    1445            1450                1455

Glu Gln Arg Ala Ala Leu Ala Leu Val Leu Pro Thr Leu Ser Ser
    1460            1465                1470

Phe Arg His Lys Arg Gln Glu Gln Ser Thr Val Asp Ala Trp Arg
    1475            1480                1485

Tyr Arg Val Thr Trp Lys Pro Leu Thr Thr Ala Ala Thr Pro Ala
    1490            1495                1500

Asp Leu Ala Gly Thr Trp Leu Leu Val Val Pro Ser Ala Leu Gly
    1505            1510                1515

Asp Asp Ala Leu Leu Ala Thr Leu Thr Glu Ala Leu Thr Arg Arg
    1520            1525                1530

Gly Ala Arg Val Leu Ala Leu Arg Val Ser Asp Ile His Ile Gly
    1535            1540                1545

Arg Ser Ala Leu Val Glu His Leu Arg Glu Ala Leu Ala Glu Thr
    1550            1555                1560

Ala Pro Leu Arg Gly Val Leu Ser Leu Leu Ala Leu Asp Glu His
    1565            1570                1575

Arg Leu Ala Asp Arg Ser Ala Leu Pro Ala Gly Leu Ala Leu Ser
    1580            1585                1590

Leu Ala Leu Val Gln Gly Leu Asp Asp Leu Ala Ile Glu Ala Pro
    1595            1600                1605

Leu Trp Leu Phe Thr Arg Gly Ala Val Ser Ile Gly His Ser Asp
    1610            1615                1620

Pro Ile Thr His Pro Thr Gln Ala Met Ile Trp Gly Leu Gly Arg
    1625            1630                1635

Val Val Gly Leu Glu His Pro Glu Arg Trp Gly Gly Leu Val Asp
    1640            1645                1650

Val Ser Ala Gly Val Asp Glu Ser Ala Val Gly Arg Leu Leu Pro
    1655            1660                1665

Ala Leu Ala Gln Arg His Asp Glu Asp Gln Leu Ala Leu Arg Pro
    1670            1675                1680

Ala Gly Leu Tyr Ala Arg Arg Ile Val Arg Ala Pro Leu Gly Asp
    1685            1690                1695
```

```
Ala Pro Pro Ala Arg Glu Phe Arg Pro Arg Gly Thr Ile Leu Ile
1700            1705                1710

Thr Gly Gly Thr Gly Ala Leu Gly Ala His Val Ala Arg Trp Leu
1715            1720                1725

Ala Arg Gln Gly Ala Glu His Leu Ile Leu Ile Ser Arg Arg Gly
1730            1735                1740

Ala Glu Ala Pro Gly Ala Ser Glu Leu His Ala Glu Leu Asn Ala
1745            1750                1755

Leu Gly Val Arg Thr Thr Leu Ala Ala Cys Asp Val Ala Asp Arg
1760            1765                1770

Ser Ala Leu Gln Ala Leu Leu Asp Ser Ile Pro Ser Asp Cys Pro
1775            1780                1785

Leu Thr Ala Val Phe His Thr Ala Gly Ala Arg Asp Asp Gly Leu
1790            1795                1800

Ile Gly Asp Met Thr Pro Glu Arg Ile Glu Arg Val Leu Ala Pro
1805            1810                1815

Lys Leu Asp Ser Ala Leu His Leu His Glu Leu Thr Lys Asn Ser
1820            1825                1830

Ala Leu Asp Ala Phe Val Leu Tyr Ala Ser Leu Ser Gly Val Leu
1835            1840                1845

Gly Asn Pro Gly Gln Ala Asn Tyr Ala Ala Ala Asn Ala Phe Leu
1850            1855                1860

Asp Ala Leu Ala Glu His Arg Arg Ser Leu Gly Leu Thr Ala Thr
1865            1870                1875

Ser Val Ala Trp Gly Gly Trp Gly Gly Gly Gly Met Ala Thr Glu
1880            1885                1890

Arg Val Ala Ala Gln Leu Gln Gln Arg Gly Leu Leu Gln Met Ala
1895            1900                1905

Pro Ser Leu Ala Leu Ala Ala Leu Ala Gln Ala Leu Gln Gln Asp
1910            1915                1920

Glu Thr Thr Ile Thr Val Ala Asp Ile Asp Trp Ser Arg Phe Ala
1925            1930                1935

Pro Ala Phe Ser Val Ala Arg Gln Arg Pro Leu Leu Arg Asp Leu
1940            1945                1950

Pro Glu Ala Gln Arg Ala Leu Gln Ala Ser Glu Gly Ala Ser Ser
1955            1960                1965

Glu His Gly Pro Ala Thr Gly Leu Leu Asp Glu Leu Arg Ser Arg
1970            1975                1980

Ser Glu Ser Glu Gln Leu Asp Leu Leu Ala Thr Leu Val Arg Gly
1985            1990                1995

Glu Thr Ala Thr Val Leu Gly His Ala Glu Ala Ser His Val Asp
2000            2005                2010

Pro Asp Lys Gly Phe Met Asp Leu Gly Leu Asp Ser Leu Met Thr
2015            2020                2025

Val Glu Leu Arg Arg Arg Leu Gln Lys Ala Thr Gly Val Lys Leu
2030            2035                2040

Pro Pro Thr Leu Ala Phe Asp His Pro Ser Pro His Arg Val Ala
2045            2050                2055

Phe Phe Leu Arg Asp Ser Leu Ser Glu Asp Asn Leu Ala Thr Gln
2060            2065                2070

Pro Ser Pro Thr Ser Leu Glu Ile Phe Ala Thr Lys Ser Ser Pro
2075            2080                2085

Ser Gly Asn Ser Ala Arg Pro Ala Ser Val Ser Ser Arg Leu Pro
```

-continued

```
                2090                2095                2100
Gly Ile Ile Phe Ile Leu Ser Ser Pro Arg Ser Gly Ser Thr Leu
            2105                2110                2115
Leu Arg Val Met Leu Ala Gly His Ser Ser Leu Phe Ser Pro Pro
            2120                2125                2130
Glu Leu His Leu Leu Pro Phe Asn Thr Met Lys Glu Arg Gln Glu
            2135                2140                2145
Gln Leu Asn Leu Ser Tyr Leu Gly Glu Gly Leu Gln Lys Thr Phe
            2150                2155                2160
Met Glu Val Lys Asn Leu Asp Ala Thr Ala Ser Gln Ala Leu Ile
            2165                2170                2175
Lys Asp Leu Glu Ser Gln Asn Leu Ser Ile Gln Gln Val Tyr Gly
            2180                2185                2190
Met Leu Gln Glu Asn Ile Ala Pro Arg Leu Leu Val Asp Lys Ser
            2195                2200                2205
Pro Thr Tyr Ala Met Glu Pro Thr Ile Leu Glu Arg Gly Glu Ala
            2210                2215                2220
Leu Phe Ala Asn Ser Lys Tyr Ile Tyr Leu Val Arg His Pro Tyr
            2225                2230                2235
Ser Val Ile Glu Ser Phe Val Arg Met Arg Met Gln Lys Leu Val
            2240                2245                2250
Gly Leu Gly Glu Glu Asn Pro Tyr Arg Val Ala Glu Gln Val Trp
            2255                2260                2265
Ala Lys Ser Asn Gln Asn Ile Leu Asn Phe Leu Ser Gln Leu Glu
            2270                2275                2280
Pro Glu Arg Gln His Gln Ile Arg Tyr Glu Asp Leu Val Lys Lys
            2285                2290                2295
Pro Gln Gln Val Leu Ser Gln Leu Cys Asp Phe Leu Asn Val Pro
            2300                2305                2310
Phe Glu Pro Glu Leu Leu Gln Pro Tyr Gln Gly Asp Arg Met Thr
            2315                2320                2325
Gly Gly Val His Gln Lys Ser Leu Ser Ile Ser Asp Pro Asn Phe
            2330                2335                2340
Leu Lys His Asn Thr Ile Asp Glu Ser Leu Ala Asp Lys Trp Lys
            2345                2350                2355
Thr Ile Gln Leu Pro Tyr Pro Leu Lys Ser Glu Thr Gln Arg Ile
            2360                2365                2370
Ala Ser Gln Leu Ser Tyr Glu Leu Pro Asn Leu Val Thr Thr Pro
            2375                2380                2385
Thr Asn Gln Gln Pro Gln Val Ser Thr Thr Pro Ser Thr Glu Gln
            2390                2395                2400
Pro Ile Met Glu Glu Lys Phe Leu Glu Phe Gly Gly Asn Gln Ile
            2405                2410                2415
Cys Leu Cys Ser Trp Gly Ser Pro Glu His Pro Val Val Leu Cys
            2420                2425                2430
Ile His Gly Ile Leu Glu Gln Gly Leu Ala Trp Gln Glu Val Ala
            2435                2440                2445
Leu Pro Leu Ala Ala Gln Gly Tyr Arg Val Val Ala Pro Asp Leu
            2450                2455                2460
Phe Gly His Gly Arg Ser Ser His Leu Glu Met Val Thr Ser Tyr
            2465                2470                2475
Ser Ser Leu Thr Phe Leu Ala Gln Ile Asp Arg Val Ile Gln Glu
            2480                2485                2490
```

```
Leu Pro Asp Gln Pro Leu Leu Val Gly His Ser Met Gly Ala
    2495            2500                2505

Met Leu Ala Thr Ala Ile Ala Ser Val Arg Pro Lys Lys Ile Lys
    2510            2515                2520

Glu Leu Ile Leu Val Glu Leu Pro Leu Pro Ala Glu Glu Ser Lys
    2525            2530                2535

Lys Glu Ser Ala Val Asn Gln Leu Thr Thr Cys Leu Asp Tyr Leu
    2540            2545                2550

Ser Ser Thr Pro Gln His Pro Ile Phe Pro Asp Val Ala Thr Ala
    2555            2560                2565

Ala Ser Arg Leu Arg Gln Ala Ile Pro Ser Leu Ser Glu Glu Phe
    2570            2575                2580

Ser Tyr Ile Leu Ala Gln Arg Ile Thr Gln Pro Asn Gln Gly Gly
    2585            2590                2595

Val Arg Trp Ser Trp Asp Ala Ile Ile Arg Thr Arg Ser Ile Leu
    2600            2605                2610

Gly Leu Asn Asn Leu Pro Gly Gly Arg Ser Gln Tyr Leu Glu Met
    2615            2620                2625

Leu Lys Ser Ile Gln Val Pro Thr Thr Leu Val Tyr Gly Asp Ser
    2630            2635                2640

Ser Lys Leu Asn Arg Pro Glu Asp Leu Gln Gln Gln Lys Met Thr
    2645            2650                2655

Met Thr Gln Ala Lys Arg Val Phe Leu Ser Gly Gly His Asn Leu
    2660            2665                2670

His Ile Asp Ala Ala Ala Ala Leu Ala Ser Leu Ile Leu Thr Ser
    2675            2680                2685

<210> SEQ ID NO 8
<211> LENGTH: 3177
<212> TYPE: PRT
<213> ORGANISM: Artificial sequence
<220> FEATURE:
<223> OTHER INFORMATION: Hybrid polyketide synthase capable of producing
      pentene

<400> SEQUENCE: 8

Met Arg Ala Pro Tyr Gly Asn Arg Gln Val Asn Arg Arg Phe Leu Arg
1               5                   10                  15

Glu Phe Arg Ala Lys Arg Pro His Cys Val Ser Pro Leu His Phe Leu
                20                  25                  30

Ala Glu Phe Ser Glu Ser Arg Gln Thr Thr Gly Ser Ala Gly Val Thr
            35                  40                  45

Ala Pro Ile Asp Arg Pro Gly Val Ser Met Ala Pro Lys Ser Gly Ala
        50                  55                  60

Gln Arg Ser Ser Asp Ile Ala Val Val Gly Met Ser Cys Arg Leu Pro
65                  70                  75                  80

Gly Ala Pro Gly Ile Asp Glu Phe Trp His Leu Leu Thr Thr Gly Gly
                85                  90                  95

Ser Ala Ile Glu Arg Arg Ala Asp Gly Thr Trp Arg Gly Ser Leu Asp
                100                 105                 110

Gly Ala Ala Asp Phe Asp Ala Ala Phe Phe Asp Met Thr Pro Arg Gln
            115                 120                 125

Ala Ala Ala Ala Asp Pro Gln Gln Arg Leu Met Leu Glu Leu Gly Trp
        130                 135                 140

Thr Ala Leu Glu Asn Ala Gly Ile Val Pro Gly Ser Leu Ala Gly Thr
```

```
            145                 150                 155                 160
Asp Thr Gly Val Phe Val Gly Ile Ala Ala Asp Asp Tyr Ala Ala Leu
                    165                 170                 175

Leu His Arg Ser Ala Thr Pro Val Ser Gly His Thr Ala Thr Gly Leu
                    180                 185                 190

Ser Arg Gly Met Ala Ala Asn Arg Leu Ser Tyr Leu Leu Gly Leu Arg
                    195                 200                 205

Gly Pro Ser Leu Ala Val Asp Ser Ala Gln Ser Ser Leu Val Ala
    210                 215                 220

Val His Leu Ala Cys Glu Ser Leu Arg Arg Gly Glu Ser Asp Leu Ala
225                 230                 235                 240

Ile Val Gly Gly Val Ser Leu Ile Leu Ala Glu Asp Ser Thr Ala Gly
                    245                 250                 255

Met Glu Leu Met Gly Ala Leu Ser Pro Asp Gly Arg Cys His Thr Phe
                260                 265                 270

Asp Ala Arg Ala Asn Gly Tyr Val Arg Gly Glu Gly Gly Ala Cys Val
                275                 280                 285

Val Leu Lys Pro Leu Glu Arg Ala Leu Ala Asp Gly Asp Arg Val His
    290                 295                 300

Cys Val Val Arg Gly Ser Ala Val Asn Asn Asp Gly Gly Ser Thr
305                 310                 315                 320

Leu Thr Thr Pro His Arg Glu Ala Gln Ala Ala Val Leu Arg Ala Ala
                    325                 330                 335

Tyr Glu Arg Ala Gly Val Gly Pro Asp Gln Val Ser Tyr Val Glu Leu
                340                 345                 350

His Gly Thr Gly Thr Pro Val Gly Asp Pro Val Glu Ala Ala Ala Leu
                355                 360                 365

Gly Ala Val Leu Gly Thr Ala His Gly Arg Asn Ala Pro Leu Ser Val
            370                 375                 380

Gly Ser Val Lys Thr Asn Val Gly His Leu Glu Ala Ala Gly Leu
385                 390                 395                 400

Val Gly Phe Val Lys Ala Ala Leu Cys Val Arg Glu Gly Val Val Pro
                405                 410                 415

Pro Ser Leu Asn His Ala Thr Pro Asn Pro Ala Ile Pro Met Asp Arg
                420                 425                 430

Leu Asn Leu Arg Val Pro Thr Arg Leu Glu Pro Trp Pro His Pro Asp
            435                 440                 445

Asp Arg Ala Thr Gly Arg Leu Arg Leu Ala Gly Val Ser Ser Phe Gly
    450                 455                 460

Met Gly Gly Thr Asn Ala His Val Val Val Glu Glu Ala Pro Leu Pro
465                 470                 475                 480

Glu Ala Gly Glu Pro Val Gly Ala Gly Val Pro Leu Ala Val Val Pro
                485                 490                 495

Val Val Val Ser Gly Arg Ser Ala Gly Ala Val Ala Glu Leu Ala Ser
                500                 505                 510

Arg Leu Asn Glu Ser Val Arg Ser Asp Arg Leu Val Asp Val Gly Leu
            515                 520                 525

Ser Ser Val Val Ser Arg Ser Val Phe Glu His Arg Ser Val Val Leu
            530                 535                 540

Ala Gly Asp Ser Ala Glu Leu Ser Ala Gly Leu Asp Ala Leu Ala Ala
545                 550                 555                 560

Asp Gly Val Ser Pro Val Leu Val Ser Gly Val Ala Ser Val Gly Gly
                565                 570                 575
```

```
Gly Arg Ser Val Phe Val Pro Gly Ala Gly Val Lys Trp Ala Gly
            580                 585                 590

Met Ala Leu Gly Leu Trp Ala Glu Ser Ala Val Phe Ala Glu Ser Met
            595                 600                 605

Ala Arg Cys Glu Ala Ala Phe Ala Gly Leu Val Glu Trp Arg Leu Ala
            610                 615                 620

Asp Val Leu Gly Asp Gly Ala Ala Leu Glu Arg Glu Asp Val Val Gln
625                 630                 635                 640

Pro Ala Ser Phe Ala Val Met Val Ser Leu Ala Ala Leu Trp Arg Ser
                645                 650                 655

Leu Gly Val Val Pro Asp Ala Val Val Gly His Ser Gln Gly Glu Ile
            660                 665                 670

Ala Ala Ala Val Val Ala Gly Gly Leu Ser Leu Glu Asp Gly Ala Arg
            675                 680                 685

Val Val Val Leu Arg Ala Arg Val Ala Glu Glu Val Leu Ser Gly Gly
            690                 695                 700

Gly Ile Ala Ser Val Arg Leu Ser Arg Ala Glu Val Glu Glu Arg Leu
705                 710                 715                 720

Ala Gly Gly Gly Gly Leu Ser Val Ala Val Val Asn Ala Pro Ser
                725                 730                 735

Ser Thr Val Val Ala Gly Glu Leu Gly Asp Leu Asp Arg Phe Val Ala
            740                 745                 750

Ala Cys Glu Ala Glu Gly Val Arg Ala Arg Arg Leu Glu Phe Gly Tyr
            755                 760                 765

Ala Ser His Ser Arg Phe Val Glu Pro Val Arg Glu Arg Leu Leu Glu
            770                 775                 780

Gly Leu Ala Asp Val Arg Pro Val Arg Gly Arg Ile Pro Phe Tyr Ser
785                 790                 795                 800

Thr Val Glu Ala Ala Glu Phe Asp Thr Ala Gly Leu Asp Ala Glu Tyr
                805                 810                 815

Trp Phe Gly Asn Leu Arg Arg Pro Val Arg Phe Gln Glu Thr Val Glu
            820                 825                 830

Arg Leu Leu Ala Asp Gly Phe Arg Val Phe Val Glu Cys Gly Ala His
            835                 840                 845

Pro Val Leu Thr Gly Ala Val Gln Glu Thr Ala Glu Thr Ala Gly Arg
            850                 855                 860

Glu Ile Cys Ser Val Gly Ser Leu Arg Arg Asp Glu Gly Gly Leu Arg
865                 870                 875                 880

Arg Phe Leu Thr Ser Ala Ala Glu Ala Phe Val Gln Gly Val Glu Val
                885                 890                 895

Ser Trp Pro Val Leu Phe Asp Gly Thr Gly Ala Arg Thr Val Asp Leu
            900                 905                 910

Pro Thr Tyr Pro Phe Gln Arg Arg His His Trp Ala Pro Asp Gly Ser
            915                 920                 925

Ala Ser Ala Ala Pro Thr Arg Asp Ile Arg Pro Glu Thr Ala Ala
            930                 935                 940

Val Pro Ala Asp Thr Met Asp Leu Ala Gly Gln Leu Arg Ala Asp Val
945                 950                 955                 960

Ala Ser Leu Pro Thr Thr Glu Gln Ile Ala Arg Leu Leu Asp Gln Val
                965                 970                 975

Arg Asp Gly Val Ala Thr Val Leu Gly Leu Asp Ala Arg Asp Glu Val
            980                 985                 990
```

```
Arg Ala Glu Ala Thr Phe Lys Glu  Leu Gly Val Glu Ser  Leu Thr Gly
    995             1000                     1005

Val Glu Leu Lys Asn His Leu  Arg Ala Arg Thr Gly  Leu His Val
1010             1015                 1020

Pro Thr Ser Leu Ile Tyr Asp  Cys Pro Thr Pro Leu  Ala Ala Ala
1025             1030                 1035

His Tyr Leu Arg Asp Glu Leu  Leu Gly Arg Pro Ala  Glu Gln Ala
1040             1045                 1050

Val Val Pro Ala Gly Ile Pro  Val Asp Glu Pro Ile  Ala Ile Val
1055             1060                 1065

Gly Met Gly Cys Arg Leu Pro  Gly Gly Val Ser Ser  Pro Glu Gly
1070             1075                 1080

Leu Trp Asp Leu Val Ala Ser  Gly Val Asp Ala Val  Ser Pro Phe
1085             1090                 1095

Pro Thr Asp Arg Gly Trp Asp  Val Gly Gly Leu Phe  Asp Pro Glu
1100             1105                 1110

Pro Gly Val Pro Gly Arg Ser  Tyr Val Arg Glu Gly  Gly Phe Leu
1115             1120                 1125

His Glu Ala Gly Glu Phe Asp  Ala Gly Phe Phe Gly  Ile Ser Pro
1130             1135                 1140

Arg Glu Ala Leu Ala Met Asp  Pro Gln Gln Arg Leu  Leu Leu Glu
1145             1150                 1155

Thr Ser Trp Glu Ala Leu Glu  Arg Ala Gly Ile Asp  Pro His Thr
1160             1165                 1170

Leu Arg Gly Ser Arg Thr Gly  Val Tyr Ala Gly Val  Met Ala Gln
1175             1180                 1185

Glu Tyr Gly Pro Arg Leu His  Glu Gly Ala Asp Gly  Tyr Glu Gly
1190             1195                 1200

Tyr Leu Leu Thr Gly Ser Ser  Ser Ser Val Ala Ser  Gly Arg Ile
1205             1210                 1215

Ser Tyr Val Leu Gly Leu Glu  Gly Pro Ala Val Thr  Val Asp Thr
1220             1225                 1230

Ala Cys Ser Ser Ser Leu Val  Ala Leu His Leu Ala  Val Arg Ala
1235             1240                 1245

Leu Arg Ser Gly Glu Cys Asp  Leu Ala Leu Ala Gly  Gly Ala Thr
1250             1255                 1260

Val Met Ala Glu Pro Gly Met  Phe Val Glu Phe Ser  Arg Gln Arg
1265             1270                 1275

Gly Leu Ser Ala His Gly Arg  Cys Lys Ala Tyr Ser  Asp Ser Ala
1280             1285                 1290

Asp Gly Thr Gly Trp Ala Glu  Gly Ala Gly Val Leu  Leu Val Glu
1295             1300                 1305

Arg Leu Ser Asp Ala Val Arg  His Gly Arg Arg Val  Leu Ala Val
1310             1315                 1320

Val Arg Gly Ser Ala Val Asn  Gln Asp Gly Ala Ser  Asn Gly Leu
1325             1330                 1335

Thr Ala Pro Asn Gly Arg Ser  Gln Ser Arg Leu Ile  Arg Gln Ala
1340             1345                 1350

Leu Ala Asp Ala Arg Leu Gly  Val Ala Asp Val Asp  Val Val Glu
1355             1360                 1365

Gly His Gly Thr Gly Thr Arg  Leu Gly Asp Pro Ile  Glu Ala Gln
1370             1375                 1380

Ala Leu Leu Ala Thr Tyr Gly  Gln Arg Asp Ala Gly  Arg Pro Leu
```

```
         1385             1390              1395
Arg Leu Gly Ser Leu Lys Ser Asn Val Gly His Thr Gln Ala Ala
    1400              1405             1410
Ala Gly Val Ala Gly Val Ile Lys Met Val Met Ala Met Arg His
    1415             1420              1425
Gly Val Leu Pro Lys Thr Leu His Val Asp Glu Pro Thr Ala Glu
    1430             1435              1440
Val Asp Trp Ser Ala Gly Ala Val Ser Leu Leu Arg Glu Gln Glu
    1445             1450              1455
Ala Trp Pro Arg Gly Glu Val Arg Arg Ala Gly Val Ser Ser
    1460             1465              1470
Phe Gly Val Ser Gly Thr Asn Ala His Val Ile Leu Glu Gln Pro
    1475             1480              1485
Pro Gly Val Pro Ser Gln Ser Ala Gly Pro Gly Ser Gly Ser Val
    1490             1495              1500
Val Asp Val Pro Val Val Pro Trp Met Val Ser Gly Lys Thr Pro
    1505             1510              1515
Glu Ala Leu Ser Ala Gln Ala Thr Ala Leu Met Thr Tyr Leu Asp
    1520             1525              1530
Glu Arg Pro Asp Val Ser Ser Leu Asp Val Gly Tyr Ser Leu Ala
    1535             1540              1545
Leu Thr Arg Ser Ala Leu Asp Glu Arg Ala Val Val Leu Gly Ser
    1550             1555              1560
Asp Arg Glu Thr Leu Leu Cys Gly Val Lys Ala Leu Ser Ala Gly
    1565             1570              1575
His Glu Ala Ser Gly Leu Val Thr Gly Ser Val Gly Ala Gly Gly
    1580             1585              1590
Arg Ile Gly Phe Val Phe Ser Gly Gln Gly Gly Gln Trp Leu Gly
    1595             1600              1605
Met Gly Arg Gly Leu Tyr Arg Ala Phe Pro Val Phe Ala Ala Ala
    1610             1615              1620
Phe Asp Glu Ala Cys Ala Glu Leu Asp Ala His Leu Gly Gln Glu
    1625             1630              1635
Ile Gly Val Arg Glu Val Val Ser Gly Ser Asp Ala Gln Leu Leu
    1640             1645              1650
Asp Arg Thr Leu Trp Ala Gln Ser Gly Leu Phe Ala Leu Gln Val
    1655             1660              1665
Gly Leu Leu Lys Leu Leu Asp Ser Trp Gly Val Arg Pro Ser Val
    1670             1675              1680
Val Leu Gly His Ser Val Gly Glu Leu Ala Ala Ala Phe Ala Ala
    1685             1690              1695
Gly Val Val Ser Leu Ser Gly Ala Ala Arg Leu Val Ala Gly Arg
    1700             1705              1710
Ala Arg Leu Met Gln Ala Leu Pro Ser Gly Gly Met Leu Ala
    1715             1720              1725
Val Pro Ala Gly Glu Glu Leu Leu Trp Ser Leu Leu Ala Asp Gln
    1730             1735              1740
Gly Asp Arg Val Gly Ile Ala Ala Val Asn Ala Ala Gly Ser Val
    1745             1750              1755
Val Leu Ser Gly Asp Arg Asp Val Leu Asp Asp Leu Ala Gly Arg
    1760             1765              1770
Leu Asp Gly Gln Gly Ile Arg Ser Arg Trp Leu Arg Val Ser His
    1775             1780              1785
```

```
Ala Phe His Ser Tyr Arg Met Asp Pro Met Leu Ala Glu Phe Ala
    1790                1795                1800

Glu Leu Ala Arg Thr Val Asp Tyr Arg Arg Cys Glu Val Pro Ile
    1805                1810                1815

Val Ser Thr Leu Thr Gly Asp Leu Asp Asp Ala Gly Arg Met Ser
    1820                1825                1830

Gly Pro Asp Tyr Trp Val Arg Gln Val Arg Glu Pro Val Arg Phe
    1835                1840                1845

Ala Asp Gly Val Gln Ala Leu Val Glu His Asp Val Ala Thr Val
    1850                1855                1860

Val Glu Leu Gly Pro Asp Gly Ala Leu Ser Ala Leu Ile Gln Glu
    1865                1870                1875

Cys Val Ala Ala Ser Asp His Ala Gly Arg Leu Ser Ala Val Pro
    1880                1885                1890

Ala Met Arg Arg Asn Gln Asp Glu Ala Gln Lys Val Met Thr Ala
    1895                1900                1905

Leu Ala His Val His Val Arg Gly Gly Ala Val Asp Trp Arg Ser
    1910                1915                1920

Phe Phe Ala Gly Thr Gly Ala Lys Gln Ile Glu Leu Pro Thr Tyr
    1925                1930                1935

Ala Phe Gln Arg Gln Arg Tyr Trp Leu Val Pro Ser Asp Ser Gly
    1940                1945                1950

Asp Val Thr Gly Ala Gly Leu Ala Gly Ala Glu His Pro Leu Leu
    1955                1960                1965

Gly Ala Val Val Pro Val Ala Gly Gly Asp Glu Val Leu Leu Thr
    1970                1975                1980

Gly Arg Ile Ser Val Arg Thr His Pro Trp Leu Ala Glu His Arg
    1985                1990                1995

Val Leu Gly Glu Val Ile Val Ala Gly Thr Ala Leu Leu Glu Ile
    2000                2005                2010

Ala Leu His Ala Gly Glu Arg Leu Gly Cys Glu Arg Val Glu Glu
    2015                2020                2025

Leu Thr Leu Glu Ala Pro Leu Val Leu Pro Glu Arg Gly Ala Ile
    2030                2035                2040

Gln Val Gln Leu Arg Val Gly Ala Pro Glu Asn Ser Gly Arg Arg
    2045                2050                2055

Pro Met Ala Leu Tyr Ser Arg Pro Glu Gly Ala Ala Glu His Asp
    2060                2065                2070

Trp Thr Arg His Ala Thr Gly Arg Leu Ala Pro Gly Arg Gly Glu
    2075                2080                2085

Ala Ala Gly Asp Leu Ala Asp Trp Pro Ala Pro Gly Ala Leu Pro
    2090                2095                2100

Val Asp Leu Asp Glu Phe Tyr Arg Asp Leu Ala Glu Leu Gly Leu
    2105                2110                2115

Glu Tyr Gly Pro Ile Phe Gln Gly Leu Lys Ala Ala Trp Arg Gln
    2120                2125                2130

Gly Asp Glu Val Tyr Ala Glu Ala Ala Leu Pro Gly Thr Glu Asp
    2135                2140                2145

Ser Gly Phe Gly Val His Pro Ala Leu Leu Asp Ala Ala Leu His
    2150                2155                2160

Ala Thr Ala Val Arg Asp Met Asp Asp Ala Arg Leu Pro Phe Gln
    2165                2170                2175
```

```
Trp Glu Gly Val Ser Leu His Ala Lys Ala Ala Pro Ala Leu Arg
2180                2185                2190

Val Arg Val Val Pro Ala Gly Asp Asp Ala Lys Ser Leu Leu Val
2195                2200                2205

Cys Asp Gly Thr Gly Arg Pro Val Ile Ser Val Asp Arg Leu Val
2210                2215                2220

Leu Arg Ser Ala Ala Ala Arg Arg Thr Gly Ala Arg Arg Gln Ala
2225                2230                2235

His Gln Ala Arg Leu Tyr Arg Leu Ser Trp Pro Thr Val Gln Leu
2240                2245                2250

Pro Thr Ser Ala Gln Pro Pro Ser Cys Val Leu Leu Gly Thr Ser
2255                2260                2265

Glu Val Ser Ala Asp Ile Gln Val Tyr Pro Asp Leu Arg Ser Leu
2270                2275                2280

Thr Ala Ala Leu Asp Ala Gly Ala Glu Pro Pro Gly Val Val Ile
2285                2290                2295

Ala Pro Thr Pro Pro Gly Gly Gly Arg Thr Ala Asp Val Arg Glu
2300                2305                2310

Thr Thr Arg His Ala Leu Asp Leu Val Gln Gly Trp Leu Ser Asp
2315                2320                2325

Gln Arg Leu Asn Glu Ser Arg Leu Leu Leu Val Thr Gln Gly Ala
2330                2335                2340

Val Ala Val Glu Pro Gly Glu Pro Val Thr Asp Leu Ala Gln Ala
2345                2350                2355

Ala Leu Trp Gly Leu Leu Arg Ser Thr Gln Thr Glu His Pro Asp
2360                2365                2370

Arg Phe Val Leu Val Asp Val Pro Glu Pro Ala Gln Leu Leu Pro
2375                2380                2385

Ala Leu Pro Gly Val Leu Ala Cys Gly Glu Pro Gln Leu Ala Leu
2390                2395                2400

Arg Arg Gly Gly Ala His Ala Pro Arg Leu Ala Gly Leu Gly Ser
2405                2410                2415

Asp Asp Val Leu Pro Val Pro Asp Gly Thr Gly Trp Arg Leu Glu
2420                2425                2430

Ala Thr Arg Pro Gly Ser Leu Asp Gly Leu Ala Leu Val Asp Glu
2435                2440                2445

Pro Thr Ala Thr Ala Pro Leu Gly Asp Gly Glu Val Arg Ile Ala
2450                2455                2460

Met Arg Ala Ala Gly Val Asn Phe Arg Asp Ala Leu Ile Ala Leu
2465                2470                2475

Gly Met Tyr Pro Gly Val Ala Ser Leu Gly Ser Glu Gly Ala Gly
2480                2485                2490

Val Val Val Glu Thr Gly Pro Gly Val Thr Gly Leu Ala Pro Gly
2495                2500                2505

Asp Arg Val Met Gly Met Ile Pro Lys Ala Phe Gly Pro Leu Ala
2510                2515                2520

Val Ala Asp His Arg Met Val Thr Arg Ile Pro Ala Gly Trp Ser
2525                2530                2535

Phe Ala Arg Ala Ala Ser Val Pro Ile Val Phe Leu Thr Ala Tyr
2540                2545                2550

Tyr Ala Leu Val Asp Leu Ala Gly Leu Arg Pro Gly Glu Ser Leu
2555                2560                2565

Leu Val His Ser Ala Ala Gly Gly Val Gly Met Ala Ala Ile Gln
```

-continued

```
                2570                2575                2580

Leu Ala Arg His Leu Gly Ala Glu Val Tyr Ala Thr Ala Ser Glu
        2585                2590                2595

Asp Lys Trp Gln Ala Val Glu Leu Ser Arg Glu His Leu Ala Ser
    2600                2605                2610

Ser Arg Thr Cys Asp Phe Glu Gln Gln Phe Leu Gly Ala Thr Gly
    2615                2620                2625

Gly Arg Gly Val Asp Val Val Leu Asn Ser Leu Ala Gly Glu Phe
    2630                2635                2640

Ala Asp Ala Ser Leu Arg Met Leu Pro Arg Gly Gly Arg Phe Leu
    2645                2650                2655

Glu Leu Gly Lys Thr Asp Val Arg Asp Pro Val Glu Val Ala Asp
    2660                2665                2670

Ala His Pro Gly Val Ser Tyr Gln Ala Phe Asp Thr Val Glu Ala
    2675                2680                2685

Gly Pro Gln Arg Ile Gly Glu Met Leu His Glu Leu Val Glu Leu
    2690                2695                2700

Phe Glu Gly Arg Val Leu Glu Pro Leu Pro Val Thr Ala Trp Asp
    2705                2710                2715

Val Arg Gln Ala Pro Glu Ala Leu Arg His Leu Ser Gln Ala Arg
    2720                2725                2730

His Val Gly Lys Leu Val Leu Thr Met Pro Pro Val Trp Asp Ala
    2735                2740                2745

Ala Gly Thr Val Leu Val Thr Gly Gly Thr Gly Ala Leu Gly Ala
    2750                2755                2760

Glu Val Ala Arg His Leu Val Ile Glu Arg Gly Val Arg Asn Leu
    2765                2770                2775

Val Leu Val Ser Arg Arg Gly Pro Ala Ala Ser Gly Ala Ala Glu
    2780                2785                2790

Leu Val Ala Gln Leu Thr Ala Tyr Gly Ala Glu Val Ser Leu Gln
    2795                2800                2805

Ala Cys Asp Val Ala Asp Arg Glu Thr Leu Ala Lys Val Leu Ala
    2810                2815                2820

Ser Ile Pro Asp Glu His Pro Leu Thr Ala Val His Ala Ala
    2825                2830                2835

Gly Val Leu Asp Asp Gly Val Ser Glu Ser Leu Thr Val Glu Arg
    2840                2845                2850

Leu Asp Gln Val Leu Arg Pro Lys Val Asp Gly Ala Arg Asn Leu
    2855                2860                2865

Leu Glu Leu Ile Asp Pro Asp Val Ala Leu Val Leu Phe Ser Ser
    2870                2875                2880

Val Ser Gly Val Leu Gly Ser Gly Gly Gln Gly Asn Tyr Ala Ala
    2885                2890                2895

Ala Asn Ser Phe Leu Asp Ala Leu Ala Gln Gln Arg Gln Ser Arg
    2900                2905                2910

Gly Leu Pro Thr Arg Ser Leu Ala Trp Gly Pro Trp Ala Glu His
    2915                2920                2925

Gly Met Ala Ser Thr Leu Arg Glu Ala Glu Gln Asp Arg Leu Ala
    2930                2935                2940

Arg Ser Gly Leu Leu Pro Ile Ser Thr Glu Glu Gly Leu Ser Gln
    2945                2950                2955

Phe Asp Ala Ala Cys Gly Gly Ala His Thr Val Val Ala Pro Val
    2960                2965                2970
```

-continued

```
Arg Phe Ser Arg Leu Ser Asp Gly Asn Ala Ile Lys Phe Ser Val
    2975                2980                2985

Leu Gln Gly Leu Val Gly Pro His Arg Val Asn Lys Ala Ala Thr
    2990                2995                3000

Ala Asp Asp Ala Glu Ser Leu Arg Lys Arg Leu Gly Arg Leu Pro
    3005                3010                3015

Asp Ala Glu Gln His Arg Ile Leu Leu Asp Leu Val Arg Met His
    3020                3025                3030

Val Ala Ala Val Leu Gly Phe Ala Gly Ser Gln Glu Ile Thr Ala
    3035                3040                3045

Asp Gly Thr Phe Lys Val Leu Gly Phe Asp Ser Leu Thr Val Val
    3050                3055                3060

Glu Leu Arg Asn Arg Ile Asn Gly Ala Thr Gly Leu Arg Leu Pro
    3065                3070                3075

Ala Thr Leu Val Phe Asn Tyr Pro Thr Pro Asp Ala Leu Ala Ala
    3080                3085                3090

His Leu Val Thr Ala Leu Ser Ala Asp Arg Leu Ala Gly Thr Phe
    3095                3100                3105

Glu Glu Leu Asp Arg Trp Ala Ala Asn Leu Pro Thr Leu Ala Arg
    3110                3115                3120

Asp Glu Ala Thr Arg Ala Gln Ile Thr Thr Arg Leu Gln Ala Ile
    3125                3130                3135

Leu Gln Ser Leu Ala Asp Val Ser Gly Gly Thr Gly Gly Gly Ser
    3140                3145                3150

Val Pro Asp Arg Leu Arg Ser Ala Thr Asp Asp Glu Leu Phe Gln
    3155                3160                3165

Leu Leu Asp Asn Asp Leu Glu Leu Pro
    3170                3175
```

<210> SEQ ID NO 9
<211> LENGTH: 2081
<212> TYPE: PRT
<213> ORGANISM: Artificial sequence
<220> FEATURE:
<223> OTHER INFORMATION: Hybrid polyketide synthase capable of producing pentene

<400> SEQUENCE: 9

```
Met Ser Asn Glu Glu Lys Leu Arg Glu Tyr Leu Arg Arg Ala Leu Val
1               5                   10                  15

Asp Leu His Gln Ala Arg Glu Arg Leu His Glu Ala Glu Ser Gly Glu
                20                  25                  30

Arg Glu Pro Ile Ala Ile Val Ala Met Gly Cys Arg Tyr Pro Gly Gly
            35                  40                  45

Val Gln Asp Pro Glu Gly Leu Trp Lys Leu Val Ala Ser Gly Gly Asp
        50                  55                  60

Ala Ile Gly Glu Phe Pro Ala Asp Arg Gly Trp His Leu Asp Glu Leu
65                  70                  75                  80

Tyr Asp Pro Asp Pro Asp Gln Pro Gly Thr Cys Tyr Thr Arg His Gly
                85                  90                  95

Gly Phe Leu His Asp Ala Gly Glu Phe Asp Ala Gly Phe Phe Asp Ile
                100                 105                 110

Ser Pro Arg Glu Ala Leu Ala Met Asp Pro Gln Gln Arg Leu Leu Leu
            115                 120                 125

Glu Ile Ser Trp Glu Thr Val Glu Ser Ala Gly Met Asp Pro Arg Ser
```

```
              130                 135                 140
Leu Arg Gly Ser Arg Thr Gly Val Phe Ala Gly Leu Met Tyr Glu Gly
145                 150                 155                 160

Tyr Asp Thr Gly Ala His Arg Ala Gly Glu Gly Val Glu Gly Tyr Leu
                165                 170                 175

Gly Thr Gly Asn Ala Gly Ser Val Ala Ser Gly Arg Val Ala Tyr Ala
                180                 185                 190

Phe Gly Phe Glu Gly Pro Ala Val Thr Val Asp Thr Ala Cys Ser Ser
            195                 200                 205

Ser Leu Val Ala Leu His Leu Ala Cys Gln Ser Leu Arg Gln Gly Glu
    210                 215                 220

Cys Asp Leu Ala Leu Ala Gly Gly Val Thr Val Met Ser Thr Pro Glu
225                 230                 235                 240

Arg Phe Val Glu Phe Ser Arg Gln Arg Gly Leu Ala Pro Asp Gly Arg
                245                 250                 255

Cys Lys Ser Phe Ala Ala Ala Asp Gly Thr Gly Trp Gly Glu Gly
                260                 265                 270

Ala Gly Leu Val Leu Leu Glu Arg Leu Ser Asp Ala Arg Arg Asn Gly
            275                 280                 285

His Arg Val Leu Ala Val Val Arg Gly Ser Ala Val Asn Gln Asp Gly
    290                 295                 300

Ala Ser Asn Gly Leu Thr Ala Pro Asn Gly Leu Ala Gln Glu Arg Val
305                 310                 315                 320

Ile Gln Gln Val Leu Thr Ser Ala Gly Leu Ser Ala Ser Asp Val Asp
                325                 330                 335

Ala Val Glu Ala His Gly Thr Gly Thr Arg Leu Gly Asp Pro Ile Glu
            340                 345                 350

Ala Gln Ala Leu Ile Ala Ala Tyr Gly Gln Asp Arg Asp Arg Asp Arg
    355                 360                 365

Pro Leu Trp Leu Gly Ser Val Lys Ser Asn Ile Gly His Thr Gln Ala
370                 375                 380

Ala Ala Gly Val Ala Gly Val Ile Lys Met Val Met Ala Met Arg His
385                 390                 395                 400

Gly Glu Leu Pro Arg Thr Leu His Val Asp Glu Pro Asn Ser His Val
                405                 410                 415

Asp Trp Ser Ala Gly Ala Val Arg Leu Leu Thr Glu Asn Ile Arg Trp
            420                 425                 430

Pro Gly Thr Gly Thr Arg Arg Ala Gly Val Ser Ser Phe Gly Val Ser
    435                 440                 445

Gly Thr Asn Ala His Val Ile Val Gly Asp Tyr Ala Gln Gln Lys Ser
    450                 455                 460

Pro Leu Ala Pro Pro Ala Thr Gln Asp Arg Pro Trp His Leu Leu Thr
465                 470                 475                 480

Leu Ser Ala Lys Asn Ala Gln Ala Leu Asn Ala Leu Gln Lys Ser Tyr
                485                 490                 495

Gly Asp Tyr Leu Ala Gln His Pro Ser Val Asp Pro Arg Asp Leu Cys
            500                 505                 510

Leu Ser Ala Asn Thr Gly Arg Ser Pro Leu Lys Glu Arg Arg Phe Phe
    515                 520                 525

Val Phe Lys Gln Val Ala Asp Leu Gln Gln Thr Leu Asn Gln Asp Phe
    530                 535                 540

Leu Ala Gln Pro Arg Leu Ser Ser Pro Ala Lys Ile Ala Phe Leu Phe
545                 550                 555                 560
```

```
Thr Gly Gln Gly Ser Gln Tyr Tyr Gly Met Gly Gln Leu Tyr Gln
                565                 570                 575

Thr Ser Pro Val Phe Arg Gln Val Leu Asp Glu Cys Asp Arg Leu Trp
            580                 585                 590

Gln Thr Tyr Ser Pro Glu Ala Pro Ala Leu Thr Asp Leu Leu Tyr Gly
        595                 600                 605

Asn His Asn Pro Asp Leu Val His Glu Thr Val Tyr Thr Gln Pro Leu
    610                 615                 620

Leu Phe Ala Val Glu Tyr Ala Ile Ala Gln Leu Trp Leu Ser Trp Gly
625                 630                 635                 640

Val Thr Pro Asp Phe Cys Met Gly His Ser Val Gly Glu Tyr Val Ala
                645                 650                 655

Ala Cys Leu Ala Gly Val Phe Ser Leu Ala Asp Gly Met Lys Leu Ile
            660                 665                 670

Thr Ala Arg Gly Lys Leu Met His Ala Leu Pro Ser Asn Gly Ser Met
        675                 680                 685

Ala Ala Val Phe Ala Asp Lys Thr Val Ile Lys Pro Tyr Leu Ser Glu
    690                 695                 700

His Leu Thr Val Gly Ala Glu Asn Gly Ser His Leu Val Leu Ser Gly
705                 710                 715                 720

Lys Thr Pro Cys Leu Glu Ala Ser Ile His Lys Leu Gln Ser Gln Gly
                725                 730                 735

Ile Lys Thr Lys Pro Leu Lys Val Ser His Ala Phe His Ser Pro Leu
            740                 745                 750

Met Ala Pro Met Leu Ala Glu Phe Arg Glu Ile Ala Glu Gln Ile Thr
        755                 760                 765

Phe His Pro Pro Arg Ile Pro Leu Ile Ser Asn Val Thr Gly Gly Gln
    770                 775                 780

Ile Glu Ala Glu Ile Ala Gln Ala Asp Tyr Trp Val Lys His Val Ser
785                 790                 795                 800

Gln Pro Val Lys Phe Val Gln Ser Ile Gln Thr Leu Ala Gln Ala Gly
                805                 810                 815

Val Asn Val Tyr Leu Glu Ile Gly Val Lys Pro Val Leu Leu Ser Met
            820                 825                 830

Gly Arg His Cys Leu Ala Glu Gln Glu Ala Val Trp Leu Pro Ser Leu
        835                 840                 845

Arg Pro His Ser Glu Pro Trp Pro Glu Ile Leu Thr Ser Leu Gly Lys
    850                 855                 860

Leu Tyr Glu Gln Gly Leu Asn Ile Asp Trp Gln Thr Val Glu Ala Gly
865                 870                 875                 880

Asp Arg Arg Arg Lys Leu Ile Leu Pro Thr Tyr Pro Phe Gln Arg Gln
                885                 890                 895

Arg Tyr Trp Phe Asn Gln Gly Ser Trp Gln Thr Val Glu Thr Glu Ser
            900                 905                 910

Val Asn Pro Gly Pro Asp Asp Leu Asn Asp Trp Leu Tyr Gln Val Ala
        915                 920                 925

Trp Thr Pro Leu Asp Thr Leu Pro Pro Ala Glu Pro Ser Ala Lys
    930                 935                 940

Leu Trp Leu Ile Leu Gly Asp Arg His Asp His Gln Pro Ile Glu Ala
945                 950                 955                 960

Gln Phe Lys Asn Ala Gln Arg Val Tyr Leu Gly Gln Ser Asn His Phe
                965                 970                 975
```

-continued

Pro Thr Asn Ala Pro Trp Glu Val Ser Ala Asp Ala Leu Asp Asn Leu
            980                 985                 990

Phe Thr His Val Gly Ser Gln Asn Leu Ala Gly Ile Leu Tyr Leu Cys
        995                 1000                1005

Pro Pro Gly Glu Asp Pro Glu Asp Leu Asp Glu Ile Gln Lys Gln
    1010                1015                1020

Thr Ser Gly Phe Ala Leu Gln Leu Ile Gln Thr Leu Tyr Gln Gln
    1025                1030                1035

Lys Ile Ala Val Pro Cys Trp Phe Val Thr His Gln Ser Gln Arg
    1040                1045                1050

Val Leu Glu Thr Asp Ala Val Thr Gly Phe Ala Gln Gly Gly Leu
    1055                1060                1065

Trp Gly Leu Ala Gln Ala Ile Ala Leu Glu His Pro Glu Leu Trp
    1070                1075                1080

Gly Gly Ile Ile Asp Val Asp Asp Ser Leu Pro Asn Phe Ala Gln
    1085                1090                1095

Ile Cys Gln Gln Arg Gln Val Gln Gln Leu Ala Val Arg His Gln
    1100                1105                1110

Lys Leu Tyr Gly Ala Gln Leu Lys Lys Gln Pro Ser Leu Pro Gln
    1115                1120                1125

Lys Asn Leu Gln Ile Gln Pro Gln Gln Thr Tyr Leu Val Thr Gly
    1130                1135                1140

Gly Leu Gly Ala Ile Gly Arg Lys Ile Ala Gln Trp Leu Ala Ala
    1145                1150                1155

Ala Gly Ala Glu Lys Val Ile Leu Val Ser Arg Arg Ala Pro Ala
    1160                1165                1170

Ala Asp Gln Gln Thr Leu Pro Thr Asn Ala Val Val Tyr Pro Cys
    1175                1180                1185

Asp Leu Ala Asp Ala Ala Gln Val Ala Lys Leu Phe Gln Thr Tyr
    1190                1195                1200

Pro His Ile Lys Gly Ile Phe His Ala Ala Gly Thr Leu Ala Asp
    1205                1210                1215

Gly Leu Leu Gln Gln Gln Thr Trp Gln Lys Phe Gln Thr Val Ala
    1220                1225                1230

Ala Ala Lys Met Lys Gly Thr Trp His Leu His Arg His Ser Gln
    1235                1240                1245

Lys Leu Asp Leu Asp Phe Phe Val Leu Phe Ser Ser Val Ala Gly
    1250                1255                1260

Val Leu Gly Ser Pro Gly Gln Gly Asn Tyr Ala Ala Ala Asn Arg
    1265                1270                1275

Gly Met Ala Ala Ile Ala Gln Tyr Arg Gln Ala Gln Gly Leu Pro
    1280                1285                1290

Ala Leu Ala Ile His Trp Gly Pro Trp Ala Glu Gly Gly Met Ala
    1295                1300                1305

Asn Ser Leu Ser Asn Gln Asn Leu Ala Trp Leu Pro Pro Pro Gln
    1310                1315                1320

Gly Leu Thr Ile Leu Glu Lys Val Leu Gly Ala Gln Gly Glu Met
    1325                1330                1335

Gly Val Phe Lys Pro Asp Trp Gln Asn Leu Ala Lys Gln Phe Pro
    1340                1345                1350

Glu Phe Ala Lys Thr His Tyr Phe Ala Ala Val Ile Pro Ser Ala
    1355                1360                1365

Glu Ala Val Pro Pro Thr Ala Ser Ile Phe Asp Lys Leu Ile Asn

-continued

```
              1370              1375              1380
Leu Glu Ala Ser Gln Arg Ala Asp Tyr Leu Leu Asp Tyr Leu Arg
        1385              1390              1395
Arg Ser Val Ala Gln Ile Leu Lys Leu Glu Ile Glu Gln Ile Gln
        1400              1405              1410
Ser His Asp Ser Leu Leu Asp Leu Gly Met Asp Ser Leu Met Ile
        1415              1420              1425
Met Glu Ala Ile Ala Ser Leu Lys Gln Asp Leu Gln Leu Met Leu
        1430              1435              1440
Tyr Pro Arg Glu Ile Tyr Glu Arg Pro Arg Leu Asp Val Leu Thr
        1445              1450              1455
Ala Tyr Leu Ala Ala Glu Phe Thr Lys Ala His Asp Ser Glu Ala
        1460              1465              1470
Ala Thr Ala Ala Ala Ala Ile Pro Ser Gln Ser Leu Ser Val Lys
        1475              1480              1485
Thr Lys Lys Gln Trp Gln Lys Pro Asp His Lys Asn Pro Asn Pro
        1490              1495              1500
Ile Ala Phe Ile Leu Ser Ser Pro Arg Ser Gly Ser Thr Leu Leu
        1505              1510              1515
Arg Val Met Leu Ala Gly His Pro Gly Leu Tyr Ser Pro Pro Glu
        1520              1525              1530
Leu His Leu Leu Pro Phe Glu Thr Met Gly Asp Arg His Gln Glu
        1535              1540              1545
Leu Gly Leu Ser His Leu Gly Glu Gly Leu Gln Arg Ala Leu Met
        1550              1555              1560
Asp Leu Glu Asn Leu Thr Pro Glu Ala Ser Gln Ala Lys Val Asn
        1565              1570              1575
Gln Trp Val Lys Ala Asn Thr Pro Ile Ala Asp Ile Tyr Ala Tyr
        1580              1585              1590
Leu Gln Arg Gln Ala Glu Gln Arg Leu Leu Ile Asp Lys Ser Pro
        1595              1600              1605
Ser Tyr Gly Ser Asp Arg His Ile Leu Asp His Ser Glu Ile Leu
        1610              1615              1620
Phe Asp Gln Ala Lys Tyr Ile His Leu Val Arg His Pro Tyr Ala
        1625              1630              1635
Val Ile Glu Ser Phe Thr Arg Leu Arg Met Asp Lys Leu Leu Gly
        1640              1645              1650
Ala Glu Gln Gln Asn Pro Tyr Ala Leu Ala Glu Ser Ile Trp Arg
        1655              1660              1665
Thr Ser Asn Arg Asn Ile Leu Asp Leu Gly Arg Thr Val Gly Ala
        1670              1675              1680
Asp Arg Tyr Leu Gln Val Ile Tyr Glu Asp Leu Val Arg Asp Pro
        1685              1690              1695
Arg Lys Val Leu Thr Asn Ile Cys Asp Phe Leu Gly Val Asp Phe
        1700              1705              1710
Asp Glu Ala Leu Leu Asn Pro Tyr Ser Gly Asp Arg Leu Thr Asp
        1715              1720              1725
Gly Leu His Gln Gln Ser Met Gly Val Gly Asp Pro Asn Phe Leu
        1730              1735              1740
Gln His Lys Thr Ile Asp Pro Ala Leu Ala Asp Lys Trp Arg Ser
        1745              1750              1755
Ile Thr Leu Pro Ala Ala Leu Gln Leu Asp Thr Ile Gln Leu Ala
        1760              1765              1770
```

| | | | | | | | | | | | |
|---|---|---|---|---|---|---|---|---|---|---|---|
|Glu|Thr|Phe|Ala|Tyr|Asp|Leu|Pro|Gln|Glu|Pro|Gln|Leu|Thr|Pro|
| |1775| | | |1780| | | |1785| | | | | |

Glu Thr Phe Ala Tyr Asp Leu Pro Gln Glu Pro Gln Leu Thr Pro
    1775                1780                1785

Gln Thr Gln Ser Leu Pro Ser Met Val Glu Arg Phe Val Thr Val
    1790                1795                1800

Arg Gly Leu Glu Thr Cys Leu Cys Glu Trp Gly Asp Arg His Gln
    1805                1810                1815

Pro Leu Val Leu Leu His Gly Ile Leu Glu Gln Gly Ala Ser
    1820                1825                1830

Trp Gln Leu Ile Ala Pro Gln Leu Ala Ala Gln Gly Tyr Trp Val
    1835                1840                1845

Val Ala Pro Asp Leu Arg Gly His Gly Lys Ser Ala His Ala Gln
    1850                1855                1860

Ser Tyr Ser Met Leu Asp Phe Leu Ala Asp Val Asp Ala Leu Ala
    1865                1870                1875

Lys Gln Leu Gly Asp Arg Pro Phe Thr Leu Val Gly His Ser Met
    1880                1885                1890

Gly Ser Ile Ile Gly Ala Met Tyr Ala Gly Ile Arg Gln Thr Gln
    1895                1900                1905

Val Glu Lys Leu Ile Leu Val Glu Thr Ile Val Pro Asn Asp Ile
    1910                1915                1920

Asp Asp Ala Glu Thr Gly Asn His Leu Thr Thr His Leu Asp Tyr
    1925                1930                1935

Leu Ala Ala Pro Pro Gln His Pro Ile Phe Pro Ser Leu Glu Val
    1940                1945                1950

Ala Ala Arg Arg Leu Arg Gln Ala Thr Pro Gln Leu Pro Lys Asp
    1955                1960                1965

Leu Ser Ala Phe Leu Thr Gln Arg Ser Thr Lys Ser Val Glu Lys
    1970                1975                1980

Gly Val Gln Trp Arg Trp Asp Ala Phe Leu Arg Thr Arg Ala Gly
    1985                1990                1995

Ile Glu Phe Asn Gly Ile Ser Arg Arg Arg Tyr Leu Ala Leu Leu
    2000                2005                2010

Lys Asp Ile Gln Ala Pro Ile Thr Leu Ile Tyr Gly Asp Gln Ser
    2015                2020                2025

Glu Phe Asn Arg Pro Ala Asp Leu Gln Ala Ile Gln Ala Ala Leu
    2030                2035                2040

Pro Gln Ala Gln Arg Leu Thr Val Ala Gly Gly His Asn Leu His
    2045                2050                2055

Phe Glu Asn Pro Gln Ala Ile Ala Gln Ile Val Tyr Gln Gln Leu
    2060                2065                2070

Gln Thr Pro Val Pro Lys Thr Gln
    2075                2080

<210> SEQ ID NO 10
<211> LENGTH: 582
<212> TYPE: PRT
<213> ORGANISM: Lyngbya majuscula

<400> SEQUENCE: 10

Phe Ile Leu Ser Ser Pro Arg Ser Gly Ser Thr Leu Leu Arg Val Met
1               5                   10                  15

Leu Ala Gly His Ser Ser Leu Phe Ser Pro Pro Glu Leu His Leu Leu
            20                  25                  30

Pro Phe Asn Thr Met Lys Glu Arg Gln Glu Gln Leu Asn Leu Ser Tyr

```
            35                  40                  45
Leu Gly Glu Gly Leu Gln Lys Thr Phe Met Glu Val Lys Asn Leu Asp
     50                  55                  60

Ala Thr Ala Ser Gln Ala Leu Ile Lys Asp Leu Glu Ser Gln Asn Leu
 65                  70                  75                  80

Ser Ile Gln Gln Val Tyr Gly Met Leu Gln Glu Asn Ile Ala Pro Arg
                 85                  90                  95

Leu Leu Val Asp Lys Ser Pro Thr Tyr Ala Met Glu Pro Thr Ile Leu
            100                 105                 110

Glu Arg Gly Glu Ala Leu Phe Ala Asn Ser Lys Tyr Ile Tyr Leu Val
        115                 120                 125

Arg His Pro Tyr Ser Val Ile Glu Ser Phe Val Arg Met Arg Met Gln
    130                 135                 140

Lys Leu Val Gly Leu Gly Glu Gln Asn Pro Tyr Arg Val Ala Glu Gln
145                 150                 155                 160

Val Trp Ala Lys Ser Asn Gln Asn Ile Leu Asn Phe Leu Ser Gln Leu
                165                 170                 175

Glu Pro Glu Arg Gln His Gln Ile Arg Tyr Glu Asp Leu Val Lys Lys
            180                 185                 190

Pro Gln Gln Val Leu Ser Gln Leu Cys Asp Phe Leu Asn Val Pro Phe
        195                 200                 205

Glu Pro Glu Leu Leu Gln Pro Tyr Gln Gly Asp Arg Met Thr Gly Gly
    210                 215                 220

Val His Gln Lys Ser Leu Ser Ile Ser Asp Pro Asn Phe Leu Lys His
225                 230                 235                 240

Asn Thr Ile Asp Glu Ser Leu Ala Asp Lys Trp Lys Thr Ile Gln Leu
                245                 250                 255

Pro Tyr Pro Leu Lys Ser Glu Thr Gln Arg Ile Ala Ser Gln Leu Ser
            260                 265                 270

Tyr Glu Leu Pro Asn Leu Val Thr Thr Pro Thr Asn Gln Gln Pro Gln
        275                 280                 285

Val Ser Thr Thr Pro Ser Thr Glu Gln Pro Ile Met Glu Glu Lys Phe
    290                 295                 300

Leu Glu Phe Gly Gly Asn Gln Ile Cys Leu Cys Ser Trp Gly Ser Pro
305                 310                 315                 320

Glu His Pro Val Val Leu Cys Ile His Gly Ile Leu Glu Gln Gly Leu
                325                 330                 335

Ala Trp Gln Glu Val Ala Leu Pro Leu Ala Ala Gln Gly Tyr Arg Val
            340                 345                 350

Val Ala Pro Asp Leu Phe Gly His Gly Arg Ser Ser His Leu Glu Met
        355                 360                 365

Val Thr Ser Tyr Ser Ser Leu Thr Phe Leu Ala Gln Ile Asp Arg Val
    370                 375                 380

Ile Gln Glu Leu Pro Asp Gln Pro Leu Leu Val Gly His Ser Met
385                 390                 395                 400

Gly Ala Met Leu Ala Thr Ala Ile Ala Ser Val Arg Pro Lys Lys Ile
                405                 410                 415

Lys Glu Leu Ile Leu Val Glu Pro Leu Pro Ala Glu Glu Ser Lys
            420                 425                 430

Lys Glu Ser Ala Val Asn Gln Leu Thr Thr Cys Leu Asp Tyr Leu Ser
        435                 440                 445

Ser Thr Pro Gln His Pro Ile Phe Pro Asp Val Ala Thr Ala Ala Ser
    450                 455                 460
```

```
Arg Leu Arg Gln Ala Ile Pro Ser Leu Ser Glu Glu Phe Ser Tyr Ile
465                 470                 475                 480

Leu Ala Gln Arg Ile Thr Gln Pro Asn Gln Gly Gly Val Arg Trp Ser
            485                 490                 495

Trp Asp Ala Ile Ile Arg Thr Arg Ser Ile Leu Gly Leu Asn Asn Leu
        500                 505                 510

Pro Gly Gly Arg Ser Gln Tyr Leu Glu Met Leu Lys Ser Ile Gln Val
    515                 520                 525

Pro Thr Thr Leu Val Tyr Gly Asp Ser Ser Lys Leu Asn Arg Pro Glu
530                 535                 540

Asp Leu Gln Gln Gln Lys Met Thr Met Thr Gln Ala Lys Arg Val Phe
545                 550                 555                 560

Leu Ser Gly Gly His Asn Leu His Ile Asp Ala Ala Ala Leu Ala
                565                 570                 575

Ser Leu Ile Leu Thr Ser
            580

<210> SEQ ID NO 11
<211> LENGTH: 261
<212> TYPE: PRT
<213> ORGANISM: Lyngbya majuscula

<400> SEQUENCE: 11

Phe Ile Leu Ser Ser Pro Arg Ser Gly Ser Thr Leu Leu Arg Val Met
1               5                   10                  15

Leu Ala Gly His Ser Ser Leu Phe Ser Pro Glu Leu His Leu Leu
            20                  25                  30

Pro Phe Asn Thr Met Lys Glu Arg Gln Glu Gln Leu Asn Leu Ser Tyr
        35                  40                  45

Leu Gly Glu Gly Leu Gln Lys Thr Phe Met Glu Val Lys Asn Leu Asp
    50                  55                  60

Ala Thr Ala Ser Gln Ala Leu Ile Lys Asp Leu Glu Ser Gln Asn Leu
65                  70                  75                  80

Ser Ile Gln Gln Val Tyr Gly Met Leu Gln Glu Asn Ile Ala Pro Arg
                85                  90                  95

Leu Leu Val Asp Lys Ser Pro Thr Tyr Ala Met Glu Pro Thr Ile Leu
            100                 105                 110

Glu Arg Gly Glu Ala Leu Phe Ala Asn Ser Lys Tyr Ile Tyr Leu Val
        115                 120                 125

Arg His Pro Tyr Ser Val Ile Glu Ser Phe Val Arg Met Arg Met Gln
130                 135                 140

Lys Leu Val Gly Leu Gly Glu Glu Asn Pro Tyr Arg Val Ala Glu Gln
145                 150                 155                 160

Val Trp Ala Lys Ser Asn Gln Asn Ile Leu Asn Phe Leu Ser Gln Leu
                165                 170                 175

Glu Pro Glu Arg Gln His Gln Ile Arg Tyr Glu Asp Leu Val Lys Lys
            180                 185                 190

Pro Gln Gln Val Leu Ser Gln Leu Cys Asp Phe Leu Asn Val Pro Phe
        195                 200                 205

Glu Pro Glu Leu Leu Gln Pro Tyr Gln Gly Asp Arg Met Thr Gly Gly
    210                 215                 220

Val His Gln Lys Ser Leu Ser Ile Ser Asp Pro Asn Phe Leu Lys His
225                 230                 235                 240

Asn Thr Ile Asp Glu Ser Leu Ala Asp Lys Trp Lys Thr Ile Gln Leu
```

```
                        245                 250                 255

Pro Tyr Pro Leu Lys
            260

<210> SEQ ID NO 12
<211> LENGTH: 281
<212> TYPE: PRT
<213> ORGANISM: Lyngbya majuscula

<400> SEQUENCE: 12

Glu Lys Phe Leu Glu Phe Gly Gly Asn Gln Ile Cys Leu Cys Ser Trp
1               5                   10                  15

Gly Ser Pro Glu His Pro Val Val Leu Cys Ile His Gly Ile Leu Glu
            20                  25                  30

Gln Gly Leu Ala Trp Gln Glu Val Ala Leu Pro Leu Ala Ala Gln Gly
        35                  40                  45

Tyr Arg Val Val Ala Pro Asp Leu Phe Gly His Gly Arg Ser Ser His
    50                  55                  60

Leu Glu Met Val Thr Ser Tyr Ser Ser Leu Thr Phe Leu Ala Gln Ile
65                  70                  75                  80

Asp Arg Val Ile Gln Glu Leu Pro Asp Gln Pro Leu Leu Val Gly
                85                  90                  95

His Ser Met Gly Ala Met Leu Ala Thr Ala Ile Ala Ser Val Arg Pro
            100                 105                 110

Lys Lys Ile Lys Glu Leu Ile Leu Val Glu Leu Pro Leu Pro Ala Glu
        115                 120                 125

Glu Ser Lys Lys Glu Ser Ala Val Asn Gln Leu Thr Thr Cys Leu Asp
    130                 135                 140

Tyr Leu Ser Ser Thr Pro Gln His Pro Ile Phe Pro Asp Val Ala Thr
145                 150                 155                 160

Ala Ala Ser Arg Leu Arg Gln Ala Ile Pro Ser Leu Ser Glu Glu Phe
                165                 170                 175

Ser Tyr Ile Leu Ala Gln Arg Ile Thr Gln Pro Asn Gln Gly Gly Val
            180                 185                 190

Arg Trp Ser Trp Asp Ala Ile Ile Arg Thr Arg Ser Ile Leu Gly Leu
        195                 200                 205

Asn Asn Leu Pro Gly Gly Arg Ser Gln Tyr Leu Glu Met Leu Lys Ser
    210                 215                 220

Ile Gln Val Pro Thr Thr Leu Val Tyr Gly Asp Ser Ser Lys Leu Asn
225                 230                 235                 240

Arg Pro Glu Asp Leu Gln Gln Lys Met Thr Met Thr Gln Ala Lys
                245                 250                 255

Arg Val Phe Leu Ser Gly Gly His Asn Leu His Ile Asp Ala Ala Ala
            260                 265                 270

Ala Leu Ala Ser Leu Ile Leu Thr Ser
        275                 280

<210> SEQ ID NO 13
<211> LENGTH: 626
<212> TYPE: PRT
<213> ORGANISM: Salmonella typhimurium

<400> SEQUENCE: 13

Met Ser Phe Ser Glu Phe Tyr Gln Arg Ser Ile Asn Glu Pro Glu Ala
1               5                   10                  15

Phe Trp Ala Glu Gln Ala Arg Arg Ile Asp Trp Arg Gln Pro Phe Thr
```

-continued

```
                20                  25                  30
Gln Thr Leu Asp His Ser Arg Pro Pro Phe Ala Arg Trp Phe Cys Gly
                35                  40                  45
Gly Thr Thr Asn Leu Cys His Asn Ala Val Asp Arg Trp Arg Asp Lys
 50                  55                  60
Gln Pro Glu Ala Leu Ala Leu Ile Ala Val Ser Ser Glu Thr Asp Glu
 65                  70                  75                  80
Glu Arg Thr Phe Thr Phe Ser Gln Leu His Asp Glu Val Asn Ile Val
                85                  90                  95
Ala Ala Met Leu Leu Ser Leu Gly Val Gln Arg Gly Asp Arg Val Leu
                100                 105                 110
Val Tyr Met Pro Met Ile Ala Glu Ala Gln Ile Thr Leu Leu Ala Cys
                115                 120                 125
Ala Arg Ile Gly Ala Ile His Ser Val Val Phe Gly Gly Phe Ala Ser
                130                 135                 140
His Ser Val Ala Ala Arg Ile Asp Asp Ala Arg Pro Ala Leu Ile Val
145                 150                 155                 160
Ser Ala Asp Ala Gly Ala Arg Gly Gly Lys Ile Leu Pro Tyr Lys Lys
                165                 170                 175
Leu Leu Asp Asp Ala Ile Ala Gln Ala Gln His Gln Pro Lys His Val
                180                 185                 190
Leu Leu Val Asp Arg Gly Leu Ala Lys Met Ala Trp Val Asp Gly Arg
                195                 200                 205
Asp Leu Asp Phe Ala Thr Leu Arg Gln Gln His Leu Gly Ala Ser Val
210                 215                 220
Pro Val Ala Trp Leu Glu Ser Asn Glu Thr Ser Cys Ile Leu Tyr Thr
225                 230                 235                 240
Ser Gly Thr Thr Gly Lys Pro Lys Gly Val Gln Arg Asp Val Gly Gly
                245                 250                 255
Tyr Ala Val Ala Leu Ala Thr Ser Met Asp Thr Ile Phe Gly Gly Lys
                260                 265                 270
Ala Gly Gly Val Phe Phe Cys Ala Ser Asp Ile Gly Trp Val Val Gly
                275                 280                 285
His Ser Tyr Ile Val Tyr Ala Pro Leu Leu Ala Gly Met Ala Thr Ile
    290                 295                 300
Val Tyr Glu Gly Leu Pro Thr Tyr Pro Asp Cys Gly Val Trp Trp Lys
305                 310                 315                 320
Ile Val Glu Lys Tyr Gln Val Asn Arg Met Phe Ser Ala Pro Thr Ala
                325                 330                 335
Ile Arg Val Leu Lys Lys Phe Pro Thr Ala Gln Ile Arg Asn His Asp
                340                 345                 350
Leu Ser Ser Leu Glu Ala Leu Tyr Leu Ala Gly Glu Pro Leu Asp Glu
                355                 360                 365
Pro Thr Ala Ser Trp Val Thr Glu Thr Leu Gly Val Pro Val Ile Asp
                370                 375                 380
Asn Tyr Trp Gln Thr Glu Ser Gly Trp Pro Ile Met Ala Leu Ala Arg
385                 390                 395                 400
Ala Leu Asp Asp Arg Pro Ser Arg Leu Gly Ser Pro Gly Val Pro Met
                405                 410                 415
Tyr Gly Tyr Asn Val Gln Leu Leu Asn Glu Val Thr Gly Glu Pro Cys
                420                 425                 430
Gly Ile Asn Glu Lys Gly Met Leu Val Ile Glu Gly Pro Leu Pro Pro
                435                 440                 445
```

```
Gly Cys Ile Gln Thr Ile Trp Gly Asp Asp Ala Arg Phe Val Lys Thr
    450                 455                 460

Tyr Trp Ser Leu Phe Asn Arg Gln Val Tyr Ala Thr Phe Asp Trp Gly
465                 470                 475                 480

Ile Arg Asp Ala Glu Gly Tyr Tyr Phe Ile Leu Gly Arg Thr Asp Asp
                485                 490                 495

Val Ile Asn Ile Ala Gly His Arg Leu Gly Thr Arg Glu Ile Glu Glu
                500                 505                 510

Ser Ile Ser Ser Tyr Pro Asn Val Ala Glu Val Ala Val Val Gly Ile
                515                 520                 525

Lys Asp Ala Leu Lys Gly Gln Val Ala Val Ala Phe Val Ile Pro Lys
530                 535                 540

Gln Ser Asp Thr Leu Ala Asp Arg Glu Ala Ala Arg Asp Glu Glu Asn
545                 550                 555                 560

Ala Ile Met Ala Leu Val Asp Asn Gln Ile Gly His Phe Gly Arg Pro
                565                 570                 575

Ala His Val Trp Phe Val Ser Gln Leu Pro Lys Thr Arg Ser Gly Lys
                580                 585                 590

Met Leu Arg Arg Thr Ile Gln Ala Glu Gly Arg Asp Pro Gly Asp Leu
                595                 600                 605

Thr Thr Ile Asp Asp Pro Ala Ser Leu Gln Gln Ile Arg Gln Ala Ile
610                 615                 620

Glu Glu
625

<210> SEQ ID NO 14
<211> LENGTH: 410
<212> TYPE: PRT
<213> ORGANISM: Mus musculus

<400> SEQUENCE: 14

Met Ala Ala Ala Leu Leu Ala Arg Ala Arg Gly Pro Leu Arg Arg Ala
1               5                   10                  15

Leu Gly Val Arg Asp Trp Arg Arg Leu His Thr Val Tyr Gln Ser Val
                20                  25                  30

Glu Leu Pro Glu Thr His Gln Met Leu Arg Gln Thr Cys Arg Asp Phe
                35                  40                  45

Ala Glu Lys Glu Leu Val Pro Ile Ala Ala Gln Leu Asp Arg Glu His
    50                  55                  60

Leu Phe Pro Thr Ala Gln Val Lys Lys Met Gly Glu Leu Gly Leu Leu
65                  70                  75                  80

Ala Met Asp Val Pro Glu Glu Leu Ser Gly Ala Gly Leu Gly Tyr Leu
                85                  90                  95

Ala Tyr Ser Ile Ala Leu Glu Glu Ile Ser Arg Ala Cys Ala Ser Thr
                100                 105                 110

Gly Val Ile Met Ser Val Asn Asn Ser Leu Tyr Leu Gly Pro Ile Leu
                115                 120                 125

Lys Phe Gly Ser Ala Gln Gln Lys Gln Gln Trp Ile Thr Pro Phe Thr
130                 135                 140

Asn Gly Asp Lys Ile Gly Cys Phe Ala Leu Ser Glu Pro Gly Asn Gly
145                 150                 155                 160

Ser Asp Ala Gly Ala Ala Ser Thr Thr Ala Arg Glu Glu Gly Asp Ser
                165                 170                 175

Trp Val Leu Asn Gly Thr Lys Ala Trp Ile Thr Asn Ser Trp Glu Ala
```

```
                180             185             190
Ser Ala Thr Val Val Phe Ala Ser Thr Asp Arg Ser Arg Gln Asn Lys
            195                 200                 205
Gly Ile Ser Ala Phe Leu Val Pro Met Pro Thr Pro Gly Leu Thr Leu
            210                 215                 220
Gly Lys Lys Glu Asp Lys Leu Gly Ile Arg Ala Ser Ser Thr Ala Asn
225                 230                 235                 240
Leu Ile Phe Glu Asp Cys Arg Ile Pro Lys Glu Asn Leu Leu Gly Glu
                245                 250                 255
Pro Gly Met Gly Phe Lys Ile Ala Met Gln Thr Leu Asp Met Gly Arg
                260                 265                 270
Ile Gly Ile Ala Ser Gln Ala Leu Gly Ile Ala Gln Ala Ser Leu Asp
                275                 280                 285
Cys Ala Val Lys Tyr Ala Glu Asn Arg Asn Ala Phe Gly Ala Pro Leu
                290                 295                 300
Thr Lys Leu Gln Asn Ile Gln Phe Lys Leu Ala Asp Met Ala Leu Ala
305                 310                 315                 320
Leu Glu Ser Ala Arg Leu Leu Thr Trp Arg Ala Ala Met Leu Lys Asp
                325                 330                 335
Asn Lys Lys Pro Phe Thr Lys Glu Ser Ala Met Arg Lys Leu Ala Ala
                340                 345                 350
Ser Glu Ala Ala Thr Ala Ile Ser Ala Ile Gln Ile Leu Gly Ser Met
                355                 360                 365
Gly Tyr Val Thr Glu Met Pro Ala Glu Arg Tyr Tyr Arg Asp Ala Arg
                370                 375                 380
Ile Thr Glu Ile Tyr Glu Gly Thr Ser Glu Ile Gln Arg Leu Val Ile
385                 390                 395                 400
Ala Gly His Leu Leu Arg Ser Tyr Arg Ser
                405                 410

<210> SEQ ID NO 15
<211> LENGTH: 292
<212> TYPE: PRT
<213> ORGANISM: Escherichia coli

<400> SEQUENCE: 15

Thr Ala Lys Thr Ala Asn Gly Cys Glu Ala Val Cys Ile Phe Val Asn
1               5                   10                  15
Asp Asp Gly Ser Arg Pro Val Leu Glu Glu Leu Lys Lys His Gly Val
                20                  25                  30
Lys Tyr Ile Ala Leu Arg Cys Ala Gly Phe Asn Asn Val Asp Leu Asp
                35                  40                  45
Ala Ala Lys Glu Leu Gly Leu Lys Val Val Arg Val Pro Ala Tyr Asp
            50                  55                  60
Pro Glu Ala Val Ala Glu His Ala Ile Gly Met Met Met Thr Leu Asn
65                  70                  75                  80
Arg Arg Ile His Arg Ala Tyr Gln Arg Thr Arg Asp Ala Asn Phe Ser
                85                  90                  95
Leu Glu Gly Leu Thr Gly Phe Thr Met Tyr Gly Lys Thr Ala Gly Val
                100                 105                 110
Ile Gly Thr Gly Lys Ile Gly Val Ala Met Leu Arg Ile Leu Lys Gly
                115                 120                 125
Phe Gly Met Arg Leu Leu Ala Phe Asp Pro Tyr Pro Ser Ala Ala Ala
                130                 135                 140
```

```
Leu Glu Leu Gly Val Glu Tyr Val Asp Leu Pro Thr Leu Phe Ser Glu
145                 150                 155                 160

Ser Asp Val Ile Ser Leu His Cys Pro Leu Thr Pro Glu Asn Tyr His
            165                 170                 175

Leu Leu Asn Glu Ala Ala Phe Asp Gln Met Lys Asn Gly Val Met Ile
        180                 185                 190

Val Asn Thr Ser Arg Gly Ala Leu Ile Asp Ser Gln Ala Ala Ile Glu
    195                 200                 205

Ala Leu Lys Asn Gln Lys Ile Gly Ser Leu Gly Met Asp Val Tyr Glu
210                 215                 220

Asn Glu Arg Asp Leu Phe Phe Glu Asp Lys Ser Asn Asp Val Ile Gln
225                 230                 235                 240

Asp Asp Val Phe Arg Arg Leu Ser Ala Cys His Asn Val Leu Phe Thr
                245                 250                 255

Gly His Gln Ala Phe Leu Thr Ala Glu Ala Leu Thr Ser Ile Ser Gln
            260                 265                 270

Thr Thr Leu Gln Asn Leu Ser Asn Leu Glu Lys Gly Thr Cys Pro
        275                 280                 285

Asn Glu Leu Val
    290

<210> SEQ ID NO 16
<211> LENGTH: 522
<212> TYPE: PRT
<213> ORGANISM: Clostridium proponicum

<400> SEQUENCE: 16

Met Arg Lys Val Pro Ile Ile Thr Ala Asp Glu Ala Ala Lys Leu Ile
1               5                   10                  15

Lys Asp Gly Asp Thr Val Thr Thr Ser Gly Phe Val Gly Asn Ala Ile
                20                  25                  30

Pro Glu Ala Leu Asp Arg Ala Val Glu Lys Arg Phe Leu Glu Thr Gly
            35                  40                  45

Glu Pro Lys Asn Ile Thr Tyr Val Tyr Cys Gly Ser Gln Gly Asn Arg
50                  55                  60

Asp Gly Arg Gly Ala Glu His Phe Ala His Glu Gly Leu Leu Lys Arg
65                  70                  75                  80

Tyr Ile Ala Gly His Trp Ala Thr Val Pro Ala Leu Gly Lys Met Ala
                85                  90                  95

Met Glu Asn Lys Met Glu Ala Tyr Asn Val Ser Gln Gly Ala Leu Cys
            100                 105                 110

His Leu Phe Arg Asp Ile Ala Ser His Lys Pro Gly Val Phe Thr Lys
        115                 120                 125

Val Gly Ile Gly Thr Phe Ile Asp Pro Arg Asn Gly Gly Gly Lys Val
    130                 135                 140

Asn Asp Ile Thr Lys Glu Asp Ile Val Glu Leu Val Glu Ile Lys Gly
145                 150                 155                 160

Gln Glu Tyr Leu Phe Tyr Pro Ala Phe Pro Ile His Val Ala Leu Ile
                165                 170                 175

Arg Gly Thr Tyr Ala Asp Glu Ser Gly Asn Ile Thr Phe Glu Lys Glu
            180                 185                 190

Val Ala Pro Leu Glu Gly Thr Ser Val Cys Gln Ala Val Lys Asn Ser
        195                 200                 205

Gly Gly Ile Val Val Val Gln Val Glu Arg Val Val Lys Ala Gly Thr
    210                 215                 220
```

```
Leu Asp Pro Arg His Val Lys Val Pro Gly Ile Tyr Val Asp Tyr Val
225                 230                 235                 240

Val Val Ala Asp Pro Glu Asp His Gln Gln Ser Leu Asp Cys Glu Tyr
            245                 250                 255

Asp Pro Ala Leu Ser Gly Glu His Arg Arg Pro Glu Val Val Gly Glu
            260                 265                 270

Pro Leu Pro Leu Ser Ala Lys Lys Val Ile Gly Arg Arg Gly Ala Ile
            275                 280                 285

Glu Leu Glu Lys Asp Val Ala Val Asn Leu Gly Val Gly Ala Pro Glu
            290                 295                 300

Tyr Val Ala Ser Val Ala Asp Glu Gly Ile Val Asp Phe Met Thr
305                 310                 315                 320

Leu Thr Ala Glu Ser Gly Ala Ile Gly Gly Val Pro Ala Gly Gly Val
            325                 330                 335

Arg Phe Gly Ala Ser Tyr Asn Ala Asp Ala Leu Ile Asp Gln Gly Tyr
            340                 345                 350

Gln Phe Asp Tyr Tyr Asp Gly Gly Gly Leu Asp Leu Cys Tyr Leu Gly
            355                 360                 365

Leu Ala Glu Cys Asp Glu Lys Gly Asn Ile Asn Val Ser Arg Phe Gly
370                 375                 380

Pro Arg Ile Ala Gly Cys Gly Gly Phe Ile Asn Ile Thr Gln Asn Thr
385                 390                 395                 400

Pro Lys Val Phe Phe Cys Gly Thr Phe Thr Ala Gly Gly Leu Lys Val
            405                 410                 415

Lys Ile Glu Asp Gly Lys Val Ile Ile Val Gln Glu Gly Lys Gln Lys
            420                 425                 430

Lys Phe Leu Lys Ala Val Glu Gln Ile Thr Phe Asn Gly Asp Val Ala
            435                 440                 445

Leu Ala Asn Lys Gln Gln Val Thr Tyr Ile Thr Glu Arg Cys Val Phe
450                 455                 460

Leu Leu Lys Glu Asp Gly Leu His Leu Ser Glu Ile Ala Pro Gly Ile
465                 470                 475                 480

Gln Thr Gln Ile Leu Asp Val Met Asp Phe Ala Pro Ile Ile Asp Arg
            485                 490                 495

Asp Ala Asn Gly Gln Ile Lys Leu Met Asp Ala Ala Leu Phe Ala Glu
            500                 505                 510

Gly Leu Met Gly Leu Lys Glu Met Lys Ser
            515                 520

<210> SEQ ID NO 17
<211> LENGTH: 124
<212> TYPE: PRT
<213> ORGANISM: Clostridium proponicum

<400> SEQUENCE: 17

Glu Phe Lys Ile Ala Ile Val Asp Asp Leu Ala Gln Glu Ser Arg
1               5                   10                  15

Gln Ile Arg Val Asp Val Leu Asp Gly Glu Gly Gly Pro Leu Tyr Arg
            20                  25                  30

Met Ala Lys Ala Trp Gln Gln Met Tyr Gly Cys Ser Leu Ala Thr Asp
            35                  40                  45

Thr Lys Lys Gly Arg Gly Arg Met Leu Ile Asn Lys Thr Ile Gln Thr
        50                  55                  60

Gly Ala Asp Ala Ile Val Val Ala Met Met Lys Phe Cys Asp Pro Glu
65                  70                  75                  80
```

```
Glu Trp Asp Tyr Pro Val Met Tyr Arg Glu Phe Glu Glu Lys Gly Val
                85                  90                  95
Lys Ser Leu Met Ile Glu Val Asp Gln Glu Val Ser Ser Phe Glu Gln
            100                 105                 110
Ile Lys Thr Arg Leu Gln Ser Phe Val Glu Met Leu
        115                 120

<210> SEQ ID NO 18
<211> LENGTH: 17
<212> TYPE: PRT
<213> ORGANISM: Streptomyces antibioticus

<400> SEQUENCE: 18

Ser Ser Ser Ala Gly Ile Asp Pro Gly Arg Ala Phe Gln Asp Met Gly
1               5                   10                  15
Ile

<210> SEQ ID NO 19
<211> LENGTH: 17
<212> TYPE: PRT
<213> ORGANISM: Saccharopolyspora erythraea

<400> SEQUENCE: 19

Ala Ser Ala Glu Arg Val Pro Ala Asp Gln Ala Phe Ala Glu Leu Gly
1               5                   10                  15
Val
```

PRODUCING ALPHA-OLEFINS USING POLYKETIDE SYNTHASES

CROSS-REFERENCE TO RELATED APPLICATIONS

This application is a continuation of U.S. application Ser. No. 13/876,727 filed Jun. 24, 2013, which is a national phase of PCT/US2011/053787 filed Sep. 28, 2011, which claims priority to U.S. provisional Application No. 61/387,435 filed Sep. 28, 2010, all of which are incorporated herein by reference in their entirety.

STATEMENT OF GOVERNMENTAL SUPPORT

This invention was made with government support under Contract No. DE-AC02-05CH11231 awarded by the U.S. Department of Energy and Award No. 0540879 awarded by the National Science Foundation. The government has certain rights in the invention

REFERENCE TO A SEQUENCE LISTING SUBMITTED AS A TEXT FILE

The Sequence Listing written in file SEQTXT_77429-011110US-0958337.TXT, created on Sep. 14, 2015, 237,019 bytes, machine format IBM-PC, MS-Windows operating system, is hereby incorporated by reference.

FIELD OF THE INVENTION

This invention relates generally to α-olefin production using polyketide synthases and so relates to the fields of chemistry, microbiology, and molecular biology.

BACKGROUND OF THE INVENTION

Type I polyketide synthases (PKSs) are programmable, multifunctional enzymes capable of possessing all of the catalytic capacity of fatty-acid synthases (FASs). However, unlike the FAS enzyme, which iteratively extends and fully reduces the β-carbonyl generated with each extension of the hydrocarbon backbone, PKS systems utilize discrete sets of enzymatic domains for each extension and reduction of the nascent chain. These sets, commonly referred to as modules, can incorporate a variety of extenders units resulting in different side chains. They also can encode between zero and three of the reducing domains associated with FASs, respectively leading to a ketone, hydroxy, double bond, or fully saturated carbon at the beta position of the growing polyketide chain (Hopwood and Sherman. 1990. Annual Review of Genetics 24:37-66).

Due to their modularity, PKS systems have been extensively explored for production of "unnatural" natural products (Weissman and Leadlay. 2005. Nature Reviews Microbiology 3:925-936). Hundreds of these molecules have been produced, ranging from basic lactones to modified versions of drugs and drug-like compounds.

SUMMARY OF THE INVENTION

The present invention provides polyketide synthases (PKSs) capable of synthesizing α-olefins, recombinant expression vectors for producing them, recombinant host cells that express them and produce the desired alpha olefin, methods for making alpha olefins, and alpha olefins produced by the methods. The PKSs of the invention are not naturally occurring and so are referred to as "recombinant" PKS enzymes. In some embodiments of the invention, the α-olefin is not a compound synthesized by a naturally occurring PKS. In some embodiments of the invention, the PKS is a hybrid PKS comprising modules and/or portions thereof, from two, three, four or more naturally occurring PKSs. A hybrid PKS can contain naturally occurring modules from two or more naturally occurring PKSs and/or it can contain one or more modules composed of portions, including intact domains, of two or more modules from the same naturally occurring PKS or from two or more naturally occurring PKS, or both. In some embodiments of the invention, a recombinant nucleic acid comprising a CurM module or portion thereof, which may be either naturally occurring or recombinant, is employed.

The present invention provides recombinant nucleic acids that encode PKSs of the invention. The recombinant nucleic acids include nucleic acids that include a portion or all of a PKS of the invention, nucleic acids that further include regulatory sequences, such as promoter and translation initiation and termination sequences, and can further include sequences that facilitate stable maintenance in a host cell, i.e., sequences that provide the function of an origin of replication or facilitate integration into host cell chromosomal or other DNA by homologous recombination. In some embodiments, the recombinant nucleic acid is stably integrated into a chromosome of a host cell. In some embodiments, the recombinant nucleic acid is a plasmid. Thus, the present invention also provides vectors, including expression vectors, comprising a recombinant nucleic acid of the present invention. The present invention also provides host cells comprising any of the recombinant nucleic acid and/or PKS of the present invention. In some embodiments, the host cell, when cultured under suitable conditions, is capable of producing the α-olefin. These host cells include, for example and without limitation, prokaryotes such as *E. coli* species, *Bacillus* species, *Streptomyces* species, *Myxobacterial* species, as well as eukaryotes including but not limited to yeast and fungal strains.

Thus, the present invention provides a wide variety of host cell comprising one or more of the recombinant nucleic acids and/or PKSs of the present invention. In some embodiments, the host cell, when cultured, is capable of producing an α-olefin that it otherwise does not produce, or produces at a lower level, in the absence of a nucleic acid of the invention.

The present invention provides methods for producing α-olefins, said methods generally comprising: providing a host cell of the present invention, and culturing said host cell in a suitable culture medium under suitable conditions such that the α-olefin is produced.

The present invention also provides compositions comprising an α-olefin from a host cell in which the α-olefin was produced, and in some embodiments may include trace residues and/or other components of the host cell. Such trace residues and/or other components may include, for example, cellular material produced by the lysis of the host cell. The present invention also provides methods of purifying α-olefins and methods for converting them to other useful products.

BRIEF DESCRIPTION OF THE DRAWINGS

The foregoing aspects and embodiments of the invention as well as others will be readily appreciated by the skilled artisan from the following detailed description of illustrative embodiments when read in conjunction with the accompanying drawings.

(FIG. 3A) a PKS system that can be used to produce 1-hexene in accordance with the invention, (FIG. 3B) how additional modules can be added to yield longer, even-chain α-olefins, and (FIG. 3C) how changing the loading module to incorporate acetate (from malonyl-CoA) will allow access to the saturated, linear, odd-chain α-olefins in accordance with the methods of the invention.

FIG. 4A shows an embodiment of the invention that illustrates utilization of the avermectin PKS loading module. The side chains illustrated (FIG. 4B) are merely examples and do not constitute the entire pool of side chains that can be incorporated using the avermectin loading module (or similar loading modules) in accordance with the methods and teaching of the invention.

FIGS. 5A-B show, in part (FIG. 5A), an example of an illustrative pathway to 3-methylenepent-4-enoic acid, an example of the carboxylated butadiene derivatives accessible using PKSs in accordance with the methods of the invention and how the distance between the diene and carboxylate moieties can be increased via the use of additional PKS modules. FIG. 5B shows the proposed mechanism of the exomethylene biosynthesis from the jamaicamide pathway (see Edwards et al. 2004. Chem Biol. 11(6):817-33; incorporated herein by reference).

FIG. 6 shows a PKS for producing butadiene in accordance with the methods of the invention. While this invention is not to be limited in any manner by any proposed mechanism of action recited or shown herein, this figure, for simplicity, illustrates loss of the hydroxyl group as a water molecule, the enzymatic mechanism utilizes sulfate as a leaving group.

FIGS. 7A-G show a PKS for producing butadiene in accordance with the methods of the invention. FIG. 7A and FIG. 7B show the loading of the acrylyl-CoA using the DEBS propionyl-CoA specific loading domain modified to accept acrylyl-CoA. FIG. 7C shows the thiotransfer of the acrylate moiety to KS domain. FIG. 7D shows the binding of the malonyl-CoA and transfer to ACP domain. FIG. 7E shows KS catalyzing the condensation of the moiety with release of $CO_2$. FIG. 7F shows KR catalyzing the reduction of the β-carbonyl group. FIG. 7G shows the final step and the release of the butadiene, $CO_2$, and water (as in FIG. 6, the loss of the hydroxyl group is illustrated with a water molecule, but the enzymatic mechanism utilizes sulfate as a leaving group).

FIG. 12A shows the loading of the acrylyl-CoA using the DEBS propionyl-CoA specific loading domain modified to accept acrylyl-CoA, and extension with malonyl-CoA to form the beta-keto ACP bound intermediate. FIG. 12B through FIG. 12F show the HMG-CoA-like mechanism involved in the replacement of the β-carbonyl group with a methyl group using PKS enzymes from the PKSX (Bacillaene) cluster from *Bacillus subtilis* (Butcher, et al. 2007. Proc Natl Acad Sci USA. 104(5):1506-9; incorporated herein by reference). This invention is not to be limited by any proposed mechanism shown herein. In this embodiment, the penultimate product is released as the free acid and subsequently decarboxylated to isoprene in accordance with the methods of the invention by either a decarboxylase, or extracellular chemical catalysis/pyrolysis.

DETAILED DESCRIPTION

Figure 1:
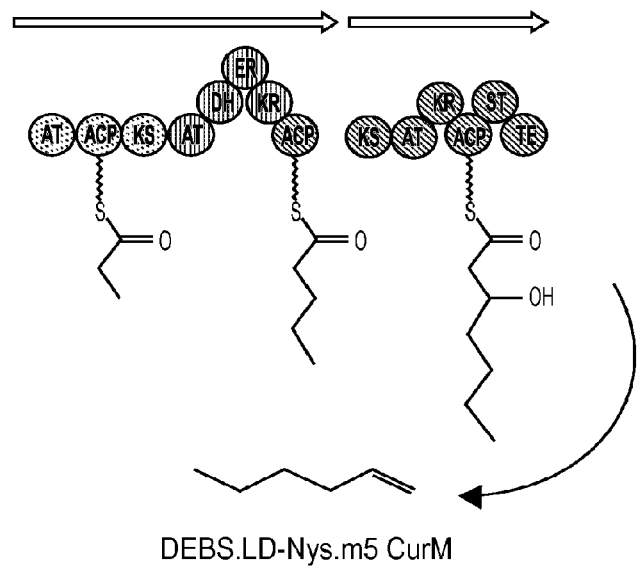
FIG. 1 shows an illustrative example of the modular organization of a biosynthetic pathway suitable for synthesizing 1-hexene in accordance with the invention. In this illustration, the proposed modules are sourced from the loading module of DEBS1 from the erythromycin PKS, module 5 from the nystatin PKS NysC, and CurM the terminal module of the curacin PKS. In another embodiment of the invention, the nystatin PKS module 5 is replaced with portions of modules 9 and 10 from the indanomycin PKS; this alternative embodiment has actually been used to produce 1-hexene.

This invention is not limited to particular embodiments described, as such may, of course, vary. The terminology used herein is for the purpose of describing particular embodiments only, and is not intended to be limiting, because the scope of the present invention will be limited only by the appended claims.

Where a range of values is provided, each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention.

Unless defined otherwise, all technical and scientific terms used herein have the meaning commonly understood by one of ordinary skill in the art to which this invention belongs. Although any methods and materials similar or equivalent to those described herein can be used in practicing the present invention, suitable methods and materials are now described. All publications cited are incorporated herein by reference to disclose and describe the methods and/or materials and/or results therein.

As used herein and in the appended claims, the singular forms "a", "and", and "the" include plural referents unless the context clearly dictates otherwise. Thus, for example, reference to "an α-olefin" includes a plurality of such α-olefins, and so forth.

The term "even-chain α-olefin" refers to an α-olefin with a carbon backbone, which, disregarding any functional groups or substituents, has an even number of carbon atoms.

The term "odd-chain α-olefin" refers to an α-olefin with a carbon backbone, which, disregarding any functional groups or substituents, has an odd number of carbon atoms.

The term "functional variant" describes an enzyme that has a polypeptide sequence that is at least 70%, 75%, 80%, 85%, 90%, 95% or 99% identical to an enzyme described herein. A "functional variant" enzyme may retain amino acids residues recognized as conserved for the enzyme in nature, and/or may have non-conserved amino acid residues. Amino acids can be, relative to the native enzyme, substituted (different), inserted, or deleted, but the variant has generally similar enzymatic activity as compared to an enzyme described herein. A "functional variant" enzyme may be found in nature or be an engineered mutant (recombinant) thereof.

The objects, advantages, and features of the invention will become more apparent to those persons skilled in the art upon reading the details of the invention as more fully described below.

Polyketide Synthases (PKS)

The present invention provides recombinant polyketide synthase (PKS) enzymes capable of synthesizing an α-olefin. The PKS enzymes of the invention are not naturally occurring PKS. In some embodiments of the invention, the α-olefin is not a compound synthesized by a naturally occurring PKS. In some embodiments of the invention, the PKS is a hybrid PKS comprising modules, domains, and/or portions thereof, or functional variants thereof, from two or more PKSs. Such α-olefins include the diketides and triketides, and polyketides of more than three ketide units, such as 4, 5, or 6 or more ketide units. The α-olefin can further include one or more functional groups in additional to the double bond that characterizes them. Such functional groups include, but are not limited to, ethyl, methyl and hydroxy side chains, internal olefins, and ketones.

In some embodiments of the invention, the α-olefin is an even-chain α-olefin having the following chemical structure:

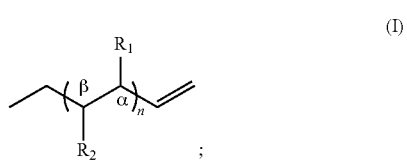
(I)

wherein each $R_1$ is independently —H or —CH$_3$, each $R_2$ is independently —H or —OH, n is an integer, and αβ is a single or double bond, with the proviso that when an αβ is a double bond then the corresponding $R_2$ is H. In some embodiments of the invention, n is an integer from 1 to 10. n indicates the number of two-carbon-chain subunits in the carbon backbone of the α-olefin. The $R_1$, $R_2$, and αβ within each two-carbon-subunit of a multiple subunit α-olefin is independent of the $R_1$, $R_2$, and αβ of any other two-carbon-subunit in the molecule. In some embodiments, however, one or more, up to all, subunits have identical $R_1$, $R_2$, and αβ.

In some embodiments of the invention, the α-olefin has the following chemical structure:

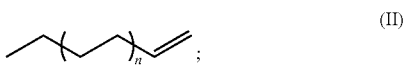
(II)

wherein n is an integer from 0 to 10.

In one embodiment, the invention provides methods, host cells, and nucleic acids for making the C3-alpha olefins propylene (propene) and polymers and products derived therefrom, including but not limited to: polypropylene, acylonitrile, propylene oxide, alcohols, cumene, acrylic acid, injection molded plastics, electronics, electrical appliances, housewares, bottle caps, toys, luggage, films, fibers, carpets, clothing, ropes, pipes, conduit, wire, cable, elastomeric polymers, acrylic fibers, nitrile rubber, acrylonitrile-butadiene-styrene (ABS) resins, styrene-acrylonitrile (SAN) resins, acrylamide, adiponitrile, polyether polyols, polyurethanes, flexible foams, rigid foams, insulation, propylene glycol, polyester resins, antifreeze, de-icing fluids, propylene glycol ethers, paints, coatings, inks, resins, cleaners, isopropanol, cosmetics, pharmaceuticals, food, ink, adhesives, 2-ethylhexanol, phthalate plasticizers, phenol, acetone, polycarbonate, phenolic resins, epoxy resins, methyl methacrylate (MMA), and acrylic esters.

In one embodiment, the invention provides methods, host cells, and nucleic acids for making the C4-alpha olefin butene and polymers and products derived therefrom, including but not limited to: polybutylene, copolymers with ethylene and/or propene, hot-melt adhesives, synthetic rubber, diesel fuel, and jet fuel.

In one embodiment, the invention provides methods, host cells, and nucleic acids for making the C4 diolefin butadiene and polymers and products derived therefrom, including but not limited to: styrene butadiene rubber (SBR), polybutadiene rubber, acrylonitrile butadiene styrene (ABS), styrene butadiene (SB) copolymer latex, nitrile rubber, adiponitrile, chloroprene, butanediol, tetrahydrofuran, tires, adhesives, coatings, high impact polystyrene, thermoplastic resins, engineering nylons (from C12 lactam), paper coating, gaskets and seals, hoses, gloves, nylon fibers, polymers, wet suits, electrical insulation, polybutylene terephthalate, spandex, and binders. Butadiene has the following chemical structure:

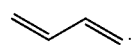

In one embodiment, the invention provides methods, host cells, and nucleic acids for making the C5 α olefin: 1-pentene and polymers and products derived therefrom, including but not limited to: gasoline, polymers, adhesives, sealants, diesel fuel, and jet fuel.

In one embodiment, the invention provides methods, host cells, and nucleic acids for making the C6 α-olefin (see FIG. 1, example): 1-hexene and polymers and products derived therefrom, including but not limited to comonomer, polyethylene, polymer, high density polyethylene (HDPE), linear low density polyethene (LLDPE), 1-heptanal, heptanoic acid, resin, film, plastic pipe, containers, diesel fuel, and jet fuel. 1-hexene has the following chemical structure:

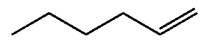

and an illustration of a 1-hexene producing PKS is provided in FIG. 1.

In one embodiment, the invention provides methods, host cells, and nucleic acids for making the C10 α-olefin: 1-decene and polymers and products derived therefrom, including but not limited to: detergent formulations, linear alkyl benzene (LAB), linear alkyl benzene sulfonate (LABS), polyalphaolefin synthetic lubricant basestocks (PAO), heat-shrink materials, electrical insulation sleeves, rash guards in clothing, polyolefin elastomers (POE), flexible foams, footwear, seat cushions, armrests, pillows, radar coolants, strings, polyol esters, detergent alcohols, plasticizer alcohols, specialty chemicals, epoxides, derivatives thereof, comonomer, intermediate in production of epoxides, amines, oxo alcohols, synthetic lubricants, synthetic fatty acids, alkylated aromatics, emulsifiers, performance waxes, cosmetic formulations, viscosity controller, solvent, decene butene copolymer, binder, film forming, decene/PVP copolymer, food additives, glazing agent, anti-foaming agent, anti-dusting agent, white mineral oil substitute, polishing agent, well fluids, alpha olefin oligomers, and the like. 1-decene has the following chemical structure:

In one embodiment, the invention provides methods, host cells, and nucleic acids for making the C8 aromatic α-olefin: styrene and polymers and products derived therefrom, including but not limited to: homopolymers, copolymers, polystyrene, expandable polystyrene (EPS), acrylonitrile-butadiene-styrene (ABS), resins, styrene-acrylonitrile (SAN), acrylonitrile-styrene-acrylate (ASA), styrene butadiene, styrene butadiene rubber, copolymer with maleic anhydride, terephthalate, unsaturated polyester resins, containers, closures, lids and vending cups, construction; electrical and electronic parts; domestic appliances and housings; household goods and home furnishings; and toys, sporting goods and recreational articles, packaging, thermoplastics, cutlery, CDs, insulating materials, polymer bonded explosives, consumer products, renewable plastics, renewable products, hardhats, tires, etc. In some embodiments of the invention, the aromatic α-olefin has the following chemical structure:

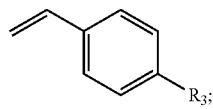
(III)

wherein R₃ is —H, —OH, —NH₃, or —NO₂.

Alpha olefins are commonly used in the cosmetics and skin care industry, and the present invention therefore provides useful starting materials for making cosmetics and skin care products. For example, alpha olefin sulfonate, sulfate free personal cleaners, soap, copolymer maleic acid, and the like are all used in these industries and provided by the invention. Alpha olefins provide by the invention can also be used in the flavor and fragrance industry. For example, 3-hydroxy-1-octene and 3-oxo-1-octene can be made using the methods and materials of the invention and are used in applications where a mushroom flavor/fragrance is desired.

The present invention can also be used to generate intermediates useful in the synthesis of pharmaceuticals. These olefins can be coupled via olefin metathesis to one another or other olefin intermediates obtained via traditional chemical syntheses to yield bioactive molecules useful as drugs.

In some embodiments, the α-olefin produced in accordance with the invention is (E)-deca-1,5-diene, which has the following chemical structure:

In some embodiments, the α-olefin produced in accordance with the invention has the following chemical structure:

(IV)

wherein R is one of the following structures:

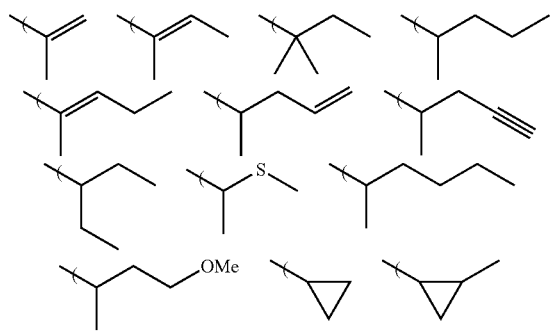

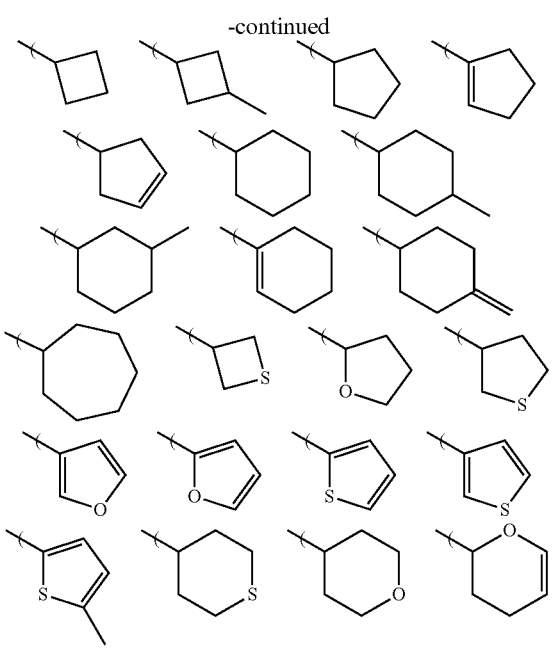

In some embodiments, the α-olefin produced in accordance with the invention is a polyolefin having chemical structure (I) and comprising at least two, three, four, five, or more C—C double bonds. Such α-olefins include, but are not limited to, diolefins, such as diolefins with two C—C double bonds on the carbon backbone. Such diolefins include, but are not limited to, butadiene, isoprene, and penta-1,3-diene. Butadiene has the chemical structure shown in [0043], above.

In some embodiments, the α-olefin produced in accordance with the invention is isoprene, which has the following chemical structure:

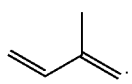

In some embodiments, the α-olefin produced in accordance with the invention is penta-1,3-diene, which has the following chemical structure:

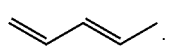

Complex polyketides comprise a large class of natural products that are synthesized in bacteria (mainly members of the actinomycete family; e.g. *Streptomyces*), fungi and plants. Polyketides form the macrolactone component of a large number of clinically important drugs, such as antibiotics (e.g. erythromycin, tylosin), antifungal agents (e.g. nystatin), anticancer agents (e.g. epothilone), immunosuppressives (e.g. rapamycin), etc. Though these compounds do not resemble each other either in their structure or their mode of action, they share a common basis for their biosynthesis, which is carried out by a group of enzymes designated polyketide synthases.

Polyketide synthases (PKS) employ short chain fatty acyl CoAs in Claisen condensation reactions to produce polyketides. Unlike fatty acid synthases that utilize acetyl CoA as the starter and malonyl CoA as the extender units, and use a single module iteratively to produce the nascent acyl chains, PKSs are composed of discrete modules, each catalyzing the chain growth of a single step. Modules can differ from each other in composition, so that, overall, a number of different starters (e.g. acetyl CoA, propionyl CoA) and extenders, some of which contain stereospecific methyl (or ethyl) side chains can be incorporated into a polyketide. In addition, PKS modules do not always reduce the 3-carbonyl formed from condensation but may leave it either unreduced (ketone), partially reduced (hydroxyl, 2,3-ene), or fully reduced (3-methylene). Many PKSs employ malonyl CoA or [S]-2-methylmalonyl CoA as the starter for polyketide synthesis. In such cases, the terminal carboxyl group is usually removed by a decarboxylase domain present at the N-terminus of the loading domain of the PKS. Thus, the structure (and chirality) of the α-carbon and β-carbonyl is determined by the module of the PKS employed in the synthesis of the growing chain at each particular step. Because of the correspondence between the modules used in the synthesis and the structure of the polyketide produced, it is possible to program PKS synthesis to produce a compound of desired structure by selection and genetic manipulation of polyketide synthases.

Figure 2:
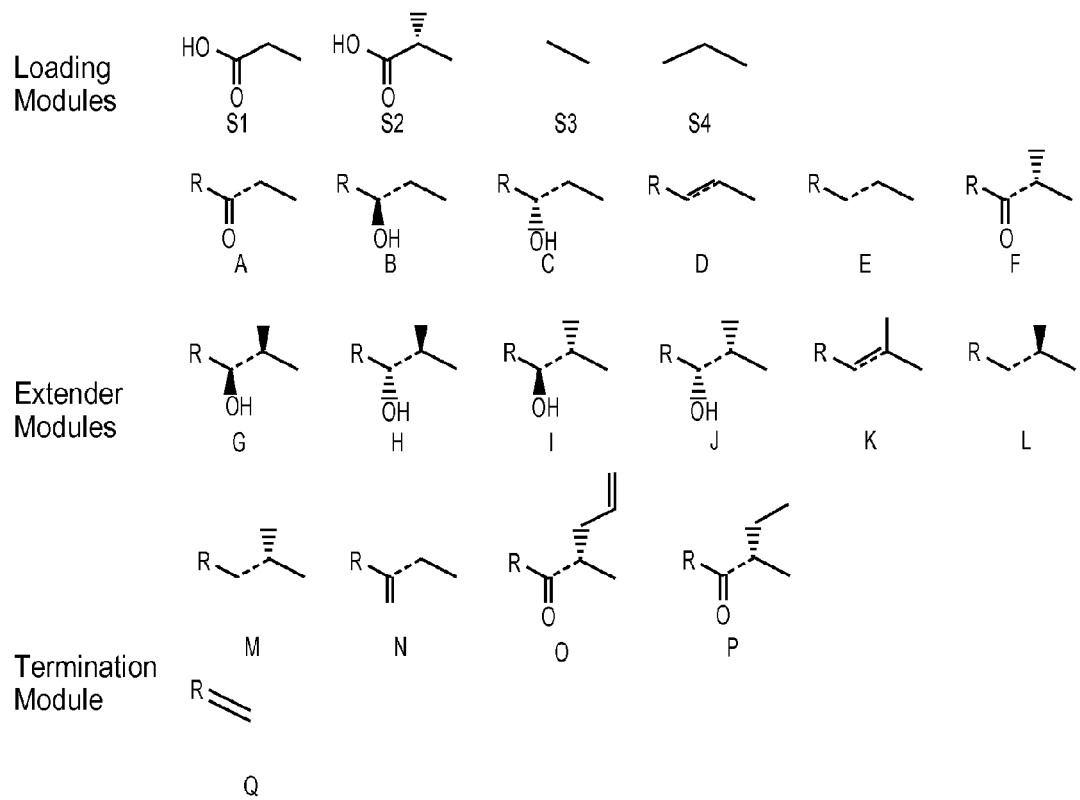
FIG. 2 shows types of modules employed and corresponding precursors utilized for incorporation into polyketide chains. The loading module is designated S. While any suitable loading domain can be used (such as those loading acetate and benzoic acid), only two examples are illustrated in this figure. The remaining compounds represent the structures incorporated into the growing polyketide chain employing extender modules A-P. The dashed line indicates the C—C bond formed through Claisen condensation; atoms to the right of the bond and the C atom at the left of the dashed line represent the structures determined by the module employed. The R group represents the existing acyl chain prior to incorporation determined by the module.

FIG. 2 shows the various modules and the precursor utilized by each module for incorporation into the corresponding nascent acyl (polyketide) chain to give rise to a range of compounds of interest. Table 1, below, provides illustrative PKS sources for each module in FIG. 2. Each PKS source (amino acid sequence and corresponding coding sequence) is well-known to one skilled in the art and readily available. In addition, for each module in Table 1, there are other modules from other PKS (or from recombinant DNA technology) that can be used. In addition, other structures can be incorporated in the ketide or polyketide that are not shown in Table 1 and FIG. 2. For example, useful loading modules includer the benzoate loading module of soraphen PKS, the isobutyrate loading module of the lipomycin PKS and bafilomycin PKS, and the acrylate loading module from the dificidin pathway. The acrylate loading module from the dificidin PKS loads and dehydrates a hydroxypropionate molecule by the use of enzymes difA-E to yield a PKS with an arylyl-ACP (Chen, 2006, J. Bact. 188:4024-4036; incorporated herein by reference).

The present invention also contemplates the use of functional variants of PKS modules, domains, and portions thereof. In one important embodiment, the invention provides a variety of recombinant modules that carry out the same enzymatic reactions conducted by the CurM module.

TABLE 1

PKS sources of the various modules.

| Module | PKS Source |
|---|---|
| S1 | Spiramycin PKS Loading Domain (with and without inactivation or deletion of the KS$^Q$ domain) |
| S2 | Pikromycin PKS Loading Domain (with and without inactivation or deletion of the KS$^Q$ domain) |
| S3 | Spiramycin PKS Loading Domain |
| S4 | Erythromycin PKS Loading Domain |
| A | Rifamycin PKS Module 2 |
| B | Oligomycin PKS Module 1 |
| C | Spiramycin PKS Module 1 |
| D | Pikromycin PKS Module 2 |
| E | Oligomycin PKS Module 3 |
| F | Erythromycin PKS Module 3 |
| G | Oligomycin PKS Module 5 |

TABLE 1-continued

PKS sources of the various modules.

| Module | PKS Source |
|---|---|
| H | Primaricin PKS Module 7 |
| I | Tylosin PKS Module 1 |
| J | Erythromycin PKS Module 1 |
| K | Avermectin PKS Module 7 |
| L | Rapamycin PKS Module 1 |
| M | Erythromycin PKS Module 4 |
| N | Pederin Module 2 |
| O | Ascomycin Module 4 |
| P | FK506 Module 4 |
| Q | Curacin A Chain Termination Module (CurM) |

All extender modules carry the β-acyl ACP synthase (commonly called the ketosynthase or KS) domain, which conducts the decarboxylative condensation step between the extender and the growing polyketide chain, and the acyl carrier protein (ACP) domain that carries the growing acyl chain and presents it to any cognate reductive domains for reduction of the β-carbonyl. Modules can differ from each other in composition so that a number of different starter and extender units, some of which contain stereospecific side chains (e.g. methyl, ethyl, propylene) can be incorporated. The acyltransferase (AT) domain of each module determines the extender unit (e.g. malonyl CoA, methylmalonyl CoA, and the like) incorporated. In addition, PKS modules do not always reduce the β-carbonyl formed from condensation but may leave it either unreduced (ketone), partially reduced (hydroxyl, 2,3-ene) or fully reduced (3-methylene), as shown in FIG. 2. The ketoreductase (KR) domain reduces the ketone to the OH function (stereospecifically); the dehydratase (DH) domain removes water from the α and β carbons leaving an α,β trans-double bond; the enoylreductase (ER) domain reduces the double bond to a β-methylene center; the reductive state of the β-carbonyl, therefore, is determined by the presence of functional reductive domains in the corresponding module. Less commonly, modules may contain an additional C-methylation domain (yielding an additional α-methyl side chain, as in epothilone).

The Curacin A Chain Termination Module is annotated as CurM. CurM catalyzes an extension of the nascent polyketide molecule with acetate (from malonyl-CoA). The resulting beta carbonyl is reduced to a hydroxyl group by a KR domain. The resulting beta hydroxyl group is then sulfonated by the ST domain (from the common metabolic precursor 3'-phosphoadenosine-5'-phosphosulfate). The TE domain releases the 3-sulfo polyketide which then undergoes loss of sulfate and a decarboxylation to form a terminal olefin moiety. The chain termination module of the PKS of the present invention can comprise the ST and TE domains of the CurM Chain Termination Module and variants thereof with similar activity. Additional PKS modules carrying the combination of a sulfotransferase (pfam00685)/thioesterase have been identified in nature and can be used in additional embodiments of the invention. One such olefination module (Ols) has been characterized from *Synechococcus* sp. strain PCC 7002 (Mendez-Perez et al. 2011. Appl. Env. Microbiol. 77:4264-4267 2011). Others include, but are not limited to, PKS enzymes from *Cyanothece* sp. PCC 7424, *Cyanothece* sp. PCC 7822, *Prochloron didemni* P1-Palau, *Pseudomonas entomophila* L48, and *Haliangium ochraceum* DSM 14365. The present invention also provides consensus sequences that differ from these naturally occurring sequences but encode similar enzymatic activities.

The makeup of the PKS, therefore, determines the choice of starter and extender acyl units incorporated, the extent of reduction at each condensation step, and the total number of units added to the chain. The wide diversity of structures of polyketides seen in nature is thus attributable to the diversity in PKS enzymes.

A partial list of PKS amino acid and corresponding nucleic acid coding sequences that can be used in the PKSs of the present invention includes, for illustration and not limitation, Ambruticin (U.S. Pat. No. 7,332,576); Avermectin (U.S. Pat. No. 5,252,474; MacNeil et al., 1993, Industrial Microorganisms: Basic and Applied Molecular Genetics, Baltz, Hegeman, & Skatrud, eds. (ASM), pp. 245-256; MacNeil et al., 1992, Gene 115: 119-25); Candicidin (FR0008) (Hu et al., 1994, Mol. Microbiol. 14: 163-72); Curacin A (Chang et al., 2004, *J. Nat. Prod.*, 67 (8), pp 1356-1367; Gu et al., 2009, *J. Am. Chem. Soc.*, 131 (44), pp 16033-16035); Epothilone (U.S. Pat. No. 6,303,342); Erythromycin (WO 93/13663; U.S. Pat. No. 5,824,513; Donadio et al., 1991, Science 252:675-79; Cortes et al., 1990, Nature 348:176-8); FK506 (Motamedi et al., 1998, Eur. J. Biochem. 256:528-34; Motamedi et al., 1997, Eur. J. Biochem. 244: 74-80); FK520 or ascomycin (U.S. Pat. No. 6,503,737; see also Nielsen et al., 1991, Biochem. 30:5789-96); Jerangolid (U.S. Pat. No. 7,285,405); Leptomycin (U.S. Pat. No. 7,288, 396); Lovastatin (U.S. Pat. No. 5,744,350); Nemadectin (MacNeil et al., 1993, supra); Niddamycin (Kakavas et al., 1997, J. Bacteriol. 179:7515-22); Oleandomycin (Swan et al., 1994, Mol. Gen. Genet. 242:358-62; U.S. Pat. No. 6,388,099; Olano et al., 1998, Mol. Gen. Genet. 259:299-308); Pederin (PCT publication no. WO 2003/044186); Pikromycin (Xue et al., 2000, Gene 245:203-211); Pimaricin (PCT publication no. WO 2000/077222); Platenolide (EP Pat. App. 791,656); Rapamycin (Schwecke et al., 1995, Proc. Natl. Acad. Sci. USA 92:7839-43); Aparicio et al., 1996, Gene 169:9-16); Rifamycin (August et al., 1998, Chemistry & Biology, 5: 69-79); Soraphen (U.S. Pat. No. 5,716,849; Schupp et al., 1995, J. Bacteriology 177: 3673-79); Spiramycin (U.S. Pat. No. 5,098,837); and Tylosin (EP 0 791,655; Kuhstoss et al., 1996, Gene 183:231-36; U.S. Pat. No. 5,876,991); each of the foregoing references is incorporated herein by reference. Additional suitable PKS coding are readily available to one skilled in the art (e.g., by cloning and sequencing of DNA from polyketide producing organisms or by reference to GenBank).

Of the more than one hundred PKSs studies and reported on in the scientific literature, the correspondence between the modules used in the biosynthesis of, and the structure of, the polyketide produced is understood both at the level of the protein sequence of the PKS and the DNA sequence of the corresponding genes. The organization of modules and correspondence with polyketide structure can be identified by amino acid and/or nucleic acid sequence determination. One can thus clone (or synthesize) DNA sequences corresponding to desired modules and transfer them as fully functioning units to heterologous hosts, including otherwise non-polyketide producing hosts such as *E. coli* (Pfeifer, et al., *Science* 291, 1790 (2001); incorporated herein by reference), and polyketide-producing hosts, such as *Streptomyces* (Kao et al., *Science* 265, 509 (1994); incorporated herein by reference).

Additional genes employed in polyketide biosynthesis have also been identified. Genes that determine phosphopantetheine:protein transferase (PPTase) that transfer the 4-phosphopantetheine co-factor of the ACP domains, commonly present in polyketide producing hosts, have been cloned in *E. coli* and other hosts (Weissman et al., *Chembiochem* 5, 116 (2004); incorporated herein by reference). While it is possible to re-program polyketide biosynthesis to produce a compound of desired structure by either genetic manipulation of a single PKS or by construction of a hybrid PKS composed of modules from two or more sources (see Weissman et al., supra), the present invention provides the first means for making an alpha-olefin by a recombinant PKS.

Recombinant methods for manipulating modular PKS genes to make the PKSs of the present invention are described in U.S. Pat. Nos. 5,672,491; 5,843,718; 5,830, 750; 5,712,146; and 6,303,342; and in PCT publication nos. WO 98/49315 and WO 97/02358; each of which is incorporated herein by reference. A number of genetic engineering strategies have been used with various PKSs to demonstrate that the structures of polyketides can be manipulated to produce novel polyketides (see the patent publications referenced supra and Hutchinson, 1998, Curr. Opin. Microbiol. 1:319-329, and Baltz, 1998, Trends Microbiol. 6:76-83; incorporated herein by reference). In some embodiments, the components of the hybrid PKS are arranged onto polypeptides having interpolypeptide linkers that direct the assembly of the polypeptides into the functional PKS protein, such that it is not required that the PKS have the same arrangement of modules in the polypeptides as observed in natural PKSs. Suitable interpolypeptide linkers to join polypeptides and intrapolypeptide linkers to join modules within a polypeptide are described in PCT publication No. WO 00/47724, incorporated herein by reference.

The vast number of polyketide pathways that have been elucidated to date and the present invention in combination provide a variety of different options to produce α-olefins in accordance with the invention. While the products can be vastly different in size and functionality, all employ similar methods for preparing the PKS and corresponding coding sequence and for producing the desired α-olefin. The interfaces between non-cognate enzyme partners can be optimized on a case-by-case basis. ACP-linker-KS and ACP-linker-TE regions from the proteins of interest will be aligned to examine the least disruptive fusion point for the hybrid synthase. Genetic constructions will employ sequence and ligation independent cloning (SLIC), or other sequence independent cloning techniques, so as to eliminate the incorporation of genetic "scarring".

In some embodiments, the PKS that produces the α-olefin of interest comprises the sulfotransferase (ST)-thioesterase (TE) domains from *Lyngbya majuscula* CurM or similar domains from another naturally occurring PKS or one of the recombinant domains provided by the invention. The α-olefins capable of being produced by the invention include, but are not limited to, the diketides propylene, 1-butene, and styrene and the triketides 1-hexene and 1-pentene. In one aspect of the invention, the host cell is fed or exogenously provided or endogenously produces acrylate and so produces diolefins such as 1,5-hexadiene and butadiene. In another aspect, feeding or exogenously providing or endogenous production of benzoic acid to the host cell comprising a PKS of the invention enables the production of styrene derivatives.

In some embodiments, host cells that are capable of producing diolefins are also capable of producing acrylate or acrylyl-CoA/ACP, thus eliminating the need for exogenous acrylate. By coupling one of many PKS thioesterase domains to the module loading acrylate from these precursor pathways, the PKS system is capable of producing acrylic acid. Acrylic acid can also be obtained from acrylyl-CoA or acrylyl-ACP by use of a non-PKS hydrolase in accordance with the invention. In some embodiments of the invention, host cells that are capable of producing diolefins are also capable of producing benzoate.

*L. majuscula* CurM ST-TE domains comprise the following amino acid sequence:

```
                                          (SEQ ID NO: 10)
F ILSSPRSGST LLRVMLAGHS SLFSPPELHL LPFNTMKERQ

EQLNLSYLGE GLQKTFMEVK NLDATASQAL IKDLESQNLS

IQQVYGMLQE NIAPRLLVDK SPTYAMEPTI LERGEALFAN

SKYIYLVRHP YSVIESFVRM RMQKLVGLGE ENPYRVAEQV

WAKSNQNILN FLSQLEPERQ HQIRYEDLVK KPQQVLSQLC

DFLNVPFEPE LLQPYQGDRM TGGVHQKSLS ISDPNFLKHN

TIDESLADKW KTIQLPYPLK SETQRIASQL SYELPNLVTT

PTNQQPQVST TPSTEQPIME EKFLEFGGNQ ICLCSWGSPE

HPVVLCIHGI LEQGLAWQEV ALPLAAQGYR VVAPDLFGHG

RSSHLEMVTS YSSLTFLAQI DRVIQELPDQ PLLLVGHSMG

AMLATAIASV RPKKIKELIL VELPLPAEES KKESAVNQLT

TCLDYLSSTP QHPIFPDVAT AASRLRQAIP SLSEEFSYIL

AQRITQPNQG GVRWSWDAII RTRSILGLNN LPGGRSQYLE

MLKSIQVPTT LVYGDSSKLN RPEDLQQQKM TMTQAKRVFL

SGGHNLHIDA AAALASLILT S
```

*L. majuscula* CurM ST domain comprises the following amino acid sequence:

```
                                          (SEQ ID NO: 11)
F ILSSPRSGST LLRVMLAGHS SLFSPPELHL LPFNTMKERQ

EQLNLSYLGE GLQKTFMEVK NLDATASQAL IKDLESQNLS

IQQVYGMLQE NIAPRLLVDK SPTYAMEPTI LERGEALFAN

SKYIYLVRHP YSVIESFVRM RMQKLVGLGE ENPYRVAEQV

WAKSNQNILN FLSQLEPERQ HQIRYEDLVK KPQQVLSQLC

DFLNVPFEPE LLQPYQGDRM TGGVHQKSLS ISDPNFLKHN

TIDESLADKW KTIQLPYPLK
```

*L. majuscula* CurM TE domain comprise the following amino acid sequence:

```
                                          (SEQ ID NO: 12)
EKFLEFGGNQ ICLCSWGSPE HPVVLCIHGI LEQGLAWQEV

ALPLAAQGYR VVAPDLFGHG RSSHLEMVTS YSSLTFLAQI

DRVIQELPDQ PLLLVGHSMG AMLATAIASV RPKKIKELIL

VELPLPAEES KKESAVNQLT TCLDYLSSTP QHPIFPDVAT

AASRLRQAIP SLSEEFSYIL AQRITQPNQG GVRWSWDAII

RTRSILGLNN LPGGRSQYLE MLKSIQVPTT LVYGDSSKLN

RPEDLQQQKM TMTQAKRVFL SGGHNLHIDA AAALASLILT S
```

In some embodiments, the PKS of the present invention comprises a naturally occurring sulfotransferase-thioesterase (ST-TE) domains, or ST or TE domain, functionally similar, but not identical, to *L. majuscula* CurM. In some embodiments, the PKS of the present invention comprises the amino acid sequences of the ST and/or TE of any of the proteins/peptides described in Tables 2-4, or functionally variants thereof. One skilled in the art can identify such *L. majuscula* CurM-like ST and/or TE domains using available bioinformatics programs. For example, the *L. majuscula* CurM ST-TE can be split in two separately functional portions by relying on its crystal structure and annotation of catalytic boundaries with programs like protein BLAST, and the sequences can be homology-modeled to get a better grasp of the boundary of catalytic domains, using *L. majuscula* CurM ST-TE as an anchoring template. Together, such methods can be employed to make solid predictions about catalytic activity and responsible amino acid regions within a larger protein.

In some embodiments, ST and/or TE domains, or functionally variants thereof, comprise one or more of the following amino acid residues (using *L. majuscula* CurM as a reference sequence): R205, H266, S100, E124, N211, and N267. In some embodiments, ST and/or TE domains, or functionally variants thereof, comprise the following amino acid residues (using *L. majuscula* CurM as a reference sequence): R205 and H266, and optionally one or more of S100, E124, N211, and N267. In some embodiments, the PKS comprises a ST domain and a TE domains that are derived or obtained from two different organisms or sources.

TABLE 2

List of proteins/peptides comprising CurM-like ST-TE domains.

| Ref. Protein/peptide [organism or source] | No. of amino acid residues | Accession No. |
|---|---|---|
| 1. polyketide synthase module [*Lyngbya majuscula* 3L] | 2211 aa protein | ZP_08432359.1 GI: 332712433 |
| 2. CurM [*Lyngbya majuscula*] | 2147 aa protein | AAT70108.1 GI: 50082961 |
| 3. beta-ketoacyl synthase [*Cyanothece* sp. PCC 7424] | 2762 aa protein | YP_002377174.1 GI: 218438845 |
| 4. beta-ketoacyl synthase [*Cyanothece* sp. PCC 7822] | 2775 aa protein | YP_003887107.1 GI: 307151723 |
| 5. polyketide synthase [*Prochloron didemni* P1-Palau] | 2999 aa protein | AEH57210.1 GI: 335387269 |
| 6. Chain A, Thioesterase Domain From Curacin Biosynthetic Pathway | 286 aa protein | 3QIT_A GI: 325534050 |
| 7. polyketide synthase module [*Lyngbya majuscula* 3L] | 2277 aa protein | ZP_08425908.1 GI: 332705832 |
| 8. polyketide synthase [*Synechococcus* sp. PCC 7002] | 2720 aa protein | YP_001734428.1 GI: 170077790 |
| 9. polyketide synthase [*Pseudomonas entomophila* L48] | 1217 aa protein | YP_610919.1 GI: 104784421 |
| 10. KR domain-containing protein [*Haliangium ochraceum* DSM 14365] | 3045 aa protein | YP_003265308.1 GI: 262194099 |
| 11. OciA [*Planktothrix agardhii* NIES-205] | 2858 aa protein | ABW84363.1 GI: 158954787 |
| 12. OciA [*Planktothrix agardhii* NIVA-CYA 116] | 3477 aa protein | ABI26077.1 GI: 112824006 |
| 13. CurM [*Burkholderia pseudomallei* 668] | 358 aa protein | YP_001062692.1 GI: 126444569 |
| 14. amino acid adenylation domain-containing protein [*Cyanothece* sp. PCC 8802] | 1470 aa protein | YP_003137597.1 GI: 257059709 |
| 15. amino acid adenylation domain-containing protein [*Cyanothece* sp. PCC 8801] | 1470 aa protein | YP_002372038.1 GI: 218246667 |
| 16. polyketide synthase [*Ostreococcus lucimarinus* CCE9901] | 18193 aa protein | XP_001416378.1 GI: 145343541 |

TABLE 3

List of proteins/peptides comprising a CurM-like ST domain.

| Ref. Protein/peptide [organism or source] | No. of amino acid residues | Accession No. |
|---|---|---|
| 1. polyketide synthase module [*Lyngbya majuscula* 3L] | 2211 aa protein | ZP_08432359.1 GI: 332712433 |
| 2. CurM [*Lyngbya majuscula*] | 2147 aa protein | AAT70108.1 GI: 50082961 |
| 3. beta-ketoacyl synthase [*Cyanothece* sp. PCC 7424] | 2762 aa protein | YP_002377174.1 GI: 218438845 |
| 4. beta-ketoacyl synthase [*Cyanothece* sp. PCC 7822] | 2775 aa protein | YP_003887107.1 GI: 307151723 |
| 5. polyketide synthase [*Prochloron didemni* P1-Palau] | 2999 aa protein | AEH57210.1 GI: 335387269 |
| 6. polyketide synthase module [*Lyngbya majuscula* 3L] | 2277 aa protein | ZP_08425908.1 GI: 332705832 |
| 7. polyketide synthase [*Synechococcus* sp. PCC 7002] | 2720 aa protein | YP_001734428.1 GI: 170077790 |
| 8. polyketide synthase [*Pseudomonas entomophila* L48] | 1217 aa protein | YP_610919.1 GI: 104784421 |
| 9. OciA [*Planktothrix agardhii* NIES-205] | 2858 aa protein | ABW84363.1 GI: 158954787 |
| 10. OciA [*Planktothrix agardhii* NIVA-CYA 116] | 3477 aa protein | ABI26077.1 GI: 112824006 |
| 11. CurM [*Burkholderia pseudomallei* 668] | 358 aa protein | YP_001062692.1 GI: 126444569 |
| 12. KR domain-containing protein [*Haliangium ochraceum* DSM 14365] | 3045 aa protein | YP_003265308.1 GI: 262194099 |
| 16. COG3321: Polyketide synthase modules and related proteins (ISS) [*Ostreococcus tauri*] | 11541 aa protein | XP_003074830.1 GI: 308800098 |
| 17. polyketide synthase [*Ostreococcus lucimarinus* CCE9901] | 18193 aa protein | XP_001416378.1 GI: 145343541 |
| 18. modular polyketide synthase type I [*Micromonas* sp. RCC299] | 14149 aa protein | XP_002507643.1 GI: 255071123 |
| 19. hypothetical protein RBXJA2T_11932 [*Rubrivivax benzoatilyticus* JA2] | 301 aa protein | ZP_08402700.1 GI: 332526592 |
| 20. hypothetical protein Dshi_1965 [*Dinoroseobacter shibae* DFL 12] | 310 aa protein | YP_001533306.1 GI: 159044512 |
| 21. hypothetical protein glr1901 [*Gloeobacter violaceus* PCC 7421] | 301 aa protein | NP_924847.1 GI: 37521470 |
| 22. hypothetical protein Sros_9233 [*Streptosporangium roseum* DSM 43021] | 290 aa protein | YP_003344594.1 GI: 271970398 |
| 23. hypothetical protein SAV_2309 [*Streptomyces avermitilis* MA-4680] | 299 aa protein | NP_823485.1 GI: 29828851 |
| 24. conserved hypothetical protein [*Streptomyces viridochromogenes* DSM 40736] | 289 aa protein | ZP_07307763.1 GI: 302555421 |
| 25. sulfotransferase [*Frankia* sp. EuI1c] | 332 aa protein | YP_004017900.1 GI: 312197839 |
| 26. hypothetical protein Nit79A3_2110 [*Nitrosomonas* sp. Is79A3] | 304 aa protein | YP_004695298.1 GI: 339483571 |
| 27. sulfotransferase [*Thermobispora bispora* DSM 43833] | 346 aa protein | YP_003651260.1 GI: 296268628 |
| 28. sulfotransferase [*Frankia* sp. EuI1c] | 264 aa protein | YP_004017815.1 GI: 312197754 |
| 29. hypothetical protein gll1899 [*Gloeobacter violaceus* PCC 7421] | 320 aa protein | NP_924845.1 GI: 37521468 |
| 30. SecC motif-containing protein [*Shewanella loihica* PV-4] | 359 aa protein | YP_001093305.1 GI: 127512108 |
| 31. predicted protein [*Micromonas pusilla* CCMP1545] | 507 aa protein | XP_003055946.1 GI: 303273170 |
| 32. Putative protein-tyrosine sulfotransferase [*Plesiocystis pacifica* SIR-1] | 305 aa protein | ZP_01905212.1 GI: 149916710 |
| 33. hypothetical protein PB2503_07444 [*Parvularcula bermudensis* HTCC2503] | 310 aa protein | YP_003854688.1 GI: 304321045 |
| 34. hypothetical protein PPE_01162 [*Paenibacillus polymyxa* E681] | 422 aa protein | YP_003869548.1 GI: 308067943 |
| 35. putative sulfotransferase [*Streptomyces griseus* subsp. *griseus* NBRC 13350] | 339 aa protein | YP_001822417.1 GI: 182434698 |
| 36. hypothetical protein LYNGBM3L_54590 [*Lyngbya majuscula* 3L] | 318 aa protein | ZP_08430625.1 GI: 332710682 |
| 37. SecC motif-containing protein [*Shewanella sediminis* HAW-EB3] | 336 aa protein | YP_001473003.1 GI: 157374403 |
| 38. sulfotransferase domain protein [*Plesiocystis pacifica* SIR-1] | 329 aa protein | ZP_01905835.1 GI: 149917336 |
| 39. sulfotransferase [*Streptomyces* cf. *griseus* XylebKG-1] | 339 aa protein | ZP_08234477.1 GI: 326775212 |
| 40. hypothetical protein Sros_1208 [*Streptosporangium roseum* DSM 43021] | 347 aa protein | YP_003336949.1 GI: 271962753 |
| 41. sulfotransferase [*Trichodesmium erythraeum* IMS101] | 430 aa protein | YP_722743.1 GI: 113476682 |
| 42. hypothetical protein Sros_1207 [*Streptosporangium roseum* DSM 43021] | 336 aa protein | YP_003336948.1 GI: 271962752 |
| 43. sulfotransferase [*Flexistipes sinusarabici* DSM 4947] | 322 aa protein | YP_004602630.1 GI: 336322663 |
| 44. Protein-tyrosine sulfotransferase [*Harpegnathos saltator*] | 381 aa protein | EFN77815.1 GI: 307196126 |
| 45. sulfotransferase domain protein [*Rhodobacterales bacterium* HTCC2083] | 346 aa protein | ZP_05076043.1 GI: 254462627 |
| 46. PREDICTED: similar to Transport and Golgi organization 13 CG32632-PB [*Tribolium castaneum*] | 382 aa protein | XP_968004.1 GI: 91090216 |
| 47. sulfotransferase [*Psychromonas ingrahamii* 37] | 335 aa protein | YP_943667.1 GI: 119945987 |
| 48. hypothetical protein sll5046 [*Synechocystis* sp. PCC 6803] | 316 aa protein | NP_942202.1 GI: 38505581 |
| 49. sulfotransferase domain-containing protein [*Roseobacter denitrificans* OCh 114] | 340 aa protein | YP_680960.1 GI: 110677953 |
| 50. putative sulfotransferase [*Burkholderia multivorans* CGD2M] | 271 aa protein | ZP_03574132.1 GI: 221201092 |
| 51. sulfotransferase [*Kangiella koreensis* DSM 16069] | 317 aa protein | YP_003146110.1 GI: 256822147 |
| 52. Protein-tyrosine sulfotransferase [*Acromyrmex echinatior*] | 381 aa protein | EGI65733.1 GI: 332025570 |
| 53. sulfotransferase [*Flexistipes sinusarabici* DSM 4947] | 325 aa protein | YP_004602624.1 GI: 336322657 |
| 54. nodulation protein noeE [*Magnetospirillum magneticum* AMB-1] | 433 aa protein | YP_420424.1 GI: 83310160 |
| 55. glycosyl transferase family 2 [*Paenibacillus polymyxa* SC2] | 421 aa protein | YP_003945463.1 GI: 310640705 |
| 56. protein-tyrosine sulfotransferase 2 [*Paenibacillus polymyxa* M1] | 423 aa protein | CCC84070.1 GI: 343095861 |
| 57. sulfotransferase [*Pedobacter* sp. BAL39] | 346 aa protein | ZP_01884054.1 GI: 149277914 |
| 58. sulfotransferase: SEC-C motif protein [*Shewanella* sp. HN-41] | 333 aa protein | ZP_08568256.1 GI: 336313314 |
| 59. sulfotransferase domain protein [*Lyngbya majuscula* 3L] | 344 aa protein | ZP_08430778.1 GI: 332710841 |
| 60. sulfotransferase domain-containing protein [*Rhodopirellula baltica* WH47] | 325 aa protein | EGF25969.1 GI: 327539348 |
| 61. hypothetical protein MettrDRAFT_3778 [*Methylosinus trichosporium* OB3b] | 396 aa protein | ZP_06890062.1 GI: 296448163 |
| 62. PREDICTED: MGC82552 protein-like [*Saccoglossus kowalevskii*] | 436 aa protein | XP_002733820.1 GI: 291227699 |
| 63. Sulfotransferase domain super family [*Microcoleus chthonoplastes* PCC 7420] | 318 aa protein | ZP_05029988.1 GI: 254416234 |
| 64. tyrosylprotein sulfotransferase-2 [*Ictalurus punctatus*] | 356 aa protein | NP_001187093.1 GI: 318064902 |
| 65. family 2 glycosyl transferase [*Nitrosococcus halophiles* Nc4] | 1043 aa protein | YP_003528062.1 GI: 292492623 |
| 66. PREDICTED: protein-tyrosine sulfotransferase [*Apis mellifera*] | 380 aa protein | XP_624657.2 GI: 328780257 |
| 67. tyrosine sulfotransferase [*Culex quinquefasciatus*] | 395 aa protein | XP_001864662.1 GI: 170057846 |
| 68. hypothetical protein L8106_07576 [*Lyngbya* sp. PCC 8106] | 281 aa protein | ZP_01622104.1 GI: 119489297 |
| 69. hypothetical protein NIDE3002 [*Candidatus Nitrospira defluvii*] | 375 aa protein | YP_003798623.1 GI: 302038301 |
| 70. SecC motif-containing protein [*Shewanella frigidimarina* NCIMB 400] | 342 aa protein | YP_749583.1 GI: 114562070 |
| 71. sulfotransferase [*Acaryochloris marina* MBIC11017] | 294 aa protein | YP_001519982.1 GI: 158338805 |
| 72. protein-tyrosine sulfotransferase 2 [*Danio rerio*] | 356 aa protein | NP_956713.1 GI: 41056257 |

TABLE 3-continued

List of proteins/peptides comprising a CurM-like ST domain.

| Ref. Protein/peptide [organism or source] | No. of amino acid residues | Accession No. |
|---|---|---|
| 73. PREDICTED: protein-tyrosine sulfotransferase-like [*Bombus terrestris*] | 380 aa protein | XP_003394254.1 GI: 340711379 |
| 74. GG17794 [*Drosophila erecta*] | 504 aa protein | XP_001978427.1 GI: 194895457 |
| 75. hypothetical protein Swit_1252 [*Sphingomonas wittichii* RW1] | 308 aa protein | YP_001261755.1 GI: 148554173 |
| 76. putative enzyme [*Lyngbya* sp. PCC 8106] | 305 aa protein | ZP_01618957.1 GI: 119484340 |
| 77. sulfotransferase [*Trichodesmium erythraeum* IMS101] | 344 aa protein | YP_722339.1 GI: 113476278 |
| 78. transport and golgi organization 13, isoform C [*Drosophila melanogaster*] | 346 aa protein | NP_001096973.1 GI: 161077803 |
| 79. hypothetical protein BRAFLDRAFT_89531 [*Branchiostoma floridae*] | 454 aa protein | XP_002590725.1 GI: 260791416 |
| 80. hypothetical protein L8106_19296 [*Lyngbya* sp. PCC 8106] | 318 aa protein | ZP_01620966.1 GI: 119487094 |
| 81. TyrosylProtein SulfoTransferase family member (tpst-1) [*Caenorhabditis elegans*] | 380 aa protein | NP_499646.3 GI: 71992370 |
| 82. methionine biosynthesis protein MetW, putative [*Nitrosococcus oceani* AFC27] | 1039 aa protein | ZP_05048086.1 GI: 254434578 |
| 83. tyrosylprotein sulfotransferase 2 [*Xenopus laevis*] | 375 aa protein | NP_001088427.1 GI: 148235112 |
| 84. glycosyl transferase family protein [*Nitrosococcus oceani* ATCC 19707] | 1037 aa protein | YP_343263.1 GI: 77164738 |
| 85. GM17618 [*Drosophila sechellia*] | 478 aa protein | XP_002042697.1 GI: 195352394 |
| 86. GE17090 [*Drosophila yakuba*] | 508 aa protein | XP_002100486.1 GI: 195478327 |
| 87. GI14854 [*Drosophila mojavensis*] | 459 aa protein | XP_002010160.1 GI: 195131443 |
| 88. GD17135 [*Drosophila simulans*] | 501 aa protein | XP_002106871.1 GI: 195566606 |
| 89. GF22576 [*Drosophila ananassae*] | 498 aa protein | XP_001965589.1 GI: 194766965 |
| 90. transport and golgi organization 13, isoform B [*Drosophila melanogaster*] | 499 aa protein | NP_727717.1 GI: 24641809 |
| 91. GL20242 [*Drosophila persimilis*] | 515 aa protein | XP_002023360.1 GI: 195165053 |
| 92. PREDICTED: protein-tyrosine sulfotransferase-like [*Acyrthosiphon pisum*] | 392 aa protein | XP_001942867.2 GI: 328706076 |
| 93. PREDICTED: similar to MGC82552 protein [*Gallus gallus*] | 379 aa protein | XP_415794.2 GI: 118100226 |
| 94. protein-tyrosine sulfotransferase A [*Loa loa*] | 384 aa protein | XP_003139556.1 GI: 312073519 |
| 95. GA26942 [*Drosophila pseudoobscura pseudoobscura*] | 521 aa protein | XP_001354726.2 GI: 198468492 |
| 96. GK16105 [*Drosophila willistoni*] | 466 aa protein | XP_002067611.1 GI: 195439384 |
| 97. PREDICTED: protein-tyrosine sulfotransferase-like [*Nasonia vitripennis*] | 396 aa protein | XP_001606792.1 GI: 156543274 |
| 98. PREDICTED: protein-tyrosine sulfotransferase 1-like [*Monodelphis domestica*] | 450 aa protein | XP_001362570.2 GI: 334324786 |
| 99. predicted protein [*Nematostella vectensis*] | 272 aa protein | XP_001630972.1 GI: 156378079 |
| 100. AGAP000900-PA [*Anopheles gambiae* str. PEST] | 392 aa protein | EAA12079.6 GI: 333469474 |

TABLE 4

List of proteins/peptides comprising a CurM-like TE domain.

| Ref. Protein/peptide [organism or source] | No. of amino acid residues | Accession No. |
|---|---|---|
| 37. hypothetical protein lpl0509 [*Legionella pneumophila* str. Lens] | 282 aa protein | YP_125875.1 GI: 54293460 |
| 38. putative lipase LipA [*Legionella pneumophila* 130b] | 282 aa protein | AAM73852.1 GI: 21666982 |
| 39. Alpha/beta hydrolase [gamma proteobacterium IMCC2047] | 294 aa protein | ZP_08648517.1 GI: 339055924 |
| 40. hypothetical protein lpp0533 [*Legionella pneumophila* str. Paris] | 282 aa protein | YP_122871.1 GI: 54296502 |
| 41. Putative hydrolase or acyltransferase of alpha/beta superfamily [*Rheinheimera* sp. A13L] | 279 aa protein | ZP_08572335.1 GI: 336317483 |
| 42. lipase A [*Legionella pneumophila* subsp. pneumophila str. Philadelphia 1] | 283 aa protein | YP_094512.1 GI: 52840713 |
| 43. alpha/beta fold family hydrolase [*Shewanella oneidensis* MR-1] | 288 aa protein | NP_718168.1 GI: 24374125 |
| 44. alpha/beta hydrolase [*Azotobacter vinelandii* DJ] | 300 aa protein | YP_002798221.1 GI: 226943148 |
| 45. lipase [*Pseudomonas syringae* pv. *mori* str. 301020] | 284 aa protein | EGH20834.1 GI: 330888173 |
| 46. alpha/beta hydrolase fold protein [*Dechlorosoma suillum* PS] | 288 aa protein | EGW60665.1 GI: 345129761 |
| 47. hydrolase, alpha/beta fold family [*Moritella* sp. PE36] | 291 aa protein | ZP_01900040.1 GI: 149911422 |
| 48. lipase [*Pseudomonas syringae* pv. *lachrymans* str. M301315] | 284 aa protein | EGH85562.1 GI: 330987459 |
| 49. lipase [*Pseudomonas syringae* pv. *tabaci* ATCC 11528] | 284 aa protein | EGH90697.1 GI: 331010641 |
| 50. Alpha/beta hydrolase fold [*Pseudomonas syringae* pv. *syringae* B728a] | 284 aa protein | YP_235108.1 GI: 66045267 |
| 51. serine hydrolase-like 2 [*Xenopus laevis*] | 304 aa protein | NP_001079604.1 GI: 147899135 |
| 52. Alpha/beta hydrolase fold protein [*Pseudomonas syringae* pv. *japonica* str. M301072PT] | 284 aa protein | EGH30625.1 GI: 330899206 |
| 53. alpha/beta hydrolase fold protein [*Shewanella halifaxensis* HAW-EB4] | 291 aa protein | YP_001674055.1 GI: 167623761 |
| 54. lipase [*Pseudomonas syringae* pv. *aesculi* str. 0893_23] | 284 aa protein | EGH02171.1 GI: 330867462 |
| 55. Alpha/beta hydrolase fold protein [*Pseudomonas syringae* pv. *morsprunorum* str. M302280PT] | 284 aa protein | EGH09818.1 GI: 330875669 |
| 56. putative hydrolase [marine gamma proteobacterium HTCC2143] | 308 aa protein | ZP_01616002.1 GI: 119475649 |
| 57. alpha/beta fold family hydrolase [*Pseudomonas syringae* pv. *actinidiae* str. M302091] | 284 aa protein | EGH65633.1 GI: 330965373 |
| 58. putative alpha/beta hydrolase [*Sphingobium japonicum* UT26S] | 290 aa protein | YP_003545632.1 GI: 294012172 |
| 59. Alpha/beta hydrolase fold protein [*Pseudomonas syringae* pv. *aptata* str. DSM 50252] | 284 aa protein | EGH78853.1 GI: 330980750 |
| 60. Alpha/beta hydrolase fold protein [*Pseudomonas syringae* pv. *pisi* str. 1704B] | 284 aa protein | EGH43451.1 GI: 330940344 |
| 61. Alpha/beta hydrolase fold protein [*Pseudomonas syringae* pv. *syringae* FF5] | 284 aa protein | ZP_06500867.1 GI: 289679977 |
| 62. hydrolase [gamma proteobacterium NOR51-B] | 299 aa protein | ZP_04957287.1 GI: 254282319 |
| 63. predicted Hydrolase or acyltransferase (alpha/beta hydrolase superfamily) protein [*Marinobacter algicola* DG893] | 305 aa protein | ZP_01893017.1 GI: 149375245 |
| 64. lipase A [*Legionella longbeachae* D-4968] | 281 aa protein | ZP_06187778.1 GI: 270159122 |
| 65. alpha/beta hydrolase fold protein [*Pseudomonas fluorescens* WH6] | 284 aa protein | ZP_07774389.1 GI: 312959874 |
| 66. alpha/beta hydrolase fold protein [*Alicycliphilus denitrificans* K601] | 300 aa protein | YP_004387755.1 GI: 330824452 |

TABLE 4-continued

List of proteins/peptides comprising a CurM-like TE domain.

| Ref. Protein/peptide [organism or source] | No. of amino acid residues | Accession No. |
|---|---|---|
| 67. hydrolase [*Sorangium cellulosum* 'So ce 56'] | 322 aa protein | YP_001615653.1 GI: 162453286 |
| 68. alpha/beta fold family hydrolase [*Shewanella violacea* DSS12] | 296 aa protein | YP_003557221.1 GI: 294141243 |
| 69. lipase [*Pseudomonas syringae* pv. *phaseolicola* 1448A] | 284 aa protein | YP_274221.1 GI: 71736540 |
| 70. putative esterase [uncultured microorganism] | 293 aa protein | BAI49930.1 GI: 269913831 |
| 71. alpha/beta fold family hydrolase [*Cellvibrio japonicus* Ueda107] | 298 aa protein | YP_001982425.1 GI: 192359104 |
| 72. alpha/beta hydrolase fold protein [*Pseudomonas fulva* 12-X] | 287 aa protein | YP_004474637.1 GI: 333900764 |
| 73. alpha/beta hydrolase [gamma proteobacterium HdN1] | 283 aa protein | YP_003810829.1 GI: 304311231 |
| 74. putative hydrolase [*Nocardia farcinica* IFM 10152] | 249 aa protein | YP_117116.1 GI: 54022874 |
| 75. alpha/beta hydrolase fold protein [*Haliangium ochraceum* DSM 14365] | 289 aa protein | YP_003269090.1 GI: 262197881 |
| 76. Alpha/beta hydrolase [*Pseudomonas syringae* pv. *syringae* 642] | 284 aa protein | ZP_07264074.1 GI: 302187401 |
| 77. Alpha/beta hydrolase fold protein [*Limnobacter* sp. MED105] | 310 aa protein | ZP_01916760.1 GI: 149928530 |
| 78. putative lipase LipA [*Legionella drancourtii* LLAP12] | 280 aa protein | ZP_05108808.1 GI: 254495899 |
| 79. hydrolase, alpha/beta fold family [*Pseudomonas syringae* pv. tomato T1] | 284 aa protein | ZP_03396309.1 GI: 213968164 |
| 80. alpha/beta hydrolase fold protein [*Rhodopseudomonas palustris* CGA009] | 340 aa protein | NP_946347.1 GI: 39934071 |
| 81. lipase, putative [*Pseudomonas syringae* pv. *glycinea* str. B076] | 284 aa protein | EFW80985.1 GI: 320324913 |
| 82. alpha/beta fold family hydrolase [*Pseudomonas syringae* pv. tomato str. DC3000] | 284 aa protein | NP_792039.1 GI: 28869420 |
| 83. hydrolase or acytransferase [*Azoarcus* sp. BH72] | 300 aa protein | YP_933620.1 GI: 119898407 |
| 84. alpha/beta super family hydrolase [*Shewanella piezotolerans* WP3] | 293 aa protein | YP_002311621.1 GI: 212635096 |
| 85. putative hydrolase [*Aromatoleum aromaticum* EbN1] | 292 aa protein | YP_158988.1 GI: 56477399 |
| 86. putative hydrolase [*Pseudomonas fluorescens* SBW25] | 284 aa protein | YP_002871482.1 GI: 229589363 |
| 87. alpha/beta hydrolase fold protein [*Rhodopseudomonas palustris* TIE-1] | 289 aa protein | YP_001990203.1 GI: 192289598 |
| 88. hydrolase [*Pseudomonas aeruginosa* PA01] | 286 aa protein | NP_250313.1 GI: 15596819 |
| 89. putative hydrolase [*Pseudomonas aeruginosa* 39016] | 286 aa protein | ZP_07792860.1 GI: 313106637 |
| 90. hydrolase, alpha/beta fold family protein [marine gamma proteobacterium HTCC2207] | 286 aa protein | ZP_01223987.1 GI: 90416054 |
| 91. PA1622 [synthetic construct] | 287 aa protein | AAT50924.1 GI: 49083048 |
| 92. lipase [*Pseudomonas syringae* pv. *maculicola* str. ES4326] | 284 aa protein | EGH59298.1 GI: 330959038 |
| 93. hydrolase [*Pseudomonas stutzeri* DSM 4166] | 282 aa protein | AEA83820.1 GI: 327480510 |
| 94. alpha/beta hydrolase [*Chromohalobacter salexigens* DSM 3043] | 289 aa protein | YP_574516.1 GI: 92114588 |
| 95. alpha/beta hydrolase fold [*Marinobacter aquaeolei* VT8] | 306 aa protein | YP_958843.1 GI: 120554492 |
| 96. hydrolase [*Pseudomonas stutzeri* A1501] | 285 aa protein | YP_001172415.1 GI: 146282262 |
| 97. Hydrolase or acetyltransferase [*Leptospira biflexa* serovar Patoc strain 'Patoc 1 (Ames)'] | 287 aa protein | YP_001964755.1 GI: 189912866 |
| 98. hypothetical hydrolase/acyltransferase [*Photobacterium profundum* 3TCK] | 299 aa protein | ZP_01219631.1 GI: 90411621 |
| 99. putative hydrolase [*Pseudomonas aeruginosa* PA7] | 286 aa protein | YP_001349005.1 GI: 152984242 |
| 100. hydrolase [*Oxalobacter formigenes* HOxBLS] | 289 aa protein | ZP_04576152.1 GI: 237745672 |

In some embodiments of the invention, a precursor molecule, such as propionate or acrylate, is provided to the PKS to produce a polyketide of interest. The precursor molecule can be fed or exogenously provided to or endogenously produced by the host cell comprising the PKS, or the host cell can produce the enzymes capable of biosynthesizing the precursor molecule from a simpler molecule that can be fed or exogenously provided to the host cell or the host cell naturally endogenously produces. For example, *Streptomyces* species produces propionyl-CoA as part of its innate metabolism, thus eliminating the need for exogenous propionate provision.

In some embodiments of the invention, the PKS capable of producing an α-olefin of interest comprises CurM, the terminal PKS from the curacin biosynthesis pathway (Chang, 2004) or a similar module. CurM is a monomodular PKS protein containing an unusual sulfotransferase domain. This domain sulfonates the beta hydroxyl group of the penultimate product and the combination of the ST-TE domains catalyze a decarboxylation and functional dehydration (with sulfate as the leaving group) to yield the terminal olefin. FIG. 1 illustrates how domains from CurM can be coupled to other PKS enzymes to produce an α-olefin, such as 1-hexene, in accordance with the methods and materials of the invention. In the example shown in FIG. 1, first PKS ORF encodes a loading module specific for propionate (via the CoA) and an extension module that incorporates acetate (via malonyl-CoA) and fully reduces the β-carbonyl. In this example shown in FIG. 1, the loading domain is from the erythromycin PKS (Donadio et al. 1991. Science 675-679; incorporated herein by reference) and module 5 is from the nystatin PKS (Brautaset et al. 2000. Chemistry & Biology 7:395-403; incorporated herein by reference), but there are other modules that can be used to provide the same product. The second and third proteins that constitute the multi-subunit PKS in this example come from the curacin PKS and corresponding gene cluster (see Chang et al. 2004. Journal of Natural Products 67:1356-1367; sequence updated in Gu et al. J Am Chem Soc. 2009 Nov. 11; 131(44):16033-5; both of which are incorporated herein by reference). Using this PKS, the first two modules can be replaced with any of several well characterized modules to yield several dozen different α-olefins. Increasing the number of upstream modules to three or more increases the number of different products into the hundreds and higher.

To ensure appropriate interactions between the two PKS proteins in this and related examples, one can use the acyl-carrier protein (ACP) and C-terminus from CurM's native enzyme partner, CurL. In general, native C- and N-terminal docking partners can be used in the combinatorial PKS enzymes of the invention. Other cognate domains from different PKS enzymes can also be used.

Figure 3A:
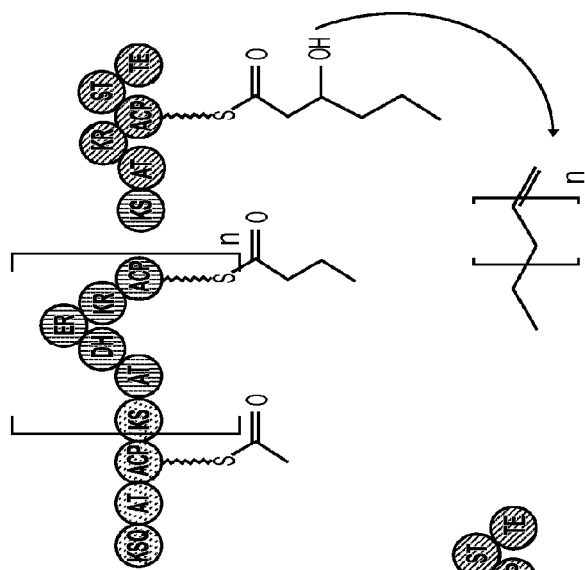
FIGS. 3A-C show.
Figure 3B:
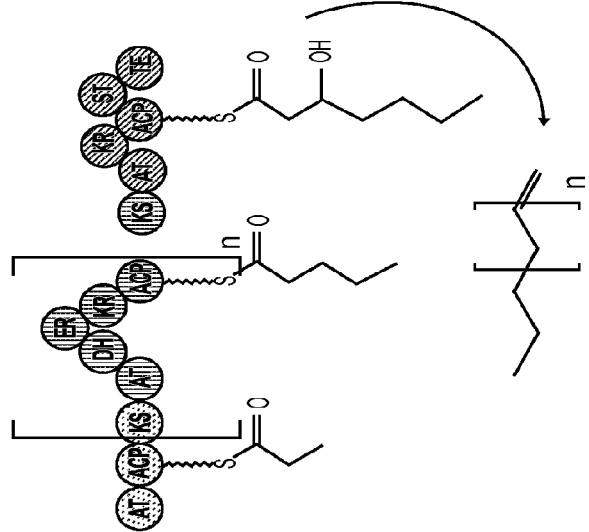
Figure 3C:
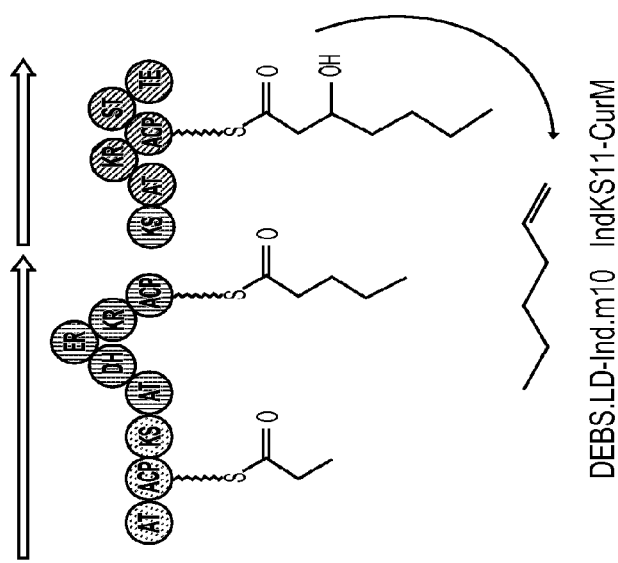
Figure 7D:
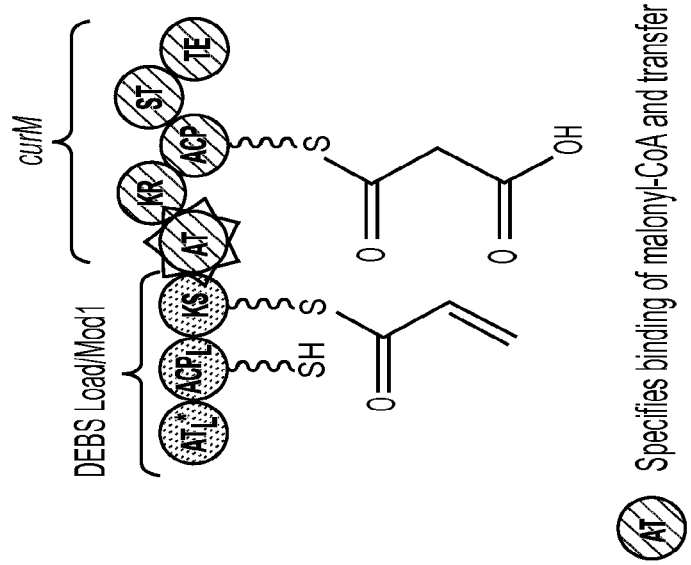
Figure 7C:
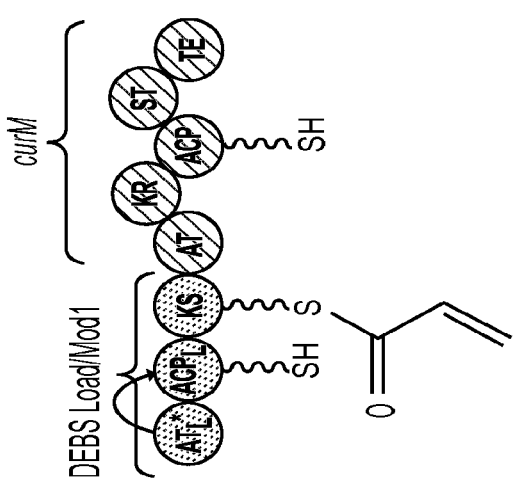
Figure 7F:
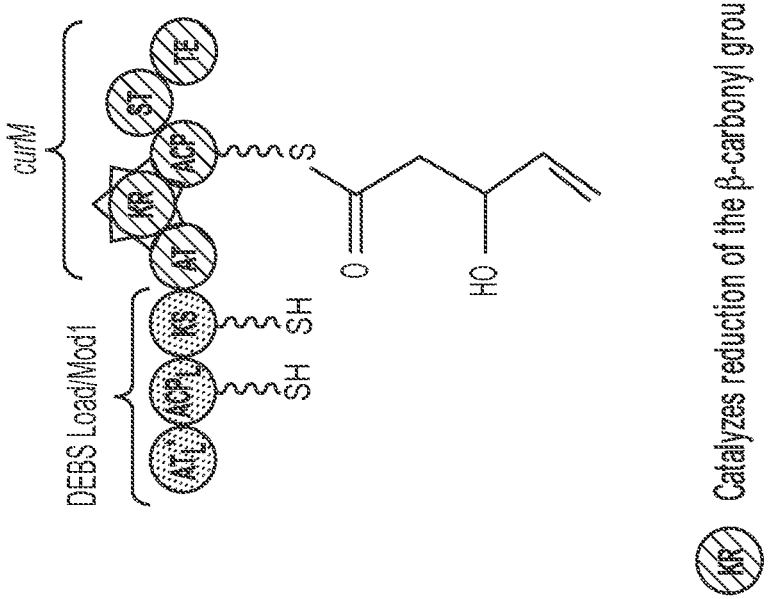
Figure 7E:
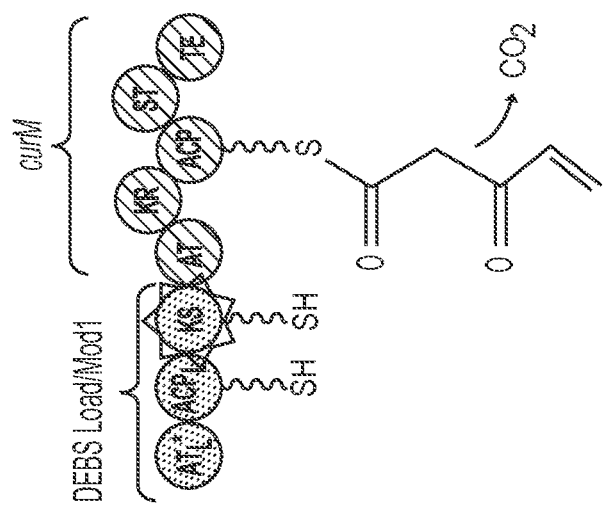
Figure 7G:
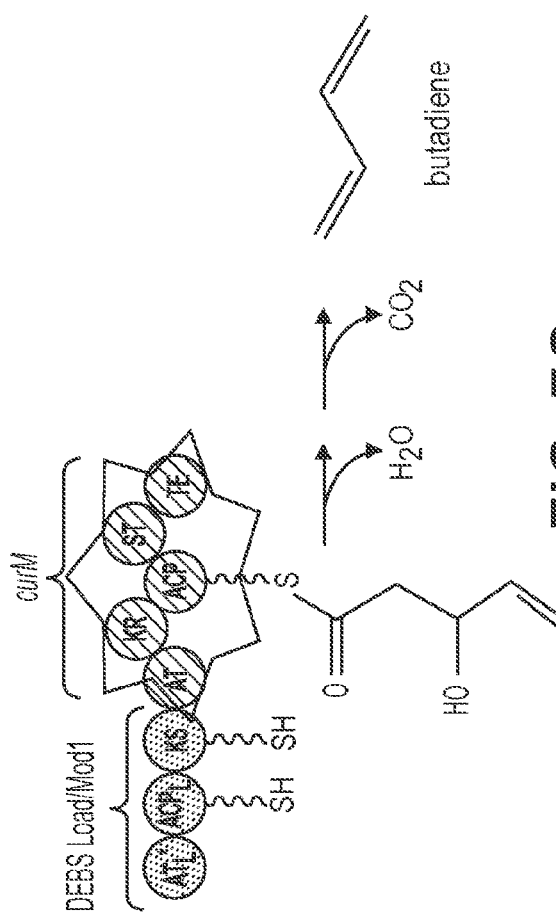

FIG. 3A shows an exemplary PKS for producing a triketide α-olefin. FIGS. 3B and 3C show exemplary extensions of this model, demonstrating how additional modules can be employed to yield longer, fully saturated, linear α-olefins.

Incorporation of the avermectin loading domain into a PKS of the invention provides access to a number of other α-olefins. Some examples of this aspect of the invention to make both known and novel α-olefins are shown in FIG. 4.

In some embodiments, the PKS of the invention produces a butadiene with a pendant acid moiety, such that the butadiene is suitable for subsequent crosslinking FIG. 5 shows such a PKS that comprises a set of enzymes comprising an HMG-like system found in several PKS enzymes and corresponding gene clusters. This system converts the β-carbonyl to a number of different chemical moieties, most pertinently an exomethylene. Briefly, one of the previously described systems for incorporating an acrylate starter (DEBS (Donadio et al. 1991. supra) or difficidin (Chen et al. 2006. J Bacteriol. 188(11):4024-36; incorporated herein by reference) loading module) can be fused to an HMG-like module, such as JamE from the jamaicamide cluster (Edwards et al. 2004. Chem Biol. 11(6):817-33; incorporated herein by reference), and a TE domain at the C-terminus. Such a bimodular PKS enzyme can be co-expressed with the genes encoding accessory proteins required for the incorporation of the desired chemistry. In this example these enzymes are JamH, JamG and JamI (Edwards et al., 2004, supra).

In some embodiments of the invention, the PKS comprises a CurM chain termination module of *Lyngbya majuscula* CurM or functionally equivalent module. In some embodiments of the invention, the PKS comprises the ST and TE domains of the curM chain termination module and sequences derived from a different CurM module or another PKS entirely. In some embodiments of the invention, the PKS comprises the KR, ACP, ST and TE domains of the CurM chain termination module and sequences derived from a different CurM module or another PKS entirely. In some embodiments of the invention, the PKS comprises the AT, KR, ACP, ST and TE domains of the CurM chain termination module and sequences derived from a different CurM module or another PKS entirely.

In some embodiments, the PKS of the invention comprises an acrylate loading module, such as the acrylate loading module from the dificidin PKS (Chen et al., 2006, supra), which incorporates the acrylyl moiety from a hydroxypropionate precursor involving the enzymes difA-E.

The present invention also provides a PKS comprising an acrylate loading module coupled to a thioesterase domain, wherein the PKS is capable of producing acrylate (acrylic acid). The erythromycin PKS, for example and without limitation, includes suitable such modules and domains.

The following depict the amino acid sequences of SEQ ID NO:1-9

*L. majuscula* CurM (GenBank: ACV42478.1) has the following amino acid sequence (SEQ ID NO:1):

```
   1 msnvskttqq dvssqevlqv lqemrsrlea vnkaktepia ivgmacrfpg gandpstywr
  61 llhdgidait pvpphrwdvn ahyepnpeip gkaytkqggf ieqvdqfdpi ffgispreai
 121 sldpqyrlll evtwealena gqtwtnlkns ktsvfmgvst ddyaslsnpi linnrslgvg
 181 rishllglqg sniqldtacs sslvaihlac qslrsgesnl alvggvnlil spistigrct
 241 mkalspdgrc ktfdaaangy gqaegcgvvv lkrlsdaitd gdlisalirg sainhdgpss
 301 gltvpngmaq kqviqqalsn arlephqvsy leahgtgtal gdpieieala aiygknrpvd
 361 qplvvgsvkt nighleaaag vsalikvvla lqhqeipphl hlkqpnpyvd wdklpikipt
 421 slmpwnceak priagissfg isgtnahlll eevpelikgq kakgksendl erplhiltls
 481 tktekaleel vsryqnhwet ypelaisdvc ytantgraqf nhrlaviasg seeltqklrq
 541 htageevvgv fsgkvpnsgs eskvaflftg qgsqylnmgr qlyetqptfr qaldtcdhil
 601 rpyldnplle ilypqdaqks ndspldqtgy tqpalfsiey allklweswg ikpnvvmghs
 661 vgeyvaatva gvfsledglk liaargrlmq glpaggemvs vmaseskvle tlkamsledk
 721 vaiaaingpe sivisgeaea iramathles vgiktkqlqv shafhsplme pmlaefeava
 781 nqityhqpri piisnvtgtk adksiataqy wvnhvrqpvr faqgmatlhq qgyetfleig
 841 akpillgmgk qclspdvgvw lpslrhgvde wqqilsslgq lyvqgakvdw sgfdrdysre
 901 kvvlptypfq rerywvetsi nqqqvvcsge pnlqgtpegt sttivkllsq gntkelaekv
 961 ektsdlppeq lkllpdllas lsqqhqqela rlttkkwfyk vqwisqaikp qrnksnnqvc
1021 hwliltdskg lgkslathlq qlgnecsvvy qadnyqnyep giyhinpshp qefeqvyqti
1081 fengklplqk vihlwsldta seqdlttetl eqaqlwgcgs tlhllqtlvk npnstppklw
1141 mitrgtqpvl sptekltvat splwglgrti asehpqlwgg lvdldpqgse devevllqqi
1201 idsqkedhla vrnrkiyvar llkhipqesq plslrsdaty litgglgalg lktaawmaek
1261 garnlvlisr rqpseqaqqt iqsleelgtq vkvlsadisv esdvanileq iqtslppllg
1321 vihaagvldd gllqqtnwer ftkvmapkvn gtwnlhkltq hlsldffvcf ssmssllgsp
1381 gqgnyaaana fmdavvhyrr emglpglsin wggwseggma trlasqhqnr mqtagislis
```

```
1441 peqgiqvlee lvrtqstaqv gvlpvdwsvl akqfssanps slllellqqe tssektderi 1501 leklqaapit erqdilknyi qlvvaktlgi npskistddn fvelgmdslm gmevvnklsg 1561 dldfiiypre fyerptidsl tqylsaelse dnlatqpspt sleifatkss psgnsarpas 1621 vssrlpgiif ilssprsgst llrvmlaghs slfsppelhl lpfntmkerq eqlnlsylge 1681 glqktfmevk nldatasqal ikdlesqnls iqqvygmlqe niaprllvdk sptyamepti 1741 lergealfan skyiylvrhp ysviesfvrm rmqklvglge enpyrvaeqv waksnqniln 1801 flsqleperq hqiryedlvk kpqqvlsqlc dflnvpfepe llqpyqgdrm tggvhqksls 1861 isdpnflkhn tidesladkw ktiqlpyplk setqriasql syelpnlvtt ptnqqpqvst 1921 tpsteqpime ekflefggnq iclcswgspe hpvvlcihgi leqglawqev alplaaqgyr 1981 vvapdlfghg rsshlemvts yssltflaqi drviqelpdq plllvghsmg amlataiasv 2041 rpkkikelil velplpaees kkesavnqlt tcldylsstp qhpifpdvat aasrlrqaip 2101 slseefsyil aqritqpnqg gvrwswdaii rtrsilglnn lpggrsqyle mlksiqvptt 2161 lvygdsskln rpedlqqqkm tmtqakrvfl sgghnlhida aaalaslilt s
```

HexORF1 has the following amino acid sequence (SEQ ID NO:2):

MADLSKLSDSRTAQPGRIVRPWPLSGCNESALRARARQLRAHLDRFPDAG
VEGVGAALAHDEQADAGPHRAVVVASSTSELLDGLAAVADGRPHASVVRG
VARPSAPVVFVFPGQGAQWAGMAGELLGESRVFAAAMDACARAFEPVTDW
TLAQVLDSPEQSRRVEVVQPALFAVQTSLAALWRSFGVTPDAVVGHSIGE
LAAAHVCGAAGAADAARAAALWSREMIPLVGNGDMAAVALSADEIEPRIA
RWDDDVVLAGVNGPRSVLLTGSPEPVARRVQELSAEGVRAQVINVSMAAH
SAQVDDIAEGMRSALAWFAPGGSEVPFYASLTGGAVDTRELVADYWRRSF
RLPVRFDEAIRSALEVGPGTFVEASPHPVLAAALQQTLDAEGSSAAVVPT
LQRGQGGMRRFLLAAAQAFTGGVAVDWTAAYDDVGAEPGSLPEFAPAEEE
DEPAESGVDWNAPPHVLRERLLAVVNGETAALAGREADAEATFRELGLDS
VLAAQLRAKVSAAIGREVNIALLYDHPTPRALAEALAAGTEVAQRETRAR
TNEAAPGEPVAVVAMACRLPGGVSTPEEFWELLSEGRDAVAGLPTDRGWD
LDSLFHPDPTRSGTAHQRGGGFLTEATAFDPAFFGMSPREALAVDPQQRL
MLELSWEVLERAGIPPTSLQASPTGVFVGLIPQEYGPRLAEGGEGVEGYL
MTGTTTSVASGRIAYTLGLEGPAISVDTACSSSLVAVHLACQSLRRGESS
LAMAGGVTVMPTPGMLVDFSRMNSLAPDGRCKAFSAGANGFGMAEGAGML
LLERLSDARRNGHPVLAVLRGTAVNSDGASNGLSAPNGRAQVRVIQQALA
ESGLGPADIDAVEAHGTGTRLGDPIEARALFEAYGRDREQPLHLGSVKSN
LGHTQAAAGVAGVIKMVLAMRAGTLPRTLHASERSKEIDWSSGAISLLDE
PEPWPAGARPRRAGVSSFGVSGTNAHVIVEEAPESSADAVAESGVRVPVP
VVPWVVSARSAEGLAAQAERLARFVGERSDQDPVDIGFSLVRSRSLLEHR
AVVLGKGRDDLVAGLASLASDGSATGVVSGVARGRARVAFGFSGQGAQRV
GMGAELASVYPVFAEALAEVTGALGLDPEVFGDVDRLGRTEVTQAALFAF
EVAVVRLLESFGVRPDVLIGHSIGEIAAAYVAGVFSLGDAAALVGARGRL
MQALPAGGVMVAVQAGEAEVVAALEGFADRVSLAAVNGPSSVVVSGEAEA
VEQVVARLGKVKSKRLRVSHAFHSPLMEPMLADFRQVAEQITYNEPQLPV
VSNVSGRLAEPGELTTPDYWVRHVREAVRFGDGVRALAADGVGVLVEVGP
DSVLTALARESLDGEDGLRAVPLLRKDRPEPETLLTGVAQAFTHGVQVDW
PALLPGGRRVELPTYAFQRRRYWLEDADPTGGDPAALGLTAADHPLLGAA
VPLAEDQGIVITSRLSLRTHPWLADHEIGGTVLLPGAGLVEIALRAGDEV
GCGRVEELTLEIPLVVPQEGGVTVQIRVGAPDESGWRPMTVHSRTDPEEE
WTRHVSGVLSPDVPTERYDLGAWPPAGATPVELDGFYEAYARLGYAYGPS
FQGLRAAWRRGDEVFAEVSLPVEEQETAGRFTLHPALLDAALQSAGAGAF
FDSGGSMRLPFAWSGVSVFAAGASTVRVRLSPAGPDAVTVALADPTGAPV
ALVERLLIPEMSPEQLERVRGEEKEAPYVLDWVPVEVPADDLVRPERWTL
LGGADAGVGLDVAGAFASLEPSDGAPEFVVLPCVPPTSPTRAADVRQSTL
QALTVLQNWVTDERHADSRLVLVTRRAVGVGAHDDVPDLTHAALWGLVRS
AQTENPGRFLLVDLDEGAELAEVLPGALGSGESQVAVRAGRVLAARLARS
GSGGAELVPPAGAPWRLDTTSPGTLENLALVPSAEEPLGPLDVRVSVRAA
GLNFRDVLIALGMYPGDARMGGEGAGVVTDVGSEVTTLAPGDRVMGMLSS
AFGPTAVSDHRALVRVPDDWSFEQAASVPTVFATAYYGLVDLAELRAGQS
VLVHAAAGGVGMAAVQLARHLGAEVFGTASTGKWDSLRAGGLDAEHIASS
RTVEFEETFLAATAGRGVDVVLDSLAGEFVDASLRLLPRGGRFVEMGKAD
IRDAERVAADHPGVTYRSFDLLEAGLDRFQEILTEVVRLFERGVLRHLPV
TAWDVRRAAEAFRFVSQARHVGKNVLVMPRVWDRDGTVLITGGTGALGAL
VARHLVAEHGMRNVLLAGRRGVDAPGARELLAELETAGAQVSVVACDVAD
RDAVAELIAKVPVEHPLTAVVHTAGVVADATLTALDAERVDTVLRAKVDA
VLHLHEATRGLDLAGFVLFSSASGIFGSPGQGNYAAANSFIDAFAHHRRA
QGLPALSLAWGLWARTSGMAGQLGHDDVARISRTGLAPITDDQGMALLDA
ALGAGRPLLVPVRLDRAALRSQATAGTLPPILRGLVRATVRRAASTAAAQ
GPSLAERLAGLPVTEHERIVVELVRADLAAVLGHSSSAGIDPGRAFQDMG

IDSLTAVELRNRLNGATGLRLAASLVFDYPTPNALATHILDELALDTAGA

GAAGEPDGPAPAPADEARFRRVINSIPLDRIRRAGLLDALLGLAGTSADT

AASDDFDQEEDGPAIASMDVDDLVRIALGESDTTADITEGTDRS*

HexORF1' has the following amino acid sequence (SEQ ID NO:3):

MADLSKLSDSRTAQPGRIVRPWPLSGCNESALRARARQLRAHLDRFPDAG

VEGVGAALAHDEQADAGPHRAVVVASSTSELLDGLAAVADGRPHASVVRG

VARPSAPVVFVFPGQGAQWAGMAGELLGESRVFAAAMDACARAFEPVTDW

TLAQVLDSPEQSRRVEVVQPALFAVQTSLAALWRSFGVTPDAVVGHSIGE

LAAAHVCGAAGAADAARAAALWSREMIPLVGNGDMAAVALSADEIEPRIA

RWDDDVVLAGVNGPRSVLLTGSPEPVARRVQELSAEGVRAQVINVSMAAH

SAQVDDIAEGMRSALAWFAPGGSEVPFYASLTGGAVDTRELVADYWRRSF

RLPVRFDEAIRSALEVGPGTFVEASPHPVLAAALQQTLDAEGSSAAVVPT

LQRGQGGMRRFLLAAAQAFTGGVAVDWTAAYDDVGAEPGSLPEFAPAEEE

DEPAESGVDWNAPPHVLRERLLAVVNGETAALAGREADAEATFRELGLDS

VLAAQLRAKVSAAIGREVNIALLYDHPTPRALAEALAAGTEVAQRETRAR

TNEAAPGEPVAVVAMACRLPGGVSTPEEFWELLSEGRDAVAGLPTDRGWD

LDSLFHPDPTRSGTAHQRGGGFLTEATAFDPAFFGMSPREALAVDPQQRL

MLELSWEVLERAGIPPTSLQASPTGVFVGLIPQEYGPRLAEGGEGVEGYL

MTGTTTSVASGRIAYTLGLEGPAISVDTACSSSLVAVHLACQSLRRGESS

LAMAGGVTVMPTPGMLVDFSRMNSLAPDGRCKAFSAGANGFGMAEGAGML

LLERLSDARRNGHPVLAVLRGTAVNSDGASNGLSAPNGRAQVRVIQQALA

ESGLGPADIDAVEAHGTGTRLGDPIEARALFEAYGRDREQPLHLGSVKSN

LGHTQAAAGVAGVIKMVLAMRAGTLPRTLHASERSKEIDWSSGAISLLDE

PEPWPAGARPRRAGVSSFGVSGTNAHVIVEEAPESSADAVAESGVRVPVP

VVPWVVSARSAEGLAAQAERLARFVGERSDQDPVDIGFSLVRSRSLLEHR

AVVLGKGRDDLVAGLASLASDGSATGVVSGVARGRARVAFGFSGQGAQRV

GMGAELASVYPVFAEALAEVTGALGLDPEVFGDVDRLGRTEVTQAALFAF

EVAVVRLLESFGVRPDVLIGHSIGEIAAAYVAGVFSLGDAAALVGARGRL

MQALPAGGVMVAVQAGEAEVVAALEGFADRVSLAAVNGPSSVVVSGEAEA

VEQVVARLGKVKSKRLRVSHAFHSPLMEPMLADFRQVAEQITYNEPQLPV

VSNVSGRLAEPGELTTPDYWVRHVREAVRFGDGVRALAADGVGVLVEVGP

DSVLTALARESLDGEDGLRAVPLLRKDRPEPETLLTGVAQAFTHGVQVDW

PALLPGGRRVELPTYAFQRRRYWLEDADPTGGDPAALGLTAADHPLLGAA

VPLAEDQGIVITSRLSLRTHPWLADHEIGGTVLLPGAGLVEIALRAGDEV

GCGRVEELTLEIPLVVPQEGGVTVQIRVGAPDESGWRPMTVHSRTDPEEE

WTRHVSGVLSPDVPTERYDLGAWPPAGATPVELDGFYEAYARLGYAYGPS

FQGLRAAWRRGDEVFAEVSLPVEEQETAGRFTLHPALLDAALQSAGAGAF

FDSGGSMRLPFAWSGVSVFAAGASTVRVRLSPAGPDAVTVALADPTGAPV

ALVERLLIPEMSPEQLERVRGEEKEAPYVLDWVPVEVPADDLVRPERWTL

LGGADAGVGLDVAGAFASLEPSDGAPEFVVLPCVPPTSPTRAADVRQSTL

QALTVLQNWVTDERHADSRLVLVTRRAVGVGAHDDVPDLTHAALWGLVRS

AQTENPGRFLLVDLDEGAELAEVLPGALGSGESQVAVRAGRVLAARLARS

GSGGAELVPPAGAPWRLDTTSPGTLENLALVPSAEEPLGPLDVRVSVRAA

GLNFRDVLIALGMYPGDARMGGEGAGVVTDVGSEVTTLAPGDRVMGMLSS

AFGPTAVSDHRALVRVPDDWSFEQAASVPTVFATAYYGLVDLAELRAGQS

VLVHAAAGGVGMAAVQLARHLGAEVFGTASTGKWDSLRAGGLDAEHIASS

RTVEFEETFLAATAGRGVDVVLDSLAGEFVDASLRLLPRGGRFVEMGKAD

IRDAERVAADHPGVTYRSFDLLEAGLDRFQEILTEVVRLFERGVLRHLPV

TAWDVRRAAEAFRFVSQARHVGKNVLVMPRVWDRDGTVLITGGTGALGAL

VARHLVAEHGMRNVLLAGRRGVDAPGARELLAELETAGAQVSVVACDVAD

RDAVAELIAKVPVEHPLTAVVHTAGVVADATLTALDAERVDTVLRAKVDA

VLHLHEATRGLDLAGFVLFSSASGIFGSPGQGNYAAANSFIDAFAHHRRA

QGLPALSLAWGLWARTSGMAGQLGHDDVARISRTGLAPITDDQGMALLDA

ALGAGRPLLVPVRLDRAALRSQATAGTLPPILRGLVRATVRRAASTAAAQ

GPSLAERLAGLPVTEHERIVVELVRADLAAVLGHASAERVPADQAFAELG

VDSLTAVELRNRLNGATGLRLAASLVFDYPTPNALATHILDELALDTAGA

GAAGEPDGPAPAPADEARFRRVINSIPLDRIRRAGLLDALLGLAGTSADT

AASDDFDQEEDGPAIASMDVDDLVRIALGESDTTADITEGTDRS*

HexORF2 has the following amino acid sequence (SEQ ID NO:4):

MSSASSEKIVEALRASLTENERLRRLNQELAAAAHEPVAIVSMACRFPGG

VESPEDFWDLISEGRDAVSGLPDNRGWDLDALYDPDPEAQGKTYVREGAF

LYDAAEFDAELFGISPREALAMDPQQRLLMETSWEVLERAGIRPDSLRGK

PVGVFTGGITSDYVTRHYASGTAPQLPSGVESHFMTGSAGSVFSGRIAYT

YGFEGPAVTVDTACSSSLVALHMAAQSLRQGECSLAFAGGVAVLPNPGTF

VGFSRQRALSPDGRCKAFSADADGTGWGEGAGLVLLEKLSDARRNGHPVL

AILRGSAVNQDGASNGLTAPNGPSQQRVIRAALANARLSPDDVDVVEAHG

TGTPLGDPIEAQALQATYGRSRSAERPLWLGSVKSNVAHAQAAAGVASVI

KVVMALRHRLLPKTLHADERSPHIDWHSGAVELLTEAREWSRTEGRARRA

GVSSFGISGTNAHVIIEEAPELIKGQKAKGKSENDLERPLHILTLSTKTE

KALEELVSRYQNHWETYPELAISDVCYTANTGRAQFNHRLAVIASGSEEL

TQKLRQHTAGEEVVGVFSGKVPNSGSESKVAFLFTGQGSQYLNMGRQLYE

TQPTFRQALDTCDHILRPYLDNPLLEILYPQDAQKSNDSPLDQTGYTQPA

LFSIEYALLKLWESWGIKPNVVMGHSVGEYVAATVAGVFSLEDGLKLIAA

RGRLMQGLPAGGEMVSVMASESKVLETLKAMSLEDKVAIAAINGPESIVI

SGEAEAIRAMATHLESVGIKTKQLQVSHAFHSPLMEPMLAEFEAVANQIT

YHQPRIPIISNVTGTKADKSIATAQYWVNHVRQPVRFAQGMATLHQQGYE

TFLEIGAKPILLGMGKQCLSPDVGVWLPSLRHGVDEWQQILSSLGQLYVQ

GAKVDWSGFDRDYSREKVVLPTYPFQRERYWVETSINQQQVVCSGEPNLQ

-continued

```
GTPEGTSTTIVKLLSQGNTKELAEKVEKTSDLPPEQLKLLPDLLASLSQQ
HQQELARLTTKKWFYKVQWISQAIKPQRNKSNNQVCHWLILTDSKGLGKS
LATHLQQLGNECSVVYQADNYQNYEPGIYHINPSHPQEFEQVYQTIFENG
KLPLQKVIHLWSLDTASEQDLTTETLEQAQLWGCGSTLHLLQTLVKNPNS
TPPKLWMITRGTQPVLSPTEKLTVATSPLWGLGRTIASEHPQLWGGLVDL
DPQGSEDEVEVLLQQIIDSQKEDHLAVRNRKIYVARLLKHIPQESQPLSL
RSDATYLITGGLGALGLKTAAWMAEKGARNLVLISRRQPSEQAQQTIQSL
EELGTQVKVLSADISVESDVANILEQIQTSLPPLLGVIHAAGVLDDGLLQ
QTNWERFTKVMAPKVNGTWNLHKLTQHLSLDFFVCFSSMSSLLGSPGQGN
YAAANAFMDAVVHYRREMGLPGLSINWGGWSEGGMATRLASQHQNRMQTA
GISLISPEQGIQVLEELVRTQSTAQVGVLPVDWSVLAKQFSSANPSSLLL
ELLQQETSSEKTDERILEKLQAAPITERQDILKNYIQLVVAKTLGINPSK
ISTDDNFVELGMDSLMGMEVVNKLSGDLDFIIYPREFYERPTIDSLTQYL
SAELSEDNLATQPSPTSLEIFATKSSPSGNSARPASVSSRLPGIIFILSS
PRSGSTLLRVMLAGHSSLFSPPELHLLPFNTMKERQEQLNLSYLGEGLQK
TFMEVKNLDATASQALIKDLESQNLSIQQVYGMLQENIAPRLLVDKSPTY
AMEPTILERGEALFANSKYIYLVRHPYSVIESFVRMRMQKLVGLGEENPY
RVAEQVWAKSNQNILNFLSQLEPERQHQIRYEDLVKKPQQVLSQLCDFLN
VPFEPELLQPYQGDRMTGGVHQKSLSISDPNFLKHNTIDESLADKWKTIQ
LPYPLKSETQRIASQLSYELPNLVTTPTNQQPQVSTTPSTEQPIMEEKFL
EFGGNQICLCSWGSPEHPVVLCIHGILEQGLAWQEVALPLAAQGYRVVAP
DLFGHGRSSHLEMVTSYSSLTFLAQIDRVIQELPDQPLLLVGHSMGAMLA
TAIASVRPKKIKELILVELPLPAEESKKESAVNQLTTCLDYLSSTPQHPI
FPDVATAASRLRQAIPSLSEEFSYILAQRITQPNQGGVRWSWDAIIRTRS
ILGLNNLPGGRSQYLEMLKSIQVPTTLVYGDSSKLNRPEDLQQQKMTMTQ
AKRVFLSGGHNLHIDAAAALASLILTS*
```

The amino acid sequence of a PKS capable of producing 1-butene has the following amino acid sequence (SEQ ID NO:5):

```
MADLSKLSDSRTAQPGRIVRPWPLSGCNESALRARARQLRAHLDRFPDAG
VEGVGAALAHDEQADAGPHRAVVVASSTSELLDGLAAVADGRPHASVVRG
VARPSAPVVFVFPGQGAQWAGMAGELLGESRVFAAAMDACARAFEPVTDW
TLAQVLDSPEQSRRVEVVQPALFAVQTSLAALWRSFGVTPDAVVGHSIGE
LAAAHVCGAAGAADAARAAALWSREMIPLVGNGDMAAVALSADEIEPRIA
RWDDDVVLAGVNGPRSVLLTGSPEPVARRVQELSAEGVRAQVINVSMAAH
SAQVDDIAEGMRSALAWFAPGGSEVPFYASLTGGAVDTRELVADYWRRSF
RLPVRFDEAIRSALEVGPGTFVEASPHPVLAAALQQTLDAEGSSAAVVPT
LQRGQGGMRRFLLAAAQAFTGGVAVDWTAAYDDVGAEPGSLPEFAPAEEE
DEPAESGVDWNAPPHVLRERLLAVVNGETAALAGREADAEATFRELGLDS
VLAAQLRAKVSAAIGREVNIALLYDHPTPRALAEALSSGTEVAQRETRAR
TNEAAPGEPIAVVAMACRLPGGVSTPEEFWELLSEGRDAVAGLPTDRGWD
LDSLFHPDPTRSGTAHQRGGGFLTEATAFDPAFFGMSPREALAVDPQQRL
MLELSWEVLERAGIPPTSLQASPTGVFVGLIPQEYGPRLAEGGEGVEGYL
MTGTTTSVASGRIAYTLGLEGPAISVDTACSSSLVAVHLACQSLRRGESS
LAMAGGVTVMPTPGMLVDFSRMNSLAPDGRCKAFSAGANGFGMAEGAGML
LLERLSDARRNGHPVLAVLRGTAVNSDGASNGLSAPNGRAQVRVIQQALA
ESGLGPADIDAVEAHGTGTRLGDPIEARALFEAYGRDREQPLHLGSVKSN
LGHTQAAAGVAGVIKMVLAMRAGTLPRTLHASERSKEIDWSSGAISLLDE
PEPWPAGARPRRAGVSSFGISGTNAHAIIEEAPELIKGQKAKGKSENDLE
RPLHILTLSTKTEKALEELVSRYQNHWETYPELAISDVCYTANTGRAQFN
HRLAVIASGSEELTQKLRQHTAGEEVVGVFSGKVPNSGSESKVAFLFTGQ
GSQYLNMGRQLYETQPTFRQALDTCDHILRPYLDNPLLEILYPQDAQKSN
DSPLDQTGYTQPALFSIEYALLKLWESWGIKPNVVMGHSVGEYVAATVAG
VFSLEDGLKLIAARGRLMQGLPAGGEMVSVMASESKVLETLKAMSLEDKV
AIAAINGPESIVISGEAEAIRAMATHLESVGIKTKQLQVSHAFHSPLMEP
MLAEFEAVANQITYHQPRIPIISNVTGTKADKSIATAQYWVNHVRQPVRF
AQGMATLHQQGYETFLEIGAKPILLGMGKQCLSPDVGVWLPSLRHGVDEW
QQILSSLGQLYVQGAKVDWSGFDRDYSREKVVLPTYPFQRERYWVETSIN
QQQVVCSGEPNLQGTPEGTSTTIVKLLSQGNTKELAEKVEKTSDLPPEQL
KLLPDLLASLSQQHQQELARLTTKKWFYKVQWISQAIKPQRNKSNNQVCH
WLILTDSKGLGKSLATHLQQLGNECSVVYQADNYQNYEPGIYHINPSHPQ
EFEQVYQTIFENGKLPLQKVIHLWSLDTASEQDLTTETLEQAQLWGCGST
LHLLQTLVKNPNSTPPKLWMITRGTQPVLSPTEKLTVATSPLWGLGRTIA
SEHPQLWGGLVDLDPQGSEDEVEVLLQQIIDSQKEDHLAVRNRKIYVARL
LKHIPQESQPLSLRSDATYLITGGLGALGLKTAAWMAEKGARNLVLISRR
QPSEQAQQTIQSLEELGTQVKVLSADISVESDVANILEQIQTSLPPLLGV
IHAAGVLDDGLLQQTNWERFTKVMAPKVNGTWNLHKLTQHLSLDFFVCFS
SMSSLLGSPGQGNYAAANAFMDAVVHYRREMGLPGLSINWGGWSEGGMAT
RLASQHQNRMQTAGISLISPEQGIQVLEELVRTQSTAQVGVLPVDWSVLA
KQFSSANPSSLLLELLQQETSSEKTDERILEKLQAAPITERQDILKNYIQ
LVVAKTLGINPSKISTDDNFVELGMDSLMGMEVVNKLSGDLDFIIYPREF
YERPTIDSLTQYLSAELSEDNLATQPSPTSLEIFATKSSPSGNSARPASV
SSRLPGIIFILSSPRSGSTLLRVMLAGHSSLFSPPELHLLPFNTMKERQE
QLNLSYLGEGLQKTFMEVKNLDATASQALIKDLESQNLSIQQVYGMLQEN
IAPRLLVDKSPTYAMEPTILERGEALFANSKYIYLVRHPYSVIESFVRMR
MQKLVGLGEENPYRVAEQVWAKSNQNILNFLSQLEPERQHQIRYEDLVKK
PQQVLSQLCDFLNVPFEPELLQPYQGDRMTGGVHQKSLSISDPNFLKHNT
IDESLADKWKTIQLPYPLKSETQRIASQLSYELPNLVTTPTNQQPQVSTT
PSTEQPIMEEKFLEFGGNQICLCSWGSPEHPVVLCIHGILEQGLAWQEVA
LPLAAQGYRVVAPDLFGHGRSSHLEMVTSYSSLTFLAQIDRVIQELPDQP
LLLVGHSMGAMLATAIASVRPKKIKELILVELPLPAEESKKESAVNQLTT
CLDYLSSTPQHPIFPDVATAASRLRQAIPSLSEEFSYILAQRITQPNQGG
```

```
VRWSWDAIIRTRSILGLNNLPGGRSQYLEMLKSIQVPTTLVYGDSSKLNR

PEDLQQQKMTMTQAKRVFLSGGHNLHIDAAAALASLILTS*
```

The amino acid sequence of a PKS capable of producing propene has the following amino acid sequence (SEQ ID NO:6):

```
MAGHGDATAQKAQDAEKSEDGSDAIAVIGMSCRFPGAPGTAEFWQLLSSG

ADAVVTAADGRRRGTIDAPADFDAAFFGMSPREAAATDPQQRLVLELGWE

ALEDAGIVPESLRGEAASVFVGAMNDDYATLLHRAGAPTDTYTATGLQHS

MIANRLSYFLGLRGPSLVVDTGQSSSLVAVALAVESLRGGTSGIALAGGV

NLVLAEEGSAAMERVGALSPDGRCHTFDARANGYVRGEGGAIVVLKPLAD

ALADGDRVYCVVRGVATGNDGGGPGLTVPDRAGQEAVLRAACDQAGVRPA

DVRFVELHGTGTPAGDPVEAEALGAVYGTGRPANEPLLVGSVKTNIGHLE

GAAGIAGFVKAALCLHERALPASLNFETPNPAIPLERLRLKVQTAHAALQ

PGTGGGPLLAGVSAFGMGGTNCHVVLEETPGGRQPAETGQADACLFSASP

MLLLSARSEQALRAQAARLREHLEDSGADPLDIAYSLATTRTRFEHRAAV

PCGDPDRLSSALAALAAGQTPRGVRIGSTDADGRLALLFTGQGAQHPGMG

QELYTTDPHFAAALDEVCEELQRCGTQNLREVMFTPDQPDLLDRTEYTQP

ALFALQTALYRTLTARGTQAHLVLGHSVGEITAAHIAGVLDLPDAARLIT

ARAHVMGQLPHGGAMLSVQAAEHDLDQLAHTHGVEIAAVNGPTHCVLSGP

RTALEETAQHLREQNVRHTWLKVSHAFHSALMDPMLGAFRDTLNTLNYQP

PTIPLISNLTGQIADPNHLCTPDYWIDHARHTVRFADAVQTAHHQGTTTY

LEIGPHPTLTTLLHHTLDNPTTIPTLHRERPEPETLTQAIAAVGVRTDGI

DWAVLCGASRPRRVELPTYAFQRRTHWAPGLTPNHAPADRPAAEPQRAMA

VGPVSREALVRLVGETTASVLGLDGPDEVALDRPFTSQGLDSMTAVELAG

LLGTAAGVALDPTLVYELPTPRAVADHLAKTLLGESAADADQEVNGRTGE

AEAKAGDPIAVIGIGCRFPGGVATPDDLWELVASGTDAISTFPTDRGWDL

DGLYDPDPSTPGKSYVRHGGFLHDAAQFDAEFFGISPREATAMDPQQRLL

LETSWEALERAGVVPESLRGGRTGVFVGTTAPEYGPRLHEGTDGYEGFLL

TGTTASVASGRIAYALGTRGPALTVDTACSSSLVALHLAVQSLRRGECDL

ALAGGTTVMSGPGMFVEFSRQRGLAPDGRCKAFSADADGTAWAEGVGMLL

VERLSDAERLGHRVLAVVRGTAVNQDGASNGLTAPSGPAQQQVIRDALSD

AGLSADDIDAVEAHGTGTALGDPIEAGALLATYGHPKRQTPVWLGSLKSN

IGHTQAAAGIAGIIKMVQALRHDTLPRTLHADHPSSKVDWDAGPLQLLTD

ARPWPADPDRPRRAGISAFGVSGTNAHVVLEEPPELIKGQKAKGKSENDL

ERPLHILTLSTKTEKALEELVSRYQNHWETYPELAISDVCYTANTGRAQF

NHRLAVIASGSEELTQKLRQHTAGEEVVGVFSGKVPNSGSESKVAFLFTG

QGSQYLNMGRQLYETQPTFRQALDTCDHILRPYLDNPLLEILYPQDAQKS

NDSPLDQTGYTQPALFSIEYALLKLWESWGIKPNVVMGHSVGEYVAATVA

GVFSLEDGLKLIAARGRLMQGLPAGGEMVSVMASESKVLETLKAMSLEDK

VAIAAINGPESIVISGEAEAIRAMATHLESVGIKTKQLQVSHAFHSPLME

PMLAEFEAVANQITYHQPRIPIISNVTGTKADKSIATAQYWVNHVRQPVR

FAQGMATLHQQGYETFLEIGAKPILLGMGKQCLSPDVGVWLPSLRHGVDE

WQQILSSLGQLYVQGAKVDWSGFDRDYSREKVVLPTYPFQRERYWVETSI

NQQQVVCSGEPNLQGTPEGTSTTIVKLLSQGNTKELAEKVEKTSDLPPEQ

LKLLPDLLASLSQQHQQELARLTTKKWFYKVQWISQAIKPQRNKSNNQVC

HWLILTDSKGLGKSLATHLQQLGNECSVVYQADNYQNYEPGIYHINPSHP

QEFEQVYQTIFENGKLPLQKVIHLWSLDTASEQDLTTETLEQAQLWGCGS

TLHLLQTLVKNPNSTPPKLWMITRGTQPVLSPTEKLTVATSPLWGLGRTI

ASEHPQLWGGLVDLDPQGSEDEVEVLLQQIIDSQKEDHLAVRNRKIYVAR

LLKHIPQESQPLSLRSDATYLITGGLGALGLKTAAWMAEKGARNLVLISR

RQPSEQAQQTIQSLEELGTQVKVLSADISVESDVANILEQIQTSLPPLLG

VIHAAGVLDDGLLQQTNWERFTKVMAPKVNGTWNLHKLTQHLSLDFFVCF

SSMSSLLGSPGQGNYAAANAFMDAVVHYRREMGLPGLSINWGGWSEGGMA

TRLASQHQNRMQTAGISLISPEQGIQVLEELVRTQSTAQVGVLPVDWSVL

AKQFSSANPSSLLLELLQQETSSEKTDERILEKLQAAPITERQDILKNYI

QLVVAKTLGINPSKISTDDNFVELGMDSLMGMEVVNKLSGDLDFIIYPRE

FYERPTIDSLTQYLSAELSEDNLATQPSPTSLEIFATKSSPSGNSARPAS

VSSRLPGIIFILSSPRSGSTLLRVMLAGHSSLFSPPELHLLPFNTMKERQ

EQLNLSYLGEGLQKTFMEVKNLDATASQALIKDLESQNLSIQQVYGMLQE

NIAPRLLVDKSPTYAMEPTILERGEALFANSKYIYLVRHPYSVIESFVRM

RMQKLVGLGEENPYRVAEQVWAKSNQNILNFLSQLEPERQHQIRYEDLVK

KPQQVLSQLCDFLNVPFEPELLQPYQGDRMTGGVHQKSLSISDPNFLKHN

TIDESLADKWKTIQLPYPLKSETQRIASQLSYELPNLVTTPTNQQPQVST

TPSTEQPIMEEKFLEFGGNQICLCSWGSPEHPVVLCIHGILEQGLAWQEV

ALPLAAQGYRVVAPDLFGHGRSSHLEMVTSYSSLTFLAQIDRVIQELPDQ

PLLLVGHSMGAMLATAIASVRPKKIKELILVELPLPAEESKKESAVNQLT

TCLDYLSSTPQHPIFPDVATAASRLRQAIPSLSEEFSYILAQRITQPNQG

GVRWSWDAIIRTRSILGLNNLPGGRSQYLEMLKSIQVPTTLVYGDSSKLN

RPEDLQQQKMTMTQAKRVFLSGGHNLHIDAAAALASLILTS
```

The amino acid sequence of a PKS capable of producing styrene has the following amino acid sequence (SEQ ID NO:7):

```
MTKEYTRPQSAPLTEGDLLTLIVAHLAERLRMDARFIDVHEPFSRHGLDS

RGAVDLVVDLRTALGRPLSPVVVWQHPTPDALARHLAGGADAREGQARAD

SAYERPGAPNEPIAIVGMACRFPGAPDVDSYWRLLSGGVDAVTEVPAGRW

DMDAFYDRDPRSLGDVSTLRGGFIDDVDRFDAMFFGISPREAVSMDPQQR

LMLELAWEALEDAGIVAERLKESLTGVFFGCIWDDYVTLIHQRGRGAIAQ

HTVTGNHRSIIANRVSYTLDLRGPSMTVDSACSSALVTIHMACESLRSGE

STLALAGGVNLNIAPESTIGVHKFGGLSPDGRCFTFDARANGYVRGEGGG

VVVLKRLSSAIADGDPIICVIRGSAVNNDGASNGLTGPNPLAQEAVLRTA

YERAGVNPADVQYVELHGTGTQLGDPVEASALGAVLGKRRPAERPLLVGS

AKTNVGHLEGAAGIVGLLKAALCLKHKQLAPNLNFETPNPHIPPFAELNLK
```

-continued
```
VQGALGPWPDMDRPLVCGVSSFGLGGTNAHVVLSEWASLEAELHPLAAES
PEALREEVQRRLLTMTSLVGRAPLSFLCGRSAAQRSAKEHRLAVTARSFE
ELKQRLLGFLEHEKHVSVSAGRVDLGAAPKVVFVFAGQGAQWFGMGRALL
QREPVFRTTIEQCSSFIQQNLGWSLLDELMTDRESSRLDEIDVSLPAIIS
IEIALAAQWRAWGVEPAFVVGHSTGEIAAAHVAGVLSIEDAMRTICAYGR
IIRKLRGKGGMGLVALSWEDAGKELTGYEGRLFRAIEHSADSTVLAGEPD
ALDALLQALERKNVFCRRVAMDVAPHCPQVDCLRDELFDALREVRPNKAQ
IPIVSEVTGTALDGERFDASHWVRNFGDPALFSTAIDHLLQEGFDIFLEL
TPHPLALPAIESNLRRSGRRGVVLPSLRRNEDERGVMLDTLGVLYVRGAP
VRWDNVYPAAFESMPLPSTAGGGKPLPPMPLLISARTDAALAAQAARLRA
HLDSHLDLELVDVAYSLAATRTHFERRAVVVARDRAGILDGLDALAHGGS
AALLGRSAAHGKLAILFTGQGSQRPTMGRALYDAFPVFRGALDAAAAHLD
RDLDRPLRDVLFAPDGSEQAARLDQTAFTQPALFALEVALFELLQSFGLK
PALLLGHSIGELVAAHVAGVLSLQDACTLVAARAKLMQALPQGGAMVTLQ
ASEQEARDLLQAAEGRVSLAAVNGHLSTVVAGDEDAVLKIARQVEALGRK
ATRLRVSHAFHSPHMDGMLDDFRRVAQGLTFHPARIPIISNVTGARATDQ
ELASPETWVRHVRDTVRFLDGVRTLHAEGARAFLELGPHPVLSALAQDAL
GHDEGPSPCAFLPTLRKGRDDAEAFTAALGALHAAGLTPDWNAFFAPFAP
CKVPLPTYTFQRERFWLDASTAHAASATPAAALEGRFWQAVESGDIDTLS
SELHVDGDEQRAALALVLPTLSSFRHKRQEQSTVDAWRYRVTWKPLTTAA
TPADLAGTWLLVVPSALGDDALLATLTEALTRRGARVLALRVSDIHIGRS
ALVEHLREALAETAPLRGVLSLLALDEHRLADRSALPAGLALSLALVQGL
DDLAIEAPLWLFTRGAVSIGHSDPITHPTQAMIWGLGRVVGLEHPERWGG
LVDVSAGVDESAVGRLLPALAQRHDEDQLALRPAGLYARRIVRAPLGDAP
PAREFRPRGTILITGGTGALGAHVARWLARQGAEHLILISRRGAEAPGAS
ELHAELNALGVRTTLAACDVADRSALQALLDSIPSDCPLTAVFHTAGARD
DGLIGDMTPERIERVLAPKLDSALHLHELTKNSALDAFVLYASLSGVLGN
PGQANYAAANAFLDALAEHRRSLGLTATSVAWGGWGGGMATERVAAQLQ
QRGLLQMAPSLALAALAQALQQDETTITVADIDWSRFAPAFSVARQRPLL
RDLPEAQRALQASEGASSEHGPATGLLDELRSRSESEQLDLLATLVRGET
ATVLGHAEASHVDPDKGFMDLGLDSLMTVELRRRLQKATGVKLPPTLAFD
HPSPHRVAFFLRDSLSEDNLATQPSPTSLEIFATKSSPSGNSARPASVSS
RLPGIIFILSSPRSGSTLLRVMLAGHSSLFSPPELHLLPFNTMKERQEQL
NLSYLGEGLQKTFMEVKNLDATASQALIKDLESQNLSIQQVYGMLQENIA
PRLLVDKSPTYAMEPTILERGEALFANSKYIYLVRHPYSVIESFVRMRMQ
KLVGLGEENPYRVAEQVWAKSNQNILNFLSQLEPERQHQIRYEDLVKKPQ
QVLSQLCDFLNVPFEPELLQPYQGDRMTGGVHQKSLSISDPNFLKHNTID
ESLADKWKTIQLPYPLKSETQRIASQLSYELPNLVTTPTNQQPQVSTTPS
TEQPIMEEKFLEFGGNQICLCSWGSPEHPVVLCIHGILEQGLAWQEVALP
LAAQGYRVVAPDLFGHGRSSHLEMVTSYSSLTFLAQIDRVIQELPDQPLL
LVGHSMGAMLATAIASVRPKKIKELILVELPLPAEESKKESAVNQLTTCL
DYLSSTPQHPIFPDVATAASRLRQAIPSLSEEFSYILAQRITQPNQGGVR
WSWDAIIRTRSILGLNNLPGGRSQYLEMLKSIQVPTTLVYGDSSKLNRPE
DLQQQKMTMTQAKRVFLSGGHNLHIDAAAALASLILTS
```

The amino acid sequence of a PKS (pentene ORF1) capable of producing pentene has the following amino acid sequence (SEQ ID NO:8):

```
MRAPYGNRQVNRRFLREFRAKRPHCVSPLHFLAEFSESRQTTGSAGVTAP
IDRPGVSMAPKSGAQRSSDIAVVGMSCRLPGAPGIDEFWHLLTTGGSAIE
RRADGTWRGSLDGAADFDAAFFDMTPRQAAAADPQQRLMLELGWTALENA
GIVPGSLAGTDTGVFVGIAADDYAALLHRSATPVSGHTATGLSRGMAANR
LSYLLGLRGPSLAVDSAQSSSLVAVHLACESLRRGESDLAIVGGVSLILA
EDSTAGMELMGALSPDGRCHTFDARANGYVRGEGGACVVLKPLERALADG
DRVHCVVRGSAVNNDGGGSTLTTPHREAQAAVLRAAYERAGVGPDQVSYV
ELHGTGTPVGDPVEAAALGAVLGTAHGRNAPLSVGSVKTNVGHLEAAAGL
VGFVKAALCVREGVVPPSLNHATPNPAIPMDRLNLRVPTRLEPWPHPDDR
ATGRLRLAGVSSFGMGGTNAHVVVEEAPLPEAGEPVGAGVPLAVVPVVVS
GRSAGAVAELASRLNESVRSDRLVDVGLSSVVSRSVFEHRSVVLAGDSAE
LSAGLDALAADGVSPVLVSGVASVGGGRSVFVFPGAGVKWAGMALGLWAE
SAVFAESMARCEAAFAGLVEWRLADVLGDGAALEREDVVQPASFAVMVSL
AALWRSLGVVPDAVVGHSQGEIAAAVVAGGLSLEDGARVVVLRARVAEEV
LSGGGIASVRLSRAEVEERLAGGGGGLSVAVVNAPSSTVVAGELGDLDRF
VAACEAEGVRARRLEFGYASHSRFVEPVRERLLEGLADVRPVRGRIPFYS
TVEAAEFDTAGLDAEYWFGNLRRPVRFQETVERLLADGFRVFVECGAHPV
LTGAVQETAETAGREICSVGSLRRDEGGLRRFLTSAAEAFVQGVEVSWPV
LFDGTGARTVDLPTYPFQRRHHWAPDGSASAAPTRDIRPDETAAVPADTM
DLAGQLRADVASLPTTEQIARLLDQVRDGVATVLGLDARDEVRAEATFKE
LGVESLTGVELKNHLRARTGLHVPTSLIYDCPTPLAAAHYLRDELLGRPA
EQAVVPAGIPVDEPIAIVGMGCRLPGGVSSPEGLWDLVASGVDAVSPFPT
DRGWDVGGLFDPEPGVPGRSYVREGGFLHEAGEFDAGFFGISPREALAMD
PQQRLLLETSWEALERAGIDPHTLRGSRTGVYAGVMAQEYGPRLHEGADG
YEGYLLTGSSSSVASGRISYVLGLEGPAVTVDTACSSSLVALHLAVRALR
SGECDLALAGGATVMAEPGMFVEFSRQRGLSAHGRCKAYSDSADGTGWAE
GAGVLLVERLSDAVRHGRRVLAVVRGSAVNQDGASNGLTAPNGRSQSRLI
RQALADARLGVADVDVVEGHGTGTRLGDPIEAQALLATYGQRDAGRPLRL
GSLKSNVGHTQAAAGVAGVIKMVMAMRHGVLPKTLHVDEPTAEVDWSAGA
VSLLREQEAWPRGERVRRAGVSSFGVSGTNAHVILEQPPGVPSQSAGPGS
GSVVDVPVVPWMVSGKTPEALSAQATALMTYLDERPDVSSLDVGYSLALT
RSALDERAVVLGSDRETLLCGVKALSAGHEASGLVTGSVGAGGRIGFVFS
GQGGQWLGMGRGLYRAFPVFAAAFDEACAELDAHLGQEIGVREVVSGSDA
QLLDRTLWAQSGLFALQVGLLKLLDSWGVRPSVVLGHSVGELAAAFAAGV
VSLSGAARLVAGRARLMQALPSGGGMLAVPAGEELLWSLLADQGDRVGIA
```

AVNAAGSVVLSGDRDVLDDLAGRLDGQGIRSRWLRVSHAFHSYRMDPMLA

EFAELARTVDYRRCEVPIVSTLTGDLDDAGRMSGPDYWVRQVREPVRFAD

GVQALVEHDVATVVELGPDGALSALIQECVAASDHAGRLSAVPAMRRNQD

EAQKVMTALAHVHVRGGAVDWRSFFAGTGAKQIELPTYAFQRQRYWLVPS

DSGDVTGAGLAGAEHPLLGAVVPVAGGDEVLLTGRISVRTHPWLAEHRVL

GEVIVAGTALLEIALHAGERLGCERVEELTLEAPLVLPERGAIQVQLRVG

APENSGRRPMALYSRPEGAAEHDWTRHATGRLAPGRGEAAGDLADWPAPG

ALPVDLDEFYRDLAELGLEYGPIFQGLKAAWRQGDEVYAEAALPGTEDSG

FGVHPALLDAALHATAVRDMDDARLPFQWEGVSLHAKAAPALRVRVVPAG

DDAKSLLVCDGTGRPVISVDRLVLRSAAARRTGARRQAHQARLYRLSWPT

VQLPTSAQPPSCVLLGTSEVSADIQVYPDLRSLTAALDAGAEPPGVVIAP

TPPGGGRTADVRETTRHALDLVQGWLSDQRLNESRLLLVTQGAVAVEPGE

PVTDLAQAALWGLLRSTQTEHPDRFVLVDVPEPAQLLPALPGVLACGEPQ

LALRRGGAHAPRLAGLGSDDVLPVPDGTGWRLEATRPGSLDGLALVDEPT

ATAPLGDGEVRIAMRAAGVNFRDALIALGMYPGVASLGSEGAGVVVETGP

GVTGLAPGDRVMGMIPKAFGPLAVADHRMVTRIPAGWSFARAASVPIVFL

TAYYALVDLAGLRPGESLLVHSAAGGVGMAAIQLARHLGAEVYATASEDK

WQAVELSREHLASSRTCDFEQQFLGATGGRGVDVVLNSLAGEFADASLRM

LPRGGRFLELGKTDVRDPVEVADAHPGVSYQAFDTVEAGPQRIGEMLHEL

VELFEGRVLEPLPVTAWDVRQAPEALRHLSQARHVGKLVLTMPPVWDAAG

TVLVTGGTGALGAEVARHLVIERGVRNLVLVSRRGPAASGAAELVAQLTA

YGAEVSLQACDVADRETLAKVLASIPDEHPLTAVVHAAGVLDDGVSESLT

VERLDQVLRPKVDGARNLLELIDPDVALVLFSSVSGVLGSGGQGNYAAAN

SFLDALAQQRQSRGLPTRSLAWGPWAEHGMASTLREAEQDRLARSGLLPI

STEEGLSQFDAACGGAHTVVAPVRFSRLSDGNAIKFSVLQGLVGPHRVNK

AATADDAESLRKRLGRLPDAEQHRILLDLVRMHVAAVLGFAGSQEITADG

TFKVLGFDSLTVVELRNRINGATGLRLPATLVFNYPTPDALAAHLVTALS

ADRLAGTFEELDRWAANLPTLARDEATRAQITTRLQAILQSLADVSGGTG

GGSVPDRLRSATDDELFQLLDNDLELP

The amino acid sequence of a PKS (pentene ORF2) capable of producing pentene has the following amino acid sequence (SEQ ID NO:9):

MSNEEKLREYLRRALVDLHQARERLHEAESGEREPIAIVAMGCRYPGGVQ

DPEGLWKLVASGGDAIGEFPADRGWHLDELYDPDPDQPGTCYTRHGGFLH

DAGEFDAGFFDISPREALAMDPQQRLLLEISWETVESAGMDPRSLRGSRT

GVFAGLMYEGYDTGAHRAGEGVEGYLGTGNAGSVASGRVAYAFGFEGPAV

TVDTACSSSLVALHLACQSLRQGECDLALAGGVTVMSTPERFVEFSRQRG

LAPDGRCKSFAAAADGTGWGEGAGLVLLERLSDARRNGHRVLAVVRGSAV

NQDGASNGLTAPNGLAQERVIQQVLTSAGLSASDVDAVEAHGTGTRLGDP

IEAQALIAAYGQDRDRDRPLWLGSVKSNIGHTQAAAGVAGVIKMVMAMRH

GELPRTLHVDEPNSHVDWSAGAVRLLTENIRWPGTGTRRAGVSSFGVSGT

NAHVIVGDYAQQKSPLAPPATQDRPWHLLTLSAKNAQALNALQKSYGDYL

AQHPSVDPRDLCLSANTGRSPLKERRFFVFKQVADLQQTLNQDFLAQPRL

SSPAKIAFLFTGQGSQYYGMGQQLYQTSPVFRQVLDECDRLWQTYSPEAP

ALTDLLYGNHNPDLVHETVYTQPLLFAVEYAIAQLWLSWGVTPDFCMGHS

VGEYVAACLAGVFSLADGMKLITARGKLMHALPSNGSMAAVFADKTVIKP

YLSEHLTVGAENGSHLVLSGKTPCLEASIHKLQSQGIKTKPLKVSHAFHS

PLMAPMLAEFREIAEQITFHPPRIPLISNVTGGQIEAEIAQADYWVKHVS

QPVKFVQSIQTLAQAGVNVYLEIGVKPVLLSMGRHCLAEQEAVWLPSLRP

HSEPWPEILTSLGKLYEQGLNIDWQTVEAGDRRRKLILPTYPFQRQRYWF

NQGSWQTVETESVNPGPDDLNDWLYQVAWTPLDTLPPAPEPSAKLWLILG

DRHDHQPIEAQFKNAQRVYLGQSNHFPTNAPWEVSADALDNLFTHVGSQN

LAGILYLCPPGEDPEDLDEIQKQTSGFALQLIQTLYQQKIAVPCWFVTHQ

SQRVLETDAVTGFAQGGLWGLAQAIALEHPELWGGIIDVDDSLPNFAQIC

QQRQVQQLAVRHQKLYGAQLKKQPSLPQKNLQIQPQQTYLVTGGLGAIGR

KIAQWLAAAGAEKVILVSRRAPAADQQTLPTNAVVYPCDLADAAQVAKLF

QTYPHIKGIFHAAGTLADGLLQQQTWQKFQTVAAAKMKGTWHLHRHSQKL

DLDFFVLFSSVAGVLGSPGQGNYAAANRGMAAIAQYRQAQGLPALAIHWG

PWAEGGMANSLSNQNLAWLPPPQGLTILEKVLGAQGEMGVFKPDWQNLAK

QFPEFAKTHYFAAVIPSAEAVPPTASIFDKLINLEASQRADYLLDYLRRS

VAQILKLEIEQIQSHDSLLDLGMDSLMIMEAIASLKQDLQLMLYPREIYE

RPRLDVLTAYLAAEFTKAHDSEAATAAAAIPSQSLSVKTKKQWQKPDHKN

PNPIAFILSSPRSGSTLLRVMLAGHPGLYSPPELHLLPFETMGDRHQELG

LSHLGEGLQRALMDLENLTPEASQAKVNQWVKANTPIADIYAYLQRQAEQ

RLLIDKSPSYGSDRHILDHSEILFDQAKYIHLVRHPYAVIESFTRLRMDK

LLGAEQQNPYALAESIWRTSNRNILDLGRTVGADRYLQVIYEDLVRDPRK

VLTNICDFLGVDFDEALLNPYSGDRLTDGLHQQSMGVGDPNFLQHKTIDP

ALADKWRSITLPAALQLDTIQLAETFAYDLPQEPQLTPQTQSLPSMVERF

VTVRGLETCLCEWGDRHQPLVLLLHGILEQGASWQLIAPQLAAQGYWVVA

PDLRGHGKSAHAQSYSMLDFLADVDALAKQLGDRPFTLVGHSMGSIIGAM

YAGIRQTQVEKLILVETIVPNDIDDAETGNHLTTHLDYLAAPPQHPIFPS

LEVAARRLRQATPQLPKDLSAFLTQRSTKSVEKGVQWRWDAFLRTRAGIE

FNGISRRRYLALLKDIQAPITLIYGDQSEFNRPADLQAIQAALPQAQRLT

VAGGHNLHFENPQAIAQIVYQQLQTPVPKTQ

Nucleic Acids Encoding the PKS

The present invention provides recombinant nucleic acids that encode the PKSs of the invention. The recombinant nucleic acids include double-stranded and single-stranded DNAs and RNA derived therefrom. The recombinant nucleic acids of the invention include those that encode an open reading frame (ORF) of a PKS of the present invention. The recombinant nucleic acids of the invention also include, in a variety of embodiments, promoter sequences for transcribing the ORF in a suitable host cell. The recombinant nucleic acids of the invention include, in some embodiments, sequences sufficient for having the recombinant nucleic acid stably replicate in a host cell, such as sequences that provide a replicon capable of stable maintenance in a host cell or sequences that direct homologous recombination of the nucleic acid into a chromosome of the host cell. In some embodiments, the nucleic acid is a plasmid, including but not limited to plasmids containing an origin of replication. The present invention also provides vectors, such as expression vectors, comprising another recombinant nucleic acid of the present invention. The present invention provides host cell comprising any of the recombinant nucleic acids and/or capable of expressing a PKS of the present invention. In some embodiments, the host cell, when cultured under suitable conditions, is capable of producing an α-olefin of the invention.

It will be apparent to one of skill in the art that a variety of recombinant vectors can be utilized in the practice of the invention. As used herein, "vector" refers to polynucleotide elements that are used to introduce recombinant nucleic acid into cells for either expression or replication (or both). Selection and use of such vectors generally is routine in the art. An "expression vector" is a recombinant nucleic acid capable of expressing (producing proteins encoded by) DNA coding sequences (and corresponding mRNA) that are operatively linked with regulatory sequences, such as promoters. Thus, an expression vector refers to a recombinant DNA or RNA construct, such as a plasmid, a phage, a recombinant virus, or other vector that, upon introduction into an appropriate host cell that when cultured under appropriate conditions, results in expression of the DNA coding sequence. Appropriate expression vector elements suitable for use in accordance with the present invention are well known to those of skill in the art and include those that are replicable in eukaryotic cells and/or prokaryotic cells and those that remain episomal as well as those that integrate into the host cell genome.

The vectors of the invention include those chosen to contain control sequences operably linked to the resulting coding sequences in a manner that expression of the coding sequences may be effected in an appropriate host. Suitable control sequences include those that function in eukaryotic and prokaryotic host cells. If the cloning vectors employed to obtain PKS genes lack control sequences for expression operably linked to the PKS-encoding nucleotide sequences, the nucleotide sequences are inserted into appropriate expression vectors. This can be done individually, or using a pool of isolated encoding nucleotide sequences, which can be inserted into "host" vectors, the resulting vectors transformed or transfected into host cells, and the resulting cells plated out into individual colonies. Suitable control sequences for single cell cultures of various types of organisms are well known in the art. Control systems for expression in yeast are widely available and are routinely used. Control elements include promoters, optionally containing operator sequences, and other elements depending on the nature of the host, such as ribosome binding sites. Particularly useful promoters for prokaryotic hosts include those from PKS gene clusters that result in the production of polyketides as secondary metabolites, including those from Type I or aromatic (Type II) PKS gene clusters. Examples are act promoters, tcm promoters, spiramycin promoters, and the like. However, other bacterial promoters, such as those derived from the genes encoding sugar metabolizing enzymes, such as those that metabolize galactose, lactose (lac) and maltose, are also useful. Additional examples include promoters derived from the genes encoding biosynthetic enzymes such as those that encode the enzymes for tryptophan (trp) biosynthesis, the β-lactamase (bla) gene promoter, bacteriophage lambda PL promoter, and the T5 promoter. In addition, synthetic promoters, such as the tac promoter (U.S. Pat. No. 4,551,433; incorporated herein by reference), can be used to construct an expression vector of the invention.

As noted, particularly useful control sequences are those which themselves, or with suitable regulatory systems, activate expression during transition from growth to stationary phase in the vegetative mycelium. Illustrative control sequences, vectors, and host cells of these types include the modified *Streptomyces coelicolor* CH999 and vectors described in PCT publication No. WO 96/40968 and similar strains of *Streptomyces lividans*. See U.S. Pat. Nos. 5,672,491; 5,830,750; 5,843,718; and 6,177,262, each of which is hereby incorporated by reference. Other regulatory sequences may also be desirable; these include those that allow for regulation of expression of the PKS sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

Selectable markers can also be included in the recombinant expression vectors of the invention. A variety of markers are known that are useful in selecting for transformed cell lines; these generally are any gene whose expression confers a selectable phenotype on transformed cells when the cells are grown in an appropriate selective medium. Such markers include, for example, genes that confer antibiotic resistance or sensitivity to a host cell.

The various PKS nucleotide sequences, or a mixture of such sequences, can be cloned into one or more recombinant vectors as individual cassettes, with separate control elements or under the control of a single promoter. The PKS encoding subunits or components can include flanking restriction sites to allow for the easy deletion and insertion of other PKS encoding subunits. The design of such restriction sites is known to those of skill in the art and can be accomplished using the techniques described in the scientific literature, such as site-directed mutagenesis and PCR. Methods for introducing the recombinant vectors of the present invention into suitable hosts are known to those of skill in the art and include the use of $CaCl_2$ or other agents, such as other divalent cations, lipofection, DMSO, protoplast transformation, conjugation, and electroporation.

Host Cells Comprising the PKS

The present invention provides host cells comprising the recombinant nucleic acid and/or PKS of the present invention. In many embodiments, the host cell, when cultured, is capable of producing an α-olefin. The host cell can be a eukaryotic or a prokaryotic cell. Suitable eukaryotic cells include yeast cells, such as from the genus *Saccharomyces, Candida,* or *Schizosaccharomyces*. A suitable species from the genus *Saccharomyces* is *Saccharomyces cerevisiae*. A suitable species from the genus *Schizosaccharomyces* is *Schizosaccharomyces pombe*. Suitable prokaryotic cells include, but are not limited to, the gram negative *Escherichia coli* and the gram positive *Streptomyces* species, such as *S. coelicolor* and *S. lividans*.

The PKSs of the invention can be in a host cell, and can isolated and purified. The PKS can synthesize the α-olefin in vivo (in a host cell) or in vitro (in a cell extract or where all necessary chemical components or starting materials are provided). The present invention provides methods of producing the α-olefin using any of these in vivo or in vitro means.

Figure 8:
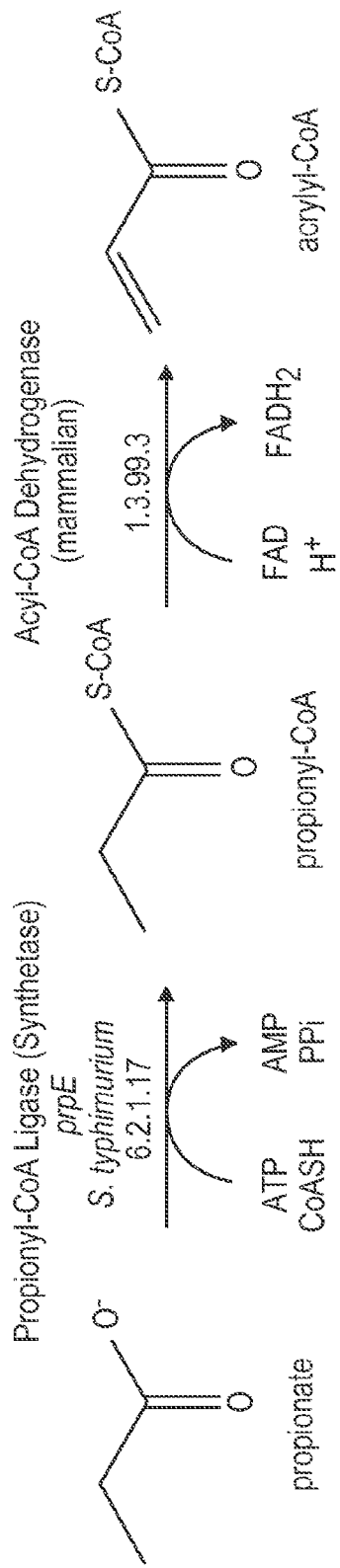
FIG. 8 shows an enzymatic pathway accessible by the methods and materials of the invention to produce acrylyl-CoA comprising exogenously supplying propionate, and expressing PrpE and acyl-CoA dehydrogenase activities. A host cell comprising this system would be provided with propionate, which could be exogenously fed to, if not produced endogenously by, the host cell selected for production.

In some embodiments of the invention, the host cell comprises a PKS which produces butadiene comprising a loading module comprising an acrylyl-ACP starter, such as a DEBS proprionyl-CoA specific loading domain which is modified to accept acrylyl-CoA, and one or more nucleic acids encoding and capable of expressing biosynthetic enzymes for synthesizing acrylyl-CoA from propionate (see FIG. 8). An example of a set of such enzymes is propionyl-CoA ligase (synthetase) (EC 6.2.1.17) and acyl-CoA dehydrogenase (mammalian) (EC 1.3.99.3), and functional variants thereof. In some embodiments, the host cell comprises a nucleic acid encoding and capable of expressing an enzyme, or functional variant thereof, capable of converting propionate into propionyl-CoA, and an enzyme, or functional variant thereof, capable of converting propionyl-CoA into acrylyl-CoA. An enzyme capable of converting propionate into propionyl-CoA is the propionyl-CoA ligase encoded by the prpE gene of *Salmonella typhimurium*. An enzyme capable of converting propionyl-CoA into acrylyl-CoA is the mammalian acyl-CoA dehydrogenase. A host cell comprising this system is provided with propionate, such as by exogenously feeding propionate to the host cell, or produces propionate endogenously.

The amino acid sequence of the propionyl-CoA ligase encoded by the prpE gene in *Salmonella typhimurium* (GenBank accession no. NP_459366) comprises:

(SEQ ID NO: 13)
```
  1 msfsefyqrs inepeafwae qarridwrqp ftqtldhsrp pfarwfcggt tnlchnavdr
 61 wrdkqpeala liavssetde ertftfsqlh devnivaaml lslgvqrgdr vlvympmiae
121 aqitllacar igaihsvvfg gfashsvaar iddarpaliv sadagarggk ilpykklldd
181 aiaqaqhqpk hvllvdrgla kmawvdgrdl dfatlrqqhl gasvpvawle snetscilyt
241 sgttgkpkgv qrdvggyava latsmdtifg gkaggvffca sdigwvvghs yivyapllag
301 mativyeglp typdcgvwwk ivekyqvnrm fsaptairvl kkfptaqirn hdlsslealy
361 lagepldept aswvtetlgv pvidnywqte sgwpimalar alddrpsrlg spgvpmygyn
421 vqllnevtge pcginekgml viegplppgc iqtiwgddar fvktywslfn rqvyatfdwg
481 irdaegyyfi lgrtddvini aghrlgtrei eesissypnv aevavvgikd alkgqvavaf
541 vipkqsdtla dreaardeen aimalvdnqi ghfgrpahvw fvsqlpktrs gkmlrrtiqa
601 egrdpgdl ttiddpaslq qirqaiee
```

The amino acid sequence of the acyl-CoA dehydrogenase of *Mus musculus* (GenBank accession no. Q07417) comprises:

(SEQ ID NO: 14)
```
  1 maaallarar gplrralgvr dwrrlhtvyq svelpethqm lrqtcrdfae kelvpiaaql
 61 drehlfptaq vkkmgelgll amdvpeelsg aglgylaysi aleeisraca stgvimsvnn
121 slylgpilkf gsaqqkqqwi tpftngdkig cfalsepgng sdagaastta reegdswvln
181 gtkawitnsw easatvvfas tdrsrqnkgi saflvpmptp gltlgkkedk lgirasstan
241 lifedcripk enllgepgmg fkiamqtldm grigiasqal giaqasldca vkyaenrnaf
301 gapltklqni qfkladmala lesarlltwr aamlkdnkkp ftkesamrkl aaseaatais
361 aiqilgsm gyvtempaer yyrdaritei yegtseiqrl viaghllrsy rs
```

Figure 9:
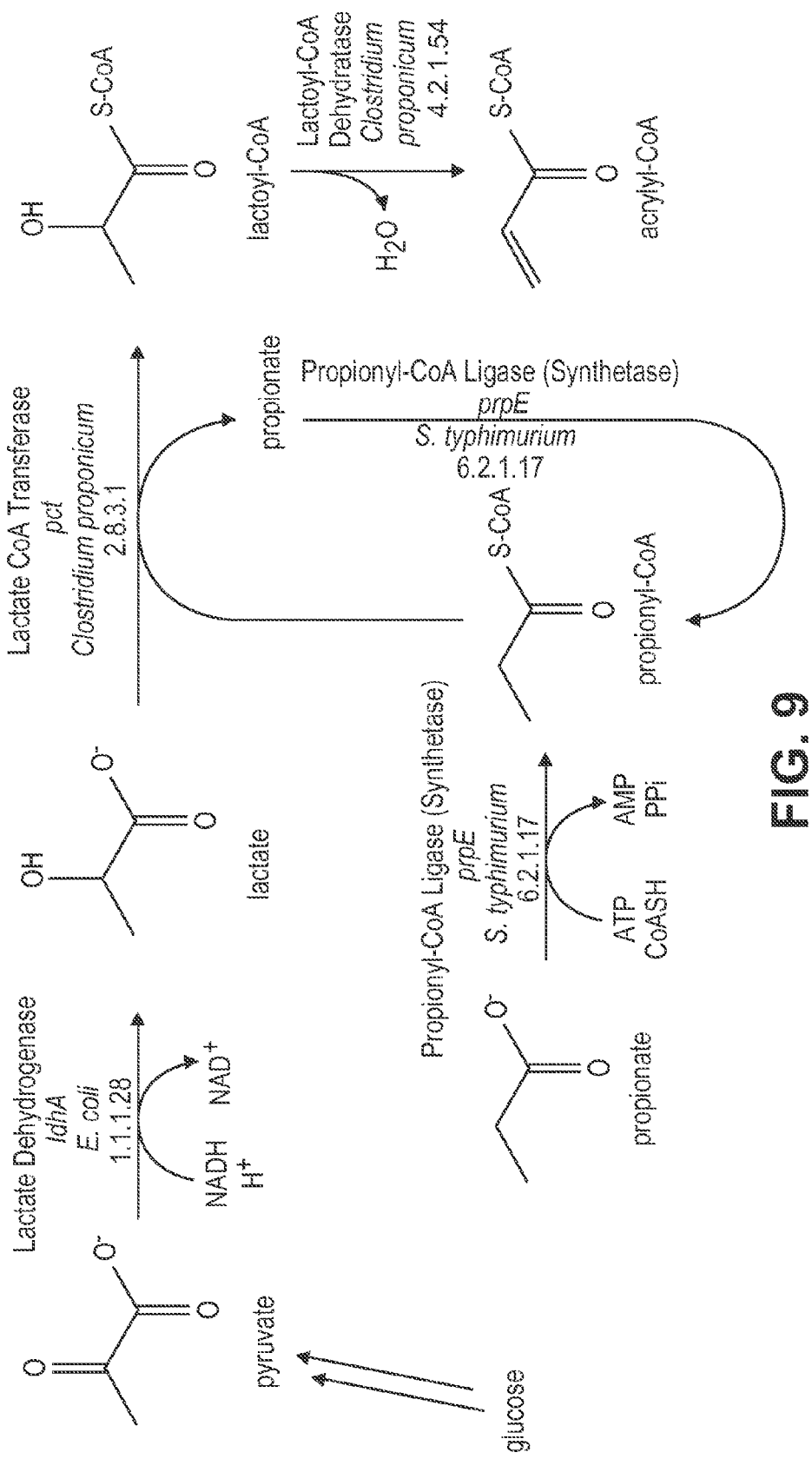
FIG. 9 shows an enzymatic pathway accessible by the methods and materials of the invention to produce acrylyl-CoA comprising exogenously supplying propionate and glucose. A host cell comprising this system would be provided with propionate, either through exogenous feeding or the introduction of propionate biosynthesis pathway, as above, and a suitable organic molecule that the host cell can directly or indirectly convert into a pyruvate. For example, if the host cell is *E. coli*, the suitable organic molecule can be glucose. This pathway utilizes the central metabolic intermediate pyruvate to produce lactate via a lactate dehydrogenase. Lactate is then converted to lacoyl-CoA by a lactate CoA trnasferase, utilizing propionyl-CoA as a cofactor and releasing propionate. Lactoyl-CoA is then dehydrated using a lactoyl-CoA dehydratase to yield acrylyl-CoA. One embodiment of this invention includes the lactate dehydrogenase, LdhA, from *E. coli*, the lactate CoA transferase, Pct, from *Clostridium proponicum*, and the lactoyl-CoA dehydratase enzymes, EI and EII, from *C. proponicum*. The introduction of this pathway into *E. coli* or yeast for diene (such as butadiene) production represents a novel application of these enzymes. An embodiment of this invention is use of this pathway for PKS-based acrylate production.

In some embodiments, the host cell of the invention comprises a PKS which produces butadiene and comprises a loading module comprising an acrylyl-ACP starter, such as a DEBS proprionyl-CoA specific loading domain which is modified to accept acrylyl-CoA, and one or more nucleic acids encoding and capable of expressing biosynthetic enzymes for synthesizing acrylyl-CoA from pyruvate (see FIG. 9). An example of a set of such enzymes is lactate dehydrogenase (EC 6.2.1.17), lactate CoA transferase (EC 2.8.3.1), propionyl-CoA ligase (synthetase) (EC 6.2.1.17), and lactoyl-CoA dehydratase (EC 4.2.1.54), or functional variants thereof. In some embodiments, the host cell comprises one or more nucleic acids encoding and capable of expressing these four enzymes. A host cell comprising this system is provided with propionate and a suitable organic molecule that the host cell can directly or indirectly convert into a pyruvate, and these compounds are either exogenously fed to or produced by the host cell. For example, if the host cell is E. coli, a suitable organic molecule is glucose.

The amino acid sequence of the lactate dehydrogenase encoded by the ldhA gene of E. coli (GenBank accession no. CAQ31881) comprises:

```
                                                            (SEQ ID NO: 15)
  1 taktangcea vcifvnddgs rpvleelkkh gvkyialrca gfnnvdldaa kelglkvvrv 61 paydpeavae haigmmmtln rrihrayqrt rdanfslegl tgftmygkta gvigtgkigv 121 amlrilkgfg mrllafdpyp saaalelgve yvdlptlfse sdvislhcpl tpenyhllne 181 aafdqmkngv mivntsrgal idsqaaieal knqkigslgm dvyenerdlf fedksndviq 241 ddvfrrlsac hnvlftghqa fltaealtsi sqttlqnlsn lekgetcpne lv
```

Figure 10:
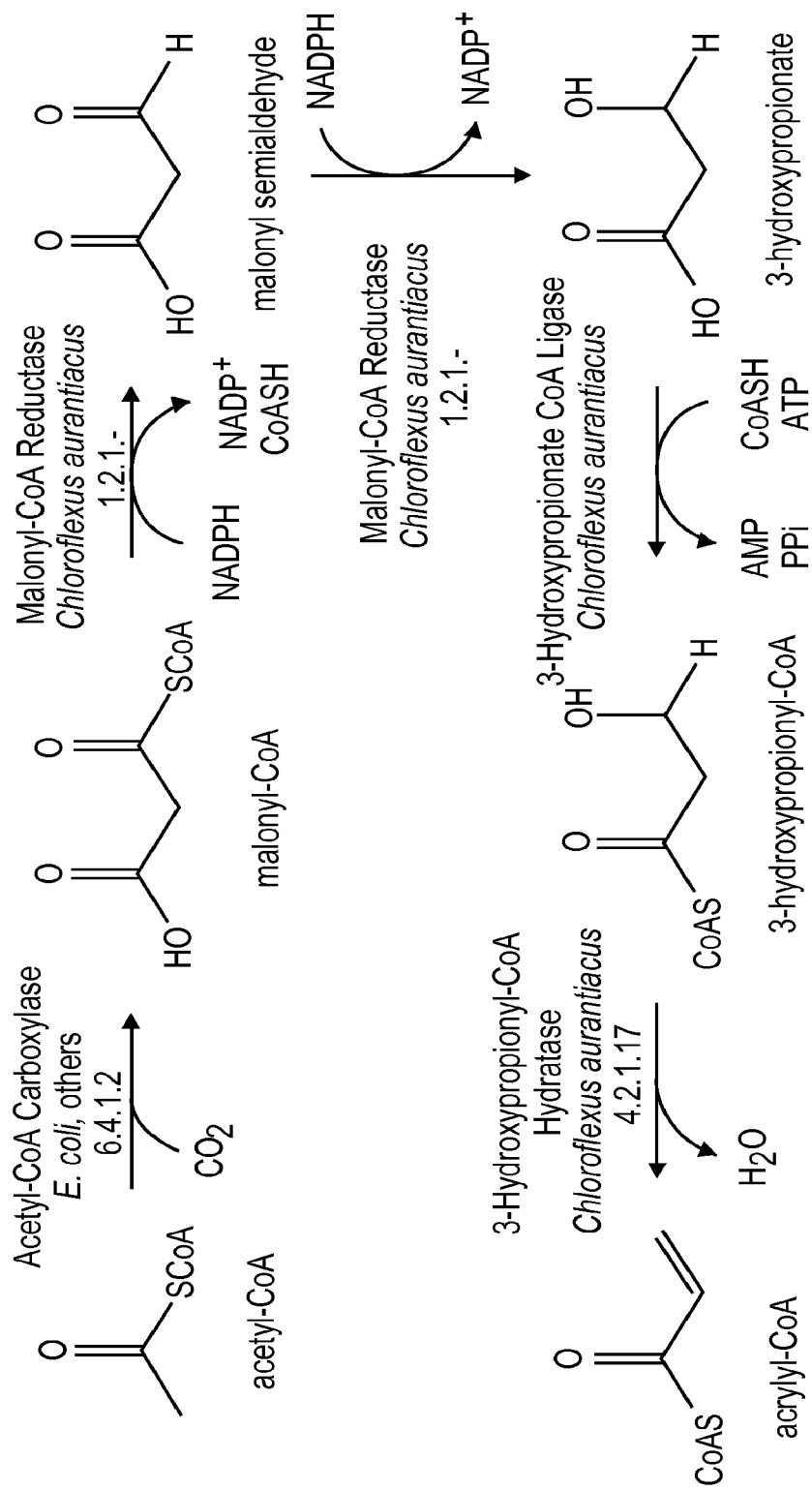
FIG. 10 shows an enzymatic pathway accessible by the methods and materials of the invention to produce acrylyl-CoA starting from the common metabolic precursor malonyl-CoA. This pathway generates malonyl-CoA using an acetyl-CoA carboxylase, acetyl-CoA and $CO_2$. Malonyl-CoA is then reduced by a malonyl-CoA reductase releasing malonyl semialdehyde. Malony semialdehyde is converted to 3-hydroxypropionate using a substrate specific oxidoreductase. A 3-hydroxypropionate CoA ligase catalyzes the formation of 3-hydroxypropionyl-CoA. This intermediate is then dehydrated to acryalyl-CoA by the reverse reaction of 3-hydroxypropionyl-CoA hydratase. In one embodiment of the invention, these enzymes are the acetyl-CoA carboxylase complex (AccA/AccD) from *E. coli*, the malonyl-CoA reductase (The introduction of this pathway into *E. coli* or yeast for diene (e.g. butadiene) production represents a novel application of these enzymes and is a unique embodiment of this invention. An embodiment of this invention is use of this pathway for PKS-based acrylate production.
Figure 11:
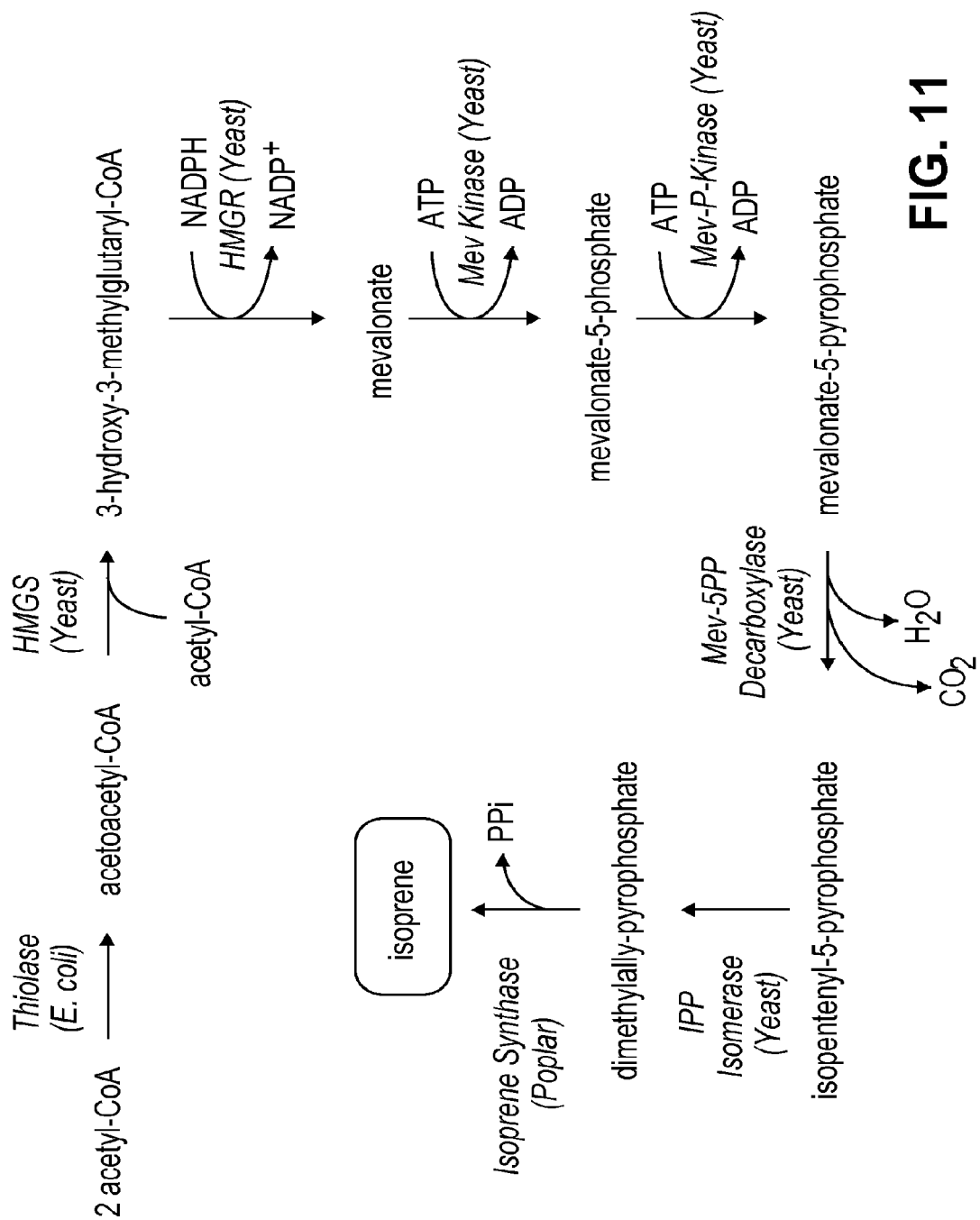
FIG. 11 shows an enzymatic pathway accessible by the methods and materials of the invention to produce isoprene via the mevalonate pathway.
Figure 12A:
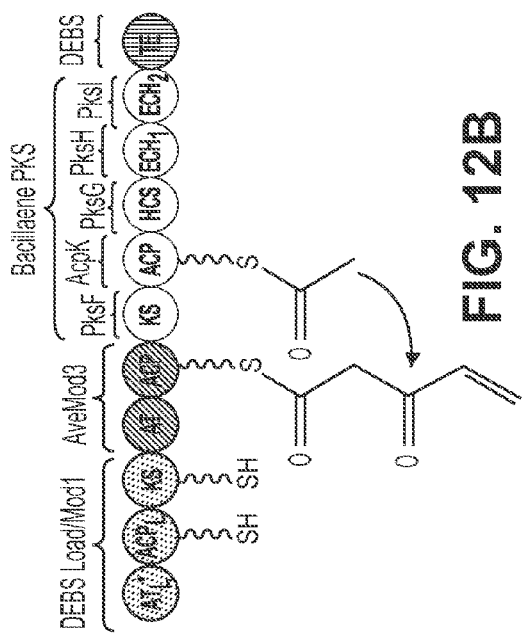
FIGS. 12A-F show an example of an illustrative pathway accessible by a PKS provided by the invention for producing isoprene.
Figure 12C:
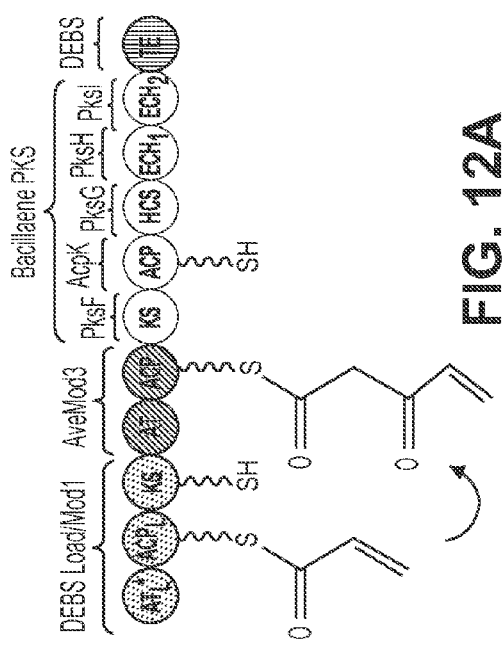
Figure 12B:
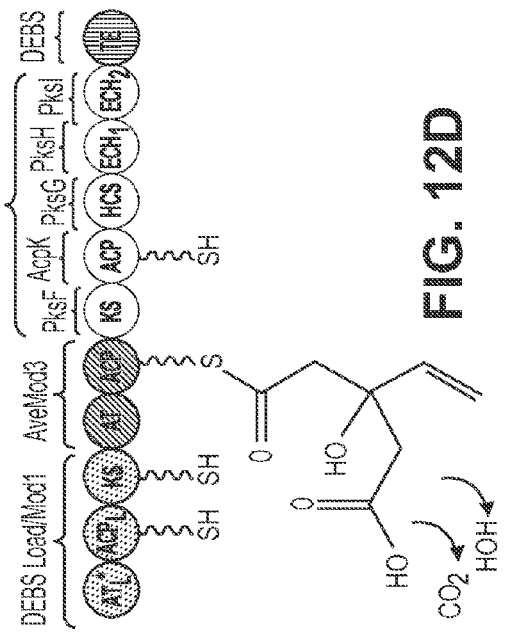
Figure 12D:
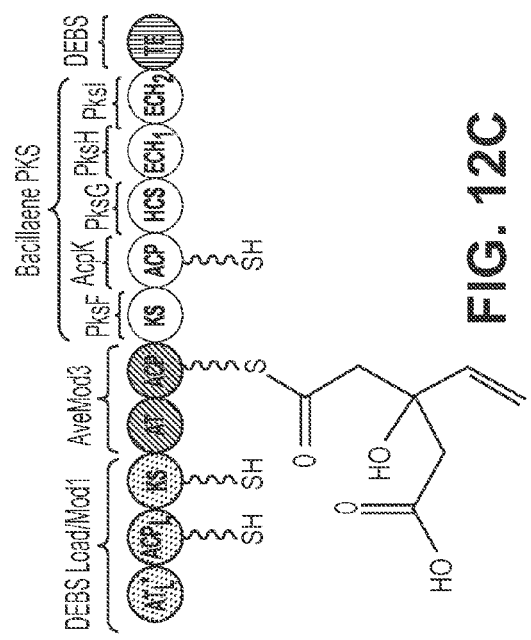
Figure 12F:
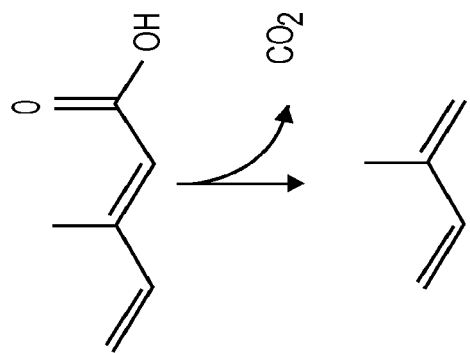
Figure 12E:
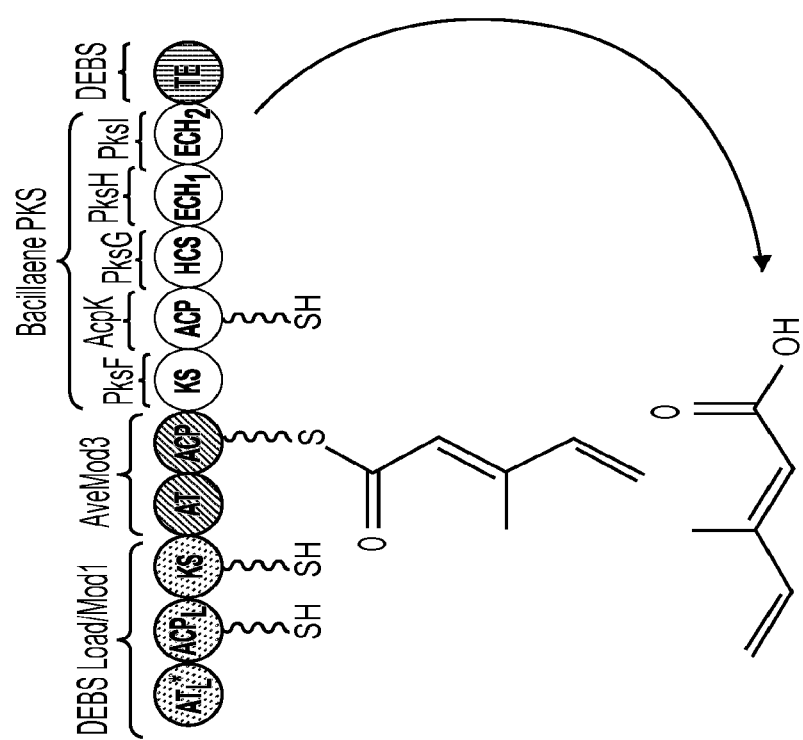

The amino acid sequence of the lactate CoA transferase encoded by the pct gene of Clostridium proponicum (GenBank accession no. CAB77207) comprises:

a loading module comprising an acrylyl-ACP starter, such as a DEBS proprionyl-CoA specific loading domain which is modified to accept acrylyl-CoA, and one or more nucleic acids encoding and capable of expressing biosynthetic enzymes for synthesizing acrylyl-CoA from acetyl CoA (see FIG. 10). An example of a set of such enzymes is acetyl-CoA carboxylase (EC 6.4.1.2), malonyl-CoA reductase (EC 1.2.1.75), 3-hydroxypropionate:CoA ligase, and 3-hydroxypropionyl-CoA hydratase (EC 4.2.1.116), or functional variants thereof. In some embodiments, the host cell comprises one or more nucleic acids encoding and capable of expressing the four enzymes described. A host cell comprising this system can be engineered to produce increased titers of acetyl-CoA.

Figure 15:
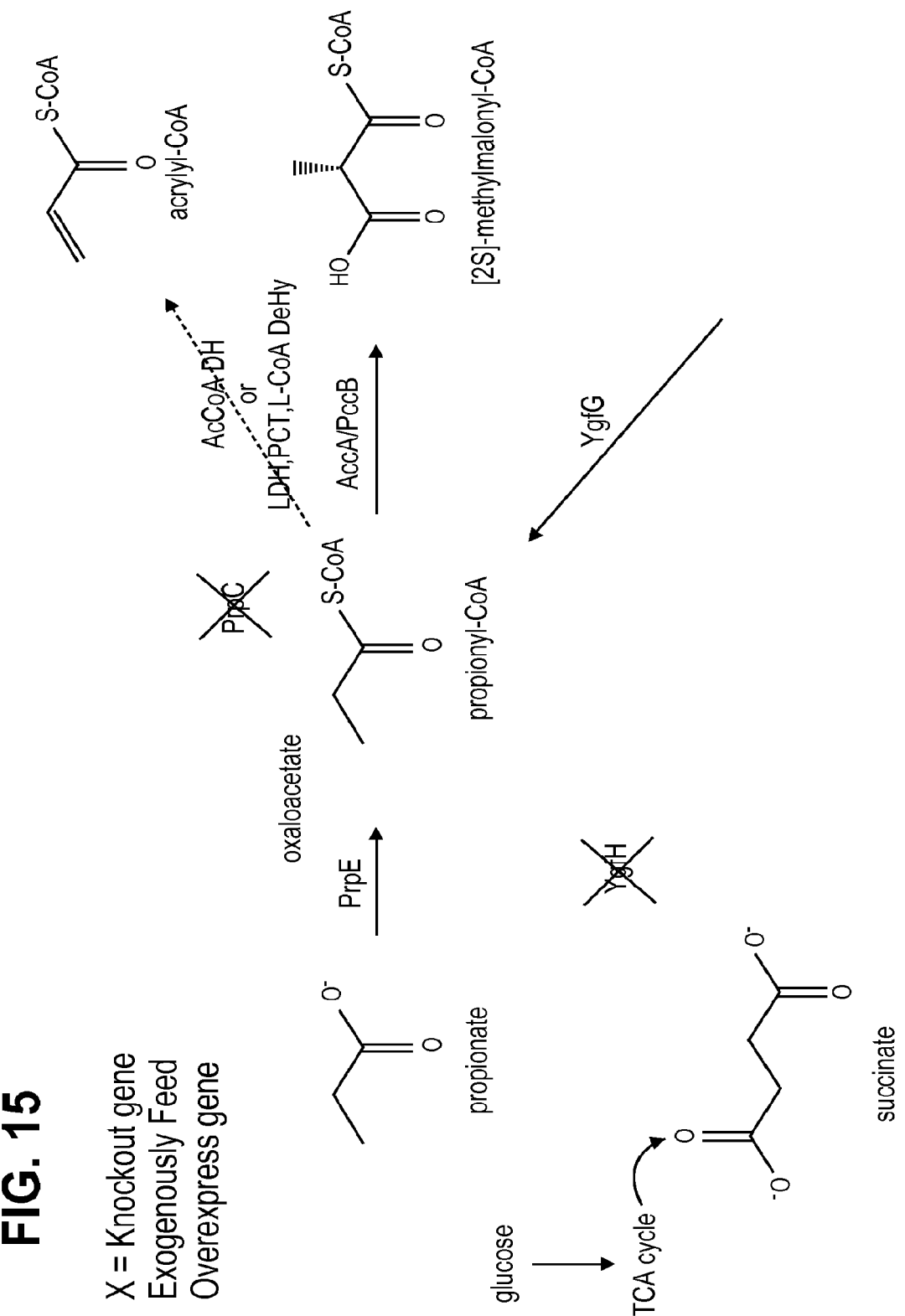
FIG. 15 shows methods and materials provided by the invention for maximizing precursor supply pathways in *E. coli*. The means to maximizing acrylyl-CoA can comprise one or more of "knocking out" (eliminating or reducing the expression of) PrpC activity, knocking out YgfH activity, exogenously feeding propionate (or producing propionate endogenously), overexpressing PrpE activity to increase cytosolic pools of propionyl-CoA. From this intermediate, the introduction of the propionyl-CoA carboxylase complex (AccA/PccB) will yield methylmalonyl-CoA (Pfeifer, et al. Science. 2001 Mar. 2; 291(5509):1790-2; incorporated herein by reference). This pool of propionyl-CoA can also be utilized in the pathways described in FIGS. 8 and 9.
Figure 16:
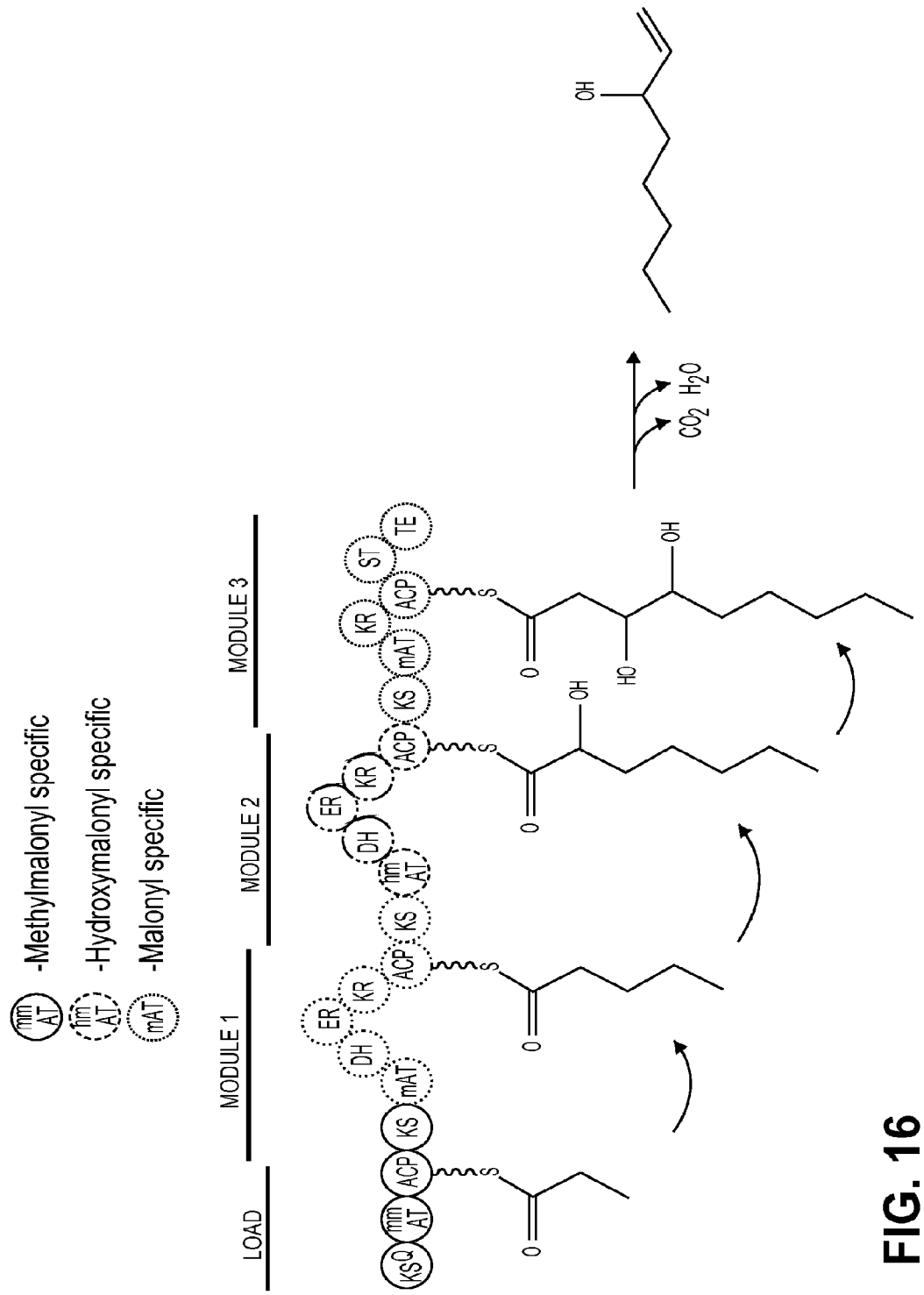
FIG. 16 shows an illustrative PKS provided by the invention to produce 3-hydroxy-1-octene. The PKS comprises the following elements: (i) Load module and KS1 from PikA1 (pikromycin), followed by (ii) Module 1 and KS2: AT-ACP segment from Module 5 and KS6 domain from the Nystatin PKS, (iii) Module 2: the hydroxymalonate-specifc AT and contiguous ACP domains from ZmaA (zwittermicin PKS) from *Bacillus cereus*, DH, ER and KR domains from nanchangmycin PKS Module 2, and (iv) Module 3: AT-TE segment of the CurM module (curacin PKS). For the production of the precursor hydroxymalonyl-ACP, enzymes ZmaD, ZmaG, and ZmaE are also produced by or provided to the host strain. This figure illustrates loss of the hydroxyl group as a water molecule, however, it should be noted that the enzymatic mechanism utilizes sulfate as a leaving group.
Figure 17:
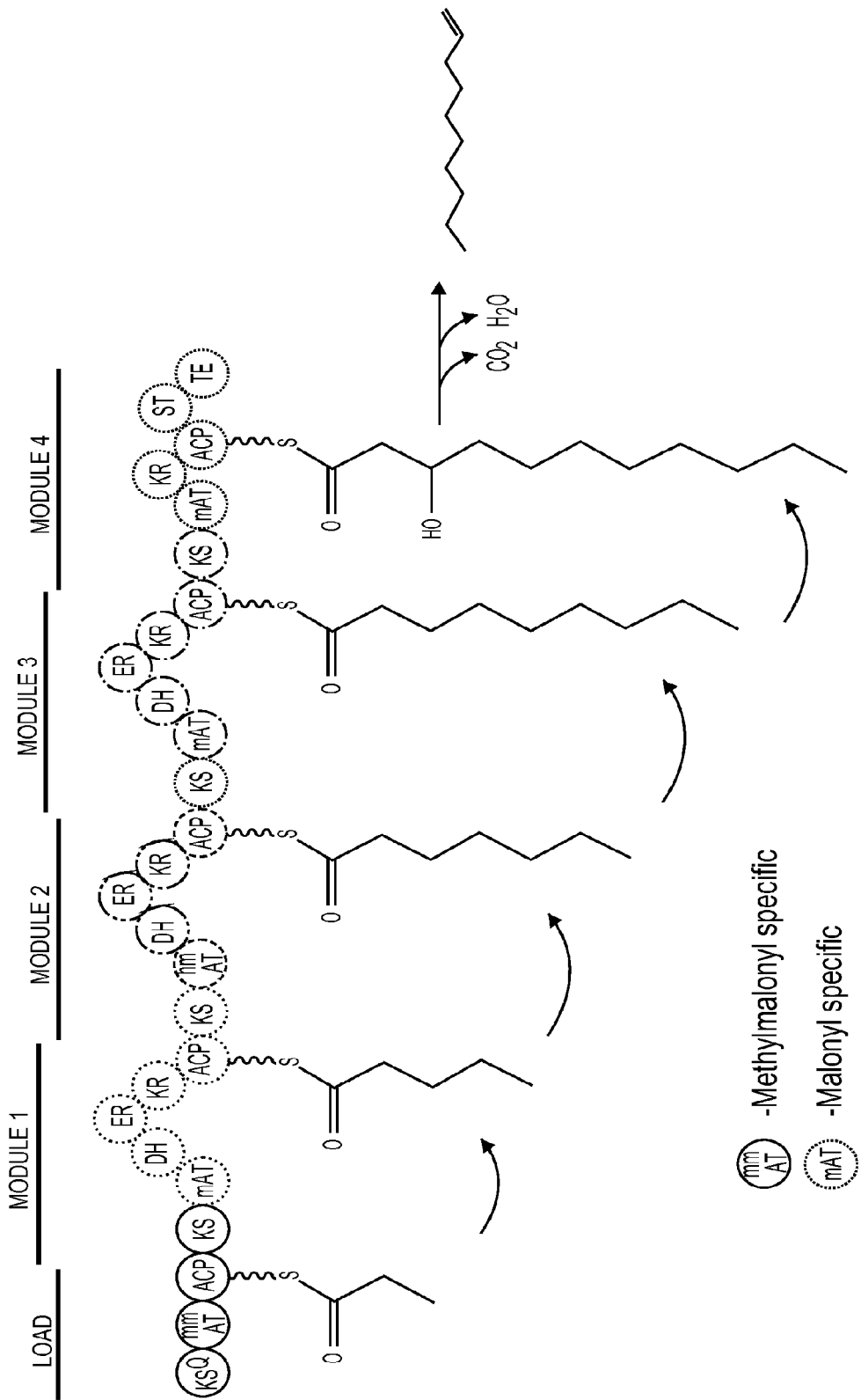
FIG. 17 shows an illustrative PKS provided by the invention to produce 1-decene. The PKS comprises the following elements: (i) Load module and KS1 from PikA1, followed by (ii) Module 1 and KS2: AT-ACP segment from Module 5 and KS6 domain from the nystatin PKS, (iii) Module 2 and KS3: AT-ACP segment from Module 15 and KS16 domain from the nystatin PKS, (iv) Module 3 and KS4: AT-ACP segment from Module 3 and K4 domain from the oligomycin PKS, and (v) Module 4: AT-TE segment from CurM. This figure illustrates loss of the hydroxyl group as a water molecule, however, it should be noted that the enzymatic mechanism utilizes sulfate as a leaving group.
Figure 18:
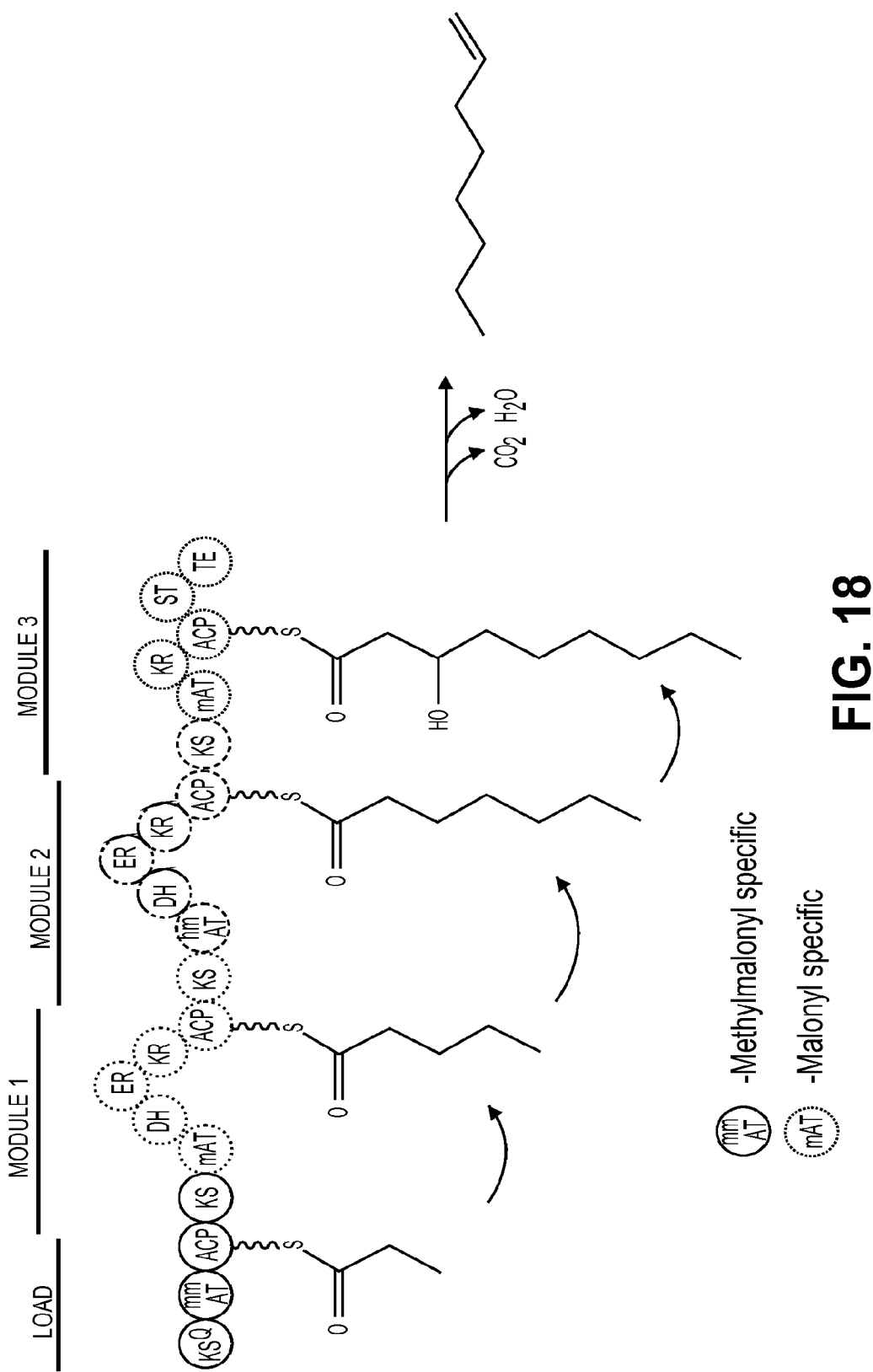
FIG. 18 shows an illustrative PKS provided by the invention to produce 1-octene. The PKS comprises the following elements: (i) Loading Module and KS1 from PikA1, followed by (ii) Module 1 and KS2: AT-ACP segment from Module 5 and KS6 domain from the nystatin PKS Module 2, (iii) and KS3: AT-ACP segment from Module 15 and KS16 domain from the nystatin PKS, and then (iv) Module 3: AT-ST segment from the CurM module. This figure illustrates loss of the hydroxyl group as a water molecule, however, it should be noted that the enzymatic mechanism utilizes sulfate as a leaving group.

In some embodiments, the host cell of the invention comprises a PKS which produces butadiene and comprises a loading module comprising an acrylyl-ACP starter, such as a DEBS proprionyl-CoA specific loading domain which is modified to accept acrylyl-CoA, and one or more nucleic acids encoding and capable of expressing biosynthetic enzymes for synthesizing acrylyl-CoA from propionate (see FIG. 15). An example of a set of such enzymes is propionyl-CoA ligase (synthetase) (EC 6.2.1.17), lactoyl-CoA dehydratase (EC 4.2.1.54), lactate dehydrogenase (EC 6.2.1.17), lactate CoA transferase (EC 2.8.3.1), or functional variants

```
                                                            (SEQ ID NO: 16)
  1 mrkvpiitad eaaklikdgd tvttsgfvgn aipealdrav ekrfletgep knityvycgs 61 qgnrdgrgae hfaheglikr yiaghwatvp algkmamenk meaynvsqga lchlfrdias 121 hkpgvftkvg igtfidprng ggkvnditke divelveikg qeylfypafp ihvalirgty 181 adesgnitfe kevaplegts vcqavknsgg ivvvqvervv kagtldprhv kvpgiyvdyv 241 vvadpedhqq sldceydpal sgehrrpevv geplplsakk vigrrgaiel ekdvavnlgv 301 gapeyvasva deegivdfmt ltaesgaigg vpaggvrfga synadalidq gyqfdyydgg 361 gldlcylgla ecdekgninv srfgpriagc ggfinitqnt pkvffcgtft agglkvkied 421 gkviivqegk qkkflkaveq itfngdvala nkqqvtyite rcvfllkedg lhlseiapgi 481 qtqildvm dfapiidrda ngqiklmdaa lfaeglmglk emks
```

The amino acid sequence of the lactoyl-CoA dehydratase encoded by the pct gene of Clostridium proponicum (GenBank accession no. CAB77206) comprises:

thereof. A host cell comprising this system is provided with propionate, either by exogenous feeding or by endogenous production.

```
                                                            (SEQ ID NO: 17)
  1 efkiaivddd laqesrqirv dvldgeggpl yrmakawqqm ygcslatdtk kgrgrmlink 61 tiqtgadaiv vammkfcdpe ewdypvmyre feekgvkslm ievdqevssf eqiktrlqsf 121 veml
```

In some embodiments, the host cell of the invention comprises a PKS which produces butadiene and comprises In some embodiments, the host cell of the invention comprises a PKS which produces 3-methyl-2,4-pentadienoic acid and comprises the modules shown in FIG. 12 including a loading module comprising an acrylyl-ACP starter, such as a DEBS proprionyl-CoA specific loading domain which is modified to accept acrylyl-CoA, and one or more nucleic acids encoding and capable of expressing biosynthetic enzymes for synthesizing acrylyl-CoA (see FIG. 12). There are several methods for enabling a host cell to synthesize acrylyl-CoA described above. 3-methyl-2,4-pentadienoic acid can be enzymatically, catalytically, or pyrolytically converted to isoprene.

Methods of Producing α-Olefins Using the PKS

The present invention provides a method of producing an α-olefin comprising: providing a host cell of the present invention, and culturing said host cell in a suitable culture medium such that the α-olefin is produced. The method can further comprise isolating said α-olefin from the host cell and/or the culture medium. The method can further comprise polymerizing the α-olefin to itself and/or any other suitable organic molecule(s), including but not limited to other compounds comprising a C—C double bond. A variety of methods for heterologous expression of PKS genes and host cells suitable for expression of these genes and production of polyketides are described, for example, in U.S. Pat. Nos. 5,843,718; 5,830,750 and 6,262,340; WO 01/31035, WO 01/27306, and WO 02/068613; and U.S. Patent Application Pub. Nos. 20020192767 and 20020045220; each of which is incorporated herein by reference.

The present invention provides for a composition comprising an α-olefin isolated from a host cell from which the α-olefin is produced, and trace residues and/or contaminants of the host cell. Such trace residues and/or contaminants include cellular material produced by the lysis of the host cell. The present invention also provides α-olefins in substantially pure form.

Certain α-olefins produced by the PKSs of the present invention can be used as fuels. In some embodiments of the invention, an α-olefin produced in accordance with the invention can be used as a "green" jet fuel. The α-olefin can be catalytically oligomerized, including but not limited to dimerized, and optionally purified. The resulting products can be dimerized again to yield a mixture of branched molecules that are then catalytically hydrogenated. For example, 1-butene produced by a PKS of the present invention can be catalytically dimerized and purified. The resulting octene products can be dimerized again to yield a mixture of branched C16 molecules that are then catalytically hydrogenated. Oligomers of butene have been validated by the US Navy as both jet and diesel fuel replacements (Harvey, 2011. Journal of Chemical Technology and Biotechnology 86(1): 2-9.). Additional benefit may come from making branched, or aromatic, α-olefins using the avermectin (or other) loading modules, as described herein.

Thus, among others, the present invention has one or more of the following advantages: (1) it reduces the dependence on oil for producing certain chemicals, and (2) it serves as a means of capture and sequestration of carbon from the atmosphere.

The invention having been described, the following examples are offered to illustrate and not limit the subject invention.

EXAMPLES

Constructs can be conveniently designed at the amino acid level and then, back translation and DNA synthesis, such as that offered commercially by service providers such as DNA 2.0, can be conducted to yield the desired nucleic acid, which may be optimized for expression in a particular host cell type. Subsequent plasmid assembly can be conducted using standard molecular biology techniques.

Example 1

Production of 1-Hexene Using a PKS-Based Enzyme System

In one embodiment of the invention, PKS modules from three different organisms were used to construct a tri-ketide pathway designed for the production of 1-hexene. In this embodiment, the 1-hexene synthase consists of two ORFs. HexORF1 combines EryA1 loading module+KS1 and AT-ACP from IdmO, HexORF2 utilizes the KS domain from IdmP and AT-TE domains from CurM. In another embodiment of this invention the loop I region of the indanomycin sourced ACP in HexORF1, SSSAGIDPGRAFQDMGI (SEQ ID NO:18), is swapped with ASAERVPADQAFA-ELGV (SEQ ID NO:19), the segment of ACP directly following EryA1. Both of these designs were back translated using software designed to optimize expression in $E.\ coli$. The genes are synthesized and ligated into two pairs of compatible, $E.\ coli$ expression vectors that are subsequently transformed into $E.\ coli$ BAP-1. The amino acid sequences for HexORF1, HexORF1', and HexORF2 are provided as SEQ ID NOs: 2-4, respectively.

Experiments have been performed demonstrating $E.\ coli$ BAP-1 utilizing exogenously added propionate. In both examples of 1-hexene production, overnight cultures of a pBbA7C-HexORF1' (or pBbA7C-HexORF1)+pBbS7k-HexORF2 cotransformed strain were grown from a single colony and used to inoculate (1% v/v) three 50-mL cultures of LB medium supplemented with 0.5% glucose and 10% glycerol in 250 mL screw cap (unsealed) flask. Cultures were grown to an OD600 of 1.0 to 1.2, induced with 50 uM IPTG and grown at (30° C.) for an additional 3 hours. Then 100 mM propionate was supplemented to the culture and a Teflon septum was used to seal the cap. The cultures were then grown at 20° C. for 24 hours after which 1-butene was detectable in the headspace of the culture using solid phase micro extraction followed by GC-MS.

Example 2

Production of Butadiene Using a PKS-Based Enzyme System

An example of a PKS system for producing butadiene is shown in FIGS. 6 and 7. The system built to produce 1-butene, described below, was fed acrylate to produce butadiene. Otherwise, all experimental details are as described as that for 1-butene production, above. While the limits of detection were inadequate to determine productivity in this instance, the invention provides several routes to increasing butadiene productivity, including: adding an acrylate specific CoA ligase to the host strain, adding an acrylate importer to the host strain, and/or utilizing a host strain less sensitive to acrylate toxicity.

Example 3

Production of 1-Butene Using a PKS-Based Enzyme System

An illustrative PKS system for producing 1-butene was constructed using the AT-TE PKS domains from CurM and the loading module for propionyl-CoA+KS1 from EryA1. For in vivo 1-butene production, overnight cultures of $E.\ coli$ BAP1 carrying pBbS7k-Butene (PKS protein sequence provided as SEQ ID NO:5) were grown from a single colony and used to inoculate (1% v/v) three 50-mL cultures of LB medium supplemented with 0.5% glucose and 10% glycerol in 250 mL screw cap (unsealed) flask. Cultures were grown to an OD600 of 1.0 to 1.2, induced with 50 uM IPTG and grown at (30° C.) for an additional 3 hours. Then 100 mM propionate was supplemented to the culture and a Teflon septum was used to seal the cap. The cultures were then grown at 20° C. for 24 hours after which 1-butene was detectable in the headspace of the culture using solid phase micro extraction followed by GC-MS.

Example 4

Production of Isoprene Using a PKS-Based Enzyme System

An example of a PKS system for producing isoprene is shown in FIG. 12.

Example 5

Production of (E)-penta-1,3-diene Using a PKS-Based Enzyme System

Figure 13:
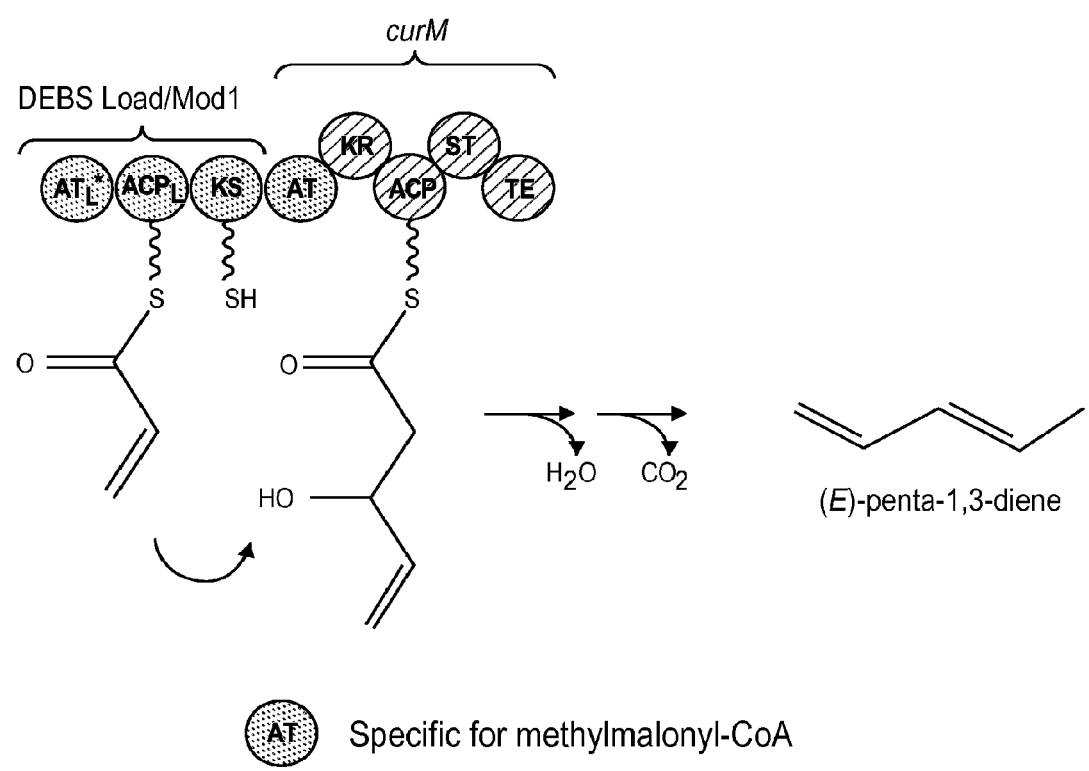
FIG. 13 shows a PKS provided by the invention for producing (E)-penta-1,3-diene. This figure illustrates loss of the hydroxyl group as a water molecule, but the enzymatic mechanism utilizes sulfate as a leaving group.
Figure 14:
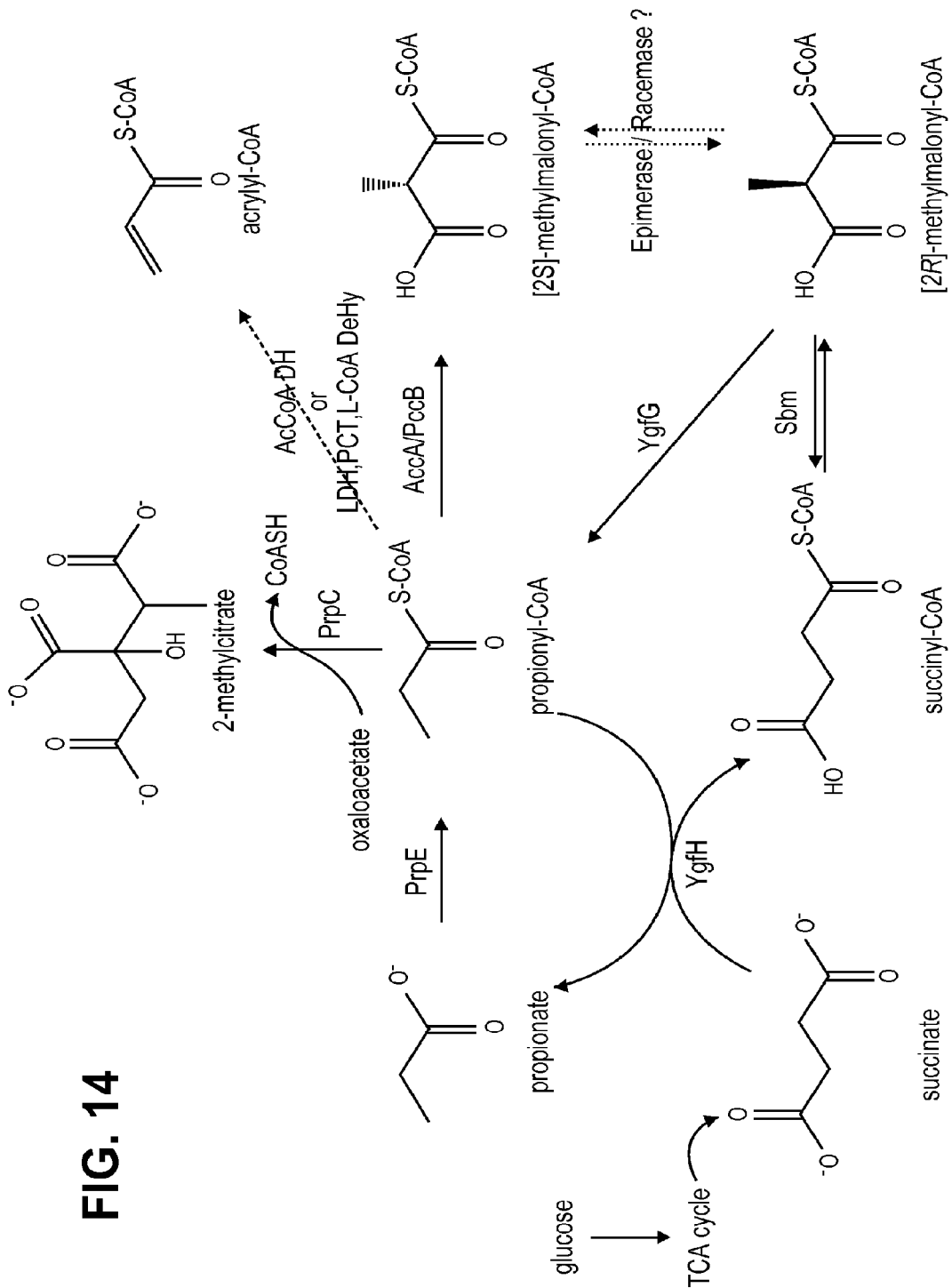
FIG. 14 shows precursor supply pathways in *E. coli* for producing acrylyl-CoA, as described in previous figures, and [2S]-methylmalonyl-CoA. Each enzymes depicted can be expressed in a host cell wherein each enzyme can be independently either endogenous or native to the host cell, or introduced into recombinant

An example of a PKS system for producing (E)-penta-1,3-diene is shown in FIG. 13.

Example 6

Production of Propene (Propylene) Using a PKS-Based Enzyme System

An illustrative propene synthase of the invention is a single enzyme consisting of the loading module+KS1 from the niddamycin PKS (Kakavas, 1997) fused to AT-TE domains from CurM (Chang, 2004; Gu, 2009) (the amino acid sequence for this construct is provided as SEQ ID NO:6). For in vivo propene production, overnight cultures of E. coli BAP1 carrying pBbS7k-propene were grown from a single colony and used to inoculate (1% v/v) three 50-mL cultures of LB medium supplemented with 0.5% glucose and 10% glycerol in 250 mL screw cap (unsealed) flask. Cultures were grown to an OD600 of 1.0 to 1.2, induced with 50 uM IPTG and grown at (30° C.) for an additional 3 hours. Then a Teflon septum was used to seal the cap. The cultures were then grown at 20° C. for 24 hours after which propene was detectable in the headspace of the culture using solid phase micro extraction followed by GC-MS.

Example 7

Production of Styrene Using a PKS-Based Enzyme System

An illustrative styrene synthase of the invention was constructed by fusing the ST and TE domains from CurM onto the loading and first extension modules from the soraphen PKS (Schupp, 1995; Wilkinson, 2001). The amino acid sequence for this construct is provided as SEQ ID NO:7. For styrene biosynthesis in the system illustrated, a pool of benzoyl-CoA is provided. To facilitate production of this essential precursor, the styrene synthase construct was coexpressed with an E. coli codon optimized gene encoding benzoate-CoA ligase, badA, from Rhodopseudomonas palustris (Egland, et al., J Bacteriol. 1995 November; 177 (22):6545-51.) and fed exogenous benzoate. For in vivo styrene production, overnight cultures of E. coli BAP1 carrying pBbS7k-SS1 (SS1 encodes SEQ ID NO:7) were grown from a single colony and used to inoculate (1% v/v) three 50-mL cultures of LB medium supplemented with 0.5% glucose and 10% glycerol in 250 mL screw cap (unsealed) flask. Cultures were grown to an OD600 of 1.0 to 1.2, induced with 50 uM IPTG and grown at (30° C.) for an additional 3 hours. Then 100 mM benzoic acid was supplemented to the culture and a Teflon septum was used to seal the cap. The cultures were then grown at 20° C. for 24 hours after which styrene was detectable in the headspace of the culture using solid phase micro extraction followed by GC-MS.

Example 8

Production of Pentene Using a PKS-Based Enzyme System

An illustrative pentene synthase of the invention was designed as two ORFs. The first ORF is built using the chalcomycin PKS loading module+KS1 fused to spinosad AT-ACP PKS module two. The second ORF is the KS from spinosad M3 fused to the olefination module (Ols) from Synechococcus sp. PCC7002 (Mendez-Perez, et al., Appl Environ Microbiol. 2011 June; 77(12):4264-7). The amino acid sequences for these chimeric proteins are provided as SEQ ID NO:8 and 9.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What we claim is:

1. A non-naturally occurring hybrid polyketide synthase (PKS) that comprises a terminal module comprising a sulfotransferase (ST) domain having at least 70% identity to the amino acid sequence of SEQ ID NO:11; and a thioesterase (TE) domain having at least 70% identity to the amino acid sequence of SEQ ID NO:12; and a loading module from an erythromycin (DEBS) loading domain, wherein the non-naturally occurring hybrid PKS synthesizes an α-olefin.

2. A recombinant nucleic acid encoding the non-naturally occurring hybrid PKS of claim 1.

3. A method of producing an α-olefin, comprising: providing a host cell comprising the recombinant nucleic acid of claim 2, and culturing said host cell in a suitable culture medium such that the α-olefin is produced.

4. A non-naturally occurring hybrid PKS that synthesizes 1-butene, wherein the non-naturally occurring hybrid PKS comprises a terminal module comprising an acyltransferase (AT) domain, a ketoreductase (KR) domain, an acyl carrier protein (ACP) domain; an ST domain having at least 90% identity to the amino acid sequence of SEQ ID NO:11; and a TE domain having at least 90% identity to the amino acid sequence of SEQ ID NO: 12; and a propionyl-CoA loading module.

5. The non-naturally occurring hybrid PKS of claim 4, wherein the terminal module comprises an AT domain, a KR domain, and an ACP domain, each of which domains is from Lyngbya majuscula CurM having the amino acid sequence of SEQ ID NO: 1; an ST domain having the amino acid sequence of SEQ ID NO: 11; and a TE domain having the amino acid sequence of SEQ ID NO: 12.

6. The non-naturally occurring hybrid PKS of claim 5, wherein the non-naturally occurring hybrid PKS comprises the loading module for propionyl-CoA and a ketosynthase (KS) domain from an erythromycin (DEBS) loading domain.

7. The non-naturally occurring hybrid PKS of claim 4, wherein the non-naturally occurring hybrid PKS comprises the loading module for propionyl-CoA and a ketosynthase (KS) domain from an erythromycin (DEBS) loading domain.

8. A recombinant nucleic acid encoding the non-naturally occurring hybrid PKS of claim 4.

9. A host cell comprising the recombinant nucleic acid of claim 8.

10. The host cell of claim 9, wherein the host cell when cultured produces 1-butene.

11. A method of producing an α-olefin, comprising: providing the host cell of claim 9, and culturing said host cell in a suitable culture medium such that 1-butene is produced.

12. The method of claim 11, further comprising isolating 1-butene.

* * * * *